US011739389B2

(12) United States Patent
Huygens

(10) Patent No.: US 11,739,389 B2
(45) Date of Patent: Aug. 29, 2023

(54) BIOMARKERS AND USES THEREOF

(71) Applicant: Microbio Pty Ltd, Westlake (AU)

(72) Inventor: Flavia Huygens, Westlake (AU)

(73) Assignee: Microbio Pty Ltd, Westlake (AU)

(*) Notice: Subject to any disclaimer, the term of this patent is extended or adjusted under 35 U.S.C. 154(b) by 480 days.

(21) Appl. No.: 16/614,697

(22) PCT Filed: May 17, 2018

(86) PCT No.: PCT/AU2018/050471
§ 371 (c)(1),
(2) Date: Nov. 18, 2019

(87) PCT Pub. No.: WO2018/209398
PCT Pub. Date: Nov. 22, 2018

(65) Prior Publication Data

US 2020/0071749 A1 Mar. 5, 2020

(30) Foreign Application Priority Data

May 17, 2017 (AU) ................................ 2017901846

(51) Int. Cl.
*C12Q 1/68* (2018.01)
*C12Q 1/689* (2018.01)
(Continued)

(52) U.S. Cl.
CPC ............. *C12Q 1/689* (2013.01); *C12Q 1/686* (2013.01); *C12Q 1/6895* (2013.01); *C12Q 2600/112* (2013.01); *C12Q 2600/156* (2013.01)

(58) Field of Classification Search
CPC ........................................................ C12Q 1/68
(Continued)

(56) References Cited

U.S. PATENT DOCUMENTS 4,656,127 A 4/1987 Mundy
5,002,867 A 3/1991 Macevicz
(Continued)

FOREIGN PATENT DOCUMENTS

CN 1683565 10/2005
CN 1746319 3/2006
(Continued)

OTHER PUBLICATIONS

Wei et al, Profiling and Identification of Small rDNA-Derived RNAs and Their Potential Biological Functions, PLoS One. 2013; 8(2): e56842. Published online Feb. 13, 2013. doi: 10.1371/journal.pone.0056842.*

(Continued)

*Primary Examiner* — Aaron A Priest
(74) *Attorney, Agent, or Firm* — Klarquist Sparkman, LLP

(57) ABSTRACT

The present invention generally relates to methods and agents for identifying and/or classifying microbes (especially bacteria), yeast organisms and filamentous fungi. In particular, the present invention concerns the discovery of unique single nucleotide polymorphisms (SNPs) in bacterial 16S ribosomal RNA (16S rRNA) and yeast organism and filamentous fungi 18S ribosomal RNA, and methods of classifying and/or identifying bacteria, yeast organisms and/or filamentous fungi in a sample based on the presence of one or more of those SNPs. The present invention also concerns probes, primers and kits that are useful in those methods.

11 Claims, 26 Drawing Sheets

Specification includes a Sequence Listing.

(51) Int. Cl.
*C12Q 1/686* (2018.01)
*C12Q 1/6895* (2018.01)

(58) Field of Classification Search
USPC ........................................................ 435/6.12
See application file for complete search history.

(56) References Cited

U.S. PATENT DOCUMENTS

| | | | | |
|---|---|---|---|---|
| 5,143,854 | A | 9/1992 | Pirrung et al. | |
| 5,422,252 | A | 6/1995 | Walker et al. | |
| 5,424,186 | A | 6/1995 | Fodor et al. | |
| 5,445,934 | A | 8/1995 | Fodor et al. | |
| 5,589,136 | A | 12/1996 | Northrup et al. | |
| 5,631,734 | A | 5/1997 | Stern et al. | |
| 6,134,854 | A | 10/2000 | Stanchfield | |
| 6,294,336 | B1 | 9/2001 | Boyce-Jacino et al. | |
| 7,381,547 | B2 | 6/2008 | Tsang et al. | |
| 7,864,230 | B2 | 1/2011 | Sugita | |
| 8,741,565 | B2 | 6/2014 | Gu et al. | |
| 2004/0010129 | A1 * | 1/2004 | Hsu | C12Q 1/689 536/23.1 |
| 2004/0241643 | A1 | 12/2004 | Yamamoto et al. | |
| 2005/0142584 | A1 | 6/2005 | Wilson et al. | |
| 2008/0199863 | A1 | 8/2008 | Haake et al. | |
| 2016/0068897 | A1 | 3/2016 | Talebpour et al. | |
| 2016/0145696 | A1 | 5/2016 | Brandon et al. | |

FOREIGN PATENT DOCUMENTS

| | | | | | |
|---|---|---|---|---|---|
| CN | 1291997 | C | | 12/2006 | |
| CN | 103436429 | A | * | 12/2013 | C12Q 1/6806 |
| CN | 103614326 | | | 3/2014 | |
| CN | 103952417 | A | * | 7/2014 | |
| CN | 104372072 | A | * | 2/2015 | C12Q 1/6851 |
| CN | 105483251 | | | 4/2016 | |
| EP | 0332435 | | | 9/1989 | |
| EP | 0785280 | A2 | | 7/1997 | |
| EP | 1464710 | A2 | | 10/2004 | |
| EP | 1953247 | A1 | | 8/2008 | |
| EP | 1997905 | A1 | * | 12/2008 | C12Q 1/689 |
| JP | 2003-284559 | | | 10/2003 | |
| JP | 2007-014351 | | | 1/2007 | |
| KR | 10-2013-0046321 | | | 5/2013 | |
| WO | WO 89/10414 | | | 11/1989 | |
| WO | WO 91/02087 | | | 2/1991 | |
| WO | WO 92/01813 | | | 2/1992 | |
| WO | WO 92/10092 | | | 6/1992 | |
| WO | WO 92/15712 | | | 9/1992 | |
| WO | WO 95/11995 | | | 5/1995 | |
| WO | WO 95/25116 | | | 9/1995 | |
| WO | WO 95/35505 | | | 12/1995 | |
| WO | WO 97/19193 | | | 5/1997 | |
| WO | WO 2002/10444 | A1 | | 2/2002 | |
| WO | WO 2003/079241 | A1 | | 9/2003 | |
| WO | WO 2003/106676 | A1 | | 12/2003 | |
| WO | WO 2008/054432 | A2 | | 5/2008 | |
| WO | WO-2011103274 | A1 | * | 8/2011 | C12Q 1/689 |
| WO | WO 2012/080754 | A2 | | 6/2012 | |
| WO | WO-2012080754 | A2 | * | 6/2012 | C12Q 1/689 |
| WO | WO 2012/110822 | | | 8/2012 | |
| WO | WO 2012/139122 | | | 10/2012 | |
| WO | WO 2013/036928 | | | 3/2013 | |
| WO | WO 2014/190394 | | | 12/2014 | |
| WO | WO-2015095796 | A1 | * | 6/2015 | C12N 15/73 |
| WO | WO 2016/012508 | A1 | | 1/2016 | |
| WO | WO 2016/013940 | A2 | | 1/2016 | |
| WO | WO 2016/193351 | | | 12/2016 | |

OTHER PUBLICATIONS

Kumar & Song, Chapter 61—Polymorphisms of the CB2 Cannabinoid Receptor, Handbook of Cannabis and Related Pathologies Biology, Pharmacology, Diagnosis, and Treatment 2017, pp. 584-591.*

Fluit et al., Molecular Detection of Antimicrobial Resistance, Clin Microbiol Rev. Oct. 2001; 14(4): 836-871. doi: 10.1128/CMR.14.4.836-871.2001.*

Nolan et al, Quantification of mRNA using real-time RT-PCR, Nature Protocols, vol. 1, No. 3, Nov. 9, 2006.*

Applied Biosystems, A Guide to High Resolution Melting (HRM) Analysis, avail at https://tools.thermofisher.com/content/sfs/manuals/cms_070283.pdf, 2010.*

Kagkli et al, Towards a Pathogenic *Escherichia coli* Detection Platform Using Multiplex SYBR® Green Real-Time PCR Methods and High Resolution Melting Analysis, PLoS ONE 7(6): e39287, //doi.org/10.1371/journal.pone.0039287, published Jun. 25, 2012.*

Tong et al, Microbiological Applications of High-Resolution Melting Analysis, J Clin Microbiol. Nov. 2012; 50(11): 3418-3421, doi: 10.1128/JCM.01709-12.*

El-Bahy, et al. "New approach to molecular characterization of *Paramphistomum cervi* and *Carmyerius gregarius* and comparative analyses with selected trematodes," *Parasitol Res.*, vol. 116, No. 5, pp. 1417-1422 (ePub 26), 2016.

Hakovirta, Jr., et al. "Identification and Analysis of Informative Single Nucleotide Polymorphisms in 16S rRNA Gene Sequences of the *Bacillus cereus* Group," *J. Clin. Microbial*, vol. 54, No. 11, pp. 2749-2756, 2016.

Imajoh, et al., "Genotypic characteristics of a *Mycobacterium* sp. Isolated from yellowtail *Seriola quinqueradiata* and striped jack *Pseudocaranx dentex* in Japan," *Microbiology and Immunology*, vol. 57, pp. 13-20, 2013.

Marques, et al., "Intraspecific sequence variation in 16S rRNA gene of *Ureaplasma diversum* isolates," *Veterinary Microbiology*, vol. 152, pp. 205-211, 2011.

Andersson et al., "Analysis of blaSHV Codon 238 and 240 Allele Mixtures Using Sybr Green High-Resolution Melting Analysis," *Antimicrob Agents Chemother*. 53.6:2679-2683, Jun. 2009.

Chee et al., "Accessing Genetic Information with High-Density DNA Arrays," *Science* 274.5287: 610-614, Oct. 1996.

Cotton et al., "Reactivity of cytosine and thymine in single-base-pair mismatches with hydroxylamine and osmium tetroxide and its application to the study of mutations," *Proc Natl Acad Sci. USA* 85: 4397-4401, Jun. 1988.

Derisi et al, "Use of cDNA microarray to analyse gene expression patterns in human cancer," *Nat Genet*. 14: 457-460, Dec. 1996.

Derisi et al., "Exploring the Metabolic and Genetic Control of Gene Expression on a Genomic Scale," *Science* 278: 680-686, Oct. 1997.

Devereux et al., "A comprehensive set of sequence analysis programs for the VAX," *Nucleic Acids Research* 12.1: 387-395, 1984.

Drmanac et al., "Accurate sequencing by hybridization for DNA diagnostics and individual genomics," *Nature Biotech*. 16: 54-58, Jan. 1998.

Gibbs et al., "Detection of single DNA base differences by competitive oligonucleotide priming," *Nucleic Acids Research* 17.7: 2437-2448, 1989.

Hacia et al., "Detection of heterozygous mutations in BRCA1 using high density oligonucleotide arrays and two-colour fluorescence analysis," *Nat Genet*. 14: 441-447, Dec. 1996.

Jobs et al., "DASH-2: Flexible, Low-Cost, and High-Throughput SNP Genotyping by Dynamic Allele-Specific Hybridization on Membrane Arrays," *Genome Res*. 13: 916-924, 2003.

Karlowsky et al. "Prevalence and antimicrobial susceptibilities of bacteria isolated from blood cultures of hospitalized patients in the United States in 2002," *Ann Clin Microbiol Antimicrob*. 3: 7, May 2004 (8 pages).

Kornher and Livak, "Mutation detection using nucleotide analogs that alter electrophoretic mobility," *Nucl Acids Res*. 17.19: 7779-7784, 1989.

Kuppuswamy et al., "Single nucleotide primer extension to detect genetic diseases: Experimental application to hemophilia B (factor IX) and cystic fibrosis genes," *Proc Natl Acad Sci. USA* 88: 1143-1147, Feb. 1991.

Liu et al, "Rolling Circle DNA Synthesis: Small Circular Oligonucleotides as Efficient Templates for DNA Polymerases," *J Am Chem Soc*. 118.7: 1587-1594, Feb. 1996.

(56) References Cited

OTHER PUBLICATIONS

Lucignano et al., "Multiplex PCR Allows Rapid and Accurate Diagnosis of Bloodstream Infections in Newborns and Children with Suspected Sepsis," *J Clin Microbiol.* 49.6: 2252-2258, Jun. 2011.
Maxam and Gilbert, "A new method for sequencing DNA," *Proc Natl Acad Sci. USA* 74.2: 560-564, Feb. 1977.
Merchant-Patel et al., "Characterisation of chicken Campylobacter jejuni isolates using resolution optimised single nucleotide polymorphisms and binary gene markers," *Int J Food Microbiol.* 128:304-308, 2008.
Merchant-Patel et al, "Campylobacter jejuni and Campylobacter coli Genotyping by High-Resolution Melting Analysis of a flaA Fragment," *Applied and Environmental Microbiology* 76.2: 493-499, Jan. 2010.
Modrich, "Mechanisms and Biological Effects of Mismatch Repair," *Ann Rev Genet.* 25: 229-253, 1991.
Moro et al., "Bacterial taxa associated with the hematophagous mite Dermanyssus gallinae detected by 16S rRNA PCR amplification and TTGE fingerprinting," *Res Microbiol.* 160.1: 63-70, Jan.-Feb. 2009.
Nagamine et al., "A PCR Artifact: Generation of Heteroduplexes," *Am J Hum Genet.* 45: 337-339, 1989.
Newton et al., "Analysis of any point mutation in DNA. The amplification refractory mutation system (ARMS)," *Nucl Acids Res.* 17.7: 2503-2516, 1989.
Novack et al., "Detection of single base-pair mismatches in DNA by chemical modification followed by electrophoresis in 15% polyacrylamide gel," *Proc Natl Acad Sci. USA* 83: 586-590, Feb. 1986.
Orita et al., "Detection of polymorphisms of human DNA by gel electrophoresis as single-strand conformation polymorphisms," *Proc Natl Acad Sci USA* 86: 2766-2770, Apr. 1989.
Price et al., "Fingerprinting of Campylobacter jejuni by Using Resolution-Optimized Binary Gene Targets Derived from Comparative Genome Hybridization Studies," *Appl Environ Microbiol.* 72.12: 7793-7803, Dec. 2006.
Prince et al., "Robust and Accurate Single Nucleotide Polymorphism Genotyping by Dynamic Allele-Specific Hybridization (DASH): Design Criteria and Assay Validation," *Genome Res.* 11: 152-162, 2001.
Reinhart et al., New Approaches to Sepsis: Molecular Diagnostics and Biomarkers, *Clinical Microbiology Reviews* 25.4: 609-634, Oct. 2012.
Salimullah et al., "Efficient SNP Analysis Enabled by Joint Application of the µTGGE and Heteroduplex Methods," *Cellular and Mol Biol Letts.* 10: 237-245, 2005.
Schena et al., "Quantitive Monitoring of Gene Expression Patterns with a Complementary DNA Microarray," *Science* 270: 467-470, Oct. 1995.
Shalon et al., "A DNA Microarray System for Analyzing Complex DNA Samples using Two-Color Fluorescent Probe Hybridization," *Genome Res.* 6: 639-645, 1996.
Sheffield et al., "Attachment of a 40-base-pair G+C-rich sequence (GC-clamp) to genomic DNA fragments by the polymerase chain reaction results in improved detection of single-base changes" *Proc Natl Acad Sci. USA* 86: 232-236, Jan. 1989.
Shenk et al., "Biochemical Method for Mapping Mutational Alterations in DNA with S1 Nuclease: The Location of Deletions and Temperature-Sensitive Mutations in Simian Virus 40," *Proc Natl Acad Sci. USA* 72.3: 989-993, Mar. 1975.
Shoemaker et al., "Quantitative phenotypic analysis of yeast deletion mutants using a highly parallel molecular bar-coding strategy," *Nat Genet.* 14: 450-456, Dec. 1996.
Sokolov, "Primer extension technique for the detection of single nucleotide in genomic DNA," *Nucl Acids Res.* 18.12: 3671, 1989.
Stephens et al., "High-Resolution Melting Analysis of the spa Repeat Region of *Staphylococcus aureus," Clinical Chemistry* 54.2: 432-436, Feb. 2008.
Syvanen et al., "Identification of Individuals by Analysis of Biallelic DNA Markers, Using PCR and Solid-Phase Minisequencing," *Amer J Hum Genet.* 52: 46-59, 1993.
Syvanen, "Accessing Genetic Variation: Genotyping Single Nucleotide Polymorphisms," *Nat Rev Genet.* 2.12: 930-942, Dec. 2001.
Thelwell et al., "Mode of action and application of Scorpion primers to mutation detection," *Nucleic Acid Res.* 28.19: 3752-3761, 2000.
Tyagi et al., "Extremely sensitive, background-free gene detection using binary probes and Qβ replicase," *Proc Natl Acad Sci. USA* 93: 5395-5400, May 1996.
Wartell et al., "Detecting base pair substitutions in DNA fragments by temperature-gradient gel electrophoresis," *Nucl Acids Res.* 18.9: 2699-2705, 1990.
Weisburg et al., "16S Ribosomal DNA Amplification for Phylogenetic Study," *Journal of Bacteriology* 173.2: 697-703, Jan. 1991.
Xiao and Kwok, "DNA Analysis by Fluorescence Quenching Detection," *Genome Research* 13.5: 932-939, 2003.
Nucleotide sequence of accession No. EF674493, Uncultured *Staphylococcus* sp. isolate TTGE gel band 11 16S (1 page).

* cited by examiner

```
Staphylococcus aureus           TTTTATGGAGAGTTTGATCCTGGCTCAGGATGAACGCTGGCGGCGTGCCTAATACATGCA
Staphylococcus epidermidis      TTTTATGGAGAGTTTGATCCTGGCTCAGGATGAACGCTGGCGGCGTGCCTAATACATGCA
Streptococcus pneumoniae        -----------GTTTGATCCTGGCTCAGGACGAACGCTGGCGGCGTGCCTAATACATGCA
Streptococcus agalactiae        ----------------------------GACGAACGCTGGCGGCGTGCCTAATACATGCA
Streptococcus pyogenes          -------GAGAGTTTGATCCTGGCTCAGGACGAACGCTGGCGGCGTGCCTAATACATGCA
Enterococcus faecalis           --------AGAGTTTGATCCTGGCTCAGGACGAACGCTGGCGGCGTGCCTAATACATGCA
Enterococcus faecium            --------AGAGTTTGATCCTGGCTCAGGACGAACGCTGGCGGCGTGCCT-ATACATGCA
Proteus mirabilis               --AATTGAAGAGTTTGATCATGGCTCAGATTGAACGCTGGCGGCAGGCCTAACACATGCA
Escherichia coli                -AAATTGAAGAGTTTGATCATGGCTCAGATTGAACGCTGGCGGCAGGCCTAACACATGCA
Serratia marcescens             ----------------------GCTCAGATTGAACGCTGGCGGCAGGCTTAACACATGCA
Enterobacter aerogenes          ---------------------------------ACGCTGGCGGCAGGCCTAACACATGCA
Enterobacter cloacae            ------------------------------TGAACGCTGGCGGCAGGCCTAACACATGCA
Klebsiella pneumoniae           --------AGAGTTTGATNNTGGCTCAGATTGAACGCTGGCGGCAGGCCTAACACATGCA
Pseudomonas aeruginosa          -GAACTGAAGAGTTTGATCATGGCTCAGATTGAACGCTGGCGGCAGGCCTAACACATGCA
Acinetobacter calcoaceticus     -------TAGAGTTTGATCCTGGCTCAGATTGAACGCTGGCGGCAGGCTTAACACATGCA
                                                                 ***********  ** * * *******

Staphylococcus aureus           AGTCGAGCGAACGGACGAGAAGCTTG----------CTTCTCTGATGTTAGCGGCGGACG
Staphylococcus epidermidis      AGTCGAGCGAACAGACGAGGAGCTTG----------CTTCTCTGACGTTAGCGGCGGACG
Streptococcus pneumoniae        AGTAGAACGCTGAAGGAGGAGCTT------------GCTTCTCTGGATGAGTTGCGAACG
Streptococcus agalactiae        AGTAGAACGCTGAGGTTTGGTGTTT----------ACACTAGACTGATGAGTTGCGAACG
Streptococcus pyogenes          AGTAGAACGCTGAGAACTGGTGCTT----------GCACCGGTTCAAGGAGTTGCGAACG
Enterococcus faecalis           AGTCGAACGCTTCTTTCCTCCCGAGTGCTTGCACTCAATTGGAAAGAGGAGTGGCGGACG
Enterococcus faecium            AGTCGAACGCTTCTTTTTCCACCGGAGCTTGCTCCACCGGAAAAAGAGGAGTGGCGAACG
Proteus mirabilis               AGTCGAGCGGTAACAGGAGAAAGCTTGCTTTCTTGC--------TGACGAGCGGCGGACG
Escherichia coli                AGTCGAACGGTAACAGGAAGAAGCTTGCTTCTTTGC--------TGACGAGTGGCGGACG
Serratia marcescens             AGTCGAGCGGTAGCACAGGGGAGCTTGCTCCCTGGG--------TGACGAGCGGCGGACG
Enterobacter aerogenes          AGTCGAGCGGTAGCACAGAGAGCT--TGCTCTCGGG--------TGACGAGCGGCGGACG
Enterobacter cloacae            AGTCGAACGGTAGCACAGAGAGCT--TGCTCTCGGG--------TGACGAGTGGCGGACG
Klebsiella pneumoniae           AGTCGAGCGGTAGCACAGAGAGCT--TGCTCTCGGG--------TGACGAGCGGCGGACG
Pseudomonas aeruginosa          AGTCGAGCGGATGAAGGGAGCTTGCT------CCTG--------GATTCAGCGGCGGACG
Acinetobacter calcoaceticus     AGTCGAGCGGGGAAAGGTAGCTTGCT------ACTG--------GACCTAGCGGCGGACG
                                *** ** **                                        **  *** ***
```

Figure 1A

```
Staphylococcus aureus         GGTGAGTAACACGTGGATAACCTACCTATAAGACTGGGATAACTTCGGGAAACCGGAGCT
Staphylococcus epidermidis    GGTGAGTAACACGTGGATAACCTACCTATAAGACTGGGATAACTTCGGGAAACCGGAGCT
Streptococcus pneumoniae      GGTGAGTAACGCGTAGGTAACCTGCCTGGTAGCGGGGGATAACTATTGGAAACGATAGCT
Streptococcus agalactiae      GGTGAGTAACGCGTAGGTAACCTGCCTCATAGCGGGGGATAACTATTGGAAACGATAGCT
Streptococcus pyogenes        GGTGAGTAACGCGTAGGTAACCTACCTCATAGCGGGGGATAACTATTGGAAACGATAGCT
Enterococcus faecalis         GGTGAGTAACACGTGGGTAACCTACCCATCAGAGGGGGATAACACTTGGAAACAGGTGCT
Enterococcus faecium          GGTGAGTAACACGTGGGTAACCTGCCCATCAGAAAGGGATAACACTTGGAAACAGGTGCT
Proteus mirabilis             GGTGAGTAATGTATG-GGGATCTGCCCGATAGAGGGGGATAACTACTGGAAACGGTGGCT
Escherichia coli              GGTGAGTAATGTCTG-GGAAACTGCCTGATGGAGGGGGATAACTACTGGAAACGGTAGCT
Serratia marcescens           GGTGAGTAATGTCTG-GGAAACTGCCTGATGGAGGGGGATAACTACTGGAAACGGTAGCT
Enterobacter aerogenes        GGTGAGTAATGTCTG-GGAAACTGCCTGATGGAGGGGGATAACTACTGGAAACGGTAGCT
Enterobacter cloacae          GGTGAGTAATGTCTG-GGAAACTGCCTGATGGAGGGGGATAACTACTGGAAACGGTAGCT
Klebsiella pneumoniae         GGTGAGTAATGTCTG-GGAAACTGCCTGATGGAGGGGGATAACTACTGGAAACGGTAGCT
Pseudomonas aeruginosa        GGTGAGTAATGCCTA-GGAATCTGCCTGGTAGTGGGGGATAACGTCCGGAAACGGGCGCT
Acinetobacter calcoaceticus   GGTGAGTAATGCTTA-GGAATCTGCCTATTAGTGGGGGACAACATTCCGAAAGGAATGCT
                              *********    *     * ** **     *   **** ***     ****     ***

Staphylococcus aureus         AATACCGGATAATATTTTGAACCGCATGGTTCAAAAGTGA--AAGACGGTCTTGCTGTCA
Staphylococcus epidermidis    AATACCGGATAATATATTGAACCGCATGGTTCAATAGTGA--AAGACGGTTTTGCTGTCA
Streptococcus pneumoniae      AATACCGCATAAGAGTGGATGTTGCATGACAT-TTGCTTAAAA--GGTGCACTTGCATCA
Streptococcus agalactiae      AATACCGCATAAGAGTAATTAACACATGTTAG-TTATTTAAAA--GGAGCAATTGCTTCA
Streptococcus pyogenes        AATACCGCATAAGAGAGACTAACGCATGTTAG-TAATTTAAAA--GGGGCAATTGCTCCA
Enterococcus faecalis         AATACCGCATAACAGTTTAT-GCCGCATGGCATAAGAGTGAAAGGCGCTTTCGGGTGTCG
Enterococcus faecium          AATACCGTATAACAAATCAAAACCGCATGGTTTTGATTTGAAAGGCGCTTTCGGGTGTCG
Proteus mirabilis             AATACCGCATAATGTCTACGGACCAAAG----------CAGGGGCTCTTCGGACCTTGCA
Escherichia coli              AATACCGCATAACGTCGCAAGACCAAAG----------AGGGGGACCTTCGGGCCTCTTG
Serratia marcescens           AATACCGCATAACGTCGCAAGACCAAAG----------AGGGGGACCTTCGGGCCTCTTG
Enterobacter aerogenes        AATACCGCATAACGTCGCAAGACCAAAG----------TGGGGGACCTTCGGGCCTCATG
Enterobacter cloacae          AATACCGCATAAYGTCGCAAGACCAAAG----------AGGGGGACCTTCGGGCCTCTTG
Klebsiella pneumoniae         AATACCGCATAACGTCGCAAGACCAAAG----------TGGGGGACCTTCGGGCCTCATG
Pseudomonas aeruginosa        AATACCGCATACGTCCTGAGGGAGAAAG----------TGGGGGATCTTCGGACCTCACG
Acinetobacter calcoaceticus   AATACCGCATACGTCCTACGGGAGAAAG----------CAGGGGACCTTCGGGCCTTGCG
                              ******* ***
```

Figure 1B

```
                                                                                SNP273
Staphylococcus aureus          CTTATAGATGGATCCGCGCTGCATTAGCTAGTTGGTAAGGTAACGGCTTACCAAGGCAAC
Staphylococcus epidermidis     CTTATAGATGGATCCGCGCCGCATTAGCTAGTTGGTAAGGTAACGGCTTACCAAGGCAAC
Streptococcus pneumoniae       CTACCAGATGGACCTGCGTTGTATTAGCTAGTTGGTGGGGTAACGGCTCACCAAGGCGAC
Streptococcus agalactiae       CTGTGAGATGGACCTGCGTTGTATTAGCTAGTTGGTGAGGTAAAGGCTCACCAAGGCGAC
Streptococcus pyogenes         CTATGAGATGGACCTGCGTTGTATTAGCTAGTTGGTGAGGTAAAGGCTCACCAAGGCGAC
Enterococcus faecalis          TTGATGGATGGACCCGCGGTGCATTAGCTAGTTGGTGAGGTAACGGCTCACCAAGGCCAC
Enterococcus faecium           CTGATGGATGGACCCGCGGTGCATTAGCTAGTTGGTGAGGTAACGGCTCACCAAGGCCAC
Proteus mirabilis              CTATCGGATGAACCCATATGGGATTAGCTAGTAGGTGGGGTAAAGGCTCACCTAGGCGAC
Escherichia coli               CCATCGGATGTGCCCAGATGGGATTAGCTAGTAGGTGGGGTAACGGCTCACCTAGGCGAC
Serratia marcescens            CCATCAGATGTGCCCAGATGGGATTAGCTAGTAGGTGGGGTAATGGCTCACCTAGGCGAC
Enterobacter aerogenes         CCATCAGATGTGCCCAGATGGGATTAGCTAGTAGGTGGGGTAATGGCTCACCTAGGCGAC
Enterobacter cloacae           CCATCAGATGTGCCCAGATGGGATTAGCTAGTAGGTGGGGTAACGGCTCACCTAGGCGAC
Klebsiella pneumoniae          CCATCAGATGTGCCCAGATGGGATTAGCTAGTAGGTGGGGTAACGGCTCACCTAGGCGAC
Pseudomonas aeruginosa         CTATCAGATGAGCCTAGGTCGGATTAGCTAGTTGGTGGGGTAAAGGCCTACCAAGGCGAC
Acinetobacter calcoaceticus    CTAATAGATGAGCCTAAGTCGGATTAGCTAGTTGGTGGGGTAAAGGCCTACCAAGGCGAC
                                     ****   *      * ********** ***  ***** ***  *** **** **

Staphylococcus aureus          GATGCATAGCCGACC-TGAGAGGGTGATCGGCCACACTGGAACTGAGACACGGTCCAGAC
Staphylococcus epidermidis     GATGCGTAGCCGACC-TGAGAGGGTGATCGGCCACACTGGAACTGAGACACGGTCCAGAC
Streptococcus pneumoniae       GATACATAGCCGACC-TGAGAGGGTGATCGGCCACACTGGGACTGAGACACGGCCCAGAC
Streptococcus agalactiae       GATACATAGCCGACC-TGAGAGGGTGATCGGCCACACTGGGACTGAGACACGGCCCAGAC
Streptococcus pyogenes         GATACATAGCCGACC-TGAGAGGGTGATCGGCCACACTGGGACTGAGACACGGCCCAGAC
Enterococcus faecalis          GATGCATAGCCGACC-TGAGAGGGTGATCGGCCACACTGGGACTGAGACACGGCCCAGAC
Enterococcus faecium           GATGCATAGCCGCACCTGAGAGGGTGATCGGCCACATTGGGACTGAGACACGGCCCA-AA
Proteus mirabilis              GATCTCTAGCTGGTC-TGAGAGGATGATCAGCCACACTGGGACTGAGACACGGCCCAGAC
Escherichia coli               GATCCCTAGCTGGTC-TGAGAGGATGACCAGCCACACTGGAACTGAGACACGGTCCAGAC
Serratia marcescens            GATCCCTAGCTGGTC-TGAGAGGATGACCAGCCACACTGGAACTGAGACACGGTCCAGAC
Enterobacter aerogenes         GATCCCTAGCTGGTC-TGAGAGGATGACCAGCCACACTGGAACTGAGACACGGTCCAGAC
Enterobacter cloacae           GATCCCTAGCTGGTC-TGAGAGGATGACCAGCCACACTGGAACTGAGACACGGTCCAGAC
Klebsiella pneumoniae          GATCCCTAGCTGGTC-TGAGAGGATGACCAGCCACACTGGAACTGAGACACGGTCCAGAC
Pseudomonas aeruginosa         GATCCGTAACTGGTC-TGAGAGGATGATCAGTCACACTGGAACTGAGACACGGTCCAGAC
Acinetobacter calcoaceticus    GATCTGTAG-CGGTC-TGAGAGGATGATCCGCCACACTGGGACTGAGACACGGCCCAGAC
                               ***   **   *  * ******* *** * * **** *** ***********  *** *
```

Figure 1C

```
                                                                          SNP378
Staphylococcus aureus           TCCTACGGGAGGCAGCAGTAGGGAATCTTCCGCAATGGGCGAAAGCCTGACGGAGCAACG
Staphylococcus epidermidis      TCCTACGGGAGGCAGCAGTAGGGAATCTTCCGCAATGGGCGAAAGCCTGACGGAGCAACG
Streptococcus pneumoniae        TCCTACGGGAGGCAGCAGTAGGGAATCTTCGGCAATGGACGGAAGTCTGACCGAGCAACG
Streptococcus agalactiae        TCCTACGGGAGGCAGCAGTAGGGAATCTTCGGCAATGGACGGAAGTCTGACCGAGCAACG
Streptococcus pyogenes          TCCTACGGGAGGCAGCAGTAGGGAATCTTCGGCAATGGGGGCAACCCTGACCGAGCAACG
Enterococcus faecalis           TCCTACGGGAGGCAGCAGTAGGGAATCTTCGGCAATGGACGAAAGTCTGACCGAGCAACG
Enterococcus faecium            CTCTACGGGAGGCAGCAGTAGGGAATCTTCGGCAATGGACGAAAGTCTGACCGAGCAACG
Proteus mirabilis               TCCTACGGGAGGCAGCAGTGGGGAATATTGCACAATGGGCGCAAGCCTGATGCAGCCATG
Escherichia coli                TCCTACGGGAGGCAGCAGTGGGGAATATTGCACAATGGGCGCAAGCCTGATGCAGCCATG
Serratia marcescens             TCCTACGGGAGGCAGCAGTGGGGAATATTGCACAATGGGCGCAAGCCTGATGCAGCCATG
Enterobacter aerogenes          TCCTACGGGAGGCAGCAGTGGGGAATATTGCACAATGGGCGCAAGCCTGATGCAGCCATG
Enterobacter cloacae            TCCTACGGGAGGCAGCAGTGGGGAATATTGCACAATGGGCGCAAGCCTGATGCAGCCATG
Klebsiella pneumoniae           TCCTACGGGAGGCAGCAGTGGGGAATATTGCACAATGGGCGCAAGCCTGATGCAGCCATG
Pseudomonas aeruginosa          TCCTACGGGAGGCAGCAGTGGGGAATATTGGACAATGGGCGAAAGCCTGATCCAGCCATG
Acinetobacter calcoaceticus     TCCTACGGGAGGCAGCAGTGGGGAATATTGGACAATGGGGGAACCCTGATCCAGCCATG
                                  **************** ****** **   ******  * **  ****   *** * *

                                             SNP412                       SNP440
Staphylococcus aureus           CCGCGTGAGTGATGAAGGTCTTCGGATCGTAAAACTCTGTTATTAGGGAAGAACATATGT
Staphylococcus epidermidis      CCGCGTGAGTGATGAAGGTCTTCGGATCGTAAAACTCTGTTATTAGGGAAGAACAAATGT
Streptococcus pneumoniae        CCGCGTGAGTGAAGAAGGTTTTCGGATCGTAAAGCTCTGTTGTAAGAGAAGAACGAGTGT
Streptococcus agalactiae        CCGCGTGAGTGAAGAAGGTTTTCGGATCGTAAAGCTCTGTTGTTAGAGAAGAACGTTGGT
Streptococcus pyogenes          CCGCGTGAGTGAAGAAGGTTTTCGGATCGTAAAGCTCTGTTGTTAGAGAAGAATGATGGT
Enterococcus faecalis           CCGCGTGAGTGAAGAAGGTTTTCGGATCGTAAAACTCTGTTGTTAGAGAAGAACAAGGAC
Enterococcus faecium            CCGCGTGAGTGAAGAAGGTTTTCGGATCGTAAAACTCTGTTGTTAGAGAAGAACAAGGAT
Proteus mirabilis               CCGCGTGTATGAAGAAGGCCTTAGGGTTGTAAAGTACTTTCAGCGGGGAGGAAGGTGATA
Escherichia coli                CCGCGTGTATGAAGAAGGCCTTCGGGTTGTAAAGTACTTTCAGCGGGGAGGAAGGGAGTA
Serratia marcescens             CCGCGTGTGTGAAGAAGGCCTTCGGGTTGTAAAGCACTTTCAGCGAGGAGGAAGGTGGTG
Enterobacter aerogenes          CCGCGTGTATGAAGAAGGCCTTCGGGTTGTAAAGTACTTTCAGCGAGGAGGAAGGCGTTA
Enterobacter cloacae            CCGCGTGTATGAAGAAGGCCTTCGGGTTGTAAAGTACTTTCAGCGGGGAGGAAGGTGTTG
Klebsiella pneumoniae           CCGCGTGTGTGAAGAAGGCCTTCGGGTTGTAAAGCACTTTCAGCGGGGAGGAAGGCGATG
Pseudomonas aeruginosa          CCGCGTGTGTGAAGAAGGTCTTCGGATTGTAAAGCACTTTAAGTTGGGAGGAAGGGCAGT
Acinetobacter calcoaceticus     CCGCGTGTGTGAAGAAGGCCTTATGGTTGTAAAGCACTTTAAGCGAGGAGGAGGCTACTA
                                *******  *** *****  **  * * *****   ** *       ** **
```

Figure 1D

```
                                                           SNP488
Staphylococcus aureus          GTAAGTAAC-TGTGCACATCTTGACGGTACCTAATCAGAAAGCCACGGCTAACTACGTGC
Staphylococcus epidermidis     GTAAGTAAC-TATGCACGTCTTGACGGTACCTAATCAGAAAGCCACGGCTAACTACGTGC
Streptococcus pneumoniae       GAGAGTGGAAAGTTCACACTGTGACGGTATCTTACCAGAAAGGGACGGCTAACTACGTGC
Streptococcus agalactiae       AGGAGTGGAAAATCTACCAAGTGACGGTAACTAACCAGAAAGGGACGGCTAACTACGTGC
Streptococcus pyogenes         GGGAGTGGAAAATCCACCAAGTGACGGTAACTAACCAGAAAGGGACGGCTAACTACGTGC
Enterococcus faecalis          GTTAGTAAC-TGAACGTCCCCTGACGGTATCTAACCAGAAAGCCACGGCTAACTACGTGC
Enterococcus faecium           GAGAGTAAC-TGTTCATCCCTTGACGGTATCTAACCAGAAAGCCACGGCTAACTACGTGC
Proteus mirabilis              AGGTTAATACCCTTGTCAATTGACGTTACC-CGCAGAAGAAGCACCGGCTAACTCCGTGC
Escherichia coli               AAGTTAATACCTTTGCTCATTGACGTTACC-CGCAGAAGAAGCACCGGCTAACTCCGTGC
Serratia marcescens            AGCTTAATACGTTCATCAATTGACGTTACT-CGCAGAAGAAGCACCGGCTAACTCCGTGC
Enterobacter aerogenes         AGGTTAATAACCTTGGCGATTGACGTTACT-CGCAGAAGAAGCACCGGCTAACTCCGTGC
Enterobacter cloacae           TGGTTAATAACCGCAGCAATTGACGTTACC-CGCAGAAGAAGCACCGGCTAACTCCGTGC
Klebsiella pneumoniae          AGGTTAATAACCTCATCGATTGACGTTACCCTGCAGAAGAAGCACCGGCTAACTCCGTGC
Pseudomonas aeruginosa         AAGTTAATAC-CTTGCTGTTTTGACGTTACCAACAGAATAAGCACCGGCTAACTTCGTGC
Acinetobacter calcoaceticus    GTATTAATACTACTGGATAGTGGACGTTACTCGCAGAATAAGCACCGGCTAACTCTGTGC
                                                                   *  ***   *********  ****

Staphylococcus aureus          CAGCAGCCGCGGTAATACGTAGGTGGCAAGCGTTATCCGGAATTATTGGGCGTAAAGCGC
Staphylococcus epidermidis     CAGCAGCCGCGGTAATACGTAGGTGGCAAGCGTTATCCGGAATTATTGGGCGTAAAGCGC
Streptococcus pneumoniae       CAGCAGCCGCGGTAATACGTAGGTCCCGAGCGTTGTCCGGATTTATTGGGCGTAAAGCGA
Streptococcus agalactiae       CAGCAGCCGCGGTAATACGTAGGTCCCGAGCGTTGTCCGGATTTATTGGGCGTAAAGCGA
Streptococcus pyogenes         CAGCAGCCGCGGTAATACGTAGGTCCCGAGCGTTGTCCGGATTTATTGGGCGTAAAGCGA
Enterococcus faecalis          CAGCAGCCGCGGTAATACGTAGGTGGCAAGCGTTGTCCGGATTTATTGGGCGTAAAGCGA
Enterococcus faecium           CAGCAGCCGCGGTAATACGTAGGTGGCAAGCGTTGTCCGGATTTATTGGGCGTAAAGCGA
Proteus mirabilis              CAGCAGCCGCGGTAATACGGAGGGTGCAAGCGTTAATCGGAATTACTGGGCGTAAAGCGC
Escherichia coli               CAGCAGCCGCGGTAATACGGAGGGTGCAAGCGTTAATCGGAATTACTGGGCGTAAAGCGC
Serratia marcescens            CAGCAGCCGCGGTAATACGGAGGGTGCAAGCGTTAATCGGAATTACTGGGCGTAAAGCGC
Enterobacter aerogenes         CAGCAGCCGCGGTAATACGGAGGGTGCAAGCGTTAATCGGAATTACTGGGCGTAAAGCGC
Enterobacter cloacae           CAGCAGCCGCGGTAATACGGAGGGTGCAAGCGTTAATCGGAATTACTGGGCGTAAAGCGC
Klebsiella pneumoniae          CAGCAGCCGCGGTAATACGGAGGGTGCAAGCGTTAATCGGAATTACTGGGCGTAAAGCGC
Pseudomonas aeruginosa         CAGCAGCCGCGGTAATACGAAGGGTGCAAGCGTTAATCGGAATTACTGGGCGTAAAGCGC
Acinetobacter calcoaceticus    CAGCAGCCGCGGTAATACAGAGGGTGCGAGCGTTAATCGGATTTACTGGGCGTAAAGCGT
                               ******************  ***   * ******   **** *** *************
```

Figure 1E

```
Staphylococcus aureus              GCGTAGGCGGTTTTTTAAGTCTGATGTGAAAGCCCACGGCTCAACCGTGGAGGGTCATTG
Staphylococcus epidermidis         GCGTAGGCGGTTTTTTAAGTCTGATGTGAAAGCCCACGGCTCAACCGTGGAGGGTCATTG
Streptococcus pneumoniae           GCGCAGGCGGTTAGATAAGTCTGAAGTTAAAGGCTGTGGCTTAACCATAGT-AGGCTTTG
Streptococcus agalactiae           GCGCAGGCGGTTCTTTAAGTCTGAAGTTAAAGGCAGTGGCTTAACCATTGT-ACGCTTTG
Streptococcus pyogenes             GCGCAGGCGGTTTTTTAAGTCTGAAGTTAAAGGCATTGGCTCAACCAATGT-ACGCTTTG
Enterococcus faecalis              GCGCAGGCGGTTTCTTAAGTCTGATGTGAAAGCCCCCGGCTCAACCGGGGAGGGTCATTG
Enterococcus faecium               GCGCAGGCGG-TTCTTAAGTCTGATGTGAAAGCCCCCGGCTCAACCGGGGAGGGTCATTG
Proteus mirabilis                  ACGCAGGCGGTCAATTAAGTCAGATGTGAAAGCCCCGAGCTTAACTTGGGAATTGCATCT
Escherichia coli                   ACGCAGGCGGTTTGTTAAGTCAGATGTGAAATCCCCGGGCTCAACCTGGGAACTGCATCT
Serratia marcescens                ACGCAGGCGGTTTGTTAAGTCAGATGTGAAATCCCCGGGCTCAACCTGGGAACTGCATTT
Enterobacter aerogenes             ACGCAGGCGGTCTGTCAAGTCGGATGTGAAATCCCCGGGCTCAACCTGGGAACTGCATTC
Enterobacter cloacae               ACGCAGGCGGTCTGTCAAGTCGGATGTGAAATCCCCGGGCTCAACCTGGGAACTGCATTC
Klebsiella pneumoniae              ACGCAGGCGGTCTGTCAAGTCGGATGTGAAATCCCCGGGCTCAACCTGGGAACTGCATTC
Pseudomonas aeruginosa             GCGTAGGTGGTTCAGCAAGTTGGATGTGAAATCCCCGGGCTCAACCTGGGAACTGCATCC
Acinetobacter calcoaceticus        GCGTAGGCGGCCATTTAAGTCAAATGTGAAATCCCCGAGCTTAACTTGGGAATTGCATTG
                                    ** *** **      ****   * ** ***  *    *** ***    *     * *

                                    SNP647  SNP653
Staphylococcus aureus              GAAACTGGAAAAACTTGAGTGCAGAAGAGGAAAGTGGAATTCCATGTGTAGCGGTGAAATG
Staphylococcus epidermidis         GAAACTGGAAAAACTTGAGTGCAGAAGAGGAAAGTGGAATTCCATGTGTAGCGGTGAAATG
Streptococcus pneumoniae           GAAACTGTTTAACTTGAGTGCAAGAGGGGAGAGTGGAATTCCATGTGTAGCGGTGAAATG
Streptococcus agalactiae           GAAACTGGAGGACTTGAGTGCAGAAGGGGAGAGTGGAATTCCATGTGTAGCGGTGAAATG
Streptococcus pyogenes             GAAACTGGAGAACTTGAGTGCAGAAGGGGAGAGTGGAATTCCATGTGTAGCGGTGAAATG
Enterococcus faecalis              GAAACTGGGAGACTTGAGTGCAGAAGAGGAGAGTGGAATTCCATGTGTAGCGGTGAAATG
Enterococcus faecium               GAAACTGGGAGACTTGAGTGCAGAAGAGGAGAGTGGAATTCCATGTGTAGCGGTGAAATG
Proteus mirabilis                  GAAACTGGTTGGCTAGAGTCTTGTAGAGGGGGGTAGAATTCCATGTGTAGCGGTGAAATG
Escherichia coli                   GATACTGGCAAGCTTGAGTCTCGTAGAGGGGGGTAGAATTCCAGGTGTAGCGGTGAAATG
Serratia marcescens                GAAACTGGCAAGCTAGAGTCTCGTAGAGGGGGGTAGAATTCCAGGTGTAGCGGTGAAATG
Enterobacter aerogenes             GAAACTGGCAGGCTAGAGTCTTGTAGAGGGGGGTAGAATTCCAGGTGTAGCGGTGAAATG
Enterobacter cloacae               GAAACTGGCAGGCTGGAGTCTTGTAGAGGGGGGTAGAATTCCAGGTGTAGCGGTGAAATG
Klebsiella pneumoniae              GAAACTGGCAGGCTAGAGTCTTGTAGAGGGGGGTAGAATTCCAGGTGTAGCGGTGAAATG
Pseudomonas aeruginosa             AAAACTACTGAGCTAGAGTACGGTAGAGGGTGGTGGAATTTCCTGTGTAGCGGTGAAATG
Acinetobacter calcoaceticus        CATACTGGATGGCTAGAGTATGGGAGAGGATGGTAGAATTCCAGGTGTAGCGGTGAAATG
                                    * ***      ** ****     ** **   ** ***** *   ***************
```

Figure 1F

```
Staphylococcus aureus             CGCAGAGATATGGAGGAACACCAGTGGCGAAGGCGACTTTCTGGTCTGTAACTGACGCTG
Staphylococcus epidermidis        CGCAGAGATATGGAGGAACACCAGTGGCGAAGGCGACTTTCTGGTCTGTAACTGACGCTG
Streptococcus pneumoniae          CGTAGATATATGGAGGAACACCGGTGGCGAAAGCGGCTCTCTGGCTTGTAACTGACGCTG
Streptococcus agalactiae          CGTAGATATATGGAGGAACACCGGTGGCGAAAGCGGCTCTCTGGTCTGTAACTGACGCTG
Streptococcus pyogenes            CGTAGATATATGGAGGAACACCGGTGGCGAAAGCGGCTCTCTGGTCTGTAACTGACGCTG
Enterococcus faecalis             CGTAGATATATGGAGGAACACCAGTGGCGAAGGCGGCTCTCTGGTCTGTAACTGACGCTG
Enterococcus faecium              CGTAGATATATGGAGGAACACCAGTGGCGAAGGCGGCTCTCTGGTCTGTAACTGACGCTG
Proteus mirabilis                 CGTAGAGATGTGGAGGAATACCGGTGGCGAAGGCGGCCCCCTGGACAAAGACTGACGCTC
ESCHERICHIA COLI                  CGTAGAGATCTGGAGGAATACCGGTGGCGAAGGCGGCCCCCTGGACGAAGACTGACGCTC
Serratia marcescens               CGTAGAGATCTGGAGGAATACCGGTGGCGAAGGCGGGCCCCTGGACGAAGACTGACGCTC
Enterobacter aerogenes            CGTAGAGATCTGGAGGAATACCGGTGGCGAAGGCGGCCCCCTGGACAAAGACTGACGCTC
Enterobacter cloacae              CGTAGAGATCTGGAGGAATACCGGTGGCGAAGGCGGCCCCCTGGACAAAGACTGACGCTC
Klebsiella pneumoniae             CGTAGAGATCTGGAGGAATACCGGTGGCGAAGGCGGCCCCCTGGACAAAGACTGACGCTC
Pseudomonas aeruginosa            CGTAGATATAGGAAGGAACACCAGTGGCGAAGGCGACCACCTGGACTGATACTGACACTG
Acinetobacter calcoaceticus       CGTAGAGATCTGGAGGAATACCGATGGCGAAGGCAGCCATCTGGCCTAATACTGACGCTG
                                  ** *** **  * ***** ***  ******* **      ****      ****** **

Staphylococcus aureus             ATGTGCGAAAGCGTGGGGATCAAACAGGATTAGATACCCTGGTAGTCCACGCCGTAAACG
Staphylococcus epidermidis        ATGTGCGAAAGCGTGGGGATCAAACAGGATTAGATACCCTGGTAGTCCACGCCGTAAACG
Streptococcus pneumoniae          AGGCTCGAAAGCGTGGGGAGCAAACAGGATTAGATACCCTGGTAGTCCACGCTGTAAACG
Streptococcus agalactiae          AGGCTCGAAAGCGTGGGGAGCAAACAGGATTAGATACCCTGGTAGTCCACGCCGTAAACG
Streptococcus pyogenes            AGGCTCGAAAGCGTGGGGAGCAAACAGGATTAGATACCCTGGTAGTCCACGCCGTAAACG
Enterococcus faecalis             AGGCTCGAAAGCGTGGGGAGCAAACAGGATTAGATACCCTGGTAGTCCACGCCGTAAACG
Enterococcus faecium              AGGCTCGAAAGCGTGGGGAGCAAACAGGATTAGATACCCTGGTAGTCCACGCCGTAAACG
Proteus mirabilis                 AGGTGCGAAAGCGTGGGGAGCAAACAGGATTAGATACCCTGGTAGTCCACGCTGTAAACG
Escherichia coli                  AGGTGCGAAAGCGTGGGGAGCAAACAGGATTAGATACCCTGGTAGTCCACGCCGTAAACG
Serratia marcescens               AGGTGCCAAAGCGTGGGGAGCAAACAGGATTAGATACCCTGGTAGTCCACGCTGTAAACG
Enterobacter aerogenes            AGGTGCGAAAGCGTGGGGAGCAAACAGGATTAGATACCCTGGTAGTCCACGCCGTAAACG
Enterobacter cloacae              AGGTGCGAAAGCGTGGGGAGCAAACAGGATTAGATACCCTGGTAGTCCACGCCGTAAACG
Klebsiella pneumoniae             AGGTGCGAAAGCGTGGGGAGCAAACAGGATTAGATACCCTGGTAGTCCACGCCGTAAACG
Pseudomonas aeruginosa            AGGTGCGAAAGCGTGGGGAGCAAACAGGATTAGATACCCTGGTAGTCCACGCCGTAAACG
Acinetobacter calcoaceticus       AGGTACGAAAGCATGGGAGCAGAACAGGATTAGATACCCTGGTAGTCCATGCCGTAAACG
                                  * *  * ***** ****     *************************** ** *******
```

Figure 1G

```
Staphylococcus aureus           ATGAGTGCTAAGTGTTAGGGGGTTTCCGCCCCTTAGTGCTGCAGCTAACGCATTAAGCAC
Staphylococcus epidermidis      ATGAGTGCTAAGTGTTAGGGGGTTTCCGCCCCTTAGTGCTGCAGCTAACGCATTAAGCAC
Streptococcus pneumoniae        ATGAGTGCTAGGTGTTAGACCCTTTCCGGGGTTTAGTGCCGTAGCTAACGCATTAAGCAC
Streptococcus agalactiae        ATGAGTGCTAGGTGTTAGGCCCTTTCCGGGGCTTAGTGCCGCAGCTAACGCATTAAGCAC
Streptococcus pyogenes          ATGAGTGCTAGGTGTTAGGCCCTTTCCGGGGCTTAGTGCCGGAGCTAACGCATTAAGCAC
Enterococcus faecalis           ATGAGTGCTAAGTGTTGGAGGGTTTCCGCCCTTCAGTGCTGCAGCAAACGCATTAAGCAC
Enterococcus faecium            ATGAGTGCTAAGTGTTGGAGGGTTTCCGCCCTTCAGTGCTGCAGCTAACGCATTAAGCAC
Proteus mirabilis               ATGTCGATTTAGAGGTTGTGGTCTTG-AACCGTGGCTTCTGGAGCTAACGCGTTAAATCG
Escherichia coli                ATGTCGACTTGGAGGTTGTGCCCTTG-AGGCGTGGCTTCCGGAGCTAACGCGTTAAGTCG
Serratia marcescens             ATGTCGATTTGGAGGTTGTGCCCTTG-AGGCGTGGCTTCCGGAGCTAACGCGTTAAATCG
Enterobacter aerogenes          ATGTCGACTTGGAGGTTGTGCCCTTG-AGGCGTGGCTTCCGGAGCTAACGCGTTAAGTCG
Enterobacter cloacae            ATGTCGATTTGGAGGTTGTGCCCTTG-AGGCGTGGCTTCCGGAGCTAACGCGTTAAATCG
Klebsiella pneumoniae           ATGTCGATTTGGAGGTTGTGCCCTTG-AGGCGTGGCTTCCGGAGCTAACGCGTTAAATCG
Pseudomonas aeruginosa          ATGTCGACTAGCCGTTGGGATCCTTG-AGATCTTAGTGGCGCAGCTAACGCGATAAGTCG
Acinetobacter calcoaceticus     ATGTTTACTAGCCGTTGGGGCCTTTG-AGGCTTTAGTGGCGCAGCTAACGCGATAAGTAG
                                ***     *    * * *     **       *   *   * *** *****  ***

Staphylococcus aureus           TCCGCCTGGGGAGTACGACCGCAAGGTTGAAACTCAAAGGAATTGACGGGGACCCGCACA
Staphylococcus epidermidis      TCCGCCTGGGGAGTACGACCGCAAGGTTGAAACTCAAAGGAATTGACGGGGACCCGCACA
Streptococcus pneumoniae        TCCGCCTGGGGAGTACGACCGCAAGGTTGAAACTCAAAGGAATTGACGGGGGCCCGCACA
Streptococcus agalactiae        TCCGCCTGGGGAGTACGACCGCAAGGTTGAAACTCAAAGGAATTGACGGGGGCCCGCACA
Streptococcus pyogenes          TCCGCCTGGGGAGTACGACCGCAAGGTTGAAACTCAAAGGAATTGACGGGGGCCCGCACA
Enterococcus faecalis           TCCGCCTGGGGAGTACGACCGCAAGGTTGAAACTCAAAGGAATTGACGGGGGCCCGCACA
Enterococcus faecium            TCCGCCTGGGGAGTACGACCGCAAGGTTGAAACTCAAAGGAATTGACGGGGGCCCGCACA
Proteus mirabilis               ACCGCCTGGGGAGTACGGCCGCAAGGTTAAAACTCAAATGAATTGACGGGGGCCCGCACA
Escherichia coli                ACCGCCTGGGGAGTACGGCCGCAAGGTTAAAACTCAAATGAATTGACGGGGGCCCGCACA
Serratia marcescens             ACCGCCTGGGGAGTACGGCCGCAAGGTTAAAACTCAAATGAATTGACGGGGGCCCGCACA
Enterobacter aerogenes          ACCGCCTGGGGAGTACGGCCGCAAGGTTAAAACTCAAATGAATTGACGGGGGCCCGCACA
Enterobacter cloacae            ACCGCCTGGGGAGTACGGCCGCAAGGTTAAAACTCAAATGAATTGACGGGGGCCCGCACA
Klebsiella pneumoniae           ACCGCCTGGGGAGTACGGCCGCAAGGTTAAAACTCAAATGAATTGACGGGGGCCCGCACA
Pseudomonas aeruginosa          ACCGCCTGGGGAGTACGGCCGCAAGGTTAAAACTCAAATGAATTGACGGGGGCCCGCACA
Acinetobacter calcoaceticus     ACCGCCTGGGGAGTACGGTCGCAAGACTAAAACTCAAATGAATTGACGGGGGCCCGCACA
                                 ****************  ******  * ********* ************ ********
```

Figure 1H

```
Staphylococcus aureus          AGCGGTGGAGCATGTGGTTTAATTCGAAGCAACGCGAAGAACCTTACCAAATCTTGACAT
Staphylococcus epidermidis     AGCGGTGGAGCATGTGGTTTAATTCGAAGCAACGCGAAGAACCTTACCAAATCTTGACAT
Streptococcus pneumoniae       AGCGGTGGAGCATGTGGTTTAATTCGAAGCAACGCGAAGAACCTTACCAGGTCTTGACAT
Streptococcus agalactiae       AGCGGTGGAGCATGTGGTTTAATTCGAAGCAACGCGAAGAACCTTACCAGGTCTTGACAT
Streptococcus pyogenes         AGCGGTGGAGCATGTGGTTTAATTCGAAGCAACGCGAAGAACCTTACCAGGTCTTGACAT
Enterococcus faecalis          AGCGGTGGAGCATGTGGTTTAATTCGAAGCAACGCGAAGAACCTTACCAGGTCTTGACAT
Enterococcus faecium           AGCGGTGGAGCATGTGGTTTAATTCGAAGCAACACGAAGAACCTTACCAGGTCTTGACAT
Proteus mirabilis              AGCGGTGGAGCATGTGGTTTAATTCGATGCAACGCGAAGAACCTTACCTACTCTTGACAT
Escherichia coli               AGCGGTGGAGCATGTGGTTTAATTCGATGCAACGCGAAGAACCTTACCTGGTCTTGACAT
Serratia marcescens            AGCGGTGGAGCATGTGGTTTAATTCGATGCAACGCGAAGAACCTTACCTACTCTTGACAT
Enterobacter aerogenes         AGCGGTGGAGCATGTGGTTTAATTCGATGCAACGCGAAGAACCTTACCTACTCTTGACAT
Enterobacter cloacae           AGCGGTGGAGCATGTGGTTTAATTCGATGCAACGCGAAGAACCTTACCTGGTCTTGACAT
Klebsiella pneumoniae          AGCGGTGGAGCATGTGGTTTAATTCGATGCAACGCGAAGAACCTTACCTGGTCTTGACAT
Pseudomonas aeruginosa         AGCGGTGGAGCATGTGGTTTAATTCGAAGCAACGCGAAGAACCTTACCTGGCCTTGACAT
Acinetobacter calcoaceticus    AGCGGTGGAGCATGTGGTTTAATTCGATGCAACGCGAAGAACCTTACCTGGCCTTGACAT
                               *************************** ***** **************    ********

Staphylococcus aureus          CCTTTGACAACTCTAGAGATAGAGCTTTCCCCTTCGGGGGACAAAGTGACAGGTGGTGCA
Staphylococcus epidermidis     CCTCTGACCCCTCTAGAGATAGAGTTTTCCCCTTCGGGGGACAGAGTGACAGGTGGTGCA
Streptococcus pneumoniae       CCCTCTGACCGCTCTAGAGATAGAGTTTT--CCTTCGGGACAGAGGTGACAGGTGGTGCA
Streptococcus agalactiae       CCTTCTGACCGGCCTAGAGATAGGCTTTC--TCTTCGGAGCAGAAGTGACAGGTGGTGCA
Streptococcus pyogenes         CCCGATGCCCGCTCTAGAGATAGAGTTTT--ACTTCGGTACATCGGTGACAGGTGGTGCA
Enterococcus faecalis          CCTTTGACCACTCTAGAGATAGAGCTTTC--CCTTCGGGGACAAAGTGACAGGTGGTGCA
Enterococcus faecium           CCTTTGACCACTCTAGAGATAGAGCTTCC--CCTTCGGGGGCAAAGTGACAGGTGGTGCA
Proteus mirabilis              CCAGCGAATCCTTTAGAGATAGAGGAGTG--CCTTCGGGAACGCTGAGACAGGTGCTGCA
Escherichia coli               CCACAGAACTTTCCAGAGATGGATTGGTG--CCTTCGGGAACTGTGAGACAGGTGCTGCA
Serratia marcescens            CCAGAGAACTTTCCAGAGATGGATTGGTG--CCTTCGGGAACTCTGAGACAGGTGCTGCA
Enterobacter aerogenes         CCAGAGAACTTAGCAGAGATGCTTTGGTG--CCTTCGGGAACTCTGAGACAGGTGCTGCA
Enterobacter cloacae           CCACAGAACTTTCCAGAGATGGATTGGTG--CCTTCGGGAACTGTGAGACAGGTGCTGCA
Klebsiella pneumoniae          CCACAGAACTTTCCAGAGATGGATTGGTG--CCTTCGGGAACTGTGAGACAGGTGCTGCA
Pseudomonas aeruginosa         GCTGAGAACTTTCCAGAGATGGATTGGTG--CCTTCGGGAACTCAGACACAGGTGCTGCA
Acinetobacter calcoaceticus    ACTAGAAACTTTCCAGAGATGGATTGGTG--CCTTCGGGAATTTAGATACAGGTGCTGCA
                                *                               *  **       *  ******* ****
```

Figure 1I

```
Staphylococcus aureus            TGGTTGTCGTCAGCTCGTGTCGTGAGATGTTGGGTTAAGTCCCGCAACGAGCGCAACCCT
Staphylococcus epidermidis       TGGTTGTCGTCAGCTCGTGTCGTGAGATGTTGGGTTAAGTCCCGCAACGAGCGCAACCCT
Streptococcus pneumoniae         TGGTTGTCGTCAGCTCGTGTCGTGAGATGTTGGGTTAAGTCCCGCAACGAGCGCAACCCC
Streptococcus agalactiae         TGGTTGTCGTCAGCTCGTGTCGTGAGATGTTGGGTTAAGTCCCGCAACGAGCGCAACCCC
Streptococcus pyogenes           TGGTTGTCGTCAGCTCGTGTCGTGAGATGTTGGGTTAAGTCCCGCAACGAGCGCAACCCC
Enterococcus faecalis            TGGTTGTCGTCAGCTCGTGTCGTGAGATGTTGGGTTAAGTCCCGCAACGAGCGCAACCCT
Enterococcus faecium             TGGTTGTCGTCAGCTCGTGTCGTGAGATGTTGGGTTAAGTCCCGCAACGAGCGCAACCCT
Proteus mirabilis                TGGCTGTCGTCAGCTCGTGTTGTGAAATGTTGGGTTAAGTCCCGCAACGAGCGCAACCCT
Escherichia coli                 TGGCTGTCGTCAGCTCGTGTTGTGAAATGTTGGGTTAAGTCCCGCAACGAGCGCAACCCT
Serratia marcescens              TGGCTGTCGTCAGCTCGTGTTGTGAAATGTTGGGTTAAGTCCCGCAACGAGCGCAACCCT
Enterobacter aerogenes           TGGCTGTCGTCAGCTCGTGTTGTGAAATGTTGGGTTAAGTCCCGCAACGAGCGCAACCCT
Enterobacter cloacae             TGGCTGTCGTCAGCTCGTGTTGTGAAATGTTGGGTTAAGTCCCGCAACGAGCGCAACCCT
Klebsiella pneumoniae            TGGCTGTCGTCAGCTCGTGTTGTGAAATGTTGGGTTAAGTCCCGCAACGAGCGCAACCCT
Pseudomonas aeruginosa           TGGCTGTCGTCAGCTCGTGTCGTGAGATGTTGGGTTAAGTCCCGTAACGAGCGCAACCCT
Acinetobacter calcoaceticus      TGGCTGTCGTCAGCTCGTGTCGTGAGATGTTGGGTTAAGTCCCGCAACGAGCGCAACCCT
                                 *** **************** **** ****************** ************** 

Staphylococcus aureus            TAAGCTTAGTTGCCATCATT--AAGTTGGGCACTCTAAGTTGACTGCCGGTGACAAACCG
Staphylococcus epidermidis       TAAGCTTAGTTGCCATCATT--AAGTTGGGCACTCTAAGTTGACTGCCGGTGACAAACCG
Streptococcus pneumoniae         TATTGTTAGTTGCCATCATT--CAGTTGGGCACTCTAGCGAGACTGCCGGTAATAAACCG
Streptococcus agalactiae         TATTGTTAGTTGCCATCATT--AAGTTGGGCACTCTAGCGAGACTGCCGGTAATAAACCG
Streptococcus pyogenes           TATTGTTAGTTGCCATCATT--AAGTTGGGCACTCTAGCGAGACTGCCGGTAATAAACCG
Enterococcus faecalis            TATTGTTAGTTGCCATCATT--TAGTTGGGCACTCTAGCGAGACTGCCGGTGACAAACCG
Enterococcus faecium             TATTGTTAGTTGCCATCATT--CAGTTGGGCACTCTAGCAAGACTGCCGGTGACAAACCG
Proteus mirabilis                TATCCTTTGTTGCCAGCACGTAATGGTGGGAACTCAAAGGAGACTGCCGGTGATAAACCG
Escherichia coli                 TATCTTTTGTTGCCAGCGGT-CCGGCCGGGAACTCAAAGGAGACTGCCAGTGATAAACTG
Serratia marcescens              TATCCTTTGTTGCCAGCGGT-TCGGCCGGGAACTCAAAGGAGACTGCCAGTGATAAACTG
Enterobacter aerogenes           TATCCTTTGTTGCCAGCGGT-CCGGCCGGGAACTCAAAGGAGACTGCCAGTGATAAACTG
Enterobacter cloacae             TATCCTTTGTTGCCAGCGGT-CCGGCCGGGAACTCAAAGGAGACTGCCAGTGATAAACTG
Klebsiella pneumoniae            TATCCTTTGTTGCCAGCGGT-TAGGCCGGGAACTCAAAGGAGACTGCCAGTGATAAACTG
Pseudomonas aeruginosa           TGTCCTTAGTTACCAGCACC-TCGGGTGGGCACTCTAAGGAGACTGCCGGTGACAAACCG
Acinetobacter calcoaceticus      TTTCCTTACTTGCCAGCATT-TCGGATGGGAACTTTAAGGATACTGCCAGTGACAAACTG
                                 *    **  ** *** *       *  *** ***  *     ****** ** * **** *
```

Figure 1J

```
Staphylococcus aureus          GAGGAAGGTGGGGATGACGTCAAATCATCATGCCCCTTATGATTTGGGCTACACACGTGC
Staphylococcus epidermidis     GAGGAAGGTGGGGATGACGTCAAATCATCATGCCCCTTATGATTTGGGCTACACACGTGC
Streptococcus pneumoniae       GAGGAAGGTGGGGATGACGTCAAATCATCATGCCCCTTATGACCTGGGCTACACACGTGC
Streptococcus agalactiae       GAGGAAGGTGGGGATGACGTCAAATCATCATGCCCCTTATGACCTGGGCTACACACGTGC
Streptococcus pyogenes         GAGGAAGGTGGGGATGACGTCAAATCATCATGCCCCTTATGACCTGGGCTACACACGTGC
Enterococcus faecalis          GAGGAAGGTGGGGATGACGTCAAATCATCATGCCCCTTATGACCTGGGCTACACACGTGC
Enterococcus faecium           GAGGAAGGTGGGGATGACGTCAAATCATCATGCCCCTTATGACCTGGGCTACACACGTGC
Proteus mirabilis              GAGGAAGGTGGGGATGACGTCAAGTCATCATGGCCCTTACGAGTAGGGCTACACACGTGC
Escherichia coli               GAGGAAGGTGGGGATGACGTCAAGTCATCATGGCCCTTACGACCAGGGCTACACACGTGC
Serratia marcescens            GAGGAAGGTGGGGATGACGTCAAGTCATCATGGCCCTTACGAGTAGGGCTACACACGTGC
Enterobacter aerogenes         GAGGAAGGTGGGGATGACGTCAAGTCATCATGGCCCTTACGAGTAGGGCTACACACGTGC
Enterobacter cloacae           GAGGAAGGTGGGGATGACGTCAAGTCATCATGGCCCTTACGACCAGGGCTACACACGTGC
Klebsiella pneumoniae          GAGGAAGGTGGGGATGACGTCAAGTCATCATGGCCCTTACGACCAGGGCTACACACGTGC
Pseudomonas aeruginosa         GAGGAAGGTGGGGATGACGTCAAGTCATCATGGCCCTTACGGCCAGGGCTACACACGTGC
Acinetobacter calcoaceticus    GAGGAAGGCGGGGACGACGTCAAGTCATCATGGCCCTTACGGCCAGGGCTACACACGTGC
                               ******** ***** ******** ******** ****** *    ***************

Staphylococcus aureus          TACAATGGACAATACAAAGGGCAGCGAAACCGTGAGGTCAAGCAAATCCCATAAAGTTGT
Staphylococcus epidermidis     TACAATGGACAATACAAAGGGCAGCGAAACCGCGAGGTCAAGCAAATCCCATAAAGTTGT
Streptococcus pneumoniae       TACAATGGCTGGTACAACGAGTCGCAAGCCGGTGACGGCAAGCTAATCTCTTAAAGCCAG
Streptococcus agalactiae       TACAATGGTTGGTACAACGAGTCGCAAGCCGGTGACGGCAAGCTAATCTCTTAAAGCCAA
Streptococcus pyogenes         TACAATGGTTGGTACAACGAGTCGCAAGCCGGTGACGGCAAGCTAATCTCTTAAAGCCAA
Enterococcus faecalis          TACAATGGGAAGTACAACGAGTCGCTAGACCGCGAGGTCATGCAAATCTCTTAAAGCTTC
Enterococcus faecium           TACAATGGGAAGTACAACGAGTTGCGAAGTCGCGAGGCTAAGCTAATCTCTTAAAGCTTC
Proteus mirabilis              TACAATGGCAGATACAAAGAGAAGCGACCTCGCGAGAGCAAGCGGAACTCATAAAGTCTG
Escherichia coli               TACAATGGCGCATACAAAGAGAAGCGACCTCGCGAGAGCAAGCGGACCTCATAAAGTGCG
Serratia marcescens            TACAATGGCATATACAAAGAGAAGCGACCTCGCGAGAGCAAGCGGACCTCATAAAGTATG
Enterobacter aerogenes         TACAATGGCATATACAAAGAGAAGCGACCTCGCGAGAGCAAGCGGACCTCATAAAGTATG
Enterobacter cloacae           TACAATGGCGCATACAAAGAGAAGCGACCTCGCGAGAGCAAGCGGACCTCATAAAGTGCG
Klebsiella pneumoniae          TACAATGGCATATACAAAGAGAAGCGACCTCGCGAGAGCAAGCGGACCTCATAAAGTATG
Pseudomonas aeruginosa         TACAATGGTCGGTACAAAGGGTTGCCAAGCCGCGAGGTGGAGCTAATCCCATAAAACCGA
Acinetobacter calcoaceticus    TACAATGGTCGGTACAAAGGGTTGCTACCTAGCGATAGGATGCTAATCTCAAAAAGCCGA
                               ********    ***** * *  ** *    * **      **  * * *  ***
```

Figure 1K

```
Staphylococcus aureus           TCTCAGTTCGGATTGTAGTCTGCAACTCGACTACATGAAGCTGGAATCGCTAGTAATCGT
Staphylococcus epidermidis      TCTCAGTTCGGATTGTAGTCTGCAACTCGACTATATGAAGCTGGAATCGCTAGTAATCGT
Streptococcus pneumoniae        TCTCAGTTCGGATTGTAGGCTGCAACTCGCCTACATGAAGTCGGAATCGCTAGTAATCGC
Streptococcus agalactiae        TCTCAGTTCGGATTGTAGGCTGCAACTCGCCTACATGAAGTCGGAATCGCTAGTAATCGC
Streptococcus pyogenes          TCTCAGTTCGGATTGTAGGCTGCAACTCGCCTACATGAAGTCGGAATCGCTAGTAATCGC
Enterococcus faecalis           TCTCAGTTCGGATTGCAGGCTGCAACTCGCCTGCATGAAGCCGGAATCGCTAGTAATCGC
Enterococcus faecium            TCTCAGTTCGGATTGCAGGCTGCAACTCGCCTGCATGAAGCCGGAATCGCTAGTAATCGC
Proteus mirabilis               TCGTAGTCCGGATTGGAGTCTGCAACTCGACTCCATGAAGTCGGAATCGCTAGTAATCGT
Escherichia coli                TCGTAGTCCGGATTGGAGTCTGCAACTCGACTCCATGAAGTCGGAATCGCTAGTAATCGT
Serratia marcescens             TCGTAGTCCGGATTGGAGTCTGCAACTCGACTCCATGAAGTCGGAATCGCTAGTAATCGT
Enterobacter aerogenes          TCGTAGTCCGGATTGGAGTCTGCAACTCGACTCCATGAAGTCGGAATCGCTAGTAATCGT
Enterobacter cloacae            TCGTAGTCCGGATTGGAGTCTGCAACTCGACTCCATGAAGTCGGAATCGCTAGTAATCGT
Klebsiella pneumoniae           TCGTAGTCCGGATTGGAGTCTGCAACTCGACTCCATGAAGTCGGAATCGCTAGTAATCGT
Pseudomonas aeruginosa          TCGTAGTCCGGATCGCAGTCTGCAACTCGACTGCGTGAAGTCGGAATCGCTAGTAATCGT
Acinetobacter calcoaceticus     TCGTAGTCCGGATTGGAGTCTGCAACTCGACTCCATGAAGTCGGAATCGCTAGTAATCGC
                                **  *** ***** * ** ********** **   *****  *****************

Staphylococcus aureus           AGATCAGCATGCTACGGTGAATACGTTCCCGGGTCTTGTACACACCGCCCGTCACACCAC
Staphylococcus epidermidis      AGATCAGCATGCTACGGTGAATACGTTCCCGGGTCTTGTACACACCGCCCGTCACACCAC
Streptococcus pneumoniae        GGATCAGCACGCCGCGGTGAATACGTTCCCGGGCCTTGTACACACCGCCCGTCACACCAC
Streptococcus agalactiae        GGATCAGCACGCCGCGGTGAATACGTTCCCGGGCCTTGTACACACCGCCCGTCACACCAC
Streptococcus pyogenes          GGATCAGCACGCCGCGGTGAATACGTTCCCGGGCCTTGTACACACCGCCCGTCACACCAC
Enterococcus faecalis           GGATCAGCACGCCGCGGTGAATACGTTCCCGGGCCTTGTACACACCGCCCGTCACACCAC
Enterococcus faecium            GGATCAGCACGCCGC-GTGAATACGTTCCCGGGCCTTGTACACACCGCCCGTCACACCAC
Proteus mirabilis               AGATCAGAATGCTACGGTGAATACGTTCCCGGGCCTTGTACACACCGCCCGTCACACCAT
Escherichia coli                GGATCAGAATGCCACGGTGAATACGTTCCCGGGCCTTGTACACACCGCCCGTCACACCAT
Serratia marcescens             AGATCAGAATGCTACGGTGAATACGTTCCCGGGCCTTGTACACACCGCCCGTCACACCAT
Enterobacter aerogenes          AGATCAGAATGCTACGGTGAATACGTTCCCGGGCCTTGTACACACCGCCCGTCACACCAT
Enterobacter cloacae            AGATCAGAATGCTACGGTGAATACGTTCCCGGGCCTTGTACACACCGCCCGTCACACCAT
Klebsiella pneumoniae           AGATCAGAATGCTACGGTGAATACGTTCCCGGGCCTTGTACACACCGCCCGTCACACCAT
Pseudomonas aeruginosa          GAATCAGAATGTCACGGTGAATACGTTCCCGGGCCTTGTACACACCGCCCGTCACACCAT
Acinetobacter calcoaceticus     GGATCAGAATGCCC--GGTGATACGTTCCCGGGCCTTGTACACACCGCCCGTCACACCAT
                                  ***** * *     *   ************* *************************
```

Figure 1L

```
Staphylococcus aureus          GAGAGTTTGTAACACCCGAAGCCGGTGGAGTAACCTTTTAGGAGCTAGCCGTCGAAGGTG
Staphylococcus epidermidis     GAGAGTTTGTAACACCCGAAGCCGGTGGAGTAACCATT-TGGAGCTAGCCGTCGAAGGTG
Streptococcus pneumoniae       GAGAGTTTGTAACACCCGAAGTCGGTGAGGTAACCG-TAAGGAGCCAGCCGCCTAAGGTG
Streptococcus agalactiae       GAGAGTTTGTAACACCCGAAGTCGGTGAGGTAACCTTTTAGGAGCCAGCCGCCTAAGGTG
Streptococcus pyogenes         GAGAGTTTGTAACACCCGAAGTCGGTGAGGTAACCTATTAGGAGCCAGCCGCCTAAGGTG
Enterococcus faecalis          GAGAGTTTGTAACACCCGAAGTCGGTGAGGTAACCTTTTTGGAGCCAGCCGCCTAAGGTG
Enterococcus faecium           GAGAGTTTGTAACACCCGAAGTCGGTGAGGTAACCTTT-TGGAGCCAGCCGCCTAAGGTG
Proteus mirabilis              GGGAGTGGGTTGCAAAAGAAGTAGGTAGCTTAACCTTC-GGGAGGGCGCTTACCACTTTG
Escherichia coli               GGGAGTGGGTTGCAAAAGAAGTAGGTAGCTTAACCTTC-GGGAGGGCGCTTACCACTTTG
Serratia marcescens            GGGAGTGGGTTGCAAAAGAAGTAGGTAGCTTAACCTTC-GGGAGGGCGCTTACCACTTTG
Enterobacter aerogenes         GGGAGTGGGTTGCAAAAGAAGTAGGTAGCTTAACCTTC-GGGAGGNCGCTTTACCACTT-
Enterobacter cloacae           GGGAGTGGGTTGCAAAAGAAGTAGGTAGCTTAACCTTC-GGGAGGGCGCTTACCACTTTG
Klebsiella pneumoniae          GGGAGTGGGTTGCAAAAGAAGTAGGTAGCTTAACCTTC-GGGAGGGCGCTTACCACTTTG
Pseudomonas aeruginosa         GGGAGTGGGTTGCTCCAGAAGTAGCTAGTCTAACCGCA-AGGGGGACGGTTACCACGGAG
Acinetobacter calcoaceticus    GGGAGTTTGTTGCACCAGAAGTAGGTAGTCTAACCGCA-AGGAGGACGCTTACCACGGTG
                               * ****  **  *    ****  * *    *****     ** *   *

Staphylococcus aureus          GGACAAATGATTGGGGTGAAGTCGTAACAAGGTAGCCGTATCGGAAGGTGCGGCTGGATC
Staphylococcus epidermidis     GGACAAATGATTGGGGTGAAGTCGTAACAAGGTAGCCGTATCGGAAGGTGCGGCTGGATC
Streptococcus pneumoniae       GGATAGATGATTGGGGTGAAGTCGTAACAAGGTAGCCGTATCGGAAG-------------
Streptococcus agalactiae       GGATAGATGATTGGGGTGAAGTCGTAACAAGGTAGCCGTATCGGAAGG------------
Streptococcus pyogenes         GGATAGATGATTGGGGTGAAGTCGTAACAAGGTAGCCGTATCGGAAGGTGCGGCTGGATC
Enterococcus faecalis          GGATAGATGATTGGGGTGAAGTCGTAACAAGGTAGCC-----------------------
Enterococcus faecium           GGATAGATGATTGGGGTGAAGTCGTAACAAGGTAGCCGTATCTGAAGGTGCGGCTGGATC
Proteus mirabilis              TGATTCATGACTGGGGTGAAGTCGTAACAAGGTAACCGTAGGGGAACCTGCGGTTGGATC
Escherichia coli               TGATTCATGACTGGGGTGAAGTCGTAACAAGGTAACCGTAGGGGAACCTGCGGTTGGATC
Serratia marcescens            TGATTCATGACTGGGGTGAAGTCGTAACAAGGTAACCGTAGGGGAACCTGCGG-------
Enterobacter aerogenes         ------------------------------------------------------------
Enterobacter cloacae           TGATTCATGACTGGGGTGAAGTCGTAACAAGGTAACCGTAGGGGAACCTGCGGCTGGATC
Klebsiella pneumoniae          TGATTCATGACTGGGGTGAAGTCGTAACAAGGTAACCGTAGGGGAACCTGCGGTTGGATC
Pseudomonas aeruginosa         TGATTCATGACTGGGGTGAAGTCGTAACAAGGTAGCCGTAGGGGAACCTGCGGCTGGATC
Acinetobacter calcoaceticus    TGGCCGATGACTGGGGTGAAGTCGTAACAAGGTAACCA----------------------
```

Figure 1M

```
Staphylococcus aureus             ACCTCCTTTCT
Staphylococcus epidermidis        ACCTCCTTTCT
Streptococcus pneumoniae          -----------
Streptococcus agalactiae          -----------
Streptococcus pyogenes            ACCTCCTTT--
Enterococcus faecalis             -----------
Enterococcus faecium              ACCTCCTTT--
Proteus mirabilis                 ACCTCCTTA--
Escherichia coli                  ACCTCCTTA--
Serratia marcescens               -----------
Enterobacter aerogenes            -----------
Enterobacter cloacae              ACCTCCTTG--
Klebsiella pneumoniae             ACCTCCTTT--
Pseudomonas aeruginosa            ACCTCCTTA--
Acinetobacter calcoaceticus       -----------
```

Figure 1N

SEQUENCE LISTING

```
<160> NUMBER OF SEQ ID NOS: 57

<210> SEQ ID NO 1
<211> LENGTH: 1542
<212> TYPE: DNA
<213> ORGANISM: Escherichia coli

<400> SEQUENCE: 1

aaattgaaga gtttgatcat ggctcagatt gaacgctggc ggcaggccta acacatgcaa      60

gtcgaacggt aacaggaaga agcttgcttc tttgctgacg agtggcggac gggtgagtaa     120

tgtctgggaa actgcctgat ggagggggat aactactgga aacggtagct aataccgcat     180
```

```
aacgtcgcaa gaccaaagag gggaccttc gggcctcttg ccatcggatg tgcccagatg    240
ggattagcta gtaggtgggg taacggctca cctaggcgac gatccctagc tggtctgaga    300
ggatgaccag ccacactgga actgagacac ggtccagact cctacgggag gcagcagtgg    360
ggaatattgc acaatgggcg caagcctgat gcagccatgc cgcgtgtatg aagaaggcct    420
tcgggttgta aagtactttc agcggggagg aagggagtaa agttaatacc tttgctcatt    480
gacgttaccc gcagaagaag caccggctaa ctccgtgcca gcagccgcgg taatacggag    540
ggtgcaagcg ttaatcggaa ttactgggcg taaagcgcac gcaggcggtt tgttaagtca    600
gatgtgaaat ccccgggctc aacctgggaa ctgcatctga tactggcaag cttgagtctc    660
gtagaggggg gtagaattcc aggtgtagcg gtgaaatgcg tagagatctg gaggaatacc    720
ggtggcgaag gcggccccct ggacgaagac tgacgctcag gtgcgaaagc gtggggagca    780
aacaggatta gataccctgg tagtccacgc cgtaaacgat gtcgacttgg aggttgtgcc    840
cttgaggcgt ggcttccgga gctaacgcgt taagtcgacc gcctggggag tacggccgca    900
aggttaaaac tcaaatgaat tgacgggggc ccgcacaagc ggtggagcat gtggtttaat    960
tcgatgcaac gcgaagaacc ttacctggtc ttgacatcca cagaactttc cagagatgga   1020
ttggtgcctt cgggaactgt gagacaggtg ctgcatggct gtcgtcagct cgtgttgtga   1080
aatgttgggt taagtcccgc aacgagcgca acccttatct tttgttgcca gcggtccggc   1140
cgggaactca aaggagactg ccagtgataa actggaggaa ggtggggatg acgtcaagtc   1200
atcatggccc ttacgaccag ggctacacac gtgctacaat ggcgcataca aagagaagcg   1260
acctcgcgag agcaagcgga cctcataaag tgcgtcgtag tccggattgg agtctgcaac   1320
tcgactccat gaagtcggaa tcgctagtaa tcgtggatca gaatgccacg gtgaatacgt   1380
tcccgggcct tgtacacacc gcccgtcaca ccatgggagt gggttgcaaa agaagtaggt   1440
agcttaacct tcgggagggc gcttaccact ttgtgattca tgactggggt gaagtcgtaa   1500
caaggtaacc gtaggggaac ctgcggttgg atcacctcct ta                      1542
```

<210> SEQ ID NO 2
<211> LENGTH: 1555
<212> TYPE: DNA
<213> ORGANISM: Staphylococcus aureus

<400> SEQUENCE: 2

```
ttttatggag agtttgatcc tggctcagga tgaacgctgg cggcgtgcct aatacatgca     60
agtcgagcga acggacgaga agcttgcttc tctgatgtta gcggcggacg ggtgagtaac    120
acgtggataa cctacctata agactgggat aacttcggga aaccggagct aataccggat    180
aatattttga accgcatggt tcaaaagtga aagacggtct tgctgtcact tatagatgga    240
tccgcgctgc attagctagt tggtaaggta acggcttacc aaggcaacga tgcatagccg    300
acctgagagg gtgatcggcc acactggaac tgagacacgg tccagactcc tacgggaggc    360
agcagtaggg aatcttccgc aatgggcgaa agcctgacgg agcaacgccg cgtgagtgat    420
gaaggtcttc ggatcgtaaa actctgttat tagggaagaa catatgtgta agtaactgtg    480
cacatcttga cggtacctaa tcagaaagcc acggctaact acgtgccagc agccgcggta    540
atacgtaggt ggcaagcgtt atccggaatt attgggcgta aagcgcgcgt aggcggtttt    600
ttaagtctga tgtgaaagcc cacggctcaa ccgtggaggg tcattggaaa ctggaaaact    660
tgagtgcaga agaggaaagt ggaattccat gtgtagcggt gaaatgcgca gagatatgga    720
```

```
ggaacaccag tggcgaaggc gactttctgg tctgtaactg acgctgatgt gcgaaagcgt    780

ggggatcaaa caggattaga taccctggta gtccacgccg taaacgatga gtgctaagtg    840

ttagggggtt tccgcccctt agtgctgcag ctaacgcatt aagcactccg cctggggagt    900

acgaccgcaa ggttgaaact caaaggaatt gacggggacc cgcacaagcg gtggagcatg    960

tggtttaatt cgaagcaacg cgaagaacct taccaaatct tgacatcctt tgacaactct   1020

agagatagag ctttcccctt cgggggacaa agtgacaggt ggtgcatggt tgtcgtcagc   1080

tcgtgtcgtg agatgttggg ttaagtcccg caacgagcgc aacccttaag cttagttgcc   1140

atcattaagt tgggcactct aagttgactg ccggtgacaa accggaggaa ggtggggatg   1200

acgtcaaatc atcatgcccc ttatgatttg ggctacacac gtgctacaat ggacaataca   1260

aagggcagcg aaaccgtgag gtcaagcaaa tcccataaag ttgttctcag ttcggattgt   1320

agtctgcaac tcgactacat gaagctggaa tcgctagtaa tcgtagatca gcatgctacg   1380

gtgaatacgt tcccgggtct tgtacacacc gcccgtcaca ccacgagagt ttgtaacacc   1440

cgaagccggt ggagtaacct tttaggagct agccgtcgaa ggtgggacaa atgattgggg   1500

tgaagtcgta acaaggtagc cgtatcggaa ggtgcggctg gatcacctcc tttct        1555
```

```
<210> SEQ ID NO 3
<211> LENGTH: 1554
<212> TYPE: DNA
<213> ORGANISM: Staphylococcus epidermidis

<400> SEQUENCE: 3

ttttatggag agtttgatcc tggctcagga tgaacgctgg cggcgtgcct aatacatgca     60

agtcgagcga acagacgagg agcttgcttc tctgacgtta gcggcggacg ggtgagtaac    120

acgtggataa cctacctata agactgggat aacttcggga aaccggagct aataccggat    180

aatatattga accgcatggt tcaatagtga aagacggttt tgctgtcact tatagatgga    240

tccgcgccgc attagctagt tggtaaggta acggcttacc aaggcaacga tgcgtagccg    300

acctgagagg gtgatcggcc acactggaac tgagacacgg tccagactcc tacgggaggc    360

agcagtaggg aatcttccgc aatgggcgaa agcctgacgg agcaacgccg cgtgagtgat    420

gaaggtcttc ggatcgtaaa actctgttat tagggaagaa caaatgtgta agtaactatg    480

cacgtcttga cggtacctaa tcagaaagcc acggctaact acgtgccagc agccgcggta    540

atacgtaggt ggcaagcgtt atccggaatt attgggcgta aagcgcgcgt aggcggtttt    600

ttaagtctga tgtgaaagcc cacggctcaa ccgtggaggg tcattggaaa ctggaaaact    660

tgagtgcaga agaggaaagt ggaattccat gtgtagcggt gaaatgcgca gagatatgga    720

ggaacaccag tggcgaaggc gactttctgg tctgtaactg acgctgatgt gcgaaagcgt    780

ggggatcaaa caggattaga taccctggta gtccacgccg taaacgatga gtgctaagtg    840

ttagggggtt tccgcccctt agtgctgcag ctaacgcatt aagcactccg cctggggagt    900

acgaccgcaa ggttgaaact caaaggaatt gacggggacc cgcacaagcg gtggagcatg    960

tggtttaatt cgaagcaacg cgaagaacct taccaaatct tgacatcctc tgacccctct   1020

agagatagag ttttcccctt cgggggacag agtgacaggt ggtgcatggt tgtcgtcagc   1080

tcgtgtcgtg agatgttggg ttaagtcccg caacgagcgc aacccttaag cttagttgcc   1140

atcattaagt tgggcactct aagttgactg ccggtgacaa accggaggaa ggtggggatg   1200

acgtcaaatc atcatgcccc ttatgatttg ggctacacac gtgctacaat ggacaataca   1260

aagggcagcg aaaccgcgag gtcaagcaaa tcccataaag ttgttctcag ttcggattgt   1320
```

agtctgcaac tcgactatat gaagctggaa tcgctagtaa tcgtagatca gcatgctacg 1380
gtgaatacgt tcccgggtct tgtacacacc gcccgtcaca ccacgagagt ttgtaacacc 1440
cgaagccggt ggagtaacca tttggagcta gccgtcgaag gtgggacaaa tgattggggt 1500
gaagtcgtaa caaggtagcc gtatcggaag gtgcggctgg atcacctcct ttct 1554

<210> SEQ ID NO 4
<211> LENGTH: 1514
<212> TYPE: DNA
<213> ORGANISM: Streptococcus pneumoniae

<400> SEQUENCE: 4
gtttgatcct ggctcaggac gaacgctggc ggcgtgccta atacatgcaa gtagaacgct 60
gaaggaggag cttgcttctc tggatgagtt gcgaacgggt gagtaacgcg taggtaacct 120
gcctggtagc gggggataac tattggaaac gatagctaat accgcataag agtggatgtt 180
gcatgacatt tgcttaaaag gtgcacttgc atcactacca gatggacctg cgttgtatta 240
gctagttggt ggggtaacgg ctcaccaagg cgacgataca tagccgacct gagagggtga 300
tcggccacac tgggactgag acacggccca gactcctacg ggaggcagca gtagggaatc 360
ttcggcaatg gacggaagtc tgaccgagca acgccgcgtg agtgaagaag gttttcggat 420
cgtaaagctc tgttgtaaga gaagaacgag tgtgagagtg gaaagttcac actgtgacgg 480
tatcttacca gaaagggacg gctaactacg tgccagcagc cgcggtaata cgtaggtccc 540
gagcgttgtc cggatttatt gggcgtaaag cgagcgcagg cggttagata agtctgaagt 600
taaaggctgt ggcttaacca tagtaggctt tggaaactgt ttaacttgag tgcaagaggg 660
gagagtggaa ttccatgtgt agcggtgaaa tgcgtagata tatggaggaa caccggtggc 720
gaaagcggct ctctggcttg taactgacgc tgaggctcga aagcgtgggg agcaaacagg 780
attagatacc ctggtagtcc acgctgtaaa cgatgagtgc taggtgttag accctttccg 840
gggtttagtg ccgtagctaa cgcattaagc actccgcctg gggagtacga ccgcaaggtt 900
gaaactcaaa ggaattgacg gggggcccgca caagcggtgg agcatgtggt ttaattcgaa 960
gcaacgcgaa gaaccttacc aggtcttgac atccctctga ccgctctaga gatagagttt 1020
tccttcggga cagaggtgac aggtggtgca tggttgtcgt cagctcgtgt cgtgagatgt 1080
tgggttaagt cccgcaacga gcgcaacccc tattgttagt tgccatcatt cagttgggca 1140
ctctagcgag actgccggta ataaaccgga ggaaggtggg gatgacgtca aatcatcatg 1200
ccccttatga cctgggctac acacgtgcta caatggctgg tacaacgagt cgcaagccgg 1260
tgacggcaag ctaatctctt aaagccagtc tcagttcgga ttgtaggctg caactcgcct 1320
acatgaagtc ggaatcgcta gtaatcgcgg atcagcacgc cgcggtgaat acgttcccgg 1380
gccttgtaca caccgcccgt cacaccacga gagtttgtaa cacccgaagt cggtgaggta 1440
accgtaagga gccagccgcc taaggtggga tagatgattg gggtgaagtc gtaacaaggt 1500
agccgtatcg gaag 1514

<210> SEQ ID NO 5
<211> LENGTH: 1501
<212> TYPE: DNA
<213> ORGANISM: Streptococcus agalactiae

<400> SEQUENCE: 5
gacgaacgct ggcggcgtgc ctaatacatg caagtagaac gctgaggttt ggtgtttaca 60

```
ctagactgat gagttgcgaa cgggtgagta acgcgtaggt aacctgcctc atagcggggg    120

ataactattg gaaacgatag ctaataccgc ataagagtaa ttaacacatg ttagttattt    180

aaaaggagca attgcttcac tgtgagatgg acctgcgttg tattagctag ttggtgaggt    240

aaaggctcac caaggcgacg atacatagcc gacctgagag ggtgatcggc cacactggga    300

ctgagacacg gcccagactc ctacgggagg cagcagtagg gaatcttcgg caatggacgg    360

aagtctgacc gagcaacgcc gcgtgagtga agaaggtttt cggatcgtaa agctctgttg    420

ttagagaaga acgttggtag gagtggaaaa tctaccaagt gacggtaact aaccagaaag    480

ggacggctaa ctacgtgcca gcagccgcgg taatacgtag gtcccgagcg ttgtccggat    540

ttattgggcg taaagcgagc gcaggcggtt ctttaagtct gaagttaaag gcagtggctt    600

aaccattgta cgctttggaa actggaggac ttgagtgcag aaggggagag tggaattcca    660

tgtgtagcgg tgaaatgcgt agatatatgg aggaacaccg gtggcgaaag cggctctctg    720

gtctgtaact gacgctgagg ctcgaaagcg tggggagcaa acaggattag ataccctggt    780

agtccacgcc gtaaacgatg agtgctaggt gttaggccct ttccggggct tagtgccgca    840

gctaacgcat taagcactcc gcctggggag tacgaccgca aggttgaaac tcaaaggaat    900

tgacgggggc ccgcacaagc ggtggagcat gtggtttaat tcgaagcaac gcgaagaacc    960

ttaccaggtc ttgacatcct tctgaccggc ctagagatag gctttctctt cggagcagaa   1020

gtgacaggtg gtgcatggtt gtcgtcagct cgtgtcgtga gatgttgggt taagtcccgc   1080

aacgagcgca acccctattg ttagttgcca tcattaagtt gggcactcta gcgagactgc   1140

cggtaataaa ccggaggaag gtggggatga cgtcaaatca tcatgcccct tatgacctgg   1200

gctacacacg tgctacaatg gttggtacaa cgagtcgcaa gccggtgacg gcaagctaat   1260

ctcttaaagc caatctcagt tcggattgta ggctgcaact cgcctacatg aagtcggaat   1320

cgctagtaat cgcggatcag cacgccgcgg tgaatacgtt cccgggcctt gtacacaccg   1380

cccgtcacac cacgagagtt tgtaacaccc gaagtcggtg aggtaacctt ttaggagcca   1440

gccgcctaag gtgggataga tgattggggt gaagtcgtaa caaggtagcc gtatcggaag   1500

g                                                                   1501
```

<210> SEQ ID NO 6
<211> LENGTH: 1543
<212> TYPE: DNA
<213> ORGANISM: Streptococcus pyogenes

<400> SEQUENCE: 6

```
gagagtttga tcctggctca ggacgaacgc tggcggcgtg cctaatacat gcaagtagaa     60

cgctgagaac tggtgcttgc accggttcaa ggagttgcga acgggtgagt aacgcgtagg    120

taacctacct catagcgggg gataactatt ggaaacgata gctaataccg cataagagag    180

actaacgcat gttagtaatt taaaaggggc aattgctcca ctatgagatg gacctgcgtt    240

gtattagcta gttggtgagg taaaggctca ccaaggcgac gatacatagc cgacctgaga    300

gggtgatcgg ccacactggg actgagacac ggcccagact cctacgggag gcagcagtag    360

ggaatcttcg gcaatggggg caaccctgac cgagcaacgc cgcgtgagtg aagaaggttt    420

tcggatcgta aagctctgtt gttagagaag aatgatggtg ggagtggaaa atccaccaag    480

tgacggtaac taaccagaaa gggacggcta actacgtgcc agcagccgcg gtaatacgta    540

ggtcccgagc gttgtccgga tttattgggc gtaaagcgag cgcaggcggt tttttaagtc    600

tgaagttaaa ggcattggct caaccaatgt acgctttgga aactggagaa cttgagtgca    660
```

```
gaaggggaga gtggaattcc atgtgtagcg gtgaaatgcg tagatatatg gaggaacacc    720
ggtggcgaaa gcggctctct ggtctgtaac tgacgctgag gctcgaaagc gtggggagca    780
aacaggatta gataccctgg tagtccacgc cgtaaacgat gagtgctagg tgttaggccc    840
tttccggggc ttagtgccgg agctaacgca ttaagcactc cgcctgggga gtacgaccgc    900
aaggttgaaa ctcaaaggaa ttgacggggg cccgcacaag cggtggagca tgtggtttaa    960
ttcgaagcaa cgcgaagaac cttaccaggt cttgacatcc cgatgcccgc tctagagata   1020
gagttttact tcggtacatc ggtgacaggt ggtgcatggt tgtcgtcagc tcgtgtcgtg   1080
agatgttggg ttaagtcccg caacgagcgc aacccctatt gttagttgcc atcattaagt   1140
tgggcactct agcgagactg ccggtaataa accggaggaa ggtggggatg acgtcaaatc   1200
atcatgcccc ttatgacctg ggctacacac gtgctacaat ggttggtaca acgagtcgca   1260
agccggtgac ggcaagctaa tctcttaaag ccaatctcag ttcggattgt aggctgcaac   1320
tcgcctacat gaagtcggaa tcgctagtaa tcgcggatca gcacgccgcg gtgaatacgt   1380
tcccgggcct tgtacacacc gcccgtcaca ccacgagagt ttgtaacacc cgaagtcggt   1440
gaggtaacct attaggagcc agccgcctaa ggtgggatag atgattgggg tgaagtcgta   1500
acaaggtagc cgtatcggaa ggtgcggctg gatcacctcc ttt                     1543
```

<210> SEQ ID NO 7
<211> LENGTH: 1522
<212> TYPE: DNA
<213> ORGANISM: Enterococcus faecalis

<400> SEQUENCE: 7

```
agagtttgat cctggctcag gacgaacgct ggcggcgtgc ctaatacatg caagtcgaac     60
gcttctttcc tcccgagtgc ttgcactcaa ttggaaagag gagtggcgga cgggtgagta    120
acacgtgggt aacctaccca tcagaggggg ataacacttg gaaacaggtg ctaataccgc    180
ataacagttt atgccgcatg gcataagagt gaaaggcgct ttcgggtgtc gttgatggat    240
ggacccgcgg tgcattagct agttggtgag gtaacggctc accaaggcca cgatgcatag    300
ccgacctgag agggtgatcg gccacactgg gactgagaca cggcccagac tcctacggga    360
ggcagcagta gggaatcttc ggcaatggac gaaagtctga ccgagcaacg ccgcgtgagt    420
gaagaaggtt ttcggatcgt aaaactctgt tgttagagaa gaacaaggac gttagtaact    480
gaacgtcccc tgacggtatc taaccagaaa gccacggcta actacgtgcc agcagccgcg    540
gtaatacgta ggtggcaagc gttgtccgga tttattgggc gtaaagcgag cgcaggcggt    600
ttcttaagtc tgatgtgaaa gcccccggct caaccgggga gggtcattgg aaactgggag    660
acttgagtgc agaagaggag agtggaattc catgtgtagc ggtgaaatgc gtagatatat    720
ggaggaacac cagtggcgaa ggcggctctc tggtctgtaa ctgacgctga ggctcgaaag    780
cgtggggagc aaacaggatt agataccctg gtagtccacg ccgtaaacga tgagtgctaa    840
gtgttggagg gtttccgccc ttcagtgctg cagcaaacgc attaagcact ccgcctgggg    900
agtacgaccg caaggttgaa actcaaagga attgacgggg gcccgcacaa gcggtggagc    960
atgtggttta attcgaagca acgcgaagaa ccttaccagg tcttgacatc ctttgaccac   1020
tctagagata gagctttccc ttcggggaca aagtgacagg tggtgcatgg ttgtcgtcag   1080
ctcgtgtcgt gagatgttgg gttaagtccc gcaacgagcg caacccttat tgttagttgc   1140
catcatttag ttgggcactc tagcgagact gccggtgaca aaccggagga aggtggggat   1200
```

```
gacgtcaaat catcatgccc cttatgacct gggctacaca cgtgctacaa tgggaagtac   1260

aacgagtcgc tagaccgcga ggtcatgcaa atctcttaaa gcttctctca gttcggattg   1320

caggctgcaa ctcgcctgca tgaagccgga atcgctagta atcgcggatc agcacgccgc   1380

ggtgaatacg ttcccgggcc ttgtacacac cgcccgtcac accacgagag tttgtaacac   1440

ccgaagtcgg tgaggtaacc tttttggagc cagccgccta aggtgggata gatgattggg   1500

gtgaagtcgt aacaaggtag cc                                            1522


<210> SEQ ID NO 8
<211> LENGTH: 1551
<212> TYPE: DNA
<213> ORGANISM: Enterococcus faecium

<400> SEQUENCE: 8

agagtttgat cctggctcag gacgaacgct ggcggcgtgc ctatacatgc aagtcgaacg     60

cttctttttc caccggagct tgctccaccg gaaaaagagg agtggcgaac gggtgagtaa    120

cacgtgggta acctgcccat cagaaaggga taacacttgg aaacaggtgc taataccgta    180

taacaaatca aaaccgcatg gttttgattt gaaaggcgct ttcgggtgtc gctgatggat    240

ggacccgcgg tgcattagct agttggtgag gtaacggctc accaaggcca cgatgcatag    300

ccgcacctga gagggtgatc ggccacattg ggactgagac acggcccaaa ctctacggga    360

ggcagcagta gggaatcttc ggcaatggac gaaagtctga ccgagcaacg ccgcgtgagt    420

gaagaaggtt ttcggatcgt aaaactctgt tgttagagaa gaacaaggat gagagtaact    480

gttcatccct tgacggtatc taaccagaaa gccacggcta actacgtgcc agcagccgcg    540

gtaatacgta ggtggcaagc gttgtccgga tttattgggc gtaaagcgag cgcaggcggt    600

tcttaagtct gatgtgaaag cccccggctc aaccggggag ggtcattgga aactgggaga    660

cttgagtgca gaagaggaga gtggaattcc atgtgtagcg gtgaaatgcg tagatatatg    720

gaggaacacc agtggcgaag gcggctctct ggtctgtaac tgacgctgag gctcgaaagc    780

gtggggagca aacaggatta gataccctgg tagtccacgc cgtaaacgat gagtgctaag    840

tgttggaggg tttccgccct tcagtgctgc agctaacgca ttaagcactc cgcctgggga    900

gtacgaccgc aaggttgaaa ctcaaaggaa ttgacggggg cccgcacaag cggtggagca    960

tgtggtttaa ttcgaagcaa cacgaagaac cttaccaggt cttgacatcc tttgaccact   1020

ctagagatag agcttcccct tcgggggcaa agtgacaggt ggtgcatggt tgtcgtcagc   1080

tcgtgtcgtg agatgttggg ttaagtcccg caacgagcgc aacccttatt gttagttgcc   1140

atcattcagt tgggcactct agcaagactg ccggtgacaa accggaggaa ggtggggatg   1200

acgtcaaatc atcatgcccc ttatgacctg ggctacacac gtgctacaat gggaagtaca   1260

acgagttgcg aagtcgcgag gctaagctaa tctcttaaag cttctctcag ttcggattgc   1320

aggctgcaac tcgcctgcat gaagccggaa tcgctagtaa tcgcggatca gcacgccgcg   1380

tgaatacgtt cccgggcctt gtacacaccg cccgtcacac cacgagagtt tgtaacaccc   1440

gaagtcggtg aggtaacctt ttggagccag ccgcctaagg tgggatagat gattggggtg   1500

aagtcgtaac aaggtagccg tatctgaagg tgcggctgga tcacctcctt t            1551


<210> SEQ ID NO 9
<211> LENGTH: 1542
<212> TYPE: DNA
<213> ORGANISM: Proteus mirabilis

<400> SEQUENCE: 9
```

```
aattgaagag tttgatcatg gctcagattg aacgctggcg gcaggcctaa cacatgcaag     60

tcgagcggta acaggagaaa gcttgctttc ttgctgacga gcggcggacg ggtgagtaat    120

gtatggggat ctgcccgata gagggggata actactggaa acggtggcta ataccgcata    180

atgtctacgg accaaagcag gggctcttcg gaccttgcac tatcggatga acccatatgg    240

gattagctag taggtggggt aaaggctcac ctaggcgacg atctctagct ggtctgagag    300

gatgatcagc cacactggga ctgagacacg gcccagactc ctacgggagg cagcagtggg    360

gaatattgca caatgggcgc aagcctgatg cagccatgcc gcgtgtatga agaaggcctt    420

agggttgtaa agtactttca gcggggagga aggtgataag gttaataccc ttgtcaattg    480

acgttacccg cagaagaagc accggctaac tccgtgccag cagccgcggt aatacggagg    540

gtgcaagcgt taatcggaat tactgggcgt aaagcgcacg caggcggtca attaagtcag    600

atgtgaaagc cccgagctta acttgggaat tgcatctgaa actggttggc tagagtcttg    660

tagagggggg tagaattcca tgtgtagcgg tgaaatgcgt agagatgtgg aggaataccg    720

gtggcgaagg cggccccctg gacaaagact gacgctcagg tgcgaaagcg tggggagcaa    780

acaggattag ataccctggt agtccacgct gtaaacgatg tcgatttaga ggttgtggtc    840

ttgaaccgtg gcttctggag ctaacgcgtt aaatcgaccg cctggggagt acggccgcaa    900

ggttaaaact caaatgaatt gacgggggcc cgcacaagcg gtggagcatg tggtttaatt    960

cgatgcaacg cgaagaacct tacctactct tgacatccag cgaatccttt agagatagag   1020

gagtgccttc gggaacgctg agacaggtgc tgcatggctg tcgtcagctc gtgttgtgaa   1080

atgttgggtt aagtcccgca acgagcgcaa cccttatcct ttgttgccag cacgtaatgg   1140

tgggaactca aaggagactg ccggtgataa accggaggaa ggtggggatg acgtcaagtc   1200

atcatggccc ttacgagtag ggctacacac gtgctacaat ggcagataca aagagaagcg   1260

acctcgcgag agcaagcgga actcataaag tctgtcgtag tccggattgg agtctgcaac   1320

tcgactccat gaagtcggaa tcgctagtaa tcgtagatca gaatgctacg gtgaatacgt   1380

tcccgggcct tgtacacacc gcccgtcaca ccatgggagt gggttgcaaa agaagtaggt   1440

agcttaacct tcgggagggc gcttaccact ttgtgattca tgactggggt gaagtcgtaa   1500

caaggtaacc gtaggggaac ctgcggttgg atcacctcct ta                       1542


<210> SEQ ID NO 10
<211> LENGTH: 1505
<212> TYPE: DNA
<213> ORGANISM: Serratia marcescens

<400> SEQUENCE: 10

gctcagattg aacgctggcg gcaggcttaa cacatgcaag tcgagcggta gcacagggga     60

gcttgctccc tgggtgacga gcggcggacg ggtgagtaat gtctgggaaa ctgcctgatg    120

gagggggata actactggaa acggtagcta ataccgcata acgtcgcaag accaaagagg    180

gggaccttcg ggcctcttgc catcagatgt gcccagatgg gattagctag taggtggggt    240

aatggctcac ctaggcgacg atccctagct ggtctgagag gatgaccagc cacactggaa    300

ctgagacacg gtccagactc ctacgggagg cagcagtggg gaatattgca caatgggcgc    360

aagcctgatg cagccatgcc gcgtgtgtga agaaggcctt cgggttgtaa agcactttca    420

gcgaggagga aggtggtgag cttaatacgt tcatcaattg acgttactcg cagaagaagc    480

accggctaac tccgtgccag cagccgcggt aatacggagg gtgcaagcgt taatcggaat    540
```

```
tactgggcgt aaagcgcacg caggcggttt gttaagtcag atgtgaaatc cccgggctca    600

acctgggaac tgcatttgaa actggcaagc tagagtctcg tagagggggg tagaattcca    660

ggtgtagcgg tgaaatgcgt agagatctgg aggaataccg gtggcgaagg cgggcccctg    720

gacgaagact gacgctcagg tgccaaagcg tggggagcaa acaggattag ataccctggt    780

agtccacgct gtaaacgatg tcgatttgga ggttgtgccc ttgaggcgtg gcttccggag    840

ctaacgcgtt aaatcgaccg cctggggagt acggccgcaa ggttaaaact caaatgaatt    900

gacgggggcc cgcacaagcg gtggagcatg tggtttaatt cgatgcaacg cgaagaacct    960

tacctactct tgacatccag agaactttcc agagatggat tggtgccttc gggaactctg   1020

agacaggtgc tgcatggctg tcgtcagctc gtgttgtgaa atgttgggtt aagtcccgca   1080

acgagcgcaa cccttatcct ttgttgccag cggttcggcc gggaactcaa aggagactgc   1140

cagtgataaa ctggaggaag gtggggatga cgtcaagtca tcatggccct tacgagtagg   1200

gctacacacg tgctacaatg gcatatacaa agagaagcga cctcgcgaga gcaagcggac   1260

ctcataaagt atgtcgtagt ccggattgga gtctgcaact cgactccatg aagtcggaat   1320

cgctagtaat cgtagatcag aatgctacgg tgaatacgtt cccgggcctt gtacacaccg   1380

cccgtcacac catgggagtg ggttgcaaaa gaagtaggta gcttaacctt cgggagggcg   1440

cttaccactt tgtgattcat gactggggtg aagtcgtaac aaggtaaccg taggggaacc   1500

tgcgg                                                               1505


<210> SEQ ID NO 11
<211> LENGTH: 1438
<212> TYPE: DNA
<213> ORGANISM: Enterobacter aerogenes
<220> FEATURE:
<221> NAME/KEY: misc_feature
<222> LOCATION: (1425)..(1425)
<223> OTHER INFORMATION: n is a, c, g, or t

<400> SEQUENCE: 11

acgctggcgg caggcctaac acatgcaagt cgagcggtag cacagagagc ttgctctcgg     60

gtgacgagcg gcggacgggt gagtaatgtc tgggaaactg cctgatggag ggggataact    120

actggaaacg gtagctaata ccgcataacg tcgcaagacc aaagtggggg accttcgggc    180

ctcatgccat cagatgtgcc cagatgggat tagctagtag gtggggtaat ggctcaccta    240

ggcgacgatc cctagctggt ctgagaggat gaccagccac actggaactg agacacggtc    300

cagactccta cgggaggcag cagtggggaa tattgcacaa tgggcgcaag cctgatgcag    360

ccatgccgcg tgtatgaaga aggccttcgg gttgtaaagt actttcagcg aggaggaagg    420

cgttaaggtt aataaccttg gcgattgacg ttactcgcag aagaagcacc ggctaactcc    480

gtgccagcag ccgcggtaat acggagggtg caagcgttaa tcggaattac tgggcgtaaa    540

gcgcacgcag gcggtctgtc aagtcggatg tgaaatcccc gggctcaacc tgggaactgc    600

attcgaaact ggcaggctag agtcttgtag aggggggtag aattccaggt gtagcggtga    660

aatgcgtaga gatctggagg aataccggtg gcgaaggcgg ccccctggac aaagactgac    720

gctcaggtgc gaaagcgtgg ggagcaaaca ggattagata ccctggtagt ccacgccgta    780

aacgatgtcg acttggaggt tgtgcccttg aggcgtggct tccggagcta acgcgttaag    840

tcgaccgcct ggggagtacg gccgcaaggt taaaactcaa atgaattgac gggggcccgc    900

acaagcggtg gagcatgtgg tttaattcga tgcaacgcga agaaccttac ctactcttga    960

catccagaga acttagcaga gatgctttgg tgccttcggg aactctgaga caggtgctgc   1020
```

```
atggctgtcg tcagctcgtg ttgtgaaatg ttgggttaag tcccgcaacg agcgcaaccc   1080

ttatcctttg ttgccagcgg tccggccggg aactcaaagg agactgccag tgataaactg   1140

gaggaaggtg gggatgacgt caagtcatca tggcccttac gagtagggct acacacgtgc   1200

tacaatggca tatacaaaga gaagcgacct cgcgagagca agcggacctc ataaagtatg   1260

tcgtagtccg gattggagtc tgcaactcga ctccatgaag tcggaatcgc tagtaatcgt   1320

agatcagaat gctacggtga atacgttccc gggccttgta cacaccgccc gtcacaccat   1380

gggagtgggt tgcaaaagaa gtaggtagct taaccttcgg gaggncgctt taccactt     1438
```

<210> SEQ ID NO 12
<211> LENGTH: 1511
<212> TYPE: DNA
<213> ORGANISM: Enterobacter cloacae

<400> SEQUENCE: 12

```
tgaacgctgg cggcaggcct aacacatgca agtcgaacgg tagcacagag agcttgctct     60

cgggtgacga gtggcggacg ggtgagtaat gtctgggaaa ctgcctgatg gagggggata    120

actactggaa acggtagcta ataccgcata aygtcgcaag accaaagagg gggaccttcg    180

ggcctcttgc catcagatgt gcccagatgg gattagctag taggtggggt aacggctcac    240

ctaggcgacg atccctagct ggtctgagag gatgaccagc cacactggaa ctgagacacg    300

gtccagactc ctacgggagg cagcagtggg gaatattgca caatgggcgc aagcctgatg    360

cagccatgcc gcgtgtatga agaaggcctt cgggttgtaa agtactttca gcggggagga    420

aggtgttgtg gttaataacc gcagcaattg acgttacccg cagaagaagc accggctaac    480

tccgtgccag cagccgcggt aatacggagg gtgcaagcgt taatcggaat tactgggcgt    540

aaagcgcacg caggcggtct gtcaagtcgg atgtgaaatc cccgggctca acctgggaac    600

tgcattcgaa actggcaggc tggagtcttg tagagggggg tagaattcca ggtgtagcgg    660

tgaaatgcgt agagatctgg aggaataccg gtggcgaagg cggccccctg gacaaagact    720

gacgctcagg tgcgaaagcg tggggagcaa acaggattag ataccctggt agtccacgcc    780

gtaaacgatg tcgatttgga ggttgtgccc ttgaggcgtg gcttccggag ctaacgcgtt    840

aaatcgaccg cctggggagt acggccgcaa ggttaaaact caaatgaatt gacgggggcc    900

cgcacaagcg gtggagcatg tggtttaatt cgatgcaacg cgaagaacct tacctggtct    960

tgacatccac agaactttcc agagatggat tggtgccttc gggaactgtg agacaggtgc   1020

tgcatggctg tcgtcagctc gtgttgtgaa atgttgggtt aagtcccgca acgagcgcaa   1080

cccttatcct ttgttgccag cggtccggcc gggaactcaa aggagactgc cagtgataaa   1140

ctggaggaag gtggggatga cgtcaagtca tcatggccct tacgaccagg gctacacacg   1200

tgctacaatg gcgcatacaa agagaagcga cctcgcgaga gcaagcggac ctcataaagt   1260

gcgtcgtagt ccggattgga gtctgcaact cgactccatg aagtcggaat cgctagtaat   1320

cgtagatcag aatgctacgg tgaatacgtt cccgggcctt gtacacaccg cccgtcacac   1380

catgggagtg ggttgcaaaa gaagtaggta gcttaacctt cgggagggcg cttaccactt   1440

tgtgattcat gactggggtg aagtcgtaac aaggtaaccg taggggaacc tgcggctgga   1500

tcacctcctt g                                                        1511
```

<210> SEQ ID NO 13
<211> LENGTH: 1534
<212> TYPE: DNA

```
<213> ORGANISM: Klebsiella pneumoniae
<220> FEATURE:
<221> NAME/KEY: misc_feature
<222> LOCATION: (11)..(12)
<223> OTHER INFORMATION: n is a, c, g, or t

<400> SEQUENCE: 13

agagtttgat nntggctcag attgaacgct ggcggcaggc ctaacacatg caagtcgagc      60

ggtagcacag agagcttgct ctcgggtgac gagcggcgga cgggtgagta atgtctggga     120

aactgcctga tggaggggga taactactgg aaacggtagc taataccgca taacgtcgca     180

agaccaaagt gggggacctt cgggcctcat gccatcagat gtgcccagat gggattagct     240

agtaggtggg gtaacggctc acctaggcga cgatccctag ctggtctgag aggatgacca     300

gccacactgg aactgagaca cggtccagac tcctacggga ggcagcagtg gggaatattg     360

cacaatgggc gcaagcctga tgcagccatg ccgcgtgtgt gaagaaggcc ttcgggttgt     420

aaagcacttt cagcggggag gaaggcgatg aggttaataa cctcatcgat tgacgttacc     480

ctgcagaaga agcaccggct aactccgtgc cagcagccgc ggtaatacgg agggtgcaag     540

cgttaatcgg aattactggg cgtaaagcgc acgcaggcgg tctgtcaagt cggatgtgaa     600

atccccgggc tcaacctggg aactgcattc gaaactggca ggctagagtc ttgtagaggg     660

gggtagaatt ccaggtgtag cggtgaaatg cgtagagatc tggaggaata ccggtggcga     720

aggcggcccc ctggacaaag actgacgctc aggtgcgaaa gcgtggggag caaacaggat     780

tagataccct ggtagtccac gccgtaaacg atgtcgattt ggaggttgtg cccttgaggc     840

gtggcttccg gagctaacgc gttaaatcga ccgcctgggg agtacggccg caaggttaaa     900

actcaaatga attgacgggg gcccgcacaa gcggtggagc atgtggttta attcgatgca     960

acgcgaagaa ccttacctgg tcttgacatc cacagaactt tccagagatg gattggtgcc    1020

ttcgggaact gtgagacagg tgctgcatgg ctgtcgtcag ctcgtgttgt gaaatgttgg    1080

gttaagtccc gcaacgagcg caacccttat cctttgttgc cagcggttag gccgggaact    1140

caaaggagac tgccagtgat aaactggagg aaggtgggga tgacgtcaag tcatcatggc    1200

ccttacgacc agggctacac acgtgctaca atggcatata caaagagaag cgacctcgcg    1260

agagcaagcg gacctcataa agtatgtcgt agtccggatt ggagtctgca actcgactcc    1320

atgaagtcgg aatcgctagt aatcgtagat cagaatgcta cggtgaatac gttcccgggc    1380

cttgtacaca ccgcccgtca caccatggga gtgggttgca aaagaagtag gtagcttaac    1440

cttcgggagg gcgcttacca ctttgtgatt catgactggg gtgaagtcgt aacaaggtaa    1500

ccgtagggga acctgcggtt ggatcacctc cttt                                1534


<210> SEQ ID NO 14
<211> LENGTH: 1536
<212> TYPE: DNA
<213> ORGANISM: Pseudomonas aeruginosa

<400> SEQUENCE: 14

gaactgaaga gtttgatcat ggctcagatt gaacgctggc ggcaggccta acacatgcaa      60

gtcgagcgga tgaagggagc ttgctcctgg attcagcggc ggacgggtga gtaatgccta     120

ggaatctgcc tggtagtggg ggataacgtc cggaaacggg cgctaatacc gcatacgtcc     180

tgagggagaa agtgggggat cttcggacct cacgctatca gatgagccta ggtcggatta     240

gctagttggt ggggtaaagg cctaccaagg cgacgatccg taactggtct gagaggatga     300

tcagtcacac tggaactgag acacggtcca gactcctacg ggaggcagca gtggggaata     360
```

```
ttggacaatg ggcgaaagcc tgatccagcc atgccgcgtg tgtgaagaag gtcttcggat    420
tgtaaagcac tttaagttgg gaggaagggc agtaagttaa taccttgctg ttttgacgtt    480
accaacagaa taagcaccgg ctaacttcgt gccagcagcc gcggtaatac gaagggtgca    540
agcgttaatc ggaattactg ggcgtaaagc gcgcgtaggt ggttcagcaa gttggatgtg    600
aaatccccgg gctcaacctg ggaactgcat ccaaaactac tgagctagag tacggtagag    660
ggtggtggaa tttcctgtgt agcggtgaaa tgcgtagata taggaaggaa caccagtggc    720
gaaggcgacc acctggactg atactgacac tgaggtgcga aagcgtgggg agcaaacagg    780
attagatacc ctggtagtcc acgccgtaaa cgatgtcgac tagccgttgg gatccttgag    840
atcttagtgg cgcagctaac gcgataagtc gaccgcctgg ggagtacggc cgcaaggtta    900
aaactcaaat gaattgacgg gggcccgcac aagcggtgga gcatgtggtt taattcgaag    960
caacgcgaag aaccttacct ggccttgaca tgctgagaac tttccagaga tggattggtg   1020
ccttcgggaa ctcagacaca ggtgctgcat ggctgtcgtc agctcgtgtc gtgagatgtt   1080
gggttaagtc ccgtaacgag cgcaaccctt gtccttagtt accagcacct cgggtgggca   1140
ctctaaggag actgccggtg acaaaccgga ggaaggtggg gatgacgtca agtcatcatg   1200
gcccttacgg ccagggctac acacgtgcta caatggtcgg tacaaagggt tgccaagccg   1260
cgaggtggag ctaatcccat aaaaccgatc gtagtccgga tcgcagtctg caactcgact   1320
gcgtgaagtc ggaatcgcta gtaatcgtga atcagaatgt cacggtgaat acgttcccgg   1380
gccttgtaca caccgcccgt cacaccatgg gagtgggttg ctccagaagt agctagtcta   1440
accgcaaggg ggacggttac cacggagtga ttcatgactg ggtgaagtc gtaacaaggt    1500
agccgtaggg gaacctgcgg ctggatcacc tcctta                             1536
```

<210> SEQ ID NO 15
<211> LENGTH: 1497
<212> TYPE: DNA
<213> ORGANISM: Acinetobacter calcoaceticus

<400> SEQUENCE: 15

```
tagagtttga tcctggctca gattgaacgc tggcggcagg cttaacacat gcaagtcgag     60
cggggaaagg tagcttgcta ctggacctag cggcggacgg gtgagtaatg cttaggaatc    120
tgcctattag tgggggacaa cattccgaaa ggaatgctaa taccgcatac gtcctacggg    180
agaaagcagg ggaccttcgg gccttgcgct aatagatgag cctaagtcgg attagctagt    240
tggtggggta aaggcctacc aaggcgacga tctgtagcgg tctgagagga tgatccgcca    300
cactgggact gagacacggc ccagactcct acgggaggca gcagtgggga atattggaca    360
atgggggggaa ccctgatcca gccatgccgc gtgtgtgaag aaggccttat ggttgtaaag    420
cactttaagc gaggaggagg ctactagtat taatactact ggatagtgga cgttactcgc    480
agaataagca ccggctaact ctgtgccagc agccgcggta atacagaggg tgcgagcgtt    540
aatcggattt actgggcgta aagcgtgcgt aggcggccat ttaagtcaaa tgtgaaatcc    600
ccgagcttaa cttgggaatt gcattgcata ctggatggct agagtatggg agaggatggt    660
agaattccag gtgtagcggt gaaatgcgta gagatctgga ggaataccga tggcgaaggc    720
agccatctgg cctaatactg acgctgaggt acgaaagcat gggagcagaa caggattaga    780
taccctggta gtccatgccg taaacgatgt ttactagccg ttggggcctt tgaggcttta    840
gtggcgcagc taacgcgata agtagaccgc ctggggagta cggtcgcaag actaaaactc    900
```

```
aaatgaattg acgggggccc gcacaagcgg tggagcatgt ggtttaattc gatgcaacgc    960

gaagaacctt acctggcctt gacatactag aaactttcca gagatggatt ggtgccttcg   1020

ggaatttaga tacaggtgct gcatggctgt cgtcagctcg tgtcgtgaga tgttgggtta   1080

agtcccgcaa cgagcgcaac ccttttcctt acttgccagc atttcggatg ggaactttaa   1140

ggatactgcc agtgacaaac tggaggaagg cggggacgac gtcaagtcat catggccctt   1200

acggccaggg ctacacacgt gctacaatgg tcggtacaaa gggttgctac ctagcgatag   1260

gatgctaatc tcaaaaagcc gatcgtagtc cggattggag tctgcaactc gactccatga   1320

agtcggaatc gctagtaatc gcggatcaga atgcccggtg atacgttccc gggccttgta   1380

cacaccgccc gtcacaccat gggagtttgt tgcaccagaa gtaggtagtc taaccgcaag   1440

gaggacgctt accacggtgt ggccgatgac tggggtgaag tcgtaacaag gtaacca      1497


<210> SEQ ID NO 16
<211> LENGTH: 19
<212> TYPE: DNA
<213> ORGANISM: Artificial Sequence
<220> FEATURE:
<223> OTHER INFORMATION: Forward Primer

<400> SEQUENCE: 16

cctcttgcca tcggatgtg                                                  19


<210> SEQ ID NO 17
<211> LENGTH: 20
<212> TYPE: DNA
<213> ORGANISM: Artificial Sequence
<220> FEATURE:
<223> OTHER INFORMATION: Reverse Primer

<400> SEQUENCE: 17

ccagtgtggc tggtcatcct                                                 20


<210> SEQ ID NO 18
<211> LENGTH: 20
<212> TYPE: DNA
<213> ORGANISM: Artificial Sequence
<220> FEATURE:
<223> OTHER INFORMATION: Forward Primer

<400> SEQUENCE: 18

cctacgggag gcagcagtag                                                 20


<210> SEQ ID NO 19
<211> LENGTH: 20
<212> TYPE: DNA
<213> ORGANISM: Artificial Sequence
<220> FEATURE:
<223> OTHER INFORMATION: Forward Primer

<400> SEQUENCE: 19

gggaggcagc agtagggaat                                                 20


<210> SEQ ID NO 20
<211> LENGTH: 22
<212> TYPE: DNA
<213> ORGANISM: Artificial Sequence
<220> FEATURE:
<223> OTHER INFORMATION: Reverse Primer

<400> SEQUENCE: 20

cgatccgaaa accttcttca ct                                              22
```

<210> SEQ ID NO 21
<211> LENGTH: 26
<212> TYPE: DNA
<213> ORGANISM: Artificial Sequence
<220> FEATURE:
<223> OTHER INFORMATION: Forward Primer

<400> SEQUENCE: 21
aagacggtct tgctgtcact tataga 26

<210> SEQ ID NO 22
<211> LENGTH: 22
<212> TYPE: DNA
<213> ORGANISM: Artificial Sequence
<220> FEATURE:
<223> OTHER INFORMATION: Reverse Primer

<400> SEQUENCE: 22
ctatgcatcg ttgccttggt aa 22

<210> SEQ ID NO 23
<211> LENGTH: 18
<212> TYPE: DNA
<213> ORGANISM: Artificial Sequence
<220> FEATURE:
<223> OTHER INFORMATION: Forward Primer

<400> SEQUENCE: 23
tgccgcgtga atgaagaa 18

<210> SEQ ID NO 24
<211> LENGTH: 21
<212> TYPE: DNA
<213> ORGANISM: Artificial Sequence
<220> FEATURE:
<223> OTHER INFORMATION: Forward Primer

<400> SEQUENCE: 24
gcgtgaagga tgaaggctct a 21

<210> SEQ ID NO 25
<211> LENGTH: 21
<212> TYPE: DNA
<213> ORGANISM: Artificial Sequence
<220> FEATURE:
<223> OTHER INFORMATION: Forward Primer

<400> SEQUENCE: 25
tgatgaaggt tttcggatcg t 21

<210> SEQ ID NO 26
<211> LENGTH: 29
<212> TYPE: DNA
<213> ORGANISM: Artificial Sequence
<220> FEATURE:
<223> OTHER INFORMATION: Reverse Primer

<400> SEQUENCE: 26
tgatgtacta ttaacacatc aaccttcct 29

<210> SEQ ID NO 27
<211> LENGTH: 22
<212> TYPE: DNA
<213> ORGANISM: Artificial Sequence
<220> FEATURE:

<223> OTHER INFORMATION: Reverse Primer

<400> SEQUENCE: 27
aacgctcgga tcttccgtat ta 22

<210> SEQ ID NO 28
<211> LENGTH: 21
<212> TYPE: DNA
<213> ORGANISM: Artificial Sequence
<220> FEATURE:
<223> OTHER INFORMATION: Reverse Primer

<400> SEQUENCE: 28
cgctcgccac ctacgtatta c 21

<210> SEQ ID NO 29
<211> LENGTH: 28
<212> TYPE: DNA
<213> ORGANISM: Artificial Sequence
<220> FEATURE:
<223> OTHER INFORMATION: Forward Primer

<400> SEQUENCE: 29
gttgtaagag aagaacgagt gtgagagt 28

<210> SEQ ID NO 30
<211> LENGTH: 22
<212> TYPE: DNA
<213> ORGANISM: Artificial Sequence
<220> FEATURE:
<223> OTHER INFORMATION: Reverse Primer

<400> SEQUENCE: 30
cgtagttagc cgtccctttc tg 22

<210> SEQ ID NO 31
<211> LENGTH: 24
<212> TYPE: DNA
<213> ORGANISM: Artificial Sequence
<220> FEATURE:
<223> OTHER INFORMATION: Forward Primer

<400> SEQUENCE: 31
gcggtttgtt aagtcagatg tgaa 24

<210> SEQ ID NO 32
<211> LENGTH: 22
<212> TYPE: DNA
<213> ORGANISM: Artificial Sequence
<220> FEATURE:
<223> OTHER INFORMATION: Forward Primer

<400> SEQUENCE: 32
ggtctgtcaa gtcggatgtg aa 22

<210> SEQ ID NO 33
<211> LENGTH: 21
<212> TYPE: DNA
<213> ORGANISM: Artificial Sequence
<220> FEATURE:
<223> OTHER INFORMATION: Forward Primer

<400> SEQUENCE: 33
tcaacctggg aactcattcg a 21

<210> SEQ ID NO 34
<211> LENGTH: 22
<212> TYPE: DNA
<213> ORGANISM: Artificial Sequence
<220> FEATURE:
<223> OTHER INFORMATION: Reverse Primer

<400> SEQUENCE: 34
ggaattctac ccccctctac ga 22

<210> SEQ ID NO 35
<211> LENGTH: 23
<212> TYPE: DNA
<213> ORGANISM: Artificial Sequence
<220> FEATURE:
<223> OTHER INFORMATION: Reverse Primer

<400> SEQUENCE: 35
ggaattctac ccccctctac aag 23

<210> SEQ ID NO 36
<211> LENGTH: 1720
<212> TYPE: DNA
<213> ORGANISM: Aspergillus fumigatus

<400> SEQUENCE: 36
ggaccgggcc tgtctaggta taagcaattt atacggtgaa actgcgaatg gctcattaaa 60
tcagttatcg tttatttgat agtaccttac tacatggata cctgtggtaa ttctagagct 120
aatacatgct aaaaacctcg acttcggaag ggtgtattt attagataaa aaaccaatgc 180
ccttcggggc tccttggtga atcataataa cttaacgaat cgcatggcct tgcgccggcg 240
atggttcatt caaatttctg ccctatcaac tttcgatggt aggatagtgg cctaccatgg 300
tggcaacggg taacggggaa ttagggttcg attccggaga gggagcctga gaaacggcta 360
ccacatccaa ggaaggcagc aggcgcgcaa attacccaat cccgacacgg ggaggtagtg 420
acaataaata ctgatacggg gctcttttgg gtctcgtaat tggaatgagt acaatctaaa 480
tcccttaacg aggaacaatt ggagggcaag tctggtgcca gcagccgcgg taattccagc 540
tccaatagcg tatattaaag ttgttgcagt taaaaagctc gtagttgaac cttgggtctg 600
gctggccggt ccgcctcacc gcgagtactg gtccggctgg acctttcctt ctggggaacc 660
tcatggcctt cactggctgt ggggggaacc aggactttta ctgtgaaaaa attagagtgt 720
tcaaagcagg cctttgctcg aatacattag catggaataa tagaatagga cgtgcggttc 780
tattttgttg gtttctagga ccgccgtaat gattaatagg gatagtcggg ggcgtcagta 840
ttcagctgtc agaggtgaaa ttcttggatt tgctgaagac taactactgc gaaagcattc 900
gccaaggatg ttttcattaa tcaggaacga aagttagggg atcgaagacg atcagatacc 960
gtcgtagtct taaccataaa ctatgccgac tagggatcgg gcggtgtttc tatgatgacc 1020
cgctcggcac cttacgagaa atcaaagttt ttgggttctg gggggagtat ggtcgcaagg 1080
ctgaaactta aagaaattga cggaagggca ccacaaggcg tggagcctgc ggcttaattt 1140
gactcaacac ggggaaactc accaggtcca gacaaaataa ggattgacag attgagagct 1200
ctttcttgat cttttggatg gtggtgcatg gccgttctta gttggtggag tgatttgtct 1260
gcttaattgc gataacgaac gagacctcgg cccttaaata gcccggtccg catttgcggg 1320
ccgctggctt cttagggga ctatcggctc aagccgatgg aagtgcgcgg caataacagg 1380
tctgtgatgc ccttagatgt tctgggccgc acgcgcgcta cactgacagg gccagcgagt 1440

```
acatcacctt ggccgagagg tctgggtaat cttgttaaac cctgtcgtgc tggggataga   1500

gcattgcaat tattgctctt caacgaggaa tgcctagtag gcacgagtca tcagctcgtg   1560

ccgattacgt ccctgccctt tgtacacacc gcccgtcgct actaccgatt gaatggctcg   1620

gtgaggcctt cggactggct caggggagtt ggcaacgact ccccagagcc ggaaagttgg   1680

tcaaacccgg tcattagagg aaagaaaaaa ttaaacacgg                         1720
```

<210> SEQ ID NO 37
<211> LENGTH: 1632
<212> TYPE: DNA
<213> ORGANISM: Candida albicans
<220> FEATURE:
<221> NAME/KEY: misc_feature
<222> LOCATION: (1587)..(1587)
<223> OTHER INFORMATION: n is a, c, g, or t

<400> SEQUENCE: 37

```
tcagttatcg tttatttgat agtaccttac tacttggata accgtggtaa ttctagagct     60

aatacatgct taaaatcccg actgtttgga agggatgtat ttattagata aaaaatcaat    120

gccttcgggc tctttgatga ttcataataa cttttcgaat cgcatggcct tgtgctggcg    180

atggttcatt caaatttctg ccctatcaac tttcgatggt aggatagtgg cctaccatgg    240

tttcaacggg taacggggaa taagggttcg attccggaga gggagcctga gaaacggcta    300

ccacatccaa ggaaggcagc aggcgcgcaa attacccaat cccgacacgg ggaggtagtg    360

acaataaata acgatacagg gcccttttgg gtcttgtaat tggaatgagt acaatgtaaa    420

taccttaacg aggaacaatt ggagggcaag tctggtgcca gcagccgcgg taattccagc    480

tccaaaagcg tatattaaag ttgttgcagt taaaaagctc gtagttgaac cttgggcttg    540

gctggccggt ccatcttttt gatgcgtact ggacccagcc gagcctttcc ttctgggtag    600

ccatttatgg cgaaccagga cttttacttt gaaaaaatta gagtgttcaa agcaggcctt    660

tgctcgaata tattagcatg gaataataga ataggacgtt atggttctat tttgttggtt    720

tctaggacca tcgtaatgat taatagggac ggtcgggggt atcagtattc agttgtcaga    780

ggtgaaattc ttggatttac tgaagactaa ctactgcgaa agcatttacc aaggacgttt    840

tcattaatca agaacgaaag ttaggggatc gaagatgatc agataccgtc gtagtcttaa    900

ccataaacta tgccgactag ggatcggttg ttgttctttt attgacgcaa tcggcacctt    960

acgagaaatc aaagtctttg ggttctgggg ggagtatggt cgcaaggctg aaacttaaag   1020

gaattgacgg aagggcacca ccaggagtgg agcctgcggc ttaatttgac tcaacacggg   1080

gaaactcacc aggtccagac acaataagga ttgacagatt gagagctctt tcttgatttt   1140

gtgggtggtg gtgcatggcc gttcttagtt ggtggagtga tttgtctgct taattgcgat   1200

aacgaacgag accttaacct actaaatagt gctgctagca tttgctggta tagtcacttc   1260

ttagagggac tatcgacttc aagtcgatgg aagtttgagg caataacagg tctgtgatgc   1320

ccttagacgt tctgggccgc acgcgcgcta cactgacgga gccagcgagt ataagccttg   1380

gccgagaggt ctgggaaatc ttgtgaaact ccgtcgtgct ggggatagag cattgtaatt   1440

gttgctcttc aacgaggaat tcctagtaag cgcaagtcat cagcttgcgt tgattacgtc   1500

cctgcccttt gtacacaccg cccgtcgcta ctaccgattg aatggcttag tgaggcctcc   1560

ggattggttt aggaaagggg gcaactncat tctggaaccg agaagctggt caaacttggt   1620

catttagagg aa                                                       1632
```

<210> SEQ ID NO 38
<211> LENGTH: 1732
<212> TYPE: DNA
<213> ORGANISM: Candida glabrata

<400> SEQUENCE: 38

```
agtatttgtc taaaaattaa gccatgcatg tctaagtata agcaatttat acagtgaaac     60
tgcgaatggc tcattaaatc agttatcgtt tatttgatag ttcctttact acatggtata    120
actgtggtaa ttctagagct aatacatgct taaaatctcg acctcttgga agagatgtat    180
ttattagata aaaaatcaat gtcttcggac tttttgatga ttcataataa cttttcgaat    240
cgcatggcct tgtgctggcg atggttcatt caaatttctg ccctatcaac tttcgatggt    300
aggatagtgg cctaccatgg tttcaacggg taacggggaa taagggttcg attccggaga    360
gggagcctga gaaacggcta ccacatccaa ggaaggcagc aggcgcgcaa attacccaat    420
cctgacacag ggaggtagtg acaataaata acgatacagg gcccattcgg gtcttgtaat    480
tggaatgagt acaatgtaaa taccttaacg aggaacaatt ggagggcaag tctggtgcca    540
gcagccgcgg taattccagc tccaatagcg tatattaaag ttgttgcagt taaaaagctc    600
gtagttgaac tttgggcctg ggtggccggt ccgatttttt cgtgtactgg aatgcacccg    660
ggcctttcct tctggctaac cccaagtcct tgtggcttgg cggcgaacca ggacttttac    720
tttgaaaaaa ttagagtgtt caaagcaggc gtattgctcg aatatattag catggaataa    780
tggaatagga cgtttggttc tattttgttg gtttctagga ccatcgtaat gattaatagg    840
gacggtcggg ggcatcagta ttcaattgtc agaggtgaaa ttcttggatt tattgaagac    900
taactactgc gaaagcattt gccaaggacg ttttcattaa tcaagaacga aagttagggg    960
atcgaagatg atcagatacc gtcgtagtct taaccataaa ctatgccgac tagggatcgg   1020
gtggtgtttt tttagtgacc cactcggcac cttacgagaa atcaaagtct ttgggttctg   1080
gggggagtat ggtcgcaagg ctgaaactta aaggaattga cggaagggca ccaccaggag   1140
tggagcctgc ggcttaattt gactcaacac ggggaaactc accaggtcca gacacaataa   1200
ggattgacag attgagagct ctttcttgat tttgtgggtg gtggtgcatg gccgttctta   1260
gttggtggag tgatttgtct gcttaattgc gataacgaac gagaccttaa cctactaaat   1320
agtggtgcta gcatttgctg gttgtccact tcttagaggg actatcggtt tcaagccgat   1380
ggaagtttga ggcaataaca ggtctgtgat gcccttagac gttctgggcc gcacgcgcgc   1440
tacactgacg gagccagcga gtctaacctt ggccgagagg tcttggtaat cttgtgaaac   1500
tccgtcgtgc tggggataga gcattgtaat tattgctctt caacgaggaa ttcctagtaa   1560
gcgcaagtca tcagcttgcg ttgattacgt ccctgccctt tgtacacacc gcccgtcgct   1620
agtaccgatt gaatggctta gtgaggcctc aggatctgct tagaagaggg ggcgactcca   1680
cttcagagcg gagaatctgg tcaaacttgg tcatttagag gaaacccaaa aa           1732
```

<210> SEQ ID NO 39
<211> LENGTH: 1223
<212> TYPE: DNA
<213> ORGANISM: Candida parapsilosis

<400> SEQUENCE: 39

```
gcctgagaaa cggctaccac atccaaggaa ggcagcaggc gcgcaaatta cccaatcccg     60
acacggggag gtagtgacaa taaataacga tacagggccc tttcgggtct tgtaattgga    120
atgagtacaa tgtaaatacc ttaacgagga acaattggag ggcaagtctg gtgccagcag    180
```

```
ccgcggtaat tccagctcca aaagcgtata ttaaagttgt tgcagttaaa aagctcgtag    240

ttgaaccttg ggcttggctg gccggtccat ctttttgat gcgtactgga cccagccgag    300

cctttccttc tggctagcct ttttggcgaa ccaggacttt tactttgaaa aaattagagt    360

gttcaaagca ggcctttgct cgaatatatt agcatggaat aatagaatag gacgttatgg    420

ttctattttg ttggtttcta ggaccatcgt aatgattaat agggacggtc gggggtatca    480

gtattcagta gtcagaggtg aaattcttgg atttactgaa gactaactac tgcgaaagca    540

tttaccaagg acgttttcat taatcaagaa cgaaagttag gggatcgaag atgatcagat    600

accgtcgtag tcttaaccat aaactatgcc gactagggat cggttgttgt tcttttattg    660

acgcaatcgg caccttacga gaaatcaaag tctttgggtt ctgggggag tatggtcgca    720

aaggctgaaa cttaaaggaa ttgacggaag ggcaccacca ggagtggagc ctgcggctta    780

atttgactca acacggggaa actcaccagg tccagacaca ataaggattg acagattgag    840

agctctttct tgattttgtg ggtggtggtg catggccgtt cttagttggt ggagtgattt    900

gtctgcttaa ttgcgataac gaacgagacc ttaacctact aaatagtgct gctagcattt    960

gctggtatag tcacttctta gagggactat cgatttcaag tcgatggaag tttgaggcaa   1020

taacaggtct gtgatgccct tagacgttct gggccgcacg cgcgctacac tgacggagcc   1080

agcgagtata aaccttggcc gagaggtctg ggaaatcttg tgaaactccg tcgtgctggg   1140

gatagagcat tgtaattatt gctcttcaac gaggaattcc tagtaagcgc aagtcatcag   1200

cttgcgttga ttacgtccct gcc                                            1223
```

<210> SEQ ID NO 40
<211> LENGTH: 1563
<212> TYPE: DNA
<213> ORGANISM: Candida tropicalis
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (631)..(631)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (723)..(822)
<223> OTHER INFORMATION: n is a, c, g, or t
<220> FEATURE:
<221> NAME/KEY: misc_feature
<222> LOCATION: (866)..(866)
<223> OTHER INFORMATION: n is a, c, g, or t
<220> FEATURE:
<221> NAME/KEY: misc_feature

```
<222> LOCATION: (1014)..(1014)
<223> OTHER INFORMATION: n is a, c, g, or t
<220> FEATURE:
<221> NAME/KEY: misc_feature
<222> LOCATION: (1509)..(1509)
<223> OTHER INFORMATION: n is a, c, g, or t
<220> FEATURE:
<221> NAME/KEY: misc_feature
<222> LOCATION: (1542)..(1542)
<223> OTHER INFORMATION: n is a, c, g, or t

<400> SEQUENCE: 40

atgcttgtct caagattaag ccatgcatgt ctaagtataa gcaatttata cagtgaaact     60

gcgaatggnt cattaaatca gttatcgttt atttgatagt accttactac ttggataacc    120

gtggtaattc tagagctaat acatgcttaa aatcccgact gtttggaagg gatgtattta    180

ttagataaaa aatcaatgtc ttcggactct ttgatgattc ataataactt ttcgaatcgc    240

atggccttgt gctggcgatg gttcattcaa atttctgccc tatcaacttt cgatggtagg    300

atagtggcct accatggttt caacgggtaa cggggaataa gggttcgatt ccggagaggg    360

agcctgagaa acggctacca catccaagga aggcagcagg cgcgcaaatt acccaatccc    420

gacacgggga ggtagtgaca ataaataacg atacagggcc ctttcgggtc ttgtaattgg    480

aatgagtaca atgtaaatac cttaacgagg aacaattgga gggcaagtct ggtgccagca    540

gcccgcggta attccagctt caaaagccgt atattaaagg tggttgcagt taaaaagctc    600

gtagttgaac cttgggcttt ggttggnccg nccatctttc tgaagcctac tggaccccaa    660

cccgagccct ttcntttggc taanccttt ggcgaaccng gacntttacc tttgaaaaaa    720

ttnnnnnnnn nnnnnnnnnn nnnnnnnnnn nnnnnnnnnn nnnnnnnnnn nnnnnnnnnn    780

nnnnnnnnnn nnnnnnnnnn nnnnnnnnnn nnnnnnnnnn nncgattagg gatcggttgt    840

tgttctttaa ttgacgccat tgggcncctt acgagaaatc aaaagtcttt gggttctggg    900

ggaagtatgg tcgcaaggtt gaaactttaa aggaattgac ggaagggcac caccaggagt    960

ggagcctgcg gcttaattt gactcaacac ggggaaactc accaggtcca gacncaataa   1020

ggattgacag attgagagct ctttcttgat tttgtgggtg gtggtgcatg gccgttctta   1080

gttggtggag tgatttgtct gcttaattgc gataacgaac gagaccttaa cctactaaat   1140

agtgctgcta gcatttgctg gtatagtcac ttcttagagg gactatcgat ttcaagtcga   1200

tggaagtttg aggcaataac aggtctgtga tgcccttaga cgttctgggc cgcacgcgcg   1260

ctacactgac ggagccagcg agtataaacc ttggccgaga ggtctgggaa atcttgtgaa   1320

actccgtcgt gctggggata gagcattgta attgttgctc ttcaacgagg aattcctagt   1380

aagcgcaagt catcagcttg cgttgattac gtccctgccc tttgtacaca ccgcccgtcg   1440

ctactaccga ttgaatggct tagtgaggct tccggattgg tttaggaaag gggcaactc   1500

cattctggna ccgagaagct agtcaaactc ggtcatttag ancaagtaaa agtcgaacaa   1560

ggt                                                                 1563


<210> SEQ ID NO 41
<211> LENGTH: 1801
<212> TYPE: DNA
<213> ORGANISM: Cryptococcus neoformans

<400> SEQUENCE: 41

acctggttga tcctgccagt agtcatatgc ttgtctcaaa gattaagcca tgcatgtcta     60

agtataaacg aattcatact gtgaaactgc gaatggctca ttaaatcagt tatagtttat    120
```

```
ttgatggtat cttgctacat ggataactgt ggtaattcta gagctaatac atgctgaaaa    180

gccccgactt ctggaagggg tgtatttatt agataaaaaa ccaatgggtt tcggccctct    240

atggtgaatc ataataactt ctcgaatcgc atggccttgt gccggcgatg cttcattcaa    300

atatctgccc tatcaacttt cgatggtagg atagaggcct accatggtat caacgggtaa    360

cggggaatta gggttcgatt ccggagaggg agcctgagaa acggctacca catccaagga    420

aggcagcagg cgcgcaaatt acccaatccc gacacgggga ggtagtgaca ataaataaca    480

atacagggct cttttgggcc ttgtaattgg aatgagtaca atttaaatcc cttaacgagg    540

aacaactgga gggcaagtct ggtgccagca gccgcggtaa ttccagctcc agtagcgtat    600

attaaagttg ttgcagttaa aaagctcgta gtcgaacttc aggtctggcg aggcggtcct    660

cctcacggag tgcactgtct tgctggacct tacctcctgg tggtcctgta tgctctttac    720

tgggtgtgca ggggaaccag gaattttacc ttgaaaaaat tagagtgttc aaagcaggca    780

atcgcccgaa tacattagca tggaataata gaataggacg tgcggttcta ttttgttggt    840

ttctaggatc gccgtaatga ttaataggga cggtcggggg cattggtatt ccgttgctag    900

aggtgaaatt cttagattga cggaagacca acaactgcga aagcatttgc caaggacgtt    960

ttcattgatc aagaacgaag gttaggggat caaaaacgat tagataccgt tgtagtctta   1020

acagtaaacg atgccgacta gggatcggcc cacgtcaatc tctgactggg tcggcacctt   1080

acgagaaatc aaagtctttg ggttctgggg ggagtatggt cgcaaggctg aaacttaaag   1140

gaattgacgg aagggcacca ccaggtgtgg agcctgcggc ttaatttgac tcaacacggg   1200

gaaactcacc aggtccagac atagtgagga ttgacagatt gatagctctt tcttgattct   1260

atgggtggtg gtgcatggcc gttcttagtt ggtggagtga tttgtctggt taattccgat   1320

aacgaacgag accttaacct gctaaatagt caggccggct ttggctggtc gtatgacttc   1380

ttagagggac tgtcggcgtc tagtcgacgg aagtttgagg caataacagg tctgtgatgc   1440

ccttagatgt tctgggccgc acgcgcgcta cactgactga gccagcgagt cttaccgcct   1500

tggccgagag gcctgggtaa tcttgtgaaa ctcagtcgtg ctggggatag agcattgcaa   1560

ttattgctct tcaacgagga atacctagta agcgtgagtc accagctcgc gttgattacg   1620

tccctgccct ttgtacacac cgcccgtcgc tactaccgat tgaatggctt agtgagatct   1680

ccggattggc gttggggagc cggcaacggc accccttggc cgagaagttg atcaaacttg   1740

gtcatttaga ggaagtaaaa gtcgtaacaa ggtttccgta ggtgaacctg cggaaggatc   1800

a                                                                   1801
```

<210> SEQ ID NO 42
<211> LENGTH: 1673
<212> TYPE: DNA
<213> ORGANISM: Fusarium sp.

<400> SEQUENCE: 42

```
gcaattatac cgcgaaactg cgaatggctc attatataag ttatcgttta tttgatagta     60

ccttactact tggataaccg tggtaattct agagctaata catgctaaaa atcccgactt    120

cggaagggat gtatttatta gattaaaaac caatgccctt cggggctcac tggtgattca    180

tgataactcc tcgaatcgca tggccttgtg ccggcgatgg ttcattcaaa tttcttccct    240

atcaactttc gatgtttggg tattggccaa acatggttgc aacgggtaac ggagggttag    300

ggctcgaccc cggagaagga gcctgagaaa cggctactac atccaaggaa ggcagcaggc    360

gcgcaaatta cccaatcccg acacggggag gtagtgacaa taaatactga tacagggctc    420
```

```
ttttgggtct tgtaattgga atgagtacaa tttaaatccc ttaacgagga acaattggag    480

ggcaagtctg gtgccagcag ccgcggtaat tccagctcca atagcgtata ttaaagttgt    540

tgtggttaaa aagctcgtag ttgaaccttg ggcctggccg tccggtccgc ctcaccgcgt    600

gtactggctc ggccgggcct ttccctctgt ggaaccccat gcccttcact gggcgtggcg    660

gggaaacagg acttttactg tgaaaaaatt agagtgctcc aggcaggcct atgctcgaat    720

acattagcat ggaataatag aataggacgt gtggttctat tttgttggtt tctaggaccg    780

ccgtaatgat taatagggac agtcgggggc atcagtattc aattgtcaga ggtgaaattc    840

ttggatttat tgaagactaa ctactgcgaa agcatttgcc aaggatgttt tcattaatca    900

ggaacgaaag ttaggggatc gaagacgatc agataccgtc gtagtcttaa ccataaacta    960

tgccgactag ggatcggacg gtgttatttt ttgacccgtt cggcacctta cgagaaatca   1020

aagtgcttgg gctccagggg gagtatggtc gcaaggctga aacttaaaga aattgacgga   1080

agggcaccac caggggtgga gcctgcggct taatttgact caacacgggg aaactcacca   1140

ggtccagaca caatgaggat tgacagattg agagctcttt cttgattttg tgggtggtgg   1200

tgcatggccg ttcttagttg gtggagtgat ttgtctgctt aattgcgata acgaacgaga   1260

ccttaacctg ctaaatagcc cgtattgctt tggcagtacg ctggcttctt agagggacta   1320

tcggctcaag ccgatggaag tttgaggcaa taacaggtct gtgatgccct tagatgttct   1380

gggccgcacg cgcgctacac tgacggagcc agcgagtact tccttgtccg aaaggtccgg   1440

gtaatcttgt taaactccgt cgtgctgggg atagagcatt gcaattattg ctcttcaacg   1500

aggaatccct agtaagcgca agtcatcagc ttgcgttgat tacgtccctg ccctttgtac   1560

acaccgcccg tcgctactac cgattgaatg gctcagtgag gcgtccggac tggcccagag   1620

aggtgggcaa ctaccactca gggccggaaa gctctccaaa ctcggtcatt aga          1673
```

<210> SEQ ID NO 43
<211> LENGTH: 1554
<212> TYPE: DNA
<213> ORGANISM: Bacillus anthracis

<400> SEQUENCE: 43

```
ttattggaga gtttgatcct ggctcaggat gaacgctggc ggcgtgccta atacatgcaa     60

gtcgagcgaa tggattaaga gcttgctctt atgaagttag cggcggacgg gtgagtaaca    120

cgtgggtaac ctgcccataa gactgggata actccgggaa accggggcta ataccggata    180

acattttgaa ccgcatggtt cgaaattgaa aggcggcttc ggctgtcact tatggatgga    240

cccgcgtcgc attagctagt tggtgaggta acggctcacc aaggcaacga tgcgtagccg    300

acctgagagg gtgatcggcc acactgggac tgagacacgg cccagactcc tacgggaggc    360

agcagtaggg aatcttccgc aatggacgaa agtctgacgg agcaacgccg cgtgagtgat    420

gaaggctttc gggtcgtaaa actctgttgt tagggaagaa caagtgctag ttgaataagc    480

tggcaccttg acggtaccta accagaaagc cacggctaac tacgtgccag cagccgcggt    540

aatacgtagg tggcaagcgt tatccggaat tattgggcgt aaagcgcgcg caggtggttt    600

cttaagtctg atgtgaaagc ccacggctca accgtggagg gtcattggaa actgggagac    660

ttgagtgcag aagaggaaag tggaattcca tgtgtagcgg tgaaatgcgt agagatatgg    720

aggaacacca gtggcgaagg cgactttctg gtctgtaact gacactgagg cgcgaaagcg    780

tggggagcaa acaggattag ataccctggt agtccacgcc gtaaacgatg agtgctaagt    840
```

gttagagggt ttccgccctt tagtgctgaa gttaacgcat taagcactcc gcctggggag 900
tacggccgca aggctgaaac tcaaaggaat tgacgggggc ccgcacaagc ggtggagcat 960
gtggtttaat tcgaagcaac gcgaagaacc ttaccaggtc ttgacatcct ctgacaaccc 1020
tagagatagg gcttctcctt cgggagcaga gtgacaggtg gtgcatggtt gtcgtcagct 1080
cgtgtcgtga gatgttgggt taagtcccgc aacgagcgca acccttgatc ttagttgcca 1140
tcattwagtt gggcactcta aggtgactgc cggtgacaaa ccggaggaag gtggggatga 1200
cgtcaaatca tcatgcccct tatgacctgg gctacacacg tgctacaatg gacggtacaa 1260
agagctgcaa gaccgcgagg tggagctaat ctcataaaac cgttctcagt tcggattgta 1320
ggctgcaact cgcctacatg aagctggaat cgctagtaat cgcggatcag catgccgcgg 1380
tgaatacgtt cccgggcctt gtacacaccg cccgtcacac cacgagagtt tgtaacaccc 1440
gaagtcggtg gggtaacctt tttggagcca gccgcctaag gtgggacaga tgattggggt 1500
gaagtcgtaa caaggtagcc gtatcggaag gtgcggctgg atcacctcct ttct 1554

<210> SEQ ID NO 44
<211> LENGTH: 1610
<212> TYPE: DNA
<213> ORGANISM: Burkholderia pseudomallei

<400> SEQUENCE: 44
tctagatgcg tgctcgagcg gccgcccagt gctgcatgga tatctgctga attcggcttg 60
agcagtttga tcctggctca gattgaacgc tggcggcatg ccttacacat gcaagtcgaa 120
cggcagcacg ggcttcggcc tggtggcgag tggcgaacgg gtgagttata catcggagca 180
tgtcctgtag tgggggatag cccggcgaaa gccgaattaa taccgcatac gatctgagga 240
tgaaagcggg ggaccttcgg gcctcgcgct atagggttgg ccgatggctg attagctagt 300
tggtggggta aaggcctacc aaggcgacga tcagtagctg gtctgagagg acgaccagcc 360
acactgggac tgagacacgg cccagactcc tacgggaggc agcagtgggg aattttggac 420
aatgggcgca agcctgatcc agcaatgccg cgtgtgtgaa gaaggccttc gggttgtaaa 480
gcacttttgt ccggaaagaa atcattctgg ctaatacccg gagtggatga cggtaccgga 540
agaataagca ccggctaact acgtgccagc agccgcggta atacgtaggg tgcgagcgtt 600
aatcgggatt actgggcgta aagcgtgcgc aggcggtttg ctaagaccga tgtgaaatcc 660
ccgggctcaa cctgggaact gcattggtga ctggcaggct agagtatggc agaggggggt 720
agaattccac gtgtagcagt gaaatgcgta gagatgtgga ggaataccga tggcgaaggc 780
agccccctgg gccaatactg acgctcatgc acgaaagcgt ggggagaaaa caggattaga 840
taccctggta gtccacgccc taaacgatgt caactagttg ttggggattc atttccttag 900
taacgtagct aacgcgcgaa gttgaccgcc tggggagtac ggtcgcaaga ttaaaactca 960
aaggaattga cggggacccg cacaagcggt ggatgatgtg gattaattcg atgcaacgcg 1020
aaaaacctta cctacccttg acatggtcgg aagcccgatg agagttgggc gtgctcgaaa 1080
gagaaccggc gcacaggtgc tgcatggctg tcgtcagctc gtgtcgtgag atgttgggtt 1140
aagtcccgca acgagcgcaa cccttgtcct tagttgctac gcaagagcac tctaaggaga 1200
ctgccggtga caaaccggag gaaggtgggg atgacgtcaa gtcctcatgg cccttatggg 1260
tagggcttca cacgtcatac aatggtcgga acagagggtc gccaacccgc gagggggagc 1320
caatcccaga aaaccgatcg tagtccggat tgcactctgc aactcgagtg catgaagctg 1380
gaatcgctag taatcgcgga tcagcatgcc gcggtgaata cgttcccggg tcttgtacac 1440
accgcccgtc acaccatggg agtgggtttt accagaagtg gctagtctaa ccgcaaggag 1500
gacggtcacc acggtaggat tcatgactgg ggtgaagtcg taacaaggta gccgtagaag 1560
ccgaattcca gcacactggc ggccgttact actggatccg agctcgtacc 1610

<210> SEQ ID NO 45
<211> LENGTH: 1511
<212> TYPE: DNA
<213> ORGANISM: Clostridium botulinum
<220> FEATURE:
<221> NAME/KEY: misc_feature
<222> LOCATION: (1)..(7)
<223> OTHER INFORMATION: n is a, c, g, or t

<400> SEQUENCE: 45
nnnnnnngag agtttgatcc tggctcagga cgaacgctgg cggcgtgctt aacacatgca 60
agtcgagcga tgaagcttcc ttcgggaagt ggattagcgg cggacgggtg agtaacacgt 120
gggtaacctg cctcaaagtg gggg atagcc ttccgaaagg aagattaata ccgcataata 180
taagagaatc gcatgatttt cttatcaaag atttattgct ttgagatgga cccgcggcgc 240
attagctagt tggtaaggta acggcttacc aaggcaacga tgcgtagccg acctgagagg 300
gtgatcggcc acattggaac tgagacacgg tccagactcc tacgggaggc agcagtgggg 360
aatattgcgc aatgggggag accctgacgc agcaacgccg cgtgggtgat gaaggtcttc 420
ggattgtaaa gccctgtttt ctaggacgat aatgacggta ctagaggagg aagccacggc 480
taactacgtg ccagcagccg cggtaatacg taggtggcga gcgttgtccg gatttactgg 540
gcgtaaaggg tgcgtaggcg gatgtttaag tgggatgtga aatccccggg cttaacctgg 600
gggctgcatt ccaaactgga tatctagagt gcaggagagg aaagcggaat tcctagtgta 660
gcggtgaaat gcgtagagat taggaagaac accagtggcg aaggcggctt tctggactgt 720
aactgacgct gaggcacgaa agcgtgggta gcaaacagga ttagataccc tggtagtcca 780
cgccgtaaac gatggatact aggtgtaggg ggtatcaact ccccctgtgc cgcagttaac 840
acaataagta tcccgcctgg ggagtacggt cgcaagatta aaactcaaag gaattgacgg 900
gggcccgcac aagcagcgga gcatgtggtt taattcgaag caacgcgaag aaccttacct 960
ggacttgaca tcccttgcat agcctagaga taggtgaagc ccttcggggc aaggagacag 1020
gtggtgcatg gttgtcgtca gctcgtgtcg tgagatgtta ggttaagtcc tgcaacgagc 1080
gcaacccttg ttattagttg ctaccattaa gttgagcact ctaatgagac tgcctgggta 1140
accaggagga aggtggggat gacgtcaaat catcatgccc cttatgtcca gggctacaca 1200
cgtgctacaa tggtaggtac aataagacgc aagaccgtga ggtggagcaa aacttataaa 1260
acctatctca gttcggattg taggctgcaa ctcgcctaca tgaagctgga gttgctagta 1320
atcgcgaatc agaatgtcgc ggtgaatacg ttcccgggcc ttgtacacac cgcccgtca 1380 caccatgaga gctggtaaca cccgaagtcc gtgaggtaac cgtaaggagc cagcggccga 1440
aggtgggatt agtgattggg gtgaagtcgt aacaaggtag ccgtaggaga acctgcggct 1500
ggatcacctc c 1511

<210> SEQ ID NO 46
<211> LENGTH: 1510
<212> TYPE: DNA
<213> ORGANISM: Clostridium botulinum
<220> FEATURE:
<221> NAME/KEY: misc_feature
<222> LOCATION: (1)..(7)

<223> OTHER INFORMATION: n is a, c, g, or t

<400> SEQUENCE: 46

```
nnnnnnngag agtttgatcc tggctcagga cgaacgctgg cggcgtgctt aacacatgca     60
agtcgagcga tgaagcttcc ttcgggaagt ggattagcgg cggacgggtg agtaacacgt    120
gggtaacctg cctcaaagtg ggggatagcc ttccgaaagg aagattaata ccgcataaca    180
taagagaatc gcatgatttt cttatcaaag atttattgct ttgagatgga cccgcggcgc    240
attagctagt tggtaaggta acggcttacc aaggcaacga tgcgtagccg acctgagagg    300
gtgatcggcc acattggaac tgagacacgg tccagactcc tacgggaggc aggagtgggg    360
aatattgcgc aatgggggaa accctgacgc agcaacgccg cgtgggtgat gaaggtcttc    420
ggattgtaaa gccctgtttt ctaggacgat aatgacggta ctagaggagg aagccacggc    480
taactacgtg ccagcagccg cggtaatacg taggtggcga gcgttgtccg gatttactgg    540
gcgtaaaggg tgcgtaggcg gatgtttaag tgggatgtga aatccccggg cttaacctgg    600
gggctgcatt ccaaactgga tatctagagt gcaggagagg aaagcggaat tcctagtgta    660
gcggtgaaat gcgtagagat taggaagaac accagtggcg aaggcggctt tctggactgt    720
aactgacgct gaggcacgaa agcgtgggta gcaaacagga ttagataccc tggtagtcca    780
cgccgtaaac gatggatact aggtgtaggg ggtatcaact ccccctgtgc cgcagttaac    840
acaataagta tcccgcctgg ggagtacggt cgcaagatta aaactcaaag gaattgacgg    900
gggcccgcac aagcagcgga gcatgtggtt taattcgaag caacgcgaag aaccttacct    960
ggacttgaca tcccttgcat agcctagaga taggtgaagc ccttcggggc aaggagacag   1020
gtggtgcatg gttgtcgtca gctcgtgtcg tgagatgtta ggttaagtcc tgcaacgagc   1080
gcaacccttg ttattagttg ctaccattaa gttgagcact ctaatgagac tgcctgggta   1140
accaggagga aggtggggat gacgtcaaat catcatgccc cttatgtcca gggctacaca   1200
cgtgctacaa tggtaggtac aataagacgc aagaccgtga ggtggagcaa aacttataaa   1260
acctatctca gttcggattg taggctgcaa ctcgcctaca tgaagctgga gttgctagta   1320
atcgcgaatc agaatgtcgc ggtgaatacg ttcccgggcc ttgtacacac cgcccgtcac   1380
accatgagag ctggtaacac ccgaagtccg tgaggtaacc gtaaggagcc agcggccgaa   1440
ggtgggatta gtgattgggg tgaagtcgta acaaggtagc cgtaggagaa cctgcggctg   1500
gatcacctcc                                                          1510
```

<210> SEQ ID NO 47
<211> LENGTH: 1516
<212> TYPE: DNA
<213> ORGANISM: Clostridium botulinum
<220> FEATURE:
<221> NAME/KEY: misc_feature
<222> LOCATION: (1)..(7)
<223> OTHER INFORMATION: n is a, c, g, or t

<400> SEQUENCE: 47

```
nnnnnnngag agtttgatcc tggctcagga cgaacgtggc ggcgtgccta acacatgcaa     60
gtcgagcgat gaagcttcct tcggggagtg gattagcggc ggacgggtga gtaacacgtg    120
ggtaacctgc ctcaaagagg gggatagcct cccgaaaggg agattaatac cgcataacat    180
tattttatgg catcatagaa taatcaaagg agcaatccgc tttgattatg gacccgcgtc    240
gcattagcta gttggtgagg taacggctca ccaaggcaac gatgcgtagc cgacctgaga    300
gggtgatcgg ccacattgga actgagacac ggtccagact cctacgggag gcagcagtgg    360
```

```
ggaatattgc gcaatggggg aaaccctgac gcagcaacgc cgcgtgagtg atgaaggttt    420

tcggatcgta aaactctgtc tttagggacg ataatgacgg tacctaagga ggaagccacg    480

gctaactacg tgccagcagc cgcggtaata cgtaggtggc aagcgttgtc cggatttact    540

gggcgtaaag agtatgtagg tgggtgctta agtcagatgt gaaattcccg ggcttaacct    600

gggcgctgca tttgaaactg ggcatctaga gtgcaggaga ggaaagtgga attcctagtg    660

tagcggtgaa atgcgtagag attaggaaga acaccagtgg cgaaggcgac tttctggact    720

gtaactgaca ctgagatacg aaagcgtggg tagcaaacag gattagatcc ccctggtagt    780

ccacgccgta aacgatgaat actaggtgtc ggggggtacc accctcggtg ccgcagcaaa    840

cgcattaagt attccgcctg gggagtacgg tcgcaagatt aaaactcaaa ggaattgacg    900

gggacccgca caagcagcgg agcatgtggt ttaattcgaa gcaacgcgaa gaaccttacc    960

tagacttgac atctcctgaa ttactcttaa tcgaggaagt cccttcgggg gacaggaaga   1020

caggtggtgc atggttgtcg tcagctcgtg tcgtgagatg ttgggttaag tcccgcaacg   1080

agcgcaaccc ttattgttag ttgctactat taagttaagc actctaacga gactgccgcg   1140

gttaacgtag aggaaggtgg ggatgacgtc aaatcatcat gccccttatg tctagggcta   1200

cacacgtgct acaatggctg gtacaacgag cagcaaaccc gcgaggggga gcaaaacttg   1260

aaagccagtc ccagttcgga ttgtaggctg aaactcgcct acatgaagtt ggagttgcta   1320

gtaatcgcgg aatcagcatg tcgcggtgaa tacgtccccg ggtcttgtac acaccgcccg   1380

tcacaccatg agagccggta acacccgaag cccgtgaggt aaccgtaagg agccagcggt   1440

cgaaggtggg attggtgatt ggggtgaagt cgtaacaagg tagccgtagg agaacctgcg   1500

gttggatcac ctcctt                                                   1516


<210> SEQ ID NO 48
<211> LENGTH: 1516
<212> TYPE: DNA
<213> ORGANISM: Clostridium botulinum
<220> FEATURE:
<221> NAME/KEY: misc_feature
<222> LOCATION: (1)..(7)
<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (789)..(790)
<223> OTHER INFORMATION: n is a, c, g, or t

<400> SEQUENCE: 48

nnnnnnngag agtttgatcc tggctcagga cgaacgctgg cggcgtgcct aacacatgca     60

agtcgagcga tgaagcttcc ttcgggaagt ggattagcgg cggacgggtg agtaacacgt    120

gggtaacctg cctcaaagag tgggatagcc tcccgaaagg gagattaata ccgcataaca    180

ttattttatg gcatcataca taaaataatc aaaggagcaa tccgctttga gatggacccg    240

cggcgcatta gctagttggt gaggtaacgg ctcaccaagg caacgatgcg tagccgacct    300

gagagggtga tcggccacat tggaactgag acacggtcca gactcctacg ggaggcagca    360

gtggggaata ttncgcaatg ggggaaaccc tgacgcagca acgccgcgtg agtgatgaag    420

gttttcggat cgtaaaactc tgtctttagg gacgataatg acggtaccta aggaggaagc    480

cacggctaac tacgtgccag cagccgcggt aatacgtagg tggcaagcgt tgtccggatt    540
```

```
tactgggcgt aaagagtatg taggtgggtg cttaagtcag atgtgaaatt cccgggctca    600

acctgggagc tgcatttgaa actgggcatc tagagtgcag gagaggaaag tggaattcct    660

agtgtagcgg tgaaatgcgt agagattagg aagaacacca gtggcgaagg cgactctctg    720

gactgtaact gacactgaga tacgaaagcg tgggtagcaa acaggattag ataccctggt    780

agtccacgnn gtaaacgatg aatactaggt gtcggggggt accaccctcg gtgccgcagc    840

aaacgcatta agtattccgc ctgggaagta cggtcgcaag attaaaactc aaaggaattg    900

acggggcccg cacaagcagc ggagcatgtg gtttaattcg aagcaacgcg aagaacctta    960

cctagacttg acatctcctg aattactctt aatcgaggaa gtcccttcgg ggacaggaag   1020

acaggtggtg catggttgtc gtcagctcgt gtcgtgagat gttgggttaa gtcccgcaac   1080

gagcgcaacc cttattgtta gttgctacta ttaagttaag cactctaacg agactgccgc   1140

ggttaacgtg gaggaaggtg gggatgacgt caaatcatca tgccccttat gtctagggct   1200

acacacgtgc tacaatggct ggtacaacga gcagcaaacc cgcgaggggg agcaaaactt   1260

gaaagccagt cccagttcgg attgtaggct gaaactcgcc tacatgaagt tggagttgct   1320

agtaatcgcg aatcagcatg tcgcggtgaa tacgttcccg ggtcttgtac acaccgcccg   1380

tcacaccatg agagccggta acacccgaag cccgtgaggt aaccgtaagg agccagcggt   1440

cgaaggtggg attggtgatt ggggtaagtc gtaacaaggt agccgtagga gaacctgcgg   1500

ctggatcacc tccttt                                                   1516


<210> SEQ ID NO 49
<211> LENGTH: 1513
<212> TYPE: DNA
<213> ORGANISM: Clostridium botulinum
<220> FEATURE:
<221> NAME/KEY: misc_feature
<222> LOCATION: (1)..(7)
<223> OTHER INFORMATION: n is a, c, g, or t

<400> SEQUENCE: 49

nnnnnnnaga gtttgatcct ggctcaggac gaacgctggc ggcgtgccta acacatgcaa     60

tcgagcgatg aagcttcctt cgggaagtgg attagcggcg gacgggtgag taacacgtgg    120

gtaacctgcc tcatagaggg gaatagcctc ccgaaaggga gattaatacc gcataaagta    180

tgaaggtcgc atgacttcat tataccaaag gagtaatccg ctatgagatg gacccgcggc    240

gcattagcta gttggtgagg taagggctca ccaaggcaac gatgcgtagc cgacctgaga    300

gggtgatcgg ccacattgga actgagacac ggtccagact cctacgggag gcagcagtgg    360

ggaatattgc gcaatggggg aaaccctgac gcagcaacgc cgcgtgaatg aagaaggcct    420

tagggttgta aagttctgtc atatgggaag ataatgacgg taccatatga ggaagccacg    480

gctaactacg tgccagcagc cgcggtaata cgtaggtggc aagcgttgtc cggatttact    540

gggcgtaaag gatgcgtagg cggacattta agtcagatgt gaaatacccg ggctcaactt    600

gggtgctgca tttgaaactg ggtgtctaga gtgcaggaga ggaaagcgga attcctagtg    660

tagcggtgaa atgcgtagag attaggaaga acaccagtgg cgaaggcggc tttctggact    720

gtaactgacg ctgaggcatg aaagcgtggg gagcaaacag gattagatac cctggtagtc    780

cacgccgtaa acgatgaata ctaggtgtag gaggtatcga ccccttctgt gccgcagtta    840

acacaataag tattccgcct ggggagtacg atcgcaagat taaaactcaa aggaattgac    900

gggggcccgc acaagcagcg gagcatgtgg tttaattcga agcaacgcga agaaccttac    960

ctagacttga catcccctga attacctgta atgagggaag cccttcgggg cagggagaca   1020
```

```
ggtggtgcat ggttgtcgtc agctcgtgtc gtgagatgtt gggttaagtc ccgcaacgag   1080

cgcaaccctt atcattagtt gctaccatta agttgagcac tctagtgaga ctgcccgggt   1140

taaccgggag gaaggtgggg atgacgtcaa atcatcatgc cccttatgtc tagggctaca   1200

cacgtgctac aatggttggt acaacaagat gcaagaccgc gaggtggagc taaacttaaa   1260

aaaccaaccc agttcggatt gtaggctgaa actcgcctac atgaagccgg agttgctagt   1320

aatcgcgaat cagcatgtcg cggtgaatac gttcccgggc cttgtacaca ccgcccgtca   1380

caccatgaga gctggtaaca cccgaagtcc gtgaggtaac cgtaaggagc cagcggccga   1440

aggtgggatt agtgattggg gtgaagtcgt aacaaggtag ccgtaggaga acctgcggtt   1500

ggatcacctc ctt                                                      1513
```

<210> SEQ ID NO 50
<211> LENGTH: 1521
<212> TYPE: DNA
<213> ORGANISM: Francisella tularensis

<400> SEQUENCE: 50

```
ttgaagagtt tgatcatggc tcagattgaa cgctggtggc atgcttaaca catgcaagtc     60

gaacggtaac aggtcttagg atgctgacga gtggcggacg ggtgagtaac gcgtaggaat    120

ctgcccattt gagggggata ccagttggaa acgactgtta ataccgcata atatctgtgg    180

attaaaggtg gctttcggcg tgtcgcagat ggatgagcct gcgttggatt agctagttgg    240

tggggtaagg gcccaccaag gctacgatcc atagctgatt tgagaggatg atcagccaca    300

ttgggactga gacacggccc aaactcctac gggaggcagc agtggggaat attggacaat    360

gggggcaacc ctgatccagc aatgccatgt gtgtgaagaa ggccctaggg ttgtaaagca    420

ctttagttgg ggaggaaagc ctcaaggtta atagccttgg gggaggacgt tacccaaaga    480

ataagcaccg gctaactccg tgccagcagc cgcggtaata cgggggggtgc aagcgttaat    540

cggaattact gggcgtaaag ggtctgtagg tggtttgtta agtcagatgt gaaagcccag    600

ggctcaacct tggaactgca tttgatactg gcaaactaga gtacggtaga ggaatgggga    660

atttctggtg tagcggtgaa atgcgtagag atcagaagga acaccaatgg cgaaggcaac    720

attctggacc gatactgaca ctgagggacg aaagcgtggg gatcaaacag gattagatac    780

cctggtagtc cacgctgtaa acgatgagta ctagctgttg gagtcggtgt aaaggctcta    840

gtggcgcacg taacgcgata agtactccgc ctggggacta cggccgcaag gctaaaactc    900

aaaggaattg acggggaccc gcacaagcgg tggagcatgt ggtttaattc gatgcaacgc    960

gaagaacctt acctggtctt gacatcctgc gaactttcta gagatagatt ggtgcttcgg   1020

aacgcagtga cagtgctgca cggctgtcgt cagctcgtgt tgtgaaatgt tgggttaagt   1080

cccgcaacga gcgcaacccc tattgatagt taccatcatt aagttgggta ctctattaag   1140

actgccgctg acaaggcgga ggaaggtggg gacgacgtca agtcatcatg gcccttacga   1200

ccagggctac acacgtgcta caatgggtat tacagagggc tgcgaaggtg cgagctggag   1260

cgaaactcaa aaaggtactc ttagtccgga ttgcagtctg caactcgact gcatgaagtc   1320

ggaatcgcta gtaatcgcag gtcagaatac tgcggtgaat acgttcccgg gtcttgtaca   1380

caccgcccgt cacaccatgg gagtgggttg ctccagaagt agatagctta acgaatgggc   1440

gtttaccacg gagtgattca tgactggggt gaagtcgtaa caatggtagc cgtagggaac   1500

ctgcggctgg atcacctcct t                                             1521
```

<210> SEQ ID NO 51
<211> LENGTH: 1464
<212> TYPE: DNA
<213> ORGANISM: Vibrio cholerae

<400> SEQUENCE: 51

```
tggctcagat tgaacgctgg cggcaggcct aacacatgca agtcgagcgg cagcacagag     60
gaacttgttc cttgggtggc gagcggcgga cgggtgagta atgcctggga aattgcccgg    120
tagaggggga taaccattgg aaacgatggc taataccgca taacctcgta agagcaaagc    180
aggggacctt cgggccttgc gctaccggat atgcccaggt gggattagct agttggtgag    240
gtaagggctc accaaggcga cgatccctag ctggtctgag aggatgatca gccacactgg    300
aactgagaca cggtccagac tcctacggga ggcagcagtg gggaatattg cacaatgggc    360
gcaagcctga tgcagccatg ccgcgtgtat gaagaaggcc ttcgggttgt aaagtacttt    420
cagtagggag gaaggtggtt aagctaatac cttaatcatt tgacgttacc tacagaagaa    480
gcaccggcta actccgtgcc agcagccgcg gtaatacgga gggtgcaagc gttaatcgga    540
attactgggc gtaaagcgca tgcaggtggt ttgttaagtc agatgtgaaa gccctgggct    600
caacctagga atcgcatttg aaactgacaa gctagagtac tgtagagggg ggtagaattt    660
caggtgtagc ggtgaaatgc gtagagatct gaaggaatac cggtggcgaa ggcggccccc    720
tggacagata ctgacactca gatgcgaaag cgtggggagc aaacaggatt agataccctg    780
gtagtccacg ccgtaaacga tgtctacttg gaggttgtga cctagagtcg tggctttcgg    840
agctaacgcg ttaagtagac cgcctgggga gtacggtcgc aagattaaaa ctcaaatgaa    900
ttgacggggg cccgcacaag cggtggagca tgtggtttaa ttcgatgcaa cgcgaagaac    960
cttacctact cttgacatcc tcagaagaga ctggagacag tcttgtgcct tcgggaactg   1020
agagacaggt gctgcatggc tgtcgtcagc tcgtgttgtg aaatgttggg ttaagtcccg   1080
caacgagcgc aacccttatc cttgtttgcc agcacgtaat ggtgggaact ccagggagac   1140
tgccggtgat aaaccggagg aaggtgggga cgacgtcaag tcatcatggc ccttacgagt   1200
agggctacac acgtgctaca atggcgtata cagagggcag cgataccgcg aggtggagcg   1260
aatctcacaa agtacgtcgt agtccggatt ggagtctgca actcgactcc atgaagtcgg   1320
aatcgctagt aatcgcaaat cagaatgttg cggtgaatac gttcccgggc cttgtacaca   1380
ccgcccgtca caccatggga gtgggctgca aaagaagcag gtagtttaac cttcgggagg   1440
acgcttgcca ctttgggtac ttgg                                          1464
```

<210> SEQ ID NO 52
<211> LENGTH: 1469
<212> TYPE: DNA
<213> ORGANISM: Yersinia pestis

<400> SEQUENCE: 52

```
ctggcggcag gcctaacaca tgcaagtcga gcggcaccgg gaagtagttt actactttgc     60
cggcgagcgg cggacgggtg agtaatgtct ggggatctgc ctgatggagg gggataacta    120
ctggaaacgg tagctaatac cgcatgacct cgcaagagca aagtggggga ccttagggcc    180
tcacgccatc ggatgaaccc agatgggatt agctagtagg tggggtaatg gctcacctag    240
gcgacgatcc ctagctggtc tgagaggatg accagccaca ctggaactga gacacggtcc    300
agactcctac gggaggcagc agtggggaat attgcacaat gggcgcaagc ctgatgcagc    360
catgccgcgt gtgtgaagaa ggccttcggg ttgtaaagca ctttcagcga ggaggaaggg    420
```

```
gttgagttta atacgctcaa tcattgacgt tactcgcaga agaagcaccg gctaactccg    480

tgccagcagc cgcggtaata cggagggtgc aagcgttaat cggaattact gggcgtaaag    540

cgcacgcagg cggtttgtta agtcagatgt gaaatccccg cgcttaacgt gggaactgca    600

tttgaaactg gcaagctaga gtcttgtaga ggggggtaga attccaggtg tagcggtgaa    660

atgcgtagag atctggagga ataccggtgg cgaaggcggc cccctggaca aagactgacg    720

ctcaggtgcg aaagcgtggg gagcaaacag gattagatac cctggtagtc cacgctgtaa    780

acgatgtcga cttggaggtt gtgcccttga ggcgtggctt ccggagctaa cgcgttaagt    840

cgaccgcctg gggagtacgg ccgcaaggtt aaaactcaaa tgaattgacg ggggcccgca    900

caagcggtgg agcatgtggt ttaattcgat gcaacgcgaa gaaccttacc tactcttgac    960

atccacagaa tttggcagag atgctaaagt gccttcggga actgtgagac aggtgctgca   1020

tggctgtcgt cagctcgtgt tgtgaaatgt tgggttaagt cccgcaacga gcgcaaccct   1080

tatcctttgt tgccagcacg taatggtggg aactcaaggg agactgccgg tgacaaaccg   1140

gaggaaggtg gggatgacgt caagtcatca tggcccttac gagtagggct acacacgtgc   1200

tacaatggca gatacaaagt gaagcgaact cgcgagagcc agcggaccac ataaagtctg   1260

tcgtagtccg gattggagtc tgcaactcga ctccatgaag tcggaatcgc tagtaatcgt   1320

agatcagaat gctacggtga atacgttccc gggccttgta cacaccgccc gtcacaccat   1380

gggagtgggt tgcaaaagaa gtaggtagct taaccttcgg gagggcgctt accactttgt   1440

gattcatgac tggggtgaag tcgtaacaa                                     1469
```

```
<210> SEQ ID NO 53
<211> LENGTH: 24
<212> TYPE: DNA
<213> ORGANISM: Artificial Sequence
<220> FEATURE:
<223> OTHER INFORMATION: Forward Primer

<400> SEQUENCE: 53

catccaagga aggcagcagg cgcg                                            24


<210> SEQ ID NO 54
<211> LENGTH: 22
<212> TYPE: DNA
<213> ORGANISM: Artificial Sequence
<220> FEATURE:
<223> OTHER INFORMATION: Reverse Primer

<400> SEQUENCE: 54

gttcaactac gagcttttta ac                                              22


<210> SEQ ID NO 55
<211> LENGTH: 22
<212> TYPE: DNA
<213> ORGANISM: Artificial Sequence
<220> FEATURE:
<223> OTHER INFORMATION: Reverse Primer

<400> SEQUENCE: 55

gttcgactac gagcttttta ac                                              22


<210> SEQ ID NO 56
<211> LENGTH: 23
<212> TYPE: DNA
<213> ORGANISM: Artificial Sequence
<220> FEATURE:
```

```
<223> OTHER INFORMATION: Forward Primer

<400> SEQUENCE: 56

gtgtagcggt gaaatgcgta gag                                              23


<210> SEQ ID NO 57
<211> LENGTH: 23
<212> TYPE: DNA
<213> ORGANISM: Artificial Sequence
<220> FEATURE:
<223> OTHER INFORMATION: Reverse Primer

<400> SEQUENCE: 57

tcgtttaccg tggactacca ggg                                              23
```

BIOMARKERS AND USES THEREOF

CROSS REFERENCE TO RELATED APPLICATIONS

This is the § 371 U.S. National Stage of International Application No. PCT/AU2018/050471, filed May 17, 2018, which was published in English under PCT Article 21(2), which in turn claims the benefit of Australian Application No. 2017901846, filed May 17, 2017, which is incorporated herein by reference in its entirety.

TECHNICAL FIELD

The present invention relates generally to methods and agents for identifying and/or classifying microbes. The methods and agents are based on the detection of polymorphisms within the 16S ribosomal RNA gene or gene products for bacteria, and within the 18S ribosomal RNA gene or gene products for yeast organisms and filamentous fungi. The invention also features methods for the treatment of infections of bacteria, yeast organisms or filamentous fungi based on the diagnostic methods of the present invention.

BACKGROUND

Rapid and accurate identification or classification of microbes (such as bacteria), yeast organisms and filamentous fungi in a sample is highly desirable.

First and foremost, rapid and accurate diagnosis of such infections can make the difference between life and death of a patient by allowing early implementation of an effective treatment or therapy.

Rapid and accurate identification or classification may assist in the implementation of effective control measures to manage, control, eradicate and/or eliminate microbes, yeast organisms or filamentous fungi in contaminated solutions, materials or foodstuffs, which may otherwise pose a threat to the wellbeing of organisms or the quality of production of the solutions, materials or foodstuffs.

Also, rapid and accurate identification or classification may assist with natural microbial, yeast organisms or filamentous fungi populations in a sample, such as, e.g., for ecological studies of microbial diversity, phylum spectrum and/or relative phylum abundance, or for monitoring deviation of a balance from a normal state in pathological conditions for an organism, such as, e.g., enteric, respiratory and skin disorders.

It may also be desirable to rapidly and accurately identify or classify microbes, yeast or filamentous fungi post therapy, treatment or modulation. For example, rapid microbial identification or classification may be of use in analysing the use of antibiotics, steroids, immune modulators, pre- and post-biotics, soil or water treatments, filtration, sterilization procedures and antiseptics.

Currently most diagnostic techniques commercially available typically require isolation and identification of live microbes, yeast organisms and filamentous fungi from a sample using culture, but this technique is negatively affected by considerable turn around time and suboptimal sensitivity, specificity and predictive value. It also can require more extensive handling of the organism, which can be particularly undesirable for some organisms such as security sensitive biological agents.

Alternative diagnostic techniques available include the use of polymerase chain reaction (PCR), particularly in conjunction with culture. However, a problem with such a technique is a lack of trust in early positive PCR results in the absence of culture results or relevant clinical or physical symptoms. Another problem with such a technique is, like with culture, a lack of sensitivity and specificity when attempting to detect small quantities of microbial nucleic acid in a background of host nucleic acid.

Hence, there is a recognized need for rapid and reliable techniques for accurate diagnosis of bacteria, yeast organisms and/or filamentous fungi.

SUMMARY OF INVENTION

In various aspects the present invention is predicated in part on high conservation of the 16S (Svedberg unit) ribosomal RNA (16S rRNA) gene between prokaryotes, including bacteria, and the high conservation of the 18S ribosomal RNA (18S rRNA) gene between yeast organisms and filamentous fungi, and also in part on the discovery of multiple single nucleotide polymorphisms (SNPs) within the 16S rRNA gene and 18S rRNA gene that may be useful in the identification and classification of microbes, particularly bacterial microbes, and yeast organisms and/or filamentous fungi in a sample.

Generally speaking, prokaryotes, including bacteria, contain 16S rRNA, which is a component of the 30S small subunit of the prokaryotic ribosome. The 16S rRNA is approximately 1,500 nucleotides in length and encoded by the 16S rRNA gene (also referred to as 16S rDNA), which is generally part of a co-transcribed operon also containing the 23S and 5S rRNA genes. Although the DNA sequence of the 16S rRNA genes (and thus the RNA sequence of the 16S rRNA molecules) is highly conserved between prokaryotes, there are regions of variation (Weisberg W. G., et al., 1991).

Similarly, the 18S rRNA gene in yeast and filamentous fungi is the homologue of the 16S rRNA gene in prokaryotes. The 18S rRNA is a component of the 40S small eukaryotic ribosomal subunit. The DNA sequence of the 18S rRNA gene (and thus the RNA sequence of the 18S rRNA molecules) is also highly conserved in yeast and filamentous fungi.

According to a first aspect of the invention, there is provided a method of identifying, partially identifying or classifying at least one bacterium, yeast organism or filamentous fungi in a sample.

In one embodiment, said method comprises analysing at least a portion of a bacterial 16S rRNA gene or gene product from the sample, or at least a portion of a yeast organism or filamentous fungi 18S rRNA gene or gene product from the sample, for the presence or absence of at least one single nucleotide polymorphism (SNP), wherein the at least one SNP in the at least a portion of the bacterial 16S rRNA gene or gene product is at a position corresponding to at least one of positions 273, 378, 412, 440, 488, 647, and 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43; or wherein the at least one bacterium, yeast organism or filamentous fungi in the sample is identified, partially identified or classified based on the presence or absence of the at least one SNP.

In another embodiment, said method comprises analysing at least a portion of a bacterial 16S rRNA gene or gene product from the sample, or at least a portion of a yeast organism or filamentous fungi 18S rRNA gene or gene product from the sample, for the presence or absence of at least one single nucleotide polymorphism (SNP), wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1; wherein the at least one bacterium, yeast organism or filamentous fungi in the sample is identified, partially identified or classified based on the presence or absence of the at least one SNP.

According to a second aspect of the present invention, there is provided a method of identifying, partially identifying, classifying or diagnosing a bacterial, yeast organism or filamentous fungi infection in a subject.

In one embodiment, said method comprises analysing the presence or absence of at least one single nucleotide polymorphism (SNP) in at least a portion of a bacterial 16S rRNA gene or gene product or in at least a portion of a yeast organism or filamentous fungi 18S rRNA gene or gene product in a sample from the subject; wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43; or wherein the presence or absence of said at least one SNP in the at least a portion of the 16S rRNA gene or gene product or in the at least a portion of the 18S rRNA gene or gene product is used to identify, partially identify, classify or diagnose the bacterial, yeast organism or filamentous fungi infection in the subject.

In another embodiment, said method comprises analysing the presence or absence of at least one single nucleotide polymorphism (SNP) in at least a portion of a bacterial 16S rRNA gene or gene product or in at least a portion of a yeast organism or filamentous fungi 18S rRNA gene or gene product in a sample from the subject;

wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1; wherein the presence or absence of said at least one SNP in the at least a portion of the 16S rRNA gene or gene product or in the at least a portion of the 18S rRNA gene or gene product is used to identify, partially identify, classify or diagnose the bacterial, yeast organism or filamentous fungi infection in the subject.

According to a third aspect of the present invention, there is provided method of treating a subject having a bacterial, yeast organism or filamentous fungi infection, said method comprising:

identifying, partially identifying, classifying or diagnosing a bacterial, yeast organism or filamentous fungi infection in a subject according to the method of the second aspect, to identify, partially identify, classify or diagnose the bacterial, yeast organism or filamentous fungi infection in the subject;

administering to the subject a therapy or treatment agent for treating the bacterial, yeast organism or filamentous fungi infection in the subject.

According to a fourth aspect of the present invention, there is provided at least one isolated probe, tool or reagent.

In one embodiment of the fourth aspect, said at least one isolated probe, tool or reagent is capable of identifying, partially identifying, or classifying at least one bacteria, yeast organism or filamentous fungi in a sample, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

In another embodiment of the fourth aspect, said at least one isolated probe, tool or reagent is capable of identifying, partially identifying, or classifying at least one bacteria, yeast organism or filamentous fungi in a sample, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to another embodiment of the fourth aspect, said at least one isolated probe, tool or reagent is capable of discriminating between a sample that comprises at least one bacteria, yeast organism or filamentous fungi and a sample that does not comprise at least one bacteria, yeast organism or filamentous fungi, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

According to another embodiment of the fourth aspect, said at least one isolated probe, tool or reagent is capable of discriminating between a sample that comprises at least one bacteria, yeast organism or filamentous fungi and a sample that does not comprise at least one bacteria, yeast organism or filamentous fungi, wherein the probe, tool or reagent is capable of binding, detecting or identifying the presence or absence of at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a fifth aspect of the present invention, there is provided a method of identifying, partially identifying, or classifying at least one bacterium, yeast organism or filamentous fungi in a sample.

In one embodiment, said method comprises:

combining with the sample the at least one isolated probe, tool or reagent of the fourth aspect; and identifying, partially identifying, or classifying the at least one bacterium, yeast organism or filamentous fungi based on the presence or absence of at least one at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

In another embodiment, said method comprises:

combining with the sample the at least one isolated probe, tool or reagent of the fourth aspect; and identifying, partially identifying, or classifying the at least one bacterium, yeast organism or filamentous fungi based on the presence or absence of at least one at least one single nucleotide polymorphism (SNP) in at least a portion of a bacterial 16S rRNA gene or gene product or at least a portion of a yeast organism or filamentous fungi 18S rRNA gene or gene product, wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a sixth aspect of the present invention, there is provided an array (especially a microarray) comprising more than one said isolated probe, tool or reagent of the fourth aspect.

According to a seventh aspect of the present invention, there is provided a biochip comprising a solid substrate and at least one isolated probe, tool or reagent of the fourth aspect.

According to an eighth aspect of the present invention, there is provided a kit or assay.

In one embodiment of the eighth aspect, the kit or assay is for classifying or identifying at least one bacterium or at least one yeast organism or filamentous fungi in a sample, said kit or assay comprising: the at least one probe, tool or reagent of the fourth aspect;

the array of the sixth aspect; and/or the biochip of the seventh aspect.

In another embodiment of the eighth aspect, the kit or assay is capable of discriminating between a sample that comprises at least one bacteria, yeast organism or filamentous fungi and a sample that does not comprise at least one bacteria, yeast organism or filamentous fungi, wherein the kit or assay comprises the probe, tool or reagent of the fourth aspect.

According to a ninth aspect of the present invention, there is provided at least one single nucleotide polymorphism (SNP).

In one embodiment, said at least one SNP is in at least a portion of a bacterial 16S rRNA gene or gene product or at least a portion of a yeast organism or filamentous fungi 18S rRNA gene or gene product for use as an indicator for classifying, identifying or partially identifying at least one bacterium, yeast organism or filamentous fungi in a sample;

wherein the at least one SNP in the at least a portion of the bacterial 16S rRNA gene or gene product is at a position corresponding to at least one of positions 273, 378, 412, 440, 488, 647, 653 of the 16S rRNA gene set forth in SEQ ID NO: 1; or wherein the at least one SNP in the at least a portion of the bacterial 16S rRNA gene or gene product is in or corresponds to the 16S rRNA gene set forth in SEQ ID NO: 43.

In another embodiment, said at least one SNP is in at least a portion of a bacterial 16S rRNA gene or gene product or at least a portion of a yeast organism or filamentous fungi 18S rRNA gene or gene product for use as an indicator for classifying, identifying or partially identifying at least one bacterium, yeast organism or filamentous fungi in a sample;

wherein the at least one SNP in the at least a portion of the bacterial 16S rRNA gene or gene product is at a position corresponding to at least one of positions 273, 378, 412, 440, 488, 647, 653, 737, 755, 762 and 776 of the 16S rRNA gene set forth in SEQ ID NO: 1.

According to a tenth aspect of the present invention, there is provided a use of at least one single nucleotide polymorphism (SNP) in at least a portion of a bacterial 16S rRNA gene or gene product or at least a portion of a yeast organism or filamentous fungi 18S rRNA gene or gene product as defined in the first aspect, or the at least one isolated probe, tool or reagent of the fourth aspect in identifying, partially identifying or classifying at least one bacterium, yeast organism or filamentous fungi in a sample, wherein said at least one bacterium, yeast organism or filamentous fungi is identified, partially identified or classified based on the presence or absence of at least one SNP in at least a portion of the 16S rRNA gene or gene product or of at least a portion of the 18S rRNA gene or gene product from the sample.

According to an eleventh aspect of the present invention, there is provided a kit comprising a probe, tool or reagent for use in the method of any one of the first, second, third or fifth aspects of the present invention.

Further aspects of the invention are provided below.

According to a twelfth aspect of the present invention, there is provided at least one single nucleotide polymorphism (SNP) in a 16S rRNA gene for use or when used in identifying at least one bacterium in a sample or classifying bacteria in the sample; or at least one single nucleotide polymorphism (SNP) in a 18S rRNA gene for use or when used in identifying at least one yeast organism or filamentous fungi in a sample or classifying a yeast organism or filamentous fungi in the sample.

According to a thirteenth aspect of the present invention, there is provided at least one probe, tool or reagent for use or when used in identifying at least one bacterium in a sample or classifying bacteria in the sample, said at least one probe, tool or reagent is capable of specifically binding, detecting or identifying at least a portion of a 16S rRNA gene in the sample containing at least one SNP; or at least one probe, tool or reagent for use or when used in identifying at least one yeast organism or filamentous fungi in a sample or classifying at least one yeast organism or filamentous fungi in the sample, said at least one probe, tool or reagent is capable of specifically binding, detecting or identifying at least a portion of a 18S rRNA gene in the sample containing at least one SNP.

According to a fourteenth aspect of the present invention, there is provided at least one probe, tool or reagent for use or when used in identifying a bacterium in a sample or classifying bacteria in the sample, said at least one probe, tool or reagent comprising an oligonucleotide having a nucleotide sequence as set forth in any one of the of SEQ ID NOs: 16-35, 56 or 57; or at least one probe, tool or reagent for use or when used in identifying at least one yeast organism or filamentous fungi in a sample or classifying at least one yeast organism or filamentous fungi in the sample, said at least one probe, tool or reagent comprising an oligonucleotide having a nucleotide sequence as set forth in any one of the of SEQ ID NOs:53-55.

According to a fifteenth aspect of the present invention, there is provided a use of the at least one SNP as defined in the twelfth aspect or the at least one probe, tool or reagent as defined in the thirteenth or fourteenth aspect in identifying at least one bacterium in a sample or classifying bacteria in the sample, wherein said at least one bacterium is identified or bacteria classified based on the presence of at least one SNP in a 16S rRNA gene from the sample as described above; or a use of the at least one SNP as defined in the twelfth aspect or the at least one probe, tool or reagent as defined in the thirteenth or fourteenth aspect in identifying at least one yeast organism or filamentous fungi in a sample or classifying at least one yeast organism or filamentous fungi in the sample, wherein said at least one yeast organism or filamentous fungi is identified or classified based on the presence of at least one SNP in a 18S rRNA gene from the sample as described above.

According to a sixteenth aspect of the present invention, there is provided a method of identifying at least one bacterium in a sample, said method comprising analysing a 16S rRNA gene from the sample for the at least one SNP as defined in the first aspect, wherein the at least one bacterium is identified based on the presence of the at least one SNP; or a method of identifying at least one yeast organism or filamentous fungi in a sample, said method comprising analysing a 18S rRNA gene from the sample for the at least one SNP as defined in the twelfth aspect, wherein the at least one yeast organism or filamentous fungi is identified based on the presence of the at least one SNP.

In one embodiment there is provided a method of identifying at least one bacterium in a sample, said method comprising analysing nucleic acid from the sample for at least one SNP in a bacterial 16S rRNA gene at a position corresponding to at least one of positions 273, 378, 412, 440, 488, 647, and 653 of the 16S rRNA gene set forth in SEQ ID NO: 1, wherein the at least one bacterium is identified based on the presence of the at least one SNP.

According to a seventeeth aspect of the present invention, there is provided a method of classifying bacteria in a sample, said method comprising analysing a 16S rRNA gene from the sample for the at least one SNP as defined in the first aspect, wherein the bacteria are classified based on the presence of the at least one SNP; or a method of classifying at least one yeast organism or filamentous fungi in a sample, said method comprising analysing a 18S rRNA gene from the sample for the at least one SNP as defined in the twelfth aspect, wherein the at least one yeast organism or filamentous fungi are classified based on the presence of the at least one SNP.

According to an eighteenth aspect of the present invention, there is provided a method of identifying at least one bacterium in a sample, said method comprising:

combining with the sample the at least one probe, tool or reagent as defined in the thirteenth or fourteenth aspects; and identifying the at least one bacterium based on the presence of at least one SNP in a 16S rRNA gene from the sample as broadly described above; or a method of identifying at least one yeast organism or filamentous fungi in a sample, said method comprising:

combining with the sample the at least one probe, tool or reagent as defined in the thirteenth or fourteenth aspects; and identifying the at least one yeast organism or filamentous fungi based on the presence of at least one SNP in a 18S rRNA gene from the sample as broadly described above.

According to a nineteenth aspect of the present invention, there is provided a method of classifying bacteria in a sample, said method comprising:

combining with the sample the at least one probe, tool or reagent as defined in the thirteenth or fourteenth aspects; and classifying the bacteria based on the presence of at least one SNP in a 16S rRNA gene from the sample as broadly described above; or a method of classifying at least one yeast organism or filamentous fungi in a sample, said method comprising:

combining with the sample the at least one probe, tool or reagent as defined in the thirteenth or fourteenth aspects; and classifying the at least one yeast organism or filamentous fungi based on the presence of at least one SNP in a 18S rRNA gene from the sample as broadly described above.

According to a twentieth aspect of the present invention, there is provided a method of diagnosing a bacterial infection in a subject, said method comprising analysing a 16S rRNA gene from a sample obtained from the subject for the at least one SNP as defined in the twelfth aspect, wherein the bacterial infection is diagnosed by identifying at least one causative bacterium in the sample based on the presence of the at least one SNP; or a method of diagnosing at least one yeast organism or filamentous fungi infection in a subject, said method comprising analysing a 18S rRNA gene from a sample obtained from the subject for the at least one SNP as defined in the twelfth aspect, wherein the at least one yeast organism or filamentous fungi infection is diagnosed by identifying at least one causative yeast organism or filamentous fungi in the sample based on the presence of the at least one SNP.

According to a twenty-first aspect of the present invention, there is provided a method of diagnosing a bacterial infection in a subject, said method comprising:

combining with a sample obtained from the subject the at least one probe, tool or reagent as defined in the thirteenth or fourteenth aspects; and diagnosing the bacterial infection by identifying at least one causative bacterium in the sample based on the presence of the at least one SNP in a 16S rRNA gene from the sample as broadly described above; or a method of diagnosing at least one yeast organism or filamentous fungi infection in a subject, said method comprising:

combining with a sample obtained from the subject the at least one probe, tool or reagent as defined in the thirteenth or fourteenth aspects; and diagnosing the at least one yeast organism or filamentous fungi infection by identifying at least one causative bacterium in the sample based on the presence of the at least one SNP in a 18S rRNA gene from the sample as broadly described above.

According to a twenty-second aspect of the present invention, there is provided a method of treating a subject having a bacterial infection, said method comprising:

diagnosing the bacterial infection by identifying the at least one causative bacterium in the sample according to the method as defined in the twentieth or twenty-first aspects; and administering to the subject a therapy or treatment agent for treating the at least one causative bacterium identified to thereby treat the bacterial infection; or a method of treating a subject having at least one yeast organism or filamentous fungi infection, said method comprising:

diagnosing the at least one yeast organism or filamentous fungi infection by identifying the at least one causative bacterium in the sample according to the method as defined in the twentieth or twenty-first aspects; and administering to the subject a therapy or treatment agent for treating the at least one causative yeast organism or filamentous fungi identified to thereby treat the bacterial infection.

According to a twenty-third aspect of the present invention, there is provided an array of oligonucleotide probes for identifying at least one bacterium in a sample or classifying bacteria in the sample, said probes comprising oligonucleotides which hybridize to at least one SNP in a 16S rRNA gene in the sample as broadly described above; or an array of oligonucleotide probes for identifying at least one yeast organism or filamentous fungi in a sample or classifying at least one yeast organism or filamentous fungi in the sample, said probes comprising oligonucleotides which hybridize to at least one SNP in a 18S rRNA gene in the sample as broadly described above.

According to a twenty-fourth aspect of the present invention, there is provided a microarray comprising oligonucleotide probes for identifying at least one bacterium in a sample or classifying bacteria in the sample, said probes comprising oligonucleotides which hybridize to at least one SNP in a 16S rRNA gene in the sample as broadly described above; or a microarray comprising oligonucleotide probes for identifying at least one yeast organism or filamentous fungi in a sample or classifying at least one yeast organism or filamentous fungi in the sample, said probes comprising oligonucleotides which hybridize to at least one SNP in a 18S rRNA gene in the sample as broadly described above.

According to a twenty-fifth aspect of the present invention, there is provided a biochip comprising a solid substrate and at least one oligonucleotide probe for identifying at least one bacterium in a sample or classifying bacteria in the sample, said at least one probe comprising an oligonucleotide which hybridize to at least one SNP in a 16S rRNA gene in the sample as broadly described above; or a biochip comprising a solid substrate and at least one oligonucleotide probe for identifying at least one yeast organism or filamentous fungi in a sample or classifying at least one yeast organism or filamentous fungi in the sample, said at least one probe comprising an oligonucleotide which hybridize to at least one SNP in a 18S rRNA gene in the sample as broadly described above.

According to a twenty-sixth aspect of the present invention, there is provided a kit or assay for identifying at least one bacterium in a sample or classifying bacteria in the sample, said kit or assay comprising: the at least one probe, tool or reagent as described above; the array of oligonucleotide probes as described above; the microarray as described above; and/or the biochip as described above; or a kit or assay for identifying at least one yeast organism or filamentous fungi in a sample or classifying at least one yeast organism or filamentous fungi in the sample, said kit or assay comprising: the at least one probe, tool or reagent as described above; the array of oligonucleotide probes as described above; the microarray as described above; and/or the biochip as described above.

According to a twenty-seventh aspect of the present invention, there is provided a method of identifying, partially identifying, classifying or diagnosing an infection in a subject. In one embodiment of the twenty-seventh aspect, said infection is a bacterial, yeast organism or filamentous fungi infection, said method comprising assaying a biological sample obtained from the subject for a property of at least one bacterial 16S rRNA gene or gene product or a portion thereof or at least one yeast organism or filamentous fungi 18S rRNA gene or gene product or a portion thereof, wherein said assay comprises detecting at least one single nucleotide polymorphism (SNP) in the at least one bacterial 16S rRNA gene or gene product or a portion thereof or at least one yeast organism or filamentous fungi 18S rRNA gene or gene product or a portion thereof, wherein the at least one SNP in the bacterial 16S rRNA gene or gene product or a portion thereof is at a position corresponding to at least one of positions 273, 378, 412, 440, 488, 647, and 653 of the 16S rRNA gene set forth in SEQ ID NO: 1; or wherein the at least one SNP in the bacterial 16S rRNA gene or gene product or a portion thereof is in or corresponds to the 16S rRNA gene set forth in SEQ ID NO: 43; or wherein the at least one bacteria, yeast organism or filamentous fungi in the sample is identified, partially identified, classified or diagnosed based on the presence or absence of the at least one SNP.

In another embodiment of the twenty-seventh aspect, said infection is a bacterial, yeast organism or filamentous fungi infection, said method comprising assaying a biological sample obtained from the subject for a property of at least one bacterial 16S rRNA gene or gene product or a portion thereof or at least one yeast organism or filamentous fungi 18S rRNA gene or gene product or a portion thereof, wherein said assay comprises detecting at least one single nucleotide polymorphism (SNP) in the at least one bacterial 16S rRNA gene or gene product or a portion thereof or at least one yeast organism or filamentous fungi 18S rRNA gene or gene product or a portion thereof, wherein the at least one SNP in the bacterial 16S rRNA gene or gene product or a portion thereof is at a position corresponding to at least one of positions 273, 378, 412, 440, 488, 647, 653, 737, 755, 762 and 776 of the 16S rRNA gene set forth in SEQ ID NO: 1;

wherein the at least one bacteria, yeast organism or filamentous fungi in the sample is identified, partially identified, classified or diagnosed based on the presence or absence of the at least one SNP.

Features of the first to twenty-seventh aspects of the present invention, where appropriate, may be as described below.

In one embodiment, said at least one SNP in the at least a portion of the bacterial 16S rRNA gene or gene product is selected from SNPs at positions corresponding to at least one of positions 273, 378, 412, 440, 488, 647, 653, 737, 755, 762 and 776 of the 16S rRNA gene as set forth in SEQ ID NO:1. In some embodiments, more than one SNP may be used in the methods of the present invention. For example, at least two SNPs, at least three SNPs, at least four SNPS, at least five SNPs, at least six SNPs, at least seven SNPs, at least eight SNPs, at least nine SNPs, at least ten SNPs, or even at least eleven SNPs may be used.

In one embodiment, said at least one SNP in the at least a portion of the bacterial 16S rRNA gene or gene product is selected from SNPs at positions corresponding to positions 273, 378, 412, 440, 488, 647 and 653 of the 16S rRNA gene as set forth in SEQ ID NO:1. In some embodiments, more than one SNP may be used in the methods of the present invention. For example, at least two SNPs, at least three SNPs, at least four SNPS, at least five SNPs, at least six SNPs, or even at least seven SNPs may be used.

In another embodiment, said at least one SNP in the at least a portion of the bacterial 16S rRNA gene or gene product may be in or correspond to the 16S rRNA gene as set forth in SEQ ID NO: 43. The at least one SNP in the at least a portion of the bacterial 16S rRNA gene or gene product set forth in SEQ ID NO: 43 may be at a position corresponding to at least one of positions 746, 764, 771, or 785 of the 16S rRNA gene set forth in SEQ ID NO: 43 (or positions 737, 755, 762, or 776 of the 16S rRNA gene as set forth in SEQ ID NO:1). At least one said SNP, at least two said SNPs, at least three said SNPs or at least four said SNPs may be used.

In another embodiment, the at least one SNP in the at least a portion of the yeast organism or filamentous fungi 18S rRNA gene or gene product may be in or correspond to the 18S rRNA gene set forth in SEQ ID NO: 37. The at least one SNP in the at least a portion of the yeast organism or filamentous fungi 18S rRNA gene or gene product may be at a position corresponding to at least one of positions 343, 371, 388, 416, and 467 of the 18S rRNA gene set forth in SEQ ID NO: 37. At least one said SNP, at least two said SNPs, at least three said SNPs, at least four said SNPs or at least five said SNPs may be used.

In a further embodiment, said method comprises analysing at least a portion of a bacterial 16S rRNA gene or gene product from the sample, or at least a portion of a yeast organism or filamentous fungi 18S rRNA gene or gene product from the sample, for the presence or absence of:

single nucleotide polymorphisms in the bacterial 16S rRNA gene at a position corresponding to positions 273, 378, 412, 440, 488, 647, and 653 of the 16S rRNA gene set forth in SEQ ID NO: 1; or single nucleotide polymorphisms in the bacterial 16S rRNA gene a position corresponding to positions 746, 764, 771, and 785 of the 16S rRNA gene set forth in SEQ ID NO: 43; or single nucleotide polymorphisms in the yeast organism or filamentous fungi 18S rRNA gene at a position corresponding to positions 343, 371, 388, 416, and 467 of the 18S rRNA gene set forth in SEQ ID NO: 37.

In a further embodiment, said method comprises analysing at least a portion of a bacterial 16S rRNA gene or gene product from the sample, or at least a portion of a yeast organism or filamentous fungi 18S rRNA gene or gene product from the sample, for the presence or absence of:

single nucleotide polymorphisms in the at least a portion of the bacterial 16S rRNA gene or gene product at a position corresponding to at least four of positions 273, 378, 412, 440, 488, 647, 653, 737, 755, 762 and 776 of the 16S rRNA gene set forth in SEQ ID NO: 1; or single nucleotide polymorphisms in the yeast organism or filamentous fungi 18S rRNA gene at a position corresponding to positions 343, 371, 388, 416, and 467 of the 18S rRNA gene set forth in SEQ ID NO: 37.

In some embodiments, the bacterium or bacteria is or are selected from among mammalian (e.g., human) associated bacteria, soil associated bacteria and water associated bacteria. In particular embodiments, the bacterium or bacteria may be a sepsis-associated bacterium or bacteria.

In some particular embodiments, the bacterium or bacteria is or are selected from among at least one of: *Acinetobacter* spp.; *Actinobaccillus* spp.; *Actinomadura* spp.; *Actinomyces* spp.; *Actinoplanes* spp.; *Aeromonas* spp.; *Agrobacterium* spp.; *Alistipes* spp.; *Anaerococcus* spp.; *Arthrobacter* spp.; *Bacillus* spp.; *Bacteroides* spp.; *Brucella* spp.; *Bulleidia* spp.; *Burkholderia* spp.; *Cardiobacterium* spp.; *Citrobacter* spp.; *Clostridium* spp.; *Cornyebacterium* spp.; *Dermatophilus* spp.; *Dorea* spp; *Enterobacter* spp.; *Enterococcus* spp.; *Erysipelothrix* spp.; *Escherichia* spp.; *Eubacterium* spp.; *Ewardsiella* spp.; *Faecalibacterium* spp.; *Filifactor* spp.; *Finegoldia* spp.; *Flavobacterium* spp.; *Francisella* spp.; *Gallicola* spp.; *Haemophilus* spp.; *Helococcus* spp.; *Holdemania* spp.; *Hyphomicrobium* spp.; *Klebsiella* spp.; *Lactobacillus* spp.; *Legionella* spp.; *Listeria* spp.; *Methylobacterium* spp.; *Micrococcus* spp.; *Micromonospora* spp.; *Mobiluncus* spp.; *Moraxella* spp.; *Morganella* spp.; *Mycobacterium* spp.; *Neisseria* spp.; *Nocardia* spp.; *Paenibacillus* spp.; *Parabacteroides* spp.; *Pasteurella* spp.; *Peptoniphilus* spp.; *Peptostreptococcus* spp.; *Planococcus* spp.; *Planomicrobium* spp.; *Plesiomonas* spp.; *Porphyromonas* spp.; *Prevotella* spp.; *Propionibacterium* spp.; *Proteus* spp.; *Providentia* spp.; *Pseudomonas* spp.; *Ralstonia* spp.; *Rhodococcus* spp.; *Roseburia* spp.; *Ruminococcus* spp.; *Salmonella* spp.; *Sedimentibacter* spp.; *Serratia* spp.; *Shigella* spp.; *Solobacterium* spp.; *Sphingomonas* spp.; *Staphylococcus* spp.; *Stenotrophomonas* spp.; *Streptococcus* spp.; *Streptomyces* spp.; *Tissierella* spp.; *Vibrio* spp.; and *Yersinia* spp.

In some more particular embodiments, the bacterium or bacteria is or are selected from among at least one of: *Acinetobacter baumannii; Acinetobacter calcoaceticus; Bacteroides fragilis; Bacteroides* vulgatus; *Citrobacter freundii; Enterobacter aerogenes; Enterobacter cloacae; Enterococcus avium; Enterococcus faecalis; Enterococcus faecium; Escherichia coli; Klebsiella oxytoca; Klebsiella pneumoniae; Proteus mirabilis; Pseudomonas aeruginosa; Serratia marcescens; Staphylococcus aureus; Staphylococcus epidermidis; Staphylococcus hominis; Staphylococcus saprophyticus; Stenotrophomonas maltophilia; Streptococcus agalactiae; Streptococcus anginosus; Streptococcus constellatus; Streptococcus intermedius; Streptococcus* milleri; *Streptococcus mitis; Streptococcus mutans; Streptococcus oralis; Streptococcus pneumoniae; Streptococcus pyogenes; Streptococcus sanguinis*; and *Streptococcus sobrinus.*

In particular embodiments, the bacterium or bacteria is or are selected from among at least one of: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes.*

In particular embodiments, the bacterium or bacteria is or are selected from among at least one of: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae; Streptococcus pyogenes; Listeria monocytogenes; Clostridium perfringens; Corynebacterium jeikeium; Bacteroides fragilis; Neisseria meningitides; Haemophilus influenzae; Salmonella* sp.; and *Staphylococcus epidermidis.* In another embodiment, the bacterium or bacteria is or are selected from among at least one of: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Ser-*

*ratia marcescens; Staphylococcus aureus; Staphylococcus epidermidis; Streptococcus agalactiae; Streptococcus pneumoniae; Streptococcus pyogenes; Listeria monocytogenes; Clostridium perfringens; Corynebacterium jeikeium; Bacteroides fragilis; Neisseria meningitides; Haemophilus influenzae; Salmonella* sp.; *Staphylococcus epidermidis; Bacillus anthracis, Clostridium botulinum, Yersinia pestis, Francisella tularensis, Vibrio cholerae*, and *Burkholderia pseudomallei.*

In one embodiment the bacterium or bacteria is a Security Sensitive Biological Agent (SSBA). The SSBA may be a Tier 1 agent or a Tier 2 agent. Exemplary Tier 1 agents include one or more of: *Bacillus anthracis* (Anthrax), and Yesinia *pestis* (Plague). Exemplary Tier 2 agents include one or more of: *Clostridium botulinum* (botulism, especially toxin producing strains); *Francisella tularensis* (Tularaemia); *Salmonella Typhi* (typhoid), and *Vibrio cholerae* (especially Cholera serotypes 01 or 0139). In one embodiment the bacterium or bacteria is or are selected from among at least one of the group consisting of: *Bacillus anthracis, Clostridium botulinum, Yersinia pestis, Francisella tularensis, Vibrio cholerae*, and *Burkholderia pseudomallei.*

In one embodiment the yeast organism may be selected from among at least one of: *Candida* spp., *Cryptococcus* spp and *Rhodotorula* spp. Exemplary *Candida* spp. may include at least one of *Candida albicans, Candida tropicalis, Candida stellatoidea, Candida krusei, Candida parapsilosis, Candida glabrata, Candida guilliermondii, Candida viswanathii, Candida auris* and *Candida lusitaniae*. Exemplary *Cryptococcus* spp. may include at least one of *Cryptococcus neoformans* and *Cryptococcus gattii*. An exemplary *Rhodotorula* spp. may be *Rhodotorula mucilaginosa.*

In one embodiment the filamentous fungi may be selected from at least one of: *Aspergillus* spp. and *Fusarium* spp. Exemplary *Fusarium* spp. may include at least one of *Fusarium solani, Fusarium oxysporum, Fusarium verticillioides, Fusarium proliferatum, Fusarium avenaceum, Fusarium bubigeum, Fusarium culmorum, Fusarium graminearum, Fusarium langsethiae, Fusarium poae, Fusarium sporotrichioides, Fusarium tricinctum* and *Fusarium virguliforme*; especially at least one of *Fusarium solani, Fusarium oxysporum, Fusarium verticillioides* and *Fusarium proliferatum*. Exemplary *Aspergillus* spp. may include at least one of *Aspergillus fumigatus, Aspergillus flavus, Aspergillus clavatus, Aspergillus lentulus, Aspergillus terreus*, and *Aspergillus nidulans*; especially at least one of *Aspergillus fumigatus, Aspergillus flavus*, and *Aspergillus clavatus*; more especially *Aspergillus fumigatus.*

In one embodiment, the yeast organism or filamentous fungi is at least one of the group consisting of: *Candida albicans, Candida tropicalis, Candida parapsilosis, Candida glabrata, Fusarium* sp., *Aspergillus fumigatus*, and *Cryptococcus neoformans.*

In one embodiment, the bacteria, yeast organism or filamentous fungi is a human pathogen.

In some embodiments, the methods of the present invention may be used to analyse blood from a subject with systemic inflammatory response syndrome (SIRS) to determine the origin of the SIRS (for example bacteria, yeast organism or filamentous fungi). In other embodiments, the methods of the present invention may be used to determine whether a subject has sepsis having a bacterial, yeast organism or filamentous fungi infectious origin. In both embodiments, the methods of the present invention may be used to determine the presence of, differentiate and/or identify bacteria, yeast organism or filamentous fungi present in the sample.

SIRS is an overwhelming whole body reaction that may have an infectious aetiology or non-infectious aetiology (i.e., infection-negative SIRS, or inSIRS). Sepsis is SIRS that occurs during infection. Sepsis in this instance is diagnosed by a clinician (when there is suspected infection) or through culture of an organism. Both SIRS and sepsis are defined by a number of non-specific host response parameters including changes in heart and respiratory rate, body temperature and white cell counts (Levy et al., 2003; Reinhart et al., 2012).

In some embodiments, the at least one SNP or at least one probe, tool or reagent may be used to classify bacteria in a sample as Gram-positive bacterium or bacteria or Gram-negative bacterium or bacteria.

For example, in some embodiments, the bacterium or bacteria may be classified as Gram-positive based on any one of the above SNPs, especially at at least one of positions 273, 378, 412, 440, 488, 647, and 653 of the 16S rRNA gene set forth in SEQ ID NO: 1. In one such embodiment, the bactreria or bacterium may be classified based on SNPs at positions corresponding to positions 273 and 653 of the 16S rRNA gene as set forth in SEQ ID NO:1, wherein the bacterium or bacteria is determined to be Gram-positive when there is an A at position 273 and a T at position 653.

For example, in another embodiment, the bacterium or bacteria may be classified as Gram-positive based on at least one SNP at a position corresponding to position 440 of the 16S rRNA gene as set forth in SEQ ID NO: 1, wherein the bacterium or bacteria is determined to be Gram-positive when there is a T at position 440. Conversely, wherein the bacterium or bacteria is determined to be Gram-negative when there is not a T at position 440.

In yet other embodiments, the at least one SNP or at least one probe, tool or reagent may be used to classify groups of bacteria, yeast organisms or filamentous fungi in a sample.

For example, in some embodiments, the bacteria may be classified as belonging to a particular genus based on at least one SNP selected from the above SNPs. In one such embodiment, the bacteria may be classified as belonging to a particular genus based on at least one SNP selected from SNPs at positions corresponding to positions 412 and 647 of the 16S rRNA gene as set forth in SEQ ID NO: 1. For example, the bacterium or bacteria in a sample may be classified as belonging to the *Staphylococcus* genus when there is a T at position 412. For example, the bacterium or bacteria in a sample may be classified as belonging to the *Enterococcus* genus when there is a G at position 647.

In yet other embodiments, the at least one SNP or at least one probe, tool or reagent may be used to identify a bacterium in a sample as described above.

For example, the bacterium *Enterobacter cloacae* may be identified in a sample based on at least one SNP at a position corresponding to position 653 of the 16S rRNA gene as set forth in SEQ ID NO: 1, wherein the bacterium *Enterobacter cloacae* is identified when there is a G at position 653.

For example, bacterium selected from *Streptococcus pneumoniae, Streptococcus agalactiae* and *Streptococcus pyogenes* may be identified in a sample based on SNPs at positions corresponding to positions 378 and 488 of the 16S rRNA gene as set forth in SEQ ID NO: 1, wherein the bacterium is: *Streptococcus pneumoniae* when there is an A at position 378 and a T at position 488; *Streptococcus agalactiae* when there is an A at position 378 and an A 488; and *Streptococcus pyogenes* when there is a G at position 378 and an A at position 488.

For example, in one embodiment, bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in a sample based on SNPs at positions corresponding to positions 273, 378, 412, 440, 488, 647 and 653 of the 16S rRNA gene as set forth in SEQ ID NO: 1, wherein the bacterium is: *Acinetobacter calcoaceticus* when there is an A at positions 273, 440 and 647; *Enterobacter cloacae* when there is a G at position 653; *Escherichia coli* when there is a T at position 273 and a T at position 653; *Klebsiella pneumoniae* when there is a T at position 273, a C at positions 488 and 647 and an A at position 653; *Proteus mirabilis* when there is a C at positions 440 and 488 and a T at position 647; *Pseudomonas aeruginosa* when there is an A at position 440 and a T at position 647; *Streptococcus agalactiae* when there is an A at positions 378, 488 and 647; *Streptococcus pneumoniae* when there is T at positions 488 and 647; and *Streptococcus pyogenes* when there is G at position 378 and A at positions 488 and 647.

For example, in another embodiment, bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in a sample based on the presence of SNPs set forth in the following table:

TABLE 1

| | SNP position in the 16S rRNA gene as set forth in SEQ ID NO: 1 | | | | | | |
|---|---|---|---|---|---|---|---|
| Bacterial species | 273 | 378 | 412 | 440 | 488 | 647 | 653 |
| *Escherichia coli* | T | G | A | C | C | C | T |
| *Streptococcus pneumoniae* | A | A | A | T | T | T | T |
| *Streptococcus agalactiae* | A | A | A | T | A | A | T |
| *Streptococcus pyogenes* | A | G | A | T | A | A | T |
| *Proteus mirabilis* | T | G | A | C | C | T | A |
| *Enterobacter cloacae* | T | G | A | C | C | C | G |
| *Klebsiella pneumoniae* | T | G | A | C | C | C | A |
| *Pseudomonas aeruginosa* | A | G | A | A | C | T | A |
| *Acinetobacter calcoaceticus* | A | G | A | A | C | A | A |

For example, in another embodiment, bacterium selected from among *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella* sp., and *Staphylococcus epidermidis* may be identified in a sample based on the presence of SNPs set forth in the following table:

TABLE 2

| | SNP position in the 16S rRNA gene as set forth in SEQ ID NO: 1 | | | | | | | | | | |
|---|---|---|---|---|---|---|---|---|---|---|---|
| Bacterial species | 273 | 378 | 412 | 440 | 488 | 647 | 653 | 737 | 755 | 762 | 776 |
| *Escherichia coli* | T | G | A | C | C | C | T | C | G | T | G |
| *Streptococcus pneumoniae* | A | A | A | T | T | T | T | C | G | C | G |
| *Streptococcus agalactiae* | A | A | A | T | A | A | T | C | G | C | G |
| *Streptococcus pyogenes* | A | G | A | T | A | A | T | C | G | T | G |
| *Proteus mirabilis* | T | G | A | C | C | T | A | C | G | T | G |
| *Enterobacter cloacae* | T | G | A | C | C | C | G | C | G | T | G |
| *Klebsiella pneumoniae* | T | G | A | C | C | C | A | C | G | T | G |
| *Pseudomonas aeruginosa* | A | G | A | A | C | T | A | A | A | T | G |
| *Acinetobacter calcoaceticus* | A | G | A | A | C | A | A | A | G | T | A |
| *Enterococcus faecalis* | A | A | A | T | T | G | T | C | G | C | G |
| *Listeria monocytogenes* | A | A | A | T | T | A | G | C | G | T | G |
| *Staphylococcus aureus* | A | G | T | T | C | A | T | T | G | T | G |
| *Clostridium perfringens* | A | G | T | C | C | T | A | C | G | C | G |
| *Corynebacterium jeikeium* | A | G | T | C | C | C | A | C | G | A | G |
| *Bacteroides fragilis* | A | G | T | T | A | C | T | C | A | C | T |
| *Neisseria meningitidis* | A | G | A | T | T | G | C | T | G | C | T |
| *Haemophilus influenzae* | A | G | A | C | C | G | A | C | G | C | G |
| *Serratia marcescens* | T | G | A | C | C | C | A | C | G | T | G |
| *Salmonella* sp. | A | G | A | C | C | C | T | C | G | T | G |
| *Staphylococcus epidermidis* | C | G | A | C | T | C | T | T | G | T | G |

In another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 746, 764, 771, or 785 of the 16S rRNA gene as set forth in SEQ ID NO:43, wherein the bacterium is: *Bacillus anthracis* when there is a T at position 746, A at position 764, C at position 771 and G at position 785; *Clostridium botulinum* type A or *Clostridium botulinum* type B when there is a T at position 746, G at position 764, C at position 771 and T at position 785; *Clostridium botulinum* type C when there is a T at position 746, A at position 764, T at position 771 and T at position 785; *Clostridium botulinum* type D when there is a C at position 746, A at position 764, T at position 771 and T at position 785; *Clostridium botulinum* type G when there is a T at position 746, G at position 764, C at position 771 and G at position 785; *Yersinia pestis* when there is a C at position 746, G at position 764, T at position 771 and G at position 785; *Francisella tularensis* when there is a T at position 746, A at position 764, G at position 771 and G at position 785; *Vibrio cholerae* when there is a C at position 746, A at position 764, T at position 771 and G at position 785; and *Burkholderia pseudomallei* when there is a C at position 746, G at position 764, C at position 771 and G at position 785.

For example, in another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on the presence of SNPs set forth in the following table:

TABLE 3

| | SNP position in the 16S rRNA gene as set forth in SEQ ID NO: 43 | | | |
|---|---|---|---|---|
| Bacterial species | 746 | 764 | 771 | 785 |
| *Bacillus anthracis* | T | A | C | G |
| *Clostridium botulinum* type A | T | G | C | T |
| *Clostridium botulinum* type B | T | G | C | T |
| *Clostridium botulinum* type C | T | A | T | T |
| *Clostridium botulinum* type D | C | A | T | T |
| *Clostridium botulinum* type G | T | G | C | G |
| *Yersinia pestis* | C | G | T | G |
| *Francisella tularensis* | T | A | G | G |
| *Vibrio cholerae* | C | A | T | G |
| *Burkholderia pseudomallei* | C | G | C | G |

The cumulative discrimatory index of the four SNPs used to identify the above organisms are 0.667 for 1 SNP; 0.889 for 2 SNPs; 0.944 for 3 SNPs; and 0.972 for 4 SNPs.

Position 746 of the 16S rRNA gene set forth in SEQ ID NO:43 corresponds to position 737 of the 16S rRNA gene set forth in SEQ ID NO:1. Position 764 of the 16S rRNA gene set forth in SEQ ID NO:43 corresponds to position 755 of the 16S rRNA gene set forth in SEQ ID NO:1. Position 771 of the 16S rRNA gene set forth in SEQ ID NO:43 corresponds to position 762 of the 16S rRNA gene set forth in SEQ ID NO:1. Position 785 of the 16S rRNA gene set forth in SEQ ID NO:43 corresponds to position 776 of the 16S rRNA gene set forth in SEQ ID NO:1.

Therefore, in another embodiment, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 737, 755, 762, or 776 of the 16S rRNA gene as set forth in SEQ ID NO:1, wherein the bacterium is: *Bacillus anthracis* when there is a T at position 737, A at position 755, C at position 762 and G at position 776; *Clostridium botulinum* type A or *Clostridium botulinum* type B when there is a T at position 737, G at position 755, C at position 762 and T at position 776; *Clostridium botulinum* type C when there is a T at position 737, A at position 755, T at position 762 and T at position 776; *Clostridium botulinum* type D when there is a C at position 737, A at position 755, T at position 762 and T at position 776; *Clostridium botulinum* type G when there is a T at position 737, G at position 755, C at position 762 and G at position 776; *Yersinia pestis* when there is a C at position 737, G at position 755, T at position 762 and G at position 776; *Francisella tularensis* when there is a T at position 737, A at position 755, G at position 762 and G at position 776; *Vibrio cholerae* when there is a C at position 737, A at position 755, T at position 762 and G at position 776; and *Burkholderia pseudomallei* when there is a C at position 737, G at position 755, C at position 762 and G at position 776.

In another embodiment, yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in a sample based on SNPs at positions corresponding to positions 343, 371, 388, 416, and 467 of the 18S rRNA gene set forth in SEQ ID NO: 37, wherein the yeast organism or filamentous fungi is: *Candida albicans* when there is a C at position 343, A at position 371, T at position 388, G at position 416 and G at position 467; *Candida tropicalis* when there is a C at position 343, A at position 371, C at position 388, G at position 416 and C at position 467; *Candida parapsilosis* when there is a C at position 343, A at position 371, C at position 388, G at position 416 and G at position 467; *Candida glabrata* when there is a T at position 343, A at position 371, C at position 388, G at position 416 and G at position 467; *Fusarium* spp. when there is a C at position 343, C at position 371, T at position 388, T at position 416 and G at position 467; *Aspergillus fumigatus* when there is a C at position 343, C at position 371, T at position 388, C at position 416 and G at position 467; and *Cryptococcus neoformans* when there is a C at position 343, A at position 371, T at position 388, T at position 416 and G at position 467.

For example, in another embodiment, yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in a sample based on the presence of SNPs set forth in the following table:

TABLE 4

| Yeast organism or | SNP position in the 18S rRNA gene as set forth in SEQ ID NO: 37 | | | | |
|---|---|---|---|---|---|
| filamentous fungi species | 343 | 371 | 388 | 416 | 467 |
| *Candida albicans* | C | A | T | G | G |
| *Candida tropicalis* | C | A | C | G | C |
| *Candida parapsilosis* | C | A | C | G | G |
| *Candida glabrata* | T | A | C | G | G |
| *Fusarium* sp. | C | C | T | T | G |
| *Aspergillus fumigatus* | C | C | T | C | G |
| *Cryptococcus neoformans* | C | A | T | T | G |

The bacteria, yeast organism or filamentous fungi may be partially identified or classified based on one or more of the above SNPs.

In one embodiment nucleic acid is extracted from the sample prior to analysis in the methods of the invention (especially in the first and second aspects). In another embodiment, the step of analysing in the methods (especially in the first and second aspects) may comprise amplification of nucleic acid. The nucleic acid may be amplified by any method known in the art including, but not limited to polymerase chain reaction (PCR), ligase chain reaction (LCR) and reverse transcription-polymerase chain reaction (RT-PCR) using one or more oligonucleotides/primers that will amplify transcribed RNA.

The SNPs may be analysed by any method known in the art including, but not limited to: high resolution melt analysis, 5' nuclease digestion (including 5' nuclease digestion), molecular beacons, oligonucleotide ligation, microarray, restriction fragment length polymorphism; antibody detection methods; direct sequencing or any combination thereof. In one embodiment, the step of analysing in the methods (especially in the first and second aspects of the invention) comprises determining the presence or the absence of the at least one SNP using high resolution melt analysis, 5' nuclease digestion, molecular beacons, oligonucleotide ligation, microarray, restriction fragment length polymorphism, antibody detection methods; direct sequencing or any combination thereof. The SNPs may be detected by any method known in the art including, but not limited to: polymerase chain reaction (PCR); ligase chain reaction (LCR); hybridization analysis; high-resolution melt analysis; digestion with nucleases, including 5' nuclease digestion; molecular beacons; oligonucleotide ligations; microarray; restriction fragment length polymorphism; antibody detection methods; direct sequencing; or any combination thereof.

For example, in some embodiments, the identifying of bacterium or classifying of bacteria may further be based on DNA melting characteristics of the SNPs as broadly described above and their surrounding DNA sequences, preferably high-resolution melt analysis.

For example, in some such embodiments, the methods of the present invention may further include high-resolution melt (HRM) analysis to further analyse the DNA melting characteristics of the SNPs as broadly described above and their surrounding DNA sequences. In a particular embodiment, the HRM analysis may include forming a DNA amplification product (i.e., amplicon) containing at least one of the SNPs and at least one intercalating fluorescent dye and heating the DNA amplification product through its melting temperature ($T_m$). The HRM is monitored in real-time using the fluorescent dye incorporated into the DNA amplification product. The level of fluorescence is monitored as the temperature increases with the the fluorescence reducing as the amount of double-stranded DNA reduces. Changes in fluorescence and temperature can be plotted in a graph known as a melt curve.

As a skilled addressee will understand, the $T_m$ of the DNA amplification product at which the two DNA strands separate is predictable, being dependent on the sequence of the nucleotide bases forming the DNA amplification product. Accordingly, it is possible to differentiate between DNA amplification products including a DNA amplification product containing a polymorphism (i.e., a SNP or SNPs) as the melt curves will appear different. Indeed, in some embodiments, it is possible to differentiate between DNA amplification products containing the same polymorphism based on differences in the surrounding DNA sequences.

For example, bacterium selected from among *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes* may be identified in a sample based on the presence of SNPs set forth in the following table and DNA melting characteristics of the SNPs and their surrounding DNA sequences:

TABLE 5

| | SNP position in the 16S rRNA gene as set forth in SEQ ID NO: 1 | | | | | | |
|---|---|---|---|---|---|---|---|
| Bacterial species | 273 | 378 | 412 | 440 | 488 | 647 | 653 |
| *Escherichia coli* | T | G | A | C | C | C | T |
| *Staphylococcus aureus* | A | G | T | T | C | A | T |
| *Staphylococcus epidermidis* | A | G | T | T | C | A | T |
| *Streptococcus pneumoniae* | A | A | A | T | T | T | T |
| *Streptococcus agalactiae* | A | A | A | T | A | A | T |
| *Streptococcus pyogenes* | A | G | A | T | A | A | T |
| *Enterococcus faecalis* | A | A | A | T | T | G | T |
| *Enterococcus faecium* | A | A | A | T | T | G | T |
| *Proteus mirabilis* | T | G | A | C | C | T | A |
| *Serratia marcescens* | T | G | A | C | T | C | A |
| *Enterobacter aerogenes* | T | G | A | C | T | C | A |
| *Enterobacter cloacae* | T | G | A | C | C | C | G |
| *Klebsiella pneumoniae* | T | G | A | C | C | C | A |
| *Pseudomonas aeruginosa* | A | G | A | A | C | T | A |
| *Acinetobacter calcoaceticus* | A | G | A | A | C | A | A |

For example, bacterium selected from among *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella* sp., *Staphylococcus epidermidis* may be identified in a sample based on the presence of SNPs set forth in Table 2 and DNA melting characteristics of the SNPs and their surrounding DNA sequences.

In one embodiment, bacteria selected from *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis;*

*Pseudomonas aeruginosa; Serratia marcescens; Staphylococcus aureus; Staphylococcus epidermidis; Streptococcus agalactiae; Streptococcus pneumoniae*; and *Streptococcus pyogenes* may be identified in a sample based on SNPs at positions corresponding to positions 273, 378, 412, 440, 488, 647 and 653 of the 16S rRNA gene as set forth in SEQ ID NO: 1 and high-resolution melt curve analysis of the SNPs and their surrounding DNA.

For example, the bacterium selected from among *Acinetobacter calcoaceticus; Enterobacter cloacae; Escherichia coli; Klebsiella pneumoniae; Proteus mirabilis; Pseudomonas aeruginosa; Streptococcus agalactiae; Streptococcus pneumoniae*; and *Streptococcus pyogenes* may be identified in the sample based on the SNP positions as described above and/or high-resolution melt curve analysis of the SNPs and their surrounding DNA.

In some embodiments, the bacterium selected from *Staphylococcus aureus; Staphylococcus epidermidis; Enterococcus faecalis; Enterococcus faecium; Serratia marcescens*; and *Enterobacter aerogenes* may be individually identified in a sample based on SNPs at positions corresponding to positions 412, 440, 488 and 647 of the 16S rRNA gene as set forth in SEQ ID NO:1, wherein: *Staphylococcus aureus* and *Staphylococcus epidermidis* may be identified when there is a T at position 412 and then further distinguished from one another based on high-resolution melt curve analysis of the DNA surrounding the SNP at position 412; *Enterococcus faecalis* and *Enterococcus faecium* may be identified when there is a G at position 647 and then further distinguished from one another based on high-resolution melt curve analysis of the DNA surrounding the SNP at position 647; *Serratia marcescens* and *Enterobacter aerogenes* may be identified when there is a C at positions 440 and 647 and a T at position 488 and may then be further distinguished from one another based on high-resolution melt curve analysis of the DNA surrounding the SNPs at any one of positions 440, 488 and 647.

In other embodiments, the bacterium selected from *Enterococcus faecalis; Enterococcus faecium; Streptococcus agalactiae*; and *Streptococcus pyogenes* may be identified in a sample based on at least one SNP at a position corresponding to position 378 of the 16S rRNA gene as set forth in SEQ ID NO:1 and high-resolution melt curve analysis of the DNA surrounding the SNP at position 378.

For example, bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on the presence of SNPs set forth in the following table and DNA melting characteristics of the SNPs and their surrounding DNA sequences:

TABLE 6

| | SNP position in the 16S rRNA gene as set forth in SEQ ID NO: 43 | | | |
|---|---|---|---|---|
| Bacterial species | 746 | 764 | 771 | 785 |
| *Bacillus anthracis* | T | A | C | G |
| *Clostridium botulinum* type A | T | G | C | T |
| *Clostridium botulinum* type B | T | G | C | T |
| *Clostridium botulinum* type C | T | A | T | T |
| *Clostridium botulinum* type D | C | A | T | T |
| *Clostridium botulinum* type G | T | G | C | G |
| *Yersinia pestis* | C | G | T | G |

TABLE 6-continued

| | SNP position in the 16S rRNA gene as set forth in SEQ ID NO: 43 | | | |
|---|---|---|---|---|
| Bacterial species | 746 | 764 | 771 | 785 |
| *Francisella tularensis* | T | A | G | G |
| *Vibrio cholerae* | C | A | T | G |
| *Burkholderia pseudomallei* | C | G | C | G |

As noted above, position 746 of the 16S rRNA gene set forth in SEQ ID NO:43 corresponds to position 737 of the 16S rRNA gene set forth in SEQ ID NO:1. Position 764 of the 16S rRNA gene set forth in SEQ ID NO:43 corresponds to position 755 of the 16S rRNA gene set forth in SEQ ID NO:1. Position 771 of the 16S rRNA gene set forth in SEQ ID NO:43 corresponds to position 762 of the 16S rRNA gene set forth in SEQ ID NO:1. Position 785 of the 16S rRNA gene set forth in SEQ ID NO:43 corresponds to position 776 of the 16S rRNA gene set forth in SEQ ID NO:1.

In one embodiment, bacteria selected from *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in a sample based on SNPs at positions corresponding to positions 746, 764, 771, or 785 of the 16S rRNA gene as set forth in SEQ ID NO:43 (or positions 737, 755, 762, or 776 of the 16S rRNA gene as set forth in SEQ ID NO: 1) and high-resolution melt curve analysis of the SNPs and their surrounding DNA.

For example, the bacterium selected from among *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei* may be identified in the sample based on the SNP positions as described above and/or high-resolution melt curve analysis of the SNPs and their surrounding DNA.

In another example, yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in a sample based on the presence of SNPs set forth in the following table and DNA melting characteristics of the SNPs and their surrounding DNA sequences:

TABLE 7

| Yeast organism or | SNP position in the 18S rRNA gene as set forth in SEQ ID NO: 37 | | | | |
|---|---|---|---|---|---|
| filamentous fungi species | 343 | 371 | 388 | 416 | 467 |
| *Candida albicans* | C | A | T | G | G |
| *Candida tropicalis* | C | A | C | G | C |
| *Candida parapsilosis* | C | A | C | G | G |
| *Candida glabrata* | T | A | C | G | G |
| *Fusarium* sp. | C | C | T | T | G |
| *Aspergillus fumigatus* | C | C | T | C | G |
| *Cryptococcus neoformans* | C | A | T | T | G |

In one embodiment, yeast organism or filamentous fungi selected from *Candida albicans, Candida tropicalis, Candida parapsilosis, Candida glabrata, Fusarium* spp., *Aspergillus fumigatus*, and *Cryptococcus neoformans* may be identified in a sample based on SNPs at positions corresponding to positions 343, 371, 388, 416, and 467 of the 18S rRNA gene set forth in SEQ ID NO: 37 and high-resolution melt curve analysis of the SNPs and their surrounding DNA.

For example, the yeast organism or filamentous fungi selected from among *Candida albicans, Candida tropicalis, Candida parapsilosis, Candida glabrata, Fusarium* spp., *Aspergillus fumigatus*, and *Cryptococcus neoformans* may be identified in the sample based on the SNP positions as described above and/or high-resolution melt curve analysis of the SNPs and their surrounding DNA.

In some embodiments, nucleic acid may be extracted from the sample prior to analysis, identifying, classifying and/or diagnosing. Generally, the analysis, identifying, classifying and/or diagnosing may include amplification of the nucleic acid. In some embodiments, the analysis, identifying, classifying and/or diagnosing may further include administering a therapeutic agent to the subject, such as, e.g., an antibiotic. In another embodiment, a method of treatment (for example as in the third aspect of the present invention) may further comprise the step of determining whether the at least one bacteria, yeast organism or filamentous fungi is resistant to a therapeutic agent.

In one embodiment, any suitable sample may be used in the methods of the present invention. Exemplary samples may comprise sputum, saliva, blood, cerebrospinal fluid or urine samples.

The probe, tool or reagent may be, but is not limited to, an oligonucleotide, a primer, a nucleic acid, a polynucleotide, DNA, cDNA, RNA, a peptide or a polypeptide. These may be, for example, single stranded or double stranded, naturally occurring, isolated, purified, chemically modified, recombinant or synthetic.

The probe, tool or reagent may be, but is not limited to, an antibody or other type of molecule or chemical entity capable of specifically binding, detecting or identifying at least a portion of a 16S rRNA gene or an 18S rRNA gene in a sample containing at least one SNP.

The probe, tool or reagent may be any number or combination of the above, and the number and combination will depend on a desired result to be achieved—e.g., detection of SNP at a genomic level (genotyping) or at the RNA transcription level.

The probe, tool or reagent may be isolated. The probe, tool or reagent may be detectably labelled. A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In particular embodiments, the at least one probe, tool or reagent is for specifically binding, detecting or identifying of a SNP at the genomic level or transcription level, preferably the former.

In preferred embodiments, the at least one probe, tool or reagent is for specifically binding, detecting or identifying at least a portion of a 16S rRNA or a 18S rRNA gene or gene product in a sample containing at least one SNP as set forth in any one of Tables 1 to 7.

When identifying, partially identifying, classifying a bacterium, yeast organism or filamentous fungi, or identifying, partially identifying or diagnosing a bacterial, yeast organism or filamentous fungi infection a single probe (especially primer) may be used with each sample, or multiple probes (especially primers) may be used with each sample (i.e. in one pot). Such probes (especially primers) can be added to the raw solution obtained from amplification (such as PCR).

In one embodiment, the at least one probe, tool or reagent may comprise two primers, each of which hybridizes to at least a portion of a bacterial 16S rRNA gene (or gene product) or to at least a portion of a yeast organism or filamentous fungi 18S rRNA gene (or gene product), containing a SNP as defined above. In another embodiment, the at least one probe, tool or reagent may comprise a probe that hybridizes to at least a portion of a bacterial 16S rRNA gene or gene product or to at least a portion of a yeast organism or filamentous fungi 18S rRNA gene or gene product containing a SNP as defined above.

In one embodiment, said at least one probe, tool or reagent comprises an oligonucleotide having (or comprising or consisting of) a nucleotide sequence having at least 90%, at least 91%, at least 92%, at least 93%, at least 94%, at least 95%, at least 96%, at least 97%, at least 98%, at least 99% or 100% sequence homology or identity with the sequence as set forth in at least one of SEQ ID Nos 16-35 and 53-57. Said probe, tool or reagent may be a primer. Said probe, tool or reagent may comprise an oligonucleotide having a nucleotide sequence as set forth in at least one of SEQ ID NOs: 16-35 and 53-57.

In one aspect, the present invention provides at least one isolated probe, tool or reagent, wherein said at least one isolated probe, tool or reagent comprises an oligonucleotide having (or comprising or consisting of) a nucleotide sequence having at least 90%, at least 91%, at least 92%, at least 93%, at least 94%, at least 95%, at least 96%, at least 97%, at least 98%, at least 99% or 100% sequence homology or identity with the sequence as set forth in at least one of SEQ ID Nos 16-35 and 53-57. Said probe, tool or reagent may be a primer.

Suitable primers for identification of SNPs in the 16S rRNA sequence set forth in SEQ ID NO. 43 (especially for identification of the SNPs in Table 3) may be as shown in the Table below.

TABLE 8

| Forward primer sequence | Reverse primer sequence |
|---|---|
| 5'GTGTAGCGGTGAAATGCGTAGAG 3' (SEQ ID NO. 56) | 5'TCGTTTACCGTGGACTACCAGGG 3' (SEQ ID NO. 57) |

Suitable primers for identification of SNPs in the 18S rRNA sequence set forth in SEQ ID NO. 37 (especially for identification of the SNPs in Table 4) may be as shown in the Table below.

TABLE 9

| Forward primer sequence | Reverse primer sequence |
|---|---|
| 5'CATCCAAGGAAGGCAGCAGGCGCG 3' (SEQ ID NO. 53) | 5'GTTCAACTACGAGCTTTTTAAC 3' (SEQ ID NO. 54) |
| | 5'GTTCGACTACGAGCTTTTTAAC 3' (SEQ ID NO. 55) |

Any of the features described herein can be combined in any combination with any one or more of the other features described herein within the scope of the invention.

The above largely discusses the use of 16S rRNA and 18S rRNA genes. However, the above may also be applicable to 16S rRNA and to 18S rRNA and to other 16S rRNA and 18S rRNA gene products. Accordingly in some embodiments (and where appropriate), references to 16S rRNA gene and 18S rRNA gene above and below may be replaced with 16S rRNA gene product (or 16S rRNA) and 18S rRNA gene product (or 18S rRNA).

The reference to any prior art in this specification is not, and should not be taken as an acknowledgement or any form of suggestion that the prior art forms part of the common general knowledge.

BRIEF DESCRIPTION OF DRAWINGS

Various embodiments of the invention will be described with reference to the following drawings, in which:

FIGS. 1A-N are a CLUSTALW sequence alignment of the representative genes encoding 16S rRNA molecules from the following bacterial species: *Acinetobacter calcoaceticus* (SEQ ID NO: 15); *Enterobacter aerogenes* (SEQ ID NO: 11); *Enterobacter cloacae* (SEQ ID NO: 12); *Enterococcus faecalis* (SEQ ID NO: 7); *Enterococcus faecium* (SEQ ID NO: 8); *Escherichia coli* (SEQ ID NO: 1); *Klebsiella pneumoniae* (SEQ ID NO: 13); *Proteus mirabilis* (SEQ ID NO: 9); *Pseudomonas aeruginosa* (SEQ ID NO: 14); *Serratia marcescens* (SEQ ID NO: 10); *Staphylococcus aureus* (SEQ ID NO: 2); *Staphylococcus epidermidis* (SEQ ID NO: 3); *Streptococcus agalactiae* (SEQ ID NO: 5); *Streptococcus pneumoniae* (SEQ ID NO: 4); and *Streptococcus pyogenes* (SEQ ID NO: 6). Variable sequences, as determined by the CLUSTALW alignment were removed. The SNPs at positions corresponding to positions 273, 378, 412, 440, 488, 647 and 653 of the 16S rRNA gene from *E. coli* as set forth in SEQ ID NO:1 are highlighted together with the corresponding nucleotide in the aligned sequences.

KEY TO SEQUENCE LISTING

Figure 2:
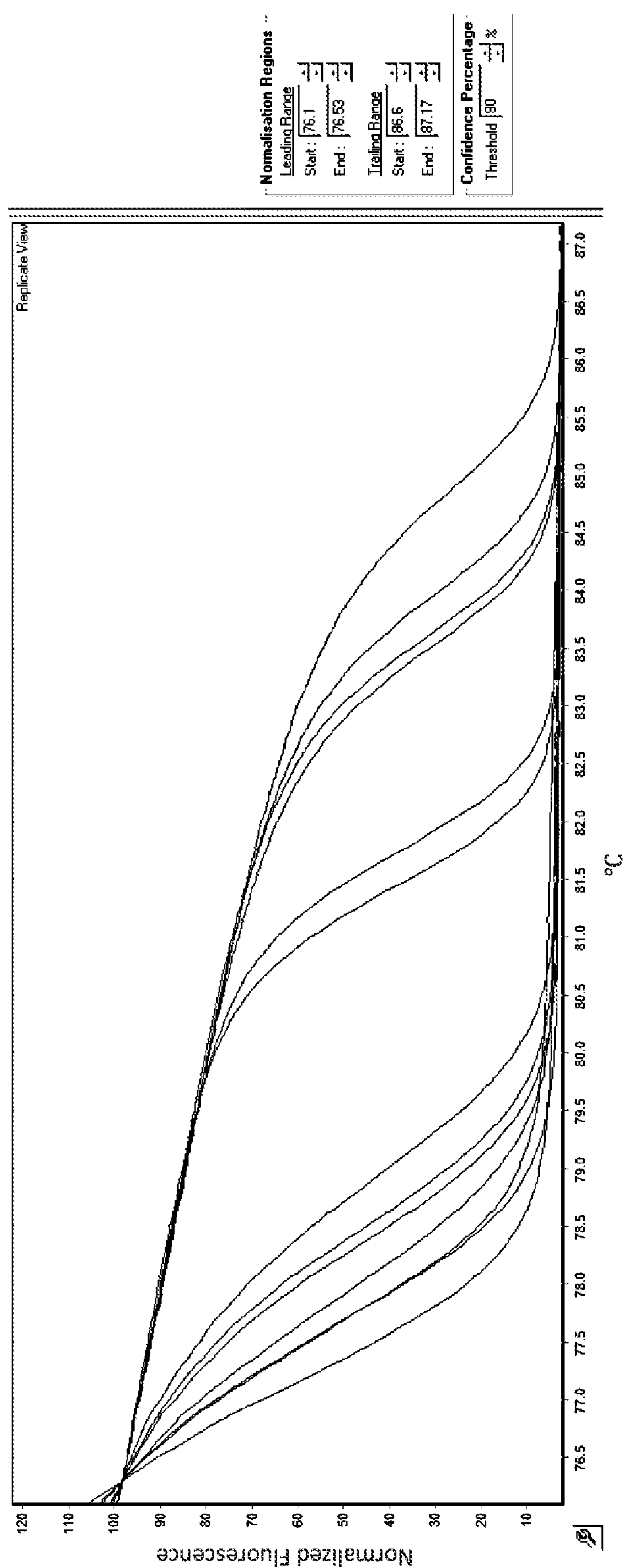
FIG. 2 shows a normalised high-resolution melt (HRM) curves plot for the following 15 bacterial species tested in Example 1: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes.*

The Sequence Listing is submitted as an ASCII text file in the form of the file named Sequence_Listing.txt, which was created on Nov. 8, 2019, and is 73 kilobytes, which is incorporated by reference herein.

SEQ ID NO:1: *Escherichia coli* 16S rRNA gene (Genbank accession NR_102804.1);

SEQ ID NO:2: *Staphylococcus aureus* 16S rRNA gene (Genbank accession NR_075000.1);

SEQ ID NO:3: *Staphylococcus epidermidis* 16S rRNA gene (Genbank accession NR_074995.1);

SEQ ID NO:4: *Streptococcus pneumoniae* 16S rRNA gene (Genbank accession NR_074564.1);

SEQ ID NO:5: *Streptococcus agalactiae* 16S rRNA gene (Genbank accession NR_040821.1);

SEQ ID NO:6: *Streptococcus pyogenes* 16S rRNA gene (Genbank accession NR_074091.1);

SEQ ID NO:7: *Enterococcus faecalis* 16S rRNA gene (Genbank accession NR_074637.1);

SEQ ID NO:8: *Enterococcus faecium* 16S rRNA gene (Genbank accession NR_042054.1);

SEQ ID NO:9: *Proteus mirabilis* 16S rRNA gene (Genbank accession NR_074898.1);

SEQ ID NO:10: *Serratia marcescens* 16S rRNA gene (Genbank accession NR_041980.1);

SEQ ID NO:11: *Enterobacter aerogenes* 16S rRNA gene (Genbank accession NR_024643.1);

SEQ ID NO:12: *Enterobacter cloacae* 16S rRNA gene (Genbank accession NR_028912.1);

SEQ ID NO:13: *Klebsiella pneumoniae* 16S rRNA gene (Genbank accession NR_036794.1);

SEQ ID NO:14: *Pseudomonas aeruginosa* 16S rRNA gene (Genbank accession NR_074828.1);

SEQ ID NO:15: *Acinetobacter calcoaceticus* 16S rRNA gene (Genbank accession AB302132.1);

SEQ ID NO:16: Forward Primer (CCTCTTGCCATCGGATGTG);

SEQ ID NO:17: Reverse Primer (CCAGTGTGGCTGGTCATCCT);

SEQ ID NO:18: Forward Primer (GGGAGGCAGCAGTAGGGAAT);

SEQ ID NO:19: Forward Primer (CCTACGGGAGGCAGCAGTAG);

SEQ ID NO:20: Reverse Primer (CGATCCGAAAACCTTCTTCACT);

SEQ ID NO:21: Forward Primer (AAGACGGTCTTGCTGTCACTTATAGA);

SEQ ID NO:22: Reverse Primer (CTATGCATCGTTGCCTTGGTAA);

SEQ ID NO:23: Forward Primer (TGCCGCGTGAATGAAGAA);

SEQ ID NO:24: Forward Primer (GCGTGAAGGATGAAGGCTCTA);

SEQ ID NO:25: Forward Primer (TGATGAAGGTTTTCGGATCGT);

SEQ ID NO:26: Reverse Primer (TGATGTACTATTAACACATCAACCTTCCT);

SEQ ID NO:27: Reverse Primer (CCAGTGTGGCTGGTCATCCT);

SEQ ID NO:28: Reverse Primer (CGCTCGCCACCTACGTATTAC);

SEQ ID NO:29: Forward Primer (GTTGTAAGAGAAGAACGAGTGTGAGAGT);

SEQ ID NO:30: Reverse Primer (CGTAGTTAGCCGTCCCTTTCTG);

SEQ ID NO:31: Forward Primer (GCGGTTTGTTAAGTCAGATGTGAA);

SEQ ID NO:32: Forward Primer (GGTCTGTCAAGTCGGATGTGAA);

SEQ ID NO:33: Forward Primer (TCAACCTGGGAACTCATTCGA);

SEQ ID NO:34: Reverse Primer (GGAATTCTACCCCCCTCTACGA);

SEQ ID NO:35: Reverse Primer (GGAATTCTACCCCCCTCTACAAG);

SEQ ID NO:36: *Aspergillus fumigatus* strain MJ-X6 18S ribosomal RNA gene, complete sequence (GenBank accession HM590663.1);

SEQ ID NO:37: *Candida albicans* 18S ribosomal RNA gene, complete sequence (GenBank accession AF114470.1);

SEQ ID NO:38: *Candida glabrata* strain SZ2 18S ribosomal RNA gene, partial sequence (GenBank accession KT229542.1);

SEQ ID NO:39: *Candida parapsilosis* 18S ribosomal RNA gene, partial sequence (GenBank accession DQ218328.1);

SEQ ID NO:40: *Candida tropicalis* 18S ribosomal RNA genes, partial sequence (GenBank accession AH009771.2);

SEQ ID NO:41: *Cryptococcus neoformans* var. *grubii* H99 18S ribosomal RNA rRNA (GenBank accession/NCBI Reference Sequence: XR_001045463.1);

SEQ ID NO:42: *Fusarium* sp. strain Z10 18S ribosomal RNA gene, partial sequence (GenBank accession MF973465.1);

SEQ ID NO:43: *Bacillus anthracis* strain 2000031664 16S ribosomal RNA gene, partial sequence (GenBank accession AY138383.1);

SEQ ID NO:44: *Burkholderia pseudomallei* 16S rRNA gene (GenBank accession AJ131790.1);

SEQ ID NO:45: *Clostridium botulinum* type A rrn gene for 16S RNA (GenBank accession X68185.1);

SEQ ID NO:46: *Clostridium botulinum* type B rrn gene for 16S RNA (GenBank accession X68186.1);

SEQ ID NO:47: *Clostridium botulinum* type C rrn gene for 16S rRNA (GenBank accession X68315.1);

SEQ ID NO:48: *Clostridium botulinum* type D rrn gene for 16S RNA (GenBank accession X68187.1);

SEQ ID NO:49: *Clostridium botulinum* type G rrn gene for 16S rRNA (GenBank accession X68317.1);

SEQ ID NO:50: *Francisella tularensis* strain B-38 16S ribosomal RNA, partial sequence (GenBank accession/NCBI Reference Sequence: NR_029362.1);

SEQ ID NO:51: *Vibrio cholerae* strain DL2 16S ribosomal RNA gene, partial sequence (GenBank accession MG062858.1);

SEQ ID NO:52: *Yersinia pestis* 16S rRNA gene, isolate: SS-Yp-116 (GenBank accession AJ232238.1);

SEQ ID NO:53: Forward Primer (CATCCAAGGAAGGCAGCAGGCGCG);

SEQ ID NO:54: Reverse Primer (GTTCAACTACGAGCTTTTTAAC);

SEQ ID NO:55: Reverse Primer (GTTCGACTACGAGCTTTTTAAC);

SEQ ID NO:56: Forward Primer (GTGTAGCGGTGAAATGCGTAGAG);

SEQ ID NO:57: Reverse Primer (TCGTTTACCGTGGACTACCAGGG).

DETAILED DESCRIPTION

1. Definitions

Unless defined otherwise, all technical and scientific terms used herein have the same meaning as commonly understood by those of ordinary skill in the art to which the invention belongs. Although any methods and materials similar or equivalent to those described herein can be used in practice or testing of the present invention, preferred methods and materials are described. For the purposes of the present invention, the following terms are defined below.

The articles "a" and "an" are used herein to refer to one or to more than one (i.e., to at least one) of the grammatical objection of the article. By way of example, "an element" means one element or more than one element.

"Amplification product" or "amplicon" refers to a nucleic acid product generated by nucleic acid amplification techniques.

The term "biological sample" as used herein refers to a sample that may be extracted, untreated, treated, diluted or concentrated from a patient or subject. Suitably, the biological sample is selected from any part of a patient or subject's body, including, but not limited to, hair, skin, nails, tissues or bodily fluids such as sputum, saliva, cerebrospinal fluid, urine and blood.

In the present specification and claims (if any), the word "comprising" and its derivatives including "comprises" and "comprise" include each of the stated integers but does not exclude the inclusion of one or more further integers.

As used herein, "corresponding" nucleic acid positions or nucleotides refer to positions or nucleotides that occur at aligned loci of two or more nucleic acid molecules. Related or variant polynucleotides can be aligned by any method known to those of skill in the art. Such methods typically maximise matches, and include methods such as using manual alignments and by using the numerous alignment programs available (e.g., BLASTN) and others known to those of skill in the art. By aligning the sequences of polynucleotides, one skilled in the art can identify corresponding nucleotides or positions using identical nucleotides as guides. For example, by aligning sequences of the gene encoding the *E. coli* 16S rRNA (set forth in SEQ ID NO:1) with a gene encoding a 16S rRNA from another species, one of skill in the art can identify corresponding positions and nucleotides using conserved nucleotides as guides.

By "gene" is meant a unit of inheritance that occupies a specific locus on a genome and consists of transcriptional and/or translational regulatory sequences and/or a coding region and/or non-translated sequences (i.e., introns, 5' and 3' untranslated sequences).

By "gene product" is meant a product of the gene. For example, a gene product of the 16S rRNA gene includes 16S rRNA. Similarly, a gene product of the 18S rRNA gene includes 18S rRNA. Gene products also include, for example, cDNA sequences derived from the rRNA sequences. Gene products may also include products of the rRNA in which a SNP in the rRNA gene would result in a corresponding change in the product.

"Homology" refers to the percentage number of nucleic acids or amino acids that are identical or constitute conservative substitutions. Homology can be determined using sequence comparison programs such as GAP (Deveraux et al. 1984), which is incorporated herein by reference. In this way, sequences of a similar or substantially different length to those cited herein could be compared by insertion of gaps into the alignment, such gaps being determined, for example, by the comparison algorithm used by GAP.

"Hybridization" is used herein to denote the pairing of complementary nucleotide sequences to produce a DNA-DNA hybrid or a DNA-RNA hybrid. In DNA, A pairs with T and C pairs with G. In RNA, U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently. The nucleotide symbols are set forth in the following table:

TABLE 10

Nucleotide Symbols

| Symbol | Description |
|---|---|
| A | Adenosine |
| C | Cytidine |
| G | Guanosine |
| T | Thymidine |
| U | Uridine |
| M | Amino (adenosine, cytosine) |
| K | Keto (guanosine, thymidine) |
| R | Purine (adenosine, guanosine) |
| Y | Pyrimidine (cytosine, thymidine) |
| N | Any nucleotide |

By "isolated" is meant material that is substantially or essentially free from components that normally accompany it in its native state.

The term "oligonucleotide" as used herein refers to a polymer composed of a multiplicity of nucleotide residues (deoxynucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length generally from about 10 to 30 nucleotide residues, but the term can refer to molecules of any length, although the term "polynucleotide" or "nucleic acid" is typically used for large oligonucleotides.

The terms "patient" and "subject" are used interchangeably and refer to patients and subjects of human or other mammal and includes any individual being examined or treated using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., koalas, bears, wild cats, wild dogs, wolves, dingoes, foxes and the like).

The term "polymorphism" as used herein refers to a difference in the nucleotide or amino acid sequence of a given region as compared to a nucleotide or amino acid sequence in a homologous-region of another individual, in particular, a difference in the nucleotide or amino acid sequence of a given region which differs between individuals of the same species. A polymorphism is generally defined in relation to a reference sequence. Polymorphisms include single nucleotide differences, differences in more than one nucleotide, and single or multiple nucleotide insertions, inversions and deletions; as well as single amino acid differences, differences in sequence of more than one amino acid, and single or multiple amino acid insertions, inversions and deletions. A "polymorphic site" is the locus at which variation occurs. It shall be understood that where a polymorphism is present in a nucleic acid sequence, and reference is made to the presence of a particular base or bases at a polymorphic site, the present invention encompasses the complementary base or bases on the complementary strand at that site.

The term "polynucleotide" or "nucleic acid" as used herein designates mRNA, RNA, rRNA, cRNA, cDNA, or DNA. The term typically refers to oligonucleotides greater than 30 nucleotides residues in length.

By "primer" it is meant an oligonucleotide which, when paired with a strand of DNA, is capable of initiating the synthesis of a primer extension product in the presence of a suitable polymerizing agent. The primer is preferably a single-stranded for maximum efficiency in amplification but can alternatively be double-stranded. A primer must be sufficiently long to prime the synthesis of extension products in the presence of the polymerization agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotide residues, although it can contain fewer nucleotide residues. Primers can be large polynucleotides, such as from about 200 nucleotides to several kilobases or more. Primers can be selected to be "substantially complementary" to the sequence on the template to which it is designed to hybridize and serve as a site for the initiation of synthesis. By "substantially complementary" it is meant that the primer is sufficiently complementary to hybridize with a target polynucleotide. In some embodiments, the primer contains no mismatches with the template to which it is designed to hybridize but this is not essential. For example, non-complementary nucleotide residues can be attached to the 5' end of the primer, with the remainder of the primer sequence being complementary to the template. Alternatively, non-complementary nucleotide residues or a stretch of non-complementary nucleotide residues can be interspersed into a primer, provided that the primer sequence has sufficient complementarity with the sequence of the template to hybridize therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another polynucleotide, often called the "target polynucleotide", through complementary base pairing. Probes can bind target polynucleotides lacking complete sequence complementarity with the probe, depending on the stringency of the hybridization conditions. Probes can be labelled directly or indirectly.

The term "sepsis" is used herein in accordance with its normal meaning in clinical medicine, and includes, for example systemic and/or blood-borne infections, such as bacterial infections.

The term "sepsis-associated bacteria" refers to bacteria that have been identified as being able to cause sepsis in a subject, or have been identified in the blood of a subject with sepsis. "Mammalian (e.g., human) sepsis-associated bacteria" therefore refers to bacteria that have been identified as being able to cause sepsis in a mammalian (e.g., human) subject, or have been identified in the blood of a mammalian (e.g., human) subject with sepsis. Examples of mammalian (e.g., human) sepsis-associated bacteria include *Acinetobacter baumannii, Actinobacillus hominis, Actinomyces massiliensis, Aeromonas hydrophila, Bacillus anthracis, Bacteroides fragilis, Brucella abortus, Burkholderia cepacia, Campylobacter coli, Campylobacter fetus, Campylobacter jejuni, Campylobacter lari, Cardiobacterium valvarum, Chlamydia trachomatis, Chlamydophila abortus, Chlamydophila pneumoniae, Citrobacter freundii, Clostridium difficile, Clostridium perfringens, Corynebacterium diphtheriae, Corynebacterium jeikeium, Corynebacterium urealyticum, Dermatophilus congolensis, Edwardsiella tarda, Enterobacter aerogenes, Enterobacter cloacae, Enterococcus faecalis, Enterococcus faecium, Erysipelothrix rhusiopathiae, Escherichia coli, Eubacterium desmolans, Flavobacterium ceti, Haemophilus ducreyi, Haemophilus influenzae, Haemophilus parahaemolyticus, Haemophilus parainfluenzae, Helicobacter cinaedi, Helicobacter pylori, Klebsiella oxytoca, Klebsiella pneumonia, Lactobacillus intestinalis, Legionella pneumophila, Leptospira interrogans, Listeria monocytogenes, Micrococcus luteus, Mobiluncus curtisii, Moraxella catarrhalis, Morganella morganii, Mycobacterium tuberculosis, Neisseria gonorrhoeae, Neisseria meningitidis, Nocardia asteroids, Nocardia brasiliensis, Pasteurella multocida, Peptostreptococcus stomatis, Porphyromonas gingivalis, Prevotella buccae, Prevotella intermedia, Prevotella melaninogenica, Proteus mirabilis, Providencia alcalifaciens, Pseudomonas aeruginosa, Rhodococcus equi, Salmonella enterica, Serratia marcescens, Shigella dysenteriae, Shigella sonnei, Staphylococcus aureus, Staphylococcus epidermidis, Staphylococcus haemolyticus, Staphylococcus hominis, Staphylococcus saprophyticus, Stenotrophomonas maltophila, Streptococcus agalactiae, Streptococcus anginosus, Streptococcus bovis, Streptococcus constellatus, Streptococcus dysgalactiae, Streptococcus intermedins, Streptococcus mitis, Streptococcus mutans, Streptococcus oralis, Streptococcus pneumoniae, Streptococcus pyogenes, Streptococcus sanguinis, Streptococcus sobrinus, Streptomyces anulatus, Streptomyces somaliensis, Veillonella atypica, Veillonella denticariosi, Veillonella dispar, Veillonella parvula, Veillonella rogosae, Vibrio cholerae, Yersinia enterocolitica* and *Yersinia pestis*.

As used herein, "sepsis" is defined as SIRS with a presumed or confirmed infectious process. Confirmation of infectious process can be determined using microbiological culture or isolation of the infectious agent. From an immunological perspective, sepsis may be seen as a systemic response to microorganisms or systemic infection.

"Systemic Inflammatory Response Syndrome (SIRS)," as used herein, refers to a clinical response arising from a non-specific insult with two or more of the following measureable clinical characteristics; a body temperature greater than 38° C. or less than 36° C., a heart rate greater than 90 beats per minute, a respiratory rate greater than 20 per minute, a white blood cell count (total leukocytes) greater than 12,000 per $mm^3$ or less than 4,000 per $mm^3$, or a band neutrophil percentage greater than 10%. From an immunological perspective, it may be seen as representing a systemic response to insult (e.g., major surgery) or systemic inflammation. As used herein, therefore, "infection-negative SIRS (inSIRS)" includes the clinical response noted above but in the absence of an identifiable infectious process.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which identical nucleic acid base (e.g., A, T, C, G) occurs in both sequence to yield the number of matched positions, dividing the number of matched positions by the total number of positions in the window of comparison (i.e., the window size), and multiplying the result by 100 to yield the percentage of sequence identity (% seq. identity).

As used herein, the term single nucleotide polymorphism (SNP) refers to nucleotide sequence variations that occur when a single nucleotide (A, T, C or G) in the genome sequence is altered (such as via substitutions, addition or deletion). SNPs can occur in both coding (gene) and non-coding regions of the genome such as the genome of a prokaryotic or eukaryotic microorganism.

As used herein, the terms "treatment", "treating" and the like, refer to obtaining a desired pharmacological and/or physiological effect. The effect may be prophylactic in terms of completely or partially preventing an infection, condition or symptom thereof and/or may be therapeutic in terms of a partial or complete cure for an infection, condition and/or adverse affect attributable to the infection or condition. "Treatment" as used herein covers any treatment of an infection or condition in a mammal (e.g., a human), and includes: (a) inhibiting the infection or condition, i.e., arresting its development; and (b) relieving the infection or condition, i.e., causing regression of the infection or condition.

2. Polymorphisms of the Invention

The present invention is based in part on the determination that SNPs within the 16S rRNA gene (and thus within the 16S rRNA molecule) of bacteria can be used to identify individual species of bacterium and/or classify bacteria based on genus or as Gram-positive or Gram-negative. The present invention is also based in part on the determination that SNPs within the 18S rRNA gene (and thus within the 18S rRNA molecule) can be used to identify, partially identify or classify yeast organisms or filamentous fungi.

2.1 Classification of Bacteria Using SNPs in 16S rRNA

The present invention provides methods for classifying bacterial species based on genus as well as methods for determining the Gram status of bacteria in a sample, i.e., determining whether the bacteria are Gram-positive or Gram-negative.

As demonstrated herein, polymorphisms at nucleotide positions of the gene encoding 16S rRNA (and thus of the 16S rRNA molecule itself) that correspond to positions 273 and 653 of the *E. coli* 16S rRNA gene as set forth in SEQ ID NO:1 can be used to determine the gram status of a selection of bacterial species within a sample, particularly including mammalian (e.g., human) pathogens (including the most commonly found bacterial species isolated by blood culture (Karlowsky et al. 2004)).

Most particularly and as shown in FIG. 1, the present invention provides methods for classifying bacterial species selected from among: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes.*

For example, the method for determining the Gram status of one of the bacterium listed in the above paragraph in a sample includes analysing nucleic acid from the sample for SNPs in the 16S rRNA gene (or 16S rRNA or DNA copy thereof) at positions corresponding to positions 273 and 653 of the 16S rRNA gene set forth in SEQ ID NO:1, wherein an A at position 273 and a T at position 653 indicates that the bacterium in the sample is Gram-positive.

Another method for determining the Gram status of one of the above said bacterium in a sample, includes analysing nucleic acid from the sample for SNPs in the 16S rRNA gene (or 16S rRNA or DNA copy thereof) at position 440 of the 16S rRNA gene set forth in SEQ ID NO: 1, wherein a T at position 440 indicates that the bacterium in the sample is Gram-positive.

The method for classifying at least one of the above said bacterium in a sample as belonging to a particular genus includes analysing nucleic acid from the sample for SNPs in the 16S rRNA gene (or 16S rRNA or DNA copy thereof) at positions corresponding to positions 412 and 647 of the 16S rRNA gene set forth in SEQ ID NO:1, wherein: a T at position 412 indicates that the bacterium belongs to *Staphylococcus* genus; or a G at position 647 indicates that the bacterium belongs to the *Enterococcus* genus.

2.2 Identification of Bacteria Using SNPs in 16S rRNA and Yeast Organisms and Filamentous Fungi Using 18S rRNA The present invention also provides methods for identifying bacterium in a sample.

As demonstrated herein, polymorphisms at nucleotide positions of the gene encoding 16S rRNA (and thus of the 16S rRNA molecule itself) that correspond to any one of positions 273, 378, 412, 440, 488, 647 and 653 of the *E. coli* 16S rRNA gene as set forth in SEQ ID NO:1 can be used to identify bacterium within a sample, particularly including mammalian (e.g., human) pathogens (including the most commonly found bacterial species isolated by blood culture (Karlowsky et al. 2004)).

In one embodiment, and as shown in FIG. 1, the present invention provides methods for identifying bacterium selected from among: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes.*

The general rules for identifying the above bacterial species within a sample using the above SNPs are depicted in Table 1 and/or Table 5.

From the above bacteria, the bacterium *Enterobacter cloacae* can be identified in a sample by analysing nucleic acid from the sample for an SNP in the 16S rRNA gene (or 16S rRNA or DNA copy thereof) at a position corresponding to position 653 of the 16S rRNA gene set forth in SEQ ID NO:1, wherein a G at position 653 indicates that the bacterium is *Enterobacter cloacae.*

From the above bacteria, bacterium selected from *Streptococcus agalactiae, Streptococcus pneumoniae* and *Streptococcus pyogenes* can be identified in a sample by analysing nucleic acid from the sample for SNPs in the 16S rRNA gene (or 16S rRNA or DNA copy thereof) at positions corresponding to positions 378 and 488 of the 16S rRNA gene set forth in SEQ ID NO:1, wherein: an A at position 378 and a T at position 488 indicate that the bacterium is *Streptococcus pneumoniae*; an A at positions 378 and 488 indicate that the bacterium is *Streptococcus agalactiae*; and a G at position 378 and an A at position 488 indicate that the bacterium is *Streptococcus pyogenes.*

From the above bacteria, the method can identify bacterium selected from *Acinetobacter calcoaceticus; Enterobacter cloacae; Escherichia coli; Klebsiella pneumoniae;*

*Proteus mirabilis; Pseudomonas aeruginosa; Streptococcus agalactiae; Streptococcus pneumoniae*; and *Streptococcus pyogenes* in a sample by analysing nucleic acid from the sample for SNPs in the 16S rRNA gene (or 16S rRNA or DNA copy thereof) at positions corresponding to positions 273, 378, 412, 440, 488, 647 and 653 of the 16S rRNA gene set forth in SEQ ID NO: 1, wherein: an A at positions 273, 440 and 647 indicates that the bacterium is *Acinetobacter calcoaceticus*; a G at position 653 indicates that the bacterium is *Enterobacter cloacae*; a T at positions 273 and 653 indicates that the bacterium is *E. coli*; a T at position 273, a C at positions 488 and 647 and an A at position 653 indicates that the bacterium is *Klebsiella pneumoniae*; a C at positions 440 and 488 and a T at position 647 indicates that the bacterium is *Proteus mirabilis*; an A at position 440 and a T at position 647 indicates that the bacterium is *Pseudomonas aeruginosa*; an A at positions 378, 488 and 647 indicates that the bacterium is *Streptococcus agalactiae*; a T at positions 488 and 647 indicates that the bacterium is *Streptococcus pneumoniae*; and a G at position 378 and an A at positions 488 and 647 indicates that the bacterium is *Streptococcus pyogenes.*

In addition to the above, the methods of the present invention can also be used to identify the presence of the following bacterium in a sample: *Staphylococcus aureus; S. epidermidis; Enterococcus faecalis; Enterococcus faecium; Serratia marcescens*; and *Enterobacter aerogenes*. The methods again include analysing nucleic acid from the sample for SNPs in the 16S rRNA gene (or 16S rRNA or DNA copy thereof) at positions corresponding to any one of positions 273, 378, 412, 440, 488, 647 and 653 of the 16S rRNA gene set forth in SEQ ID NO:1, wherein: a T at position 412 indicates that the sample includes the bacterium *Staphylococcus aureus* and/or *S. epidermidis*; a G at position 647 indicates that the sample includes the bacterium *Enterococcus faecalis* and/or *Enterococcus faecium*; and a C at positions 440 and 647 and a T at position 488 indicates that the sample includes the bacterium *Serratia marcescens* and/or *Enterobacter aerogenes.*

Further to the above, methods of the present invention can also be used to identify each of *Staphylococcus aureus; S. epidermidis; Enterococcus faecalis; Enterococcus faecium; Serratia marcescens*; and *Enterobacter aerogenes* in a sample. The methods include further analysing the nucleic acid from the sample with high-resolution melt analysis (see 3.8, below). High-resolution melt analysis allows nucleic acid sequences from different bacterium but containing the same SNP(s) to be differentiated from one another based upon variations in the surrounding nucleotide bases.

In another embodiment, the present invention provides methods for identifying bacterium selected from among: *Escherichia coli, Streptococcus pneumoniae, Streptococcus agalactiae, Streptococcus pyogenes, Proteus mirabilis, Enterobacter cloacae, Klebsiella pneumoniae, Pseudomonas aeruginosa, Acinetobacter calcoaceticus, Enterococcus faecalis, Listeria monocytogenes, Staphylococcus aureus, Clostridium perfringens, Corynebacterium jeikeium, Bacteroides fragilis, Neisseria meningitidis, Haemophilus influenzae, Serratia marcescens, Salmonella* sp., and *Staphylococcus epidermidis*. The general rules for identifying the above bacterial species within a sample using the above SNPs are depicted in Table 2.

Similarly, as demonstrated herein, polymorphisms at nucleotide positions of the gene encoding 16S rRNA (and thus of the rRNA molecule itself) that correspond to positions 746, 764, 771, or 785 of the *Bacillus anthracis* 16S rRNA gene as set forth in SEQ ID NO:43 (or positions 737, 755, 762, or 776 of the 16S rRNA gene as set forth in SEQ ID NO:1) can be used to identify bacterium within a sample, particularly including mammalian (e.g., human) pathogens (including pathogens known as Security Sensitive Biological Agents).

In one embodiment, there is provided methods for identifying bacterium selected from among: *Bacillus anthracis, Clostridium botulinum* type A, *Clostridium botulinum* type B, *Clostridium botulinum* type C, *Clostridium botulinum* type D, *Clostridium botulinum* type G, *Yersinia pestis, Francisella tularensis, Vibrio cholerae* and *Burkholderia pseudomallei.*

The general rules for identifying the above bacterial species within a sample using the above SNPs are depicted in Table 3 and/or Table 6.

From the above bacteria, the bacterium *Bacillus anthracis* can be identified in a sample by analysing nucleic acid from the sample for an SNP in the 16S rRNA gene (or 16S rRNA or DNA copy thereof) of SEQ ID NO. 43, where a T at position 746, A at position 764, C at position 771 and G at position 785 indicates that the bacterium is *Bacillus anthracis.*

From the above bacteria, bacterium selected from *Clostridium botulinum* type A or *Clostridium botulinum* type B can be identified in a sample by analysing nucleic acid from the sample for an SNP in the 16S rRNA gene (or 16S rRNA or DNA copy thereof) of SEQ ID NO. 43, where a T at position 746, G at position 764, C at position 771 and T at position 785 indicates that the bacterium is *Clostridium botulinum* type A or *Clostridium botulinum* type B.

From the above bacteria, the bacterium *Clostridium botulinum* type C can be identified in a sample by analysing nucleic acid from the sample for an SNP in the 16S rRNA gene (or 16S rRNA or DNA copy thereof) of SEQ ID NO. 43, where a T at position 746, A at position 764, T at position 771 and T at position 785 indicates that the bacterium is *Clostridium botulinum* type C.

From the above bacteria, the bacterium *Clostridium botulinum* type D can be identified in a sample by analysing nucleic acid from the sample for an SNP in the 16S rRNA gene (or 16S rRNA or DNA copy thereof) of SEQ ID NO. 43, where a C at position 746, A at position 764, T at position 771 and T at position 785 indicates that the bacterium is *Clostridium botulinum* type D.

From the above bacteria, the bacterium *Clostridium botulinum* type G can be identified in a sample by analysing nucleic acid from the sample for an SNP in the 16S rRNA gene (or 16S rRNA or DNA copy thereof) of SEQ ID NO. 43, where a T at position 746, G at position 764, C at position 771 and G at position 785 indicates that the bacterium is *Clostridium botulinum* type G.

From the above bacteria, the bacterium *Yersinia pestis* can be identified in a sample by analysing nucleic acid from the sample for an SNP in the 16S rRNA gene (or 16S rRNA or DNA copy thereof) of SEQ ID NO. 43, where a C at position 746, G at position 764, T at position 771 and G at position 785 indicates that the bacterium is *Yersinia pestis.*

From the above bacteria, the bacterium *Francisella tularensis* can be identified in a sample by analysing nucleic acid from the sample for an SNP in the 16S rRNA gene (or 16S rRNA or DNA copy thereof) of SEQ ID NO. 43, where a T at position 746, A at position 764, G at position 771 and G at position 785 indicates that the bacterium is *Francisella tularensis.*

From the above bacteria, the bacterium *Vibrio cholerae* can be identified in a sample by analysing nucleic acid from the sample for an SNP in the 16S rRNA gene (or 16S rRNA or DNA copy thereof) of SEQ ID NO. 43, where a C at position 746, A at position 764, T at position 771 and G at position 785 indicates that the bacterium is *Vibrio cholerae*.

From the above bacteria, the bacterium *Burkholderia pseudomallei* can be identified in a sample by analysing nucleic acid from the sample for an SNP in the 16S rRNA gene (or 16S rRNA or DNA copy thereof) of SEQ ID NO. 43, where a C at position 746, G at position 764, C at position 771 and G at position 785 indicates that the bacterium is *Burkholderia pseudomallei*.

Further to the above, methods of the present invention may also be used to identify each of *Bacillus anthracis*, *Clostridium botulinum* type A, *Clostridium botulinum* type B, *Clostridium botulinum* type C, *Clostridium botulinum* type D, *Clostridium botulinum* type G, *Yersinia pestis*, *Francisella tularensis*, *Vibrio cholerae* and *Burkholderia pseudomallei* in a sample. The methods include further analysing the nucleic acid from the sample with high-resolution melt analysis (see 3.8, below).

Similarly, as demonstrated herein, polymorphisms at nucleotide positions of the gene encoding 18S rRNA (and thus of the rRNA molecule itself) that correspond to positions 343, 371, 388, 416, and 467 of the *Candida albicans* 18S rRNA gene set forth in SEQ ID NO: 37 can be used to identify bacterium within a sample, particularly including mammalian (e.g., human) pathogens.

In one embodiment, there is provided methods for identifying a yeast organism or filamentous fungi selected from among: *Candida albicans*, *Candida tropicalis*, *Candida parapsilosis*, *Candida glabrata*, *Fusarium* spp., *Aspergillus fumigatus*, and *Cryptococcus neoformans*.

The general rules for identifying the above bacterial species within a sample using the above SNPs are depicted in Table 4 and/or Table 7.

From the above yeast organism or filamentous fungi, the yeast organism *Candida albicans* can be identified in a sample by analysing nucleic acid from the sample for an SNP in the 18S rRNA gene (or 18S rRNA or DNA copy thereof) of SEQ ID NO. 37, where a C at position 343, A at position 371, T at position 388, G at position 416 and G at position 467 indicates that the yeast organism is *Candida albicans*.

From the above yeast organism or filamentous fungi, the yeast organism *Candida tropicalis* can be identified in a sample by analysing nucleic acid from the sample for an SNP in the 18S rRNA gene (or 18S rRNA or DNA copy thereof) of SEQ ID NO. 37, where a C at position 343, A at position 371, C at position 388, G at position 416 and C at position 467 indicates that the yeast organism is *Candida tropicalis*.

From the above yeast organism or filamentous fungi, the yeast organism *Candida parapsilosis* can be identified in a sample by analysing nucleic acid from the sample for an SNP in the 18S rRNA gene (or 18S rRNA or DNA copy thereof) of SEQ ID NO. 37, where a C at position 343, A at position 371, C at position 388, G at position 416 and G at position 467 indicates that the yeast organism is *Candida parapsilosis*.

From the above yeast organism or filamentous fungi, the yeast organism *Candida glabrata* can be identified in a sample by analysing nucleic acid from the sample for an SNP in the 18S rRNA gene (or 18S rRNA or DNA copy thereof) of SEQ ID NO. 37, where a T at position 343, A at position 371, C at position 388, G at position 416 and G at position 467 indicates that the yeast organism is *Candida glabrata*.

From the above yeast organism or filamentous fungi, the yeast organism *Cryptococcus neoformans* can be identified in a sample by analysing nucleic acid from the sample for an SNP in the 18S rRNA gene (or 18S rRNA or DNA copy thereof) of SEQ ID NO. 37, where a C at position 343, A at position 371, T at position 388, T at position 416 and G at position 467 indicates that the yeast organism is *Cryptococcus neoformans*.

From the above yeast organism or filamentous fungi, the filamentous fungi *Fusarium* spp. can be identified in a sample by analysing nucleic acid from the sample for an SNP in the 18S rRNA gene (or 18S rRNA or DNA copy thereof) of SEQ ID NO. 37, where a C at position 343, C at position 371, T at position 388, T at position 416 and G at position 467 indicates that the filamentous fungi is *Fusarium* spp.

From the above yeast organism or filamentous fungi, the filamentous fungi *Aspergillus fumigatus* can be identified in a sample by analysing nucleic acid from the sample for an SNP in the 18S rRNA gene (or 18S rRNA or DNA copy thereof) of SEQ ID NO. 37, where a C at position 343, C at position 371, T at position 388, C at position 416 and G at position 467 indicates that the filamentous fungi is *Aspergillus fumigatus*.

Further to the above, methods of the present invention may also be used to identify each of *Candida albicans*, *Candida tropicalis*, *Candida parapsilosis*, *Candida glabrata*, *Fusarium* spp., *Aspergillus fumigatus*, and *Cryptococcus neoformans* in a sample. The methods include further analysing the nucleic acid from the sample with high-resolution melt analysis (see 3.8, below).

3. Screening for Specific Polymorphisms to Identify and/or Classify Bacteria, Yeast Organisms and Filamentous Fungi According to the Invention Steps/techniques of isolating a biological sample from a subject, processing a biological sample, genomic DNA extraction, RNA extraction, DNA detection and characterisation, RNA detection and characterisation, DNA sequencing, DNA sequence analyses, SNP genotyping studies, RNA location and identification, RNA profiling and RNA screening, RNA sequencing, RNA sequence analyses can be carried out in any suitable way.

Any method known in the art to detect one or more SNPs can be used in the methods described herein to classify and/or identify bacterial species within a sample. In particular embodiments, the methods also facilitate in the narrowing down or, in some cases, confirming of one bacterial species (or yeast organism or filamentous fungi species) over another. Numerous methods are known in the art for determining the nucleotide occurrence at a particular position corresponding to a single nucleotide polymorphism in a sample. The various tools for the detection of polymorphisms include, but are not limited to, DNA sequencing, scanning techniques, hybridization based techniques, extension based analysis, high-resolution melting analysis, incorporation based techniques, restriction enzyme based analysis and ligation based techniques.

The methods according to the present invention can identify polymorphisms described herein within the 16S rRNA or 18S rRNA genes, within the 16S rRNA or 18S rRNA molecule or within DNA copies thereof, and for either strand. In some examples, the methods of detecting the polymorphisms utilise a first step of amplification, and amplification can be from the 16S rRNA or 18S rRNA gene or from DNA copies of the 16S rRNA or 18S rRNA molecule.

The nucleic acid may be from a biological sample from a subject or from an environmental sample, such as an air, soil or water sample, a filtrate, a food or manufactured product, or swap from a surface, such as from a medical instrument or work place surface. The subject may be a human subject or non-human subject, such as a mammalian subject, such as a primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., koalas, bears, wild cats, wild dogs, wolves, dingoes, foxes and the like). Biological samples from a subject may be from any part of the subject's body, including but not limited to bodily fluids such as blood, saliva, sputum, urine, cerebrospinal fluid, faeces, cells, tissue or biopsies. In other examples, the nucleic acid is obtained from cultured cells.

The nucleic acid that is analysed according to the methods of the present invention may be analysed while within the sample, or may first be extracted from the sample, e.g., isolated from the sample prior to analysis. Any method for isolating nucleic acid from a sample can be used in the methods of the present invention, and such methods are well known to those of skill in the art. The extracted nucleic acid can include DNA and/or RNA (including mRNA or rRNA). In some examples, a further step of reverse transcription can be included in the methods prior to analysis. Thus, the nucleic acid to be analysed can include the 16S rRNA gene, 18S rRNA gene, 16S rRNA, 18S rRNA, a DNA copy of the 16S rRNA or the 18S rRNA or any combination thereof. The nucleic acid can also contain portions of the 16S rRNA gene, 18S rRNA gene, 16S rRNA, 18S rRNA or a DNA copy of the 16S rRNA or the 18S rRNA, providing the portions containing the nucleic acid positions that are being analysed for SNPs.

In some instances, the methods include amplification of the nucleic acid. In such instances, suitable nucleic acid amplification techniques are well known to a person or ordinary skill in the art, and include polymerase chain reaction (PCR) as for example described in Ausubel et al., Current Protocols in Molecular Biology (John Wiley & Sons, Inc. 1994-1998, strand displacement amplification (SDA) as for example described in U.S. Pat. No. 5,422,252, rolling circle replication (RCR) as for example described in Liu et al. (1996) and in WO 92/01813 and WO 97/19193, nucleic acid sequence-based amplification (NASBA) as for example described in Sooknanan et al., (1994), ligase chain reaction (LCR), simple sequence repeat analysis (SSR), branched DNA amplification assay (b-DNA), transcription amplification and self-sustained sequence replication, and Q-β replicase amplification as for example described in Tyagi et al. (1996).

Such methods can utilise one or more oligonucleotide probes or primers, including, for example, an amplification primer pair, that selectively hybridize to a target polynucleotide, which contains one or more SNPs. Oligonucleotide probes useful in practicing a method of the invention can include, for example, an oligonucleotide that is complementary to and spans a portion of the target polynucleotide, including the position of the SNP, which the presence of a specific nucleotide at the polymorphic site (i.e., the SNP) is detected by the presence or absence of selective hybridization of the probe. Such a method can further include contacting the target polynucleotide and hybridized oligonucleotide with an endonuclease, and detecting the presence or absence of a cleavage product of the probe, depending on whether the nucleotide occurrence at the polymorphic site is complementary to the corresponding nucleotide of the probe.

Primers may be manufactured using any convenient method of synthesis. Examples of such methods may be found in "Protocols for Oligonucleotides and Analogues; Synthesis and Properties", Methods in Molecular Biology Series, Volume 20, Ed. Sudhir Agrawal, Humana ISBN: 0-89603-247-7, 1993. The primers may also be labelled to facilitate detection.

Any method useful for the detection of SNPs can be used in the present invention, and many different methods are known in the art for SNP genotyping (for review see Syvanen, A. C. (2001); Kim, S. and Misra, A., (2007)). Such methodology may consist of the use of three steps in succession, including a "reaction" (e.g., hybridization, ligation, extension and cleavage) followed by "separation" (e.g., solid phase microtitre plates, microparticles or arrays, gel electrophoresis, solution-phase homogenous or semi-homogenous). No single ideal SNP genotyping method exists for all applications, and it is well within the skill of a skilled artisan to determine the most appropriate method given the various parameters, such as sample size and number of SNPs to be analysed.

Example technologies that particularly lend themselves to clinical use and that rely on querying small numbers of SNPs, are fast, sensitive (through amplification of nucleic acid in the sample), one-step, output measured in real-time, able to be multiplexed and automated, comparatively inexpensive, and accurate include, but are not limited to, TaqMan® assays (5' nuclease assay, Applied Biosystems), high-resolution melt analysis, molecular beacon probes such as LUX® (Invitrogen) or Scorpion® probes (Sigma Aldrich), and Template Directed Dye Incorporation (TDI, Perkin Elmer).

For example, TaqMan® (Applied Biosystems) uses a combination of hybridization with allele-specific probes, solution phase homogenous, and fluorescence resonance energy transfer. The TaqMan® assay relies on forward and reverse primers and Taq DNA polymerase to amplify nucleic acid in conjunction with 5'-nuclease activity of Taq DNA polymerase to degrade a labelled probe designed to bind across the SNP site(s). Reaction, separation and detection can all be performed at the same time and results read in real-time as the reaction proceeds. While such an approach does not lend itself to analysing large numbers of SNPs simultaneously it is particularly suitable for querying small numbers of SNPs quickly, sensitively and accurately at a reasonable cost.

Although some methods may be more suitable than others, any method known in the art to detect one or more SNPs can be used in the methods described herein to classify and/or identify bacteria and/or bacterium in a sample. Non-limiting examples of such methods are described below.

3.1 Nucleic Acid Sequencing Techniques

In some embodiments, the polymorphism is identified through nucleic acid sequencing techniques. Specifically, amplification products which span a SNP locus can be sequenced using traditional sequencing methodologies (e.g., the "dideoxy-mediated chain termination method", also known as the "Sanger Method" (Sanger, F., et al. (1975)) and the "chemical degradation method", also known as the "Maxam-Gilbert method" (Maxam, A. M., et al., 1977) both references are herein incorporated by reference to determine the nucleotide occurrence at the SNP loci.

Boyce-Jacino et al., U.S. Pat. No. 6,294,336 provides a solid phase sequencing method for determining the sequence of nucleic acid molecules (either DNA or RNA) by utilizing a primer that selectively binds a polynucleotide target at a site wherein the SNP is the most 3' nucleotide selectively bound to the target. Other sequencing technologies such as a Denaturing High Pressure Liquid Chromatography or mass spectrometry may also be employed.

In other illustrative examples, the sequencing method comprises a technique known as Pyrosequencing™. The approach is based on the generation of pyrophosphate whenever a deoxynucleotides is incorporated during polymerization of DNA. The generation of pyrophosphate is coupled to a luciferase-catalysed reaction resulting in light emission if the particular deoxynucleotides added is incorporated, yielding a quantitative and distinctive pyrogram. Sample processing includes PCR amplification with a biotinylated primer, isolation of the biotinylated single strand amplicon on streptavidin coated beads (or other solid phase) and annealing of a sequencing primer. Samples are then analysed by a Pyrosequence™, which adds a number of enzymes and substrates required for the indicator reaction, including sulfurylase and luciferase, as well as pyrase for degradation of unincorporated molecules. The sample is then interrogated by addition of the four deoxynucleotides. Light emission can be detected by a charge coupled device (CCD) camera and is proportional to the number of nucleotides incorporated. Results are automatically assigned by pattern recognition.

Alternatively, methods of the invention can identify nucleotide occurrences at polymorphic sites within a nucleic acid using a "micro-sequencing" method. Micro-sequencing methods determine the identity of only a single nucleotide at a "predetermined" site. Such methods have particular utility in determining the presence and identity of polymorphisms in a target polynucleotide. Such micro-sequencing methods, as well as other methods for determining the nucleotide occurrence at a polymorphic site are discussed in U.S. Pat. No. 6,294,336, which is incorporated herein by reference.

Micro-sequencing methods include the Genetic Bit Analysis™ method disclosed in WO 92/15712. Additional, primer-guided, nucleotide incorporation procedures for assaying polymorphic sites in DNA have also been described (Komher, J. S., et al., 1989); Sokolov, B. P., 1990; Syvanen, A. C., et al., 1990; Kuppuswamy, M. N., et al., 1991; Prezant, T. R., et al. 1992; Ugozzoli, L., et al., 1992; Nyren, P., et al. 1993; and WO 89/10414). These methods differ from Genetic Bit Analysis™ in that they all rely on incorporation of labelled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, A. C., et al. 1993).

Further micro-sequencing methods have been provided by U.S. Pat. No. 4,656,127 and French Patent No. 2,650,840 (WO 91/02087) which involve a solution-based method for determining the identity of a nucleotide of a polymorphic site. As in the method of the US patent, a primer is employed that is complementary to allelic sequences immediately 3' to a polymorphic site.

In other illustrative examples, U.S. Pat. No. 5,002,867, for example, describes a method for determining nucleic acid sequences via hybridization with multiple mixtures of oligonucleotide probes. In accordance with such methods, the sequence of a target polynucleotide is determined by permitting the target to sequentially hybridize with sets of probes having an invariant nucleotide at one position, and variant nucleotides at other positions. The method determines the nucleotide sequence of the target by hybridizing the target with a set of probes, and then determining the number of sites that at least one member of the set is capable of hybridizing to the target (i.e., the number of matches). The procedure is typically repeated until each member of a set of probes has been tested.

Alternatively, the template-directed dye-terminator incorporation assay with fluorescence polarization detection (FP-TDI) assay (Chen et al. 1999) is a version of the primer extension assay that is also called mini-sequencing or the single base extension assay (Syvanen, A. C., et al., 1990). The primer extension assay is capable of detecting SNPs. The DNA sequencing protocol ascertains the nature of the one base immediately 3' to the SNP-specific sequencing primer that is annealed to the target DNA immediately upstream from the polymorphic site. In the presence of DNA polymerase and the appropriate dideoxyribonucleoside triphosphate (ddNTP), the primer is extended specifically by one base as dictated by the target DNA sequence at the polymorphic site. By determining which ddNTP is incorporated, the allele(s) present in the target DNA can be inferred.

3.2 Polymorphism Hybridization Based Techniques

Hybridization techniques for detecting polymorphisms within a nucleotide sequence can include, but are not restricted to the TaqMan® assay (Applied Biosystems), dot blots, reverse dot blot, Multiplex-allele-specific diagnostic assays (MASDA), Dynamic allele-specific hybridization (DASH) (Jobs et al. 2003), molecular beacons and Southern Blots.

The TaqMan® assay (also known as a 5' nuclease assay or 5' digestion assay) for identifying SNPs within a nucleotide sequence is based on the nuclease activity of Taq polymerase that displaces and cleaves the oligonucleotide probe hybridized to the target DNA, generating a fluorescent signal. TaqMan® probes specific for a particular SNP are required, with each probe having different fluorescent dyes attached to the 5' end and quencher attached to the 3' end. When the probes are intact, the quencher interacts with the fluorophore by fluorescence resonance energy transfer (FRET), quenching their fluorescence. During the PCT annealing step, the TaqMan® probes hybridize to the target DNA. In the extension step, the fluorescent dye is cleaved by the nuclease activity of the Taq polymerase, leading to an increase in fluorescence by the reporter dye. Mismatch probes are displaced without fragmentation. The genotype of a sample is determined by measuring the signal intensity of the two different dyes.

Another useful SNP identification method includes DASH (dynamic allele-specific hybridization), which encompasses dynamic tracking of probe (oligonucleotide) to target (PCR product) hybridization as the reaction temperature is steadily increased to identify polymorphisms (Prince, J. A., et al. 2001).

In some embodiments, multiplex-allele-specific diagnostic assays (MASDA) can be used for the analysis of a large number of samples (>500). MASDA utilizes oligonucleotide hybridization to interrogate DNA sequences. Multiplex DNA samples are immobilized on a solid support and a single hybridization is performed with a pool of allele-specific oligonucleotides (ASO) probes. Any probes complementary to specific polymorphisms present in a given sample are in effect affinity purified from the pool by the target DNA. Sequence-specific band patterns (fingerprints), generated by chemical or enzymatic sequencing of the bound ASO(s), easily identify the specific mutation(s).

There are several alternative hybridization-based techniques, including, among others, molecular beacons, and Scorpion® probes (Tyagi, S. and Kramer, F. R. 1996; Thelwell et al., 2000). Molecular beacons are comprised of oligonucleotides that have fluorescent reporter and quencher dyes at their 5' and 3' ends. The central portion of the oligonucleotide hybridizes across the target sequence, but the 5' and 3' flanking regions are complementary to each other. When not hybridized to their target sequence, the 5' and 3' flanking regions hybridize to form a stem-loop structure, and there is little fluorescence because of the proximity of the reporter and quencher dyes. However, upon hybridization to their target sequence, the dyes are separated and there is a large increase in fluorescence. Mismatched probe-target hybrids dissociate at substantially lower temperature than exactly complementary hybrids. There are a number of variations of the "beacon" approach. Scorpion® probes are similar but incorporate a PCR primer sequence as part of the probe. A more recent "duplex" format has also been developed.

In some embodiments, a further method of identifying a SNP comprises the SNP-IT™ method (Orchid BioSciences, Inc., Princeton, N.J.). In general, SNP-IT™ is a 3-step primer extension reaction. In the first step a target polynucleotide is isolated from a sample by hybridization to a capture primer, which provides a first level of specificity. In a second step, the capture primer is extended from a terminating nucleotide triphosphate at the target SNP site, which provides a second level of specificity. In a third step, the extended nucleotide triphosphate can be detected using a variety of known formats, including: direct fluorescence, indirect fluorescence, an indirect colorimetric assay, mass spectrometry, fluorescence polarization, etc. Reactions can be processed in 384-well format in an automated format using a SNPstream™ instrument (Orchid BioSciences, Inc., Princeton, N.J.).

In these embodiments, the amplification products can be detected by Southern Blot analysis with or without using radioactive probes. In one such method, for example, a small sample of DNA containing a very low level of the nucleic acid sequence of the polymorphic locus is amplified, and analyzed via a Southern Blotting technique or similarly, using a dot blot analysis. The use of non-radioactive probes or labels is facilitated by the high level of the amplified signal. Alternatively, probes used to detect the amplified products can be directly or indirectly detectably labelled, for example, with a radioisotope, a fluorescent compound, a bioluminescent compound, a chemiluminescent compound, a metal chelator or an enzyme.

Hybridization conditions, such as salt concentration and temperature can also be adjusted for the nucleotide sequence to be screened. Southern blotting and hybridization protocols are described in Current Protocols in Molecular Biology (Greene Publishing Associates and Wiley-Interscience), pages 2.9.1-2.9.10. Probes can be labelled for hybridization with random oligomers and the Klenow fragment of DNA polymerase. Very high specific activity probes can be obtained using commercially available kits such as the Ready-To-Go DNA Labeling Beads (Pharmacia Biotech), following the manufacturer's protocol. Possible competition probes having high repeat sequence content, and stringency of hybridization and wash down will be determined individually for each probe used. Alternatively, fragments of a candidate sequence may be generated by PCR, the specificity may be verified using a rodent-human somatic cell hybrid panel, and sub-cloning the fragment. This allows for a large prep for sequencing and use as a probe. Once a given gene fragment has been characterized, small probe preparations can be achieved by gel or column purifying the PCR product.

Suitable materials that cane be used in the dot blot, reverse dot blot, multiplex and MASDA formats are well known in the art and include, but are not limited to nylon and nitrocellulose membranes.

3.3 Polymorphism Scanning Techniques

Scanning techniques contemplated by the present invention for detecting polymorphisms within a nucleotide sequence can include, but are not restricted to, chemical mismatch cleavage (CMC) (Saleeba, J. A et al., 1992), mismatch repair enzymes cleavage (MREC) (Lu, A. L. and Hsu, I. C, 1992), chemical cleavage techniques, denaturing gradient gel electrophoresis (DGGE) (Wartell et al., 1990; Sheffield et al., 1989), temperature gradient gel electrophoresis (TGGE) (Salimullah, et al. 2005), constant denaturant gel electrophoresis (CDGE), single strand conformation polymorphism (SSCP) analysis (Kumar, D. et al., 2006), heteroduplex analysis (HA) (Nagamine, C. M., et al., 1989), microsatellite marker analysis and single strand polymorphism assays (SSPA).

In some embodiments, the SNPs of the present invention are detected through CMC, wherein a radiolabeled DNA wild type sequence (i.e., probe) is hybridized to an amplified sequence containing the putative alteration to form a heteroduplex. A chemical modification, followed by piperidine cleavage, is used to remove the mismatch bubble in the heteroduplex. Gel electrophoresis of the denatured heteroduplex and autoradiography allow visualisation of the cleavage product. Osmium tetroxide is used for the modification of mispaired thymidines and hydroxylamine for mismatched cytosines. Additionally, labeling the antisense strand of the probe DNA allows the detection of adenosine and guanosine mismatches. The chemical cleavage of mismatch can be used to detect almost 100% of mutations in long DNA fragments. Moreover, this method provides the precise characterization and the exact location of the mutation within the tested fragment. Recently, the method has been amended to make CMC more suitable for automation by using fluorescent primers also enabling multiplexing and thereby reducing the number of manipulations. Alternatively, fluorescently labeled dUTPs incorporated via PCR allow the internal labelling of both target and probe DNA strands and therefore labelling of each possible hybrid, doubling the chances of mutation detection and virtually guaranteeing 100% detection.

In other embodiments, the mismatch repair enzymes cleavage (MREC) assay is used to identify SNPs of the present invention. MREC relies on nicking enzyme systems specific for mismatch-containing DNA. The sequence of interest is amplified by PCR and homo- and heteroduplex species may be generated at the end of the PCR, by denaturing and allowing to re-anneal the amplified products. These hybrids are treated with mismatch repair enzymes and then analysed by denaturing gel electrophoresis. The MREC assay makes use of three mismatch repair enzymes. The MutY endonuclease removes adenines from the mismatches and is useful to detect both A/T and C/G transversions and G/C and T/A transitions. Mammalian thymine glycosylase removes thymines from T/G, T/C and T/T mismatches and is useful to detect G/C and A/T transitions as well as A/T and G/C and T/A and A/T transversions. The all-type endonuclease or topoisomerase I from human or calf thymus can recognize all eight mismatches and can be used to scan any nucleotide substitution. MREC can use specific labels which can be incorporated into both DNA strands, thus allowing all four possible nucleotide substitutions in a given site to be identified.

In some embodiments, chemical cleavage analysis as described in U.S. Pat. No. 5,217,863 is used for identifying SNPs within nucleotide sequences. Like heteroduplex analysis, chemical cleavage detects different properties that result when mismatched allelic sequences hybridize with each other. Instead of detecting this difference as an altered migration rate on a gel, the difference is detected in altered susceptibility of the hybrid to chemical cleavage using, for example, hydroxylamine, or osmium tetroxide, followed by piperidine.

Among the cleavage methods contemplated by the present invention, RNAse A relies on the principle of heteroduplex mismatch analysis. In the RNAse A cleavage method, RNA-DNA heteroduplex between radiolabeled riboprobe and a DNA, obtained by PCR amplification, is enzymatically cleaved by RNAse A, by exploiting the ability of RNAse A to cleave single-stranded RNA at the points of mismatches in RNA:DNA hybrids. This is followed by electrophoresis and autoradiography. The presence and location of a mutation are indicated by a cleavage product of a given size (Meyers, R. M., et al., 1985; Gibbs, R. A. and Caskey, T., 1987).

DNA probes also can be used to detect mismatches, through enzymatic or chemical cleavage; see, e.g., Cotton, et al., 1988; Shenk et al., 1975; and Novack et al., 1986.

In some embodiments, the Invader® assay (Third Wave™ Technology) may be employed to scan for polymorphisms within the 16S rRNA genes of the present invention. For example, the Invader® assay is based on the specificity of recognition, and cleavage, by a Flap endonuclease, of the three dimensional structure formed when two overlapping oligonucleotides hybridize perfectly to a target DNA (Lyamichev, V. et al., 1999).

Alternatively, denaturing gradient gel electrophoresis (DGGE) is a useful technique to separate and identify sequence variants. DGGE is typically performed in constant-concentration polyacrylamide gel slabs, cast in the presence of linearly increasing amounts of a denaturing agent (usually formamide and urea, cathode to anode). A variant of DGGE employs temperature gradients along the migration path and is known as TGGE. Separation by DGGE or TGGE is based on the fact that the electrophoretic mobility in a gel of a partially melted DNA molecule is greatly reduced as compared to an unmelted molecule.

In some embodiments, constant denaturant gel electrophoresis (CDGE) is useful for detecting SNPs within a nucleotide sequence, as described in detail in Smith-Sorenson et al., 1993. A given DNA duplex melts in a predetermined, characteristic fashion in a gel of a constant denaturant. Mutations alter this movement. An abnormally migrating fragment is isolated and sequenced to determine the specific mutation.

In other embodiments, single-strand conformation polymorphism (SSCP) analysis provides a method for detecting SNPs of the present invention. SSCP is a method based on a change in mobility of separated single-strand DNA molecules in non-denaturing polyacrylamide gel electrophoresis. Electrophoretic mobility depends on both size and shape of a molecule, and single-stranded DNA molecules fold back on themselves and generate secondary structures, which are determined by intra-molecular interactions in a sequence dependent manner. A single nucleotide substitution can alter the secondary structure and, consequently, the electrophoretic mobility of the single strands, resulting in band shifts on autoradiographs. The ability of a given nucleotide variation to alter the conformation of the single strands is not predictable on the basis of an adequate theoretical model and base changes occurring in a loop or in a long stable stem of the secondary structure might not be detected by SSCP. Standard SSCP reaches maximal reliability in detecting sequence alterations in fragments of 150-200 bp. More advanced protocols, allowing the detection of mutations at sensitivity equal to that of the radioactively-based SSCP analysis, have been developed. These methods use fluorescence-labeled primers in the PCR and analyze the products with a fluorescence-based automated sequencing machine. Multi-colour fluorescent SSCP also allows including an internal standard in every lane, which can be used to compare data from each lane with respect to each other. Other variants to increase the detection rate include a dideoxy sequencing approach based on dideoxy fingerprinting (ddF) and restriction endonuclease fingerprinting (REF).

The ddF method is a combination of SSCP and Sanger dideoxy sequencing, which involves non-denaturing gel electrophoresis of a Sanger sequencing reaction with one dideoxynucleotide. In this way, for example, a 250-bp fragment can be screened to identify a SNP. REF is a more complex modification of SSCP allowing the screening of more than 1 kb fragments. For REF, a target sequence is amplified with PCR, digested independently with five to six different restriction endonucleases and analyzed by SSCP on a non-denaturing gel. In the case of six restriction enzymes being used, a sequence variation will be present in six different restriction fragments, thus generating 12 different single-stranded segments. A mobility shift in any one of these fragments is sufficient to pinpoint the presence of a SNP of the invention. The restriction pattern obtained enables localization of an alteration in the region examined.

In some embodiments, heteroduplex analysis (HA) detects single base substitutions in PCR products or nucleotide sequences. HA can be rapidly performed without radioisotopes or specialized equipment. The HA method takes advantage of the formation of heteroduplexes between sequences with differing nucleotides at one or more positions by heating and renaturing of PCR products. Due to a more open double-stranded configuration surrounding the mismatched bases, heteroduplexes migrate slower than their corresponding homoduplexes, and are then detected as bands of reduced mobility. The ability of a particular single base substitution to be detected by the HA method cannot be predicted merely by knowing the mismatched bases since the adjacent nucleotides have a substantial effect on the configuration of the mismatched region and length-based separation will clearly miss nucleotide substitutions. Optimization of the temperature, gel cross-linking and concentration of acrylamide used as well as glycerol and sucrose enhance the resolution of mutated samples. The HA method can be rapidly performed without radioisotopes or specialized equipment and screens large numbers of samples for known mutations and polymorphisms in sequenced genes. When HA is used in combination with SSCP, up to 100% of all alterations in a DNA fragment can be easily detected.

In some embodiments, the use of proteins that recognize nucleotide mismatches, such as the *E. coli* mutS protein can be used to detect a polymorphism within 16S rRNA of the present invention (Modrich 1991). In the mutS assay, the protein binds only to sequences that contain a nucleotide mismatch in a heteroduplex between two sequences.

In further embodiments, polymorphism detection can be performed using microsatellite marker analysis. Microsatellite markers with average genome spacing, for example of about 10 centimorgans (cM), can be employed using standard DNA isolation methods known in the art.

SSPA analysis and the closely related heteroduplex analysis methods described above may be used for screening for single-base polymorphisms (Orita, M. et al., 1989).

3.4 Nucleotide Arrays and Gene Chips for Polymorphism Analysis

The invention further contemplates methods of identifying SNPs through the use of an array of oligonucleotides, wherein discrete positions on the array are complementary to one or more of the sequences containing the SNPs of the present invention, e.g. oligonucleotides of at least 12 nt, at least about 15 nt, at least about 18 nt, at least about 20 nt, or at least about 25 nt, or longer, and including the sequence flanking the polymorphic position. Such an array may comprise a series of oligonucleotides, each of which can specifically hybridize to a different polymorphism. For examples of arrays, see Hacia et al., 1996 and De Risi et al., 1996.

A nucleotide array can include all or a subset of the polymorphisms of the invention, as required. One or more polymorphic forms may be present in the array. The oligonucleotide sequence on the array is generally at least about 12 nt in length, at least about 15 nt, at least about 18 nt, at least about 20 nt, or at least about 25 nt, or more, such as 100 to 200 nt in length. For examples of arrays, see Ramsay 1998; Hacia et al., 1996; Lockhart et al., 1996; and De Risi et al., 1996.

A number of methods are available for creating microarrays of biological samples, such as arrays of DNA samples to be used in DNA hybridization assays. Examples of such arrays are discussed in detail in PCT Application No. WO95/35505; U.S. Pat. No. 5,445,934; and Drmanac et al., 1993. Yershov et al. 1996 describes an alternative construction of an oligonucleotide array. The construction and use of oligonucleotide arrays are reviewed by Ramsay (1998).

Methods of using high-density oligonucleotide arrays for identifying polymorphisms within nucleotide sequences are known in the art. For example, Milosavljevic et al., 1996 describe DNA sequence recognition by hybridization to short oligomers (see also, Drmanac et al., 1998; and Drmanac and Drmanac, 1999). The use of arrays for identification of unknown mutations is proposed by Ginot 1997.

Detection of known mutations is described in Hacia et al. 1996; Cronin et al., 1996; and others. The use of arrays in genetic mapping is discussed in Chee et al., 1996; Sapolsky and Lishutz, 1996; and Shoemaker et al., 1996.

Quantitative monitoring of gene expression patterns with a complementary DNA microarray is described in Schena et al., 1995; and DeRisi et al., 1997. Wodicka et al., 1997 performs genome wide expression monitoring in *S. cerevisiae.*

High-density microarrays of oligonucleotides are known in the art and are commercially available. The sequence of oligonucleotides on the array will correspond to a known target sequences. The length of oligonucleotide present on the array is an important factor in how sensitive hybridization will be to the presence of a mismatch. Usually oligonucleotides will be at least about 12 nt in length, more usually at least about 15 nt in length, preferably at least about 20 nt in length and more preferably at least about 25 nt in length, and will be not longer than about 35 nt in length, usually not more than about 30 nt in length.

Methods of producing large arrays of oligonucleotides are described in U.S. Pat. Nos. 5,134,854 and 5,445,934 using light-directed synthesis techniques. Using a computer-controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in International Publication WO 95/35505.

Microarrays can be scanned to detect hybridization of the labeled genome samples. Methods and devices for detecting fluorescently marked targets on devices are known in the art. Generally such detection devices include a microscope and light source for directing light at a substrate. A photon counter detects fluorescence from the substrate, while an x-y translation stage varies the location of the substrate. A confocal detection device that may be used in the subject methods is described in U.S. Pat. No. 5,631,734. A scanning laser microscope is described in Shalon et al. 1996. A scan, using the appropriate excitation line, is performed for each fluorophore used. The digital images generated from the scan are then combined for subsequent analysis. For any particular array element, the ratio of the fluorescent signal from one nucleic acid sample is compared to the fluorescent signal from the other nucleic acid sample, and the relative signal intensity determined.

Methods for analysing the data collected by fluorescence detection are known in the art. Data analysis includes the steps of determining fluorescent intensity as a function of substrate position from the data collected, removing outliers, i.e., data deviating from a predetermined statistical distribution, and calculating the relative binding affinity of the targets from the remaining data. The resulting data may be displayed as an image with the intensity in each region varying according to the binding affinity between targets and probes.

Nucleic acid analysis via microchip technology is also applicable to the present invention. In this technique, thousands of distinct oligonucleotide probes can be applied in an array on a silicon chip. A nucleic acid to be analyzed is fluorescently labeled and hybridized to the probes on the chip. It is also possible to study nucleic acid-protein interactions using these nucleic acid microchips. Using this technique one can determine the presence of mutations, sequence the nucleic acid being analyzed, or measure expression levels of a gene of interest. The method is one of parallel processing of many, even thousands, of probes at once and can tremendously increase the rate of analysis.

Alteration of mRNA transcription can be detected by any techniques known to persons of ordinary skill in the art. These include Northern blot analysis, PCR amplification and RNase protection. Diminished mRNA transcription indicates an alteration of the sequence.

The array/chip technology has already been applied with success in numerous cases.

For example, the screening of mutations has been undertaken in the BRCA 1 gene, in *S. cerevisiae* mutant strains, and in the protease gene of HIV-1 virus (Hacia et al., 1996; Shoemaker et al., 1996; Kozal et al., 1996). Chips of various formats for use in detecting SNPs can be produced on a customized basis.

An array-based tiling strategy useful for detecting SNPs is described in EP 785280. Briefly, arrays may generally be "tiled" for a large number of specific polymorphisms. "Tiling" refers to the synthesis of a defined set of oligonucleotide probes that are made up of a sequence complementary to the target sequence of interest, as well as preselected variations of that sequence, e.g., substitution of one or more given positions with one or more members of the basis set of monomers, i.e., nucleotides. Tiling strategies are further described in PCT application No. WO 95/11995. In some embodiments, arrays are tiled for a number of specific SNPs. In particular, the array is tiled to include a number of detection blocks, each detection block being specific for a specific SNP or a set of SNPs. For example, a detection block may be tiled to include a number of probes that span the sequence segment that includes a specific SNP. To ensure probes that are complementary to each allele, the probes are synthesized in pairs differing at the SNP position. In addition to the probes differing at the SNP position, monosubstituted probes are also generally tiled within the detection block. Such methods can readily be applied to the SNP information disclosed herein.

These monosubstituted probes have bases at and up to a certain number of bases in either direction from the polymorphism, substituted with the remaining nucleotides (selected from A, T, G, C and U). Typically, the probes in a tiled detection block will include substitutions of the sequence positions up to and including those that are 5 bases away from the SNP. The monosubstituted probes provide internal controls for the tiled array, to distinguish actual hybridization from artificial cross-hybridization. Upon completion of hybridization with the target sequence and washing of the array, the array is scanned to determine the position on the array to which the target sequence hybridizes. The hybridization data from the scanned array is then analyzed to identify which allele or alleles of the SNP are present in the sample. Hybridization and scanning may be carried out as described in PCT application No. WO 92/10092 and WO 95/11995 and U.S. Pat. No. 5,424,186.

Thus, in some embodiments, the chips may comprise an array of nucleic acid sequences of fragments of about 15 nucleotides in length and the sequences complementary thereto, or a fragment thereof, the fragment comprising at least about 8 consecutive nucleotides, preferably 10, 15, 20, more preferably 25, 30, 40, 47, or 50 consecutive nucleotides and containing a polymorphic base. In some embodiments the polymorphic base is within 5, 4, 3, 2, or 1 nucleotides from the centre of the polynucleotide, more preferably at the centre of the polynucleotide. In other embodiments, the chip may comprise an array containing any number of polynucleotides of the present invention.

An oligonucleotide may be synthesized on the surface of the substrate by using a chemical coupling procedure and an ink jet application apparatus, as described in PCT application WO95/251116. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number which lends itself to the efficient use of commercially available instrumentation.

Using such arrays, the present invention provides methods of identifying the SNPs of the present invention in a sample. Such methods comprise incubating a test sample with an array comprising one or more oligonucleotide probes corresponding to at least one SNP position of the present invention, and assaying for binding of a nucleic acid from the test sample with one or more of the oligonucleotide probes. Such assays will typically involve arrays comprising oligonucleotide probes corresponding to many SNP positions and/or allelic variants of those SNP positions, at least one of which is a SNP of the present invention.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel SNPs disclosed herein. Examples of such assays can be found in Chard, T, An Introduction to Radioimmunoassay and Related Techniques, Elsevier Science Publishers, Amsterdam, The Netherlands (1986); Bullock, G. R. et al., Techniques in Immunocytochemistry, Academic Press, Orlando, Fla. Vol. 1 (I 982), Vol. 2 (1983), Vol. 3 (1985); Tijssen, P., Practice and Theory of Enzyme Immunoassays: Laboratory Techniques in Biochemistry and Molecular Biology, Elsevier Science Publishers, Amsterdam, The Netherlands (1985).

Multicomponent integrated systems may also be used to analyze SNPs. Such systems miniaturize and compartmentalize processes such as PCR and capillary electrophoresis reactions in a single functional device. An example of such technique is disclosed in U.S. Pat. No. 5,589,136, which describes the integration of PCR amplification and capillary electrophoresis in chips.

Integrated systems can be envisaged mainly when microfluidic systems are used. These systems comprise a pattern of micro-channels designed onto a glass, silicon, quartz, or plastic wafer included on a microchip. The movements of the samples are controlled by electric, electro-osmotic or hydrostatic forces applied across different areas of the microchip to create functional microscopic valves and pumps with no moving parts. Varying the voltage controls the liquid flow at intersections between the micro-machined channels and changes the liquid flow rate for pumping across different sections of the microchip.

For genotyping SNPs, the microfluidic system may integrate, for example, nucleic acid amplification, mini-sequencing primer extension, capillary electrophoresis, and a detection method such as laser induced fluorescence detection.

In a first step, the DNA samples are amplified, preferably by PCR. Then, the amplification products are subjected to automated mini-sequencing reactions using ddNTPs (specific fluorescence for each ddNTP) and the appropriate oligonucleotide mini-sequencing primers which hybridize just upstream of the targeted polymorphic base. Once the extension at the 3' end is completed, the primers are separated from the unincorporated fluorescent ddNTPs by capillary electrophoresis. The separation medium used in capillary electrophoresis can be, for example, polyacrylamide, polyethylene glycol or dextran. The incorporated ddNTPs in the single nucleotide primer extension products are identified by laser-induced fluorescence detection. This microchip can be used to process at least 96 to 384 samples, or more, in parallel. 3.5 Extension based techniques for the detection of polymorphisms Extension based techniques for detecting polymorphisms within a nucleotide sequence can include, but are not restricted to allele-specific amplification, also known as the amplification refractory mutation system (ARMS) as disclosed in European Patent Application Publication No. 0332435 and in Newton et al., 1989, and cloning of polymorphisms (COPS) as contemplated by Gibbs et al. 1989.

The extension-based technique, ARMS, uses allele specific oligonucleotide (ASO) PCR primers for genotyping. In this approach, one of the two oligonucleotide primers used for PCR is designed to bind to the polymorphic site, most commonly with the 3' end of the primer targeting the site. Under carefully controlled conditions (annealing temperature, magnesium concentration etc.), amplification only takes place if the nucleotide at the 3' end of the PCR primer is complementary to the base at the polymorphic site, with a mismatch being "refractory" to amplification.

A variation of the ARMS approach, termed mutagenically separated PCR (MS-PCR), comprises two ARMS primers of different lengths, each specific for different polymorphisms at a site. This method yields PCR products of different lengths for the different polymorphisms.

3.6 Ligation Based Assays for Detecting Polymorphisms

Another typical method of SNP detection encompasses the oligonucleotide ligation assay. A number of approaches make use of DNA ligase, an enzyme that can join two adjacent oligonucleotides hybridized to a DNA template. The specificity of the approach comes from the requirement for a perfect match between the hybridized oligonucleotides and the DNA template at the ligation site. In the oligonucleotide ligation assay (OLA), or ligase chain reaction (LCR) assay the sequence surrounding the mutation site is first amplified, and one strand serves as a template for three ligation probes, two of these are allele specific oligonucleotides (ASO) and the third a common probe. Numerous approaches can be used for the detection of the ligated products. For example, the two ASOs can be differentially labeled with fluorescent or hapten labels and ligated products detected by fluorimetric or colorimetric enzyme-linked immunosorbent assays, respectively. For electrophoresis-based systems, use of mobility modifier tags or variation in probe lengths coupled with fluorescence detection enables the multiplex genotyping of several single nucleotide substitutions in a single tube. When used on arrays, ASOs can be spotted at specific locations or addresses on a chip. PCR amplified DNA can then be added and ligation to labeled oligonucleotides at specific addresses on the array can be measured.

3.7 Signal Generating Polymorphism Detection Assays

In some embodiments, fluorescence resonance energy transfer (FRET) is contemplated as a method to identify a polymorphism within the 16S rRNA gene. FRET occurs due to the interaction between the electronic excited states of two dye molecules. The excitation is transferred from one (the donor) dye molecule to the other (the acceptor) dye molecule without emission of a photon. This is distance-dependent, that is the donor and the acceptor dye must be in close proximity. The hybridization probe system consists of two oligonucleotides labeled with fluorescent dyes. The hybridization probe pair is designed to hybridize to adjacent regions on the target DNA. Each probe is labeled with a different marker dye. Interaction of the two dyes can only occur when both are bound to their target. The donor probe is labeled with fluorophore at the 3' end and the acceptor probe at the 5' end. During PCR, the two different oligonucleotides hybridize to adjacent regions of the target DNA such that the fluorophores, which are coupled to the oligonucleotides, are in close proximity in the hybrid structure. The donor fluorophore (F1) is excited by an external light source, and then passes part of its excitation energy to the adjacent acceptor fluorophore (F2). The excited acceptor fluorophore (F2) emits light at a different wavelength which can then be detected and measured for molecular proximity.

In other embodiments, the MagSNiPer method, based on single base extension, magnetic separation, and chemiluminescence provides a further method for SNP identification in a nucleotide sequence. Single base nucleotide extension reaction is performed with a biotinylated primer whose 3' terminus is contiguous to the SNP site with a tag-labeled ddNTP. Then the primers are captured by magnetic-coated beads with streptavidin, and unincorporated labeled ddNTP is removed by magnetic separation. The magnetic beads are incubated with anti-tag antibody conjugated with alkaline phosphatase. After the removal of excess conjugates by magnetic separation, SNP typing is performed by measuring chemilummescence. The incorporation of labeled ddNTP is monitored by chemilummescence induced by alkaline phosphatase.

In some embodiments, fluorescence polarization provides a method for identifying polymorphisms within a nucleotide sequence. For example, amplified DNA containing a polymorphic is incubated with oligonucleotide primers (designed to hybridize to the DNA template adjacent to the polymorphic site) in the presence of allele-specific dye-labeled dideoxyribonucleoside triphosphates and a commercially available modified Taq DNA polymerase. The primer is extended by the dye-terminator specific for the allele present on the template, increasing approximately 10-fold the molecular weight of the fluorophore. At the end of the reaction, the fluorescence polarization of the two dye-terminators in the reaction mixture is analyzed directly without separation or purification. This homogeneous DNA diagnostic method is shown to be highly sensitive and specific and is suitable for automated genotyping of large number of samples.

In other embodiments, surface enhanced Raman scattering can be used as a method for detecting and identifying single base differences in double stranded DNA fragments (see Chumanov, G 1999). SERS has also been used for single molecule detection (Kneipp, K, 1997). SERS results in strongly increased Raman signals from molecules that have been attached to nanometer sized metallic structures.

Illustrative examples include a genotyping method discussed by Xiao and Kwok 2003 based on a primer extension assay with fluorescence quenching as the detection. The template-directed dye-terminator incorporation with fluorescence quenching detection (FQ-TDI) assay is based on the observation that the intensity of fluorescent dye R110- and R6G-labeled acycloterminators is universally quenched once they are incorporated onto a DNA oligonucleotide primer. By comparing the rate of fluorescence quenching of the two allelic dyes in real time, the frequency of SNPs in DNA samples can be measured. The kinetic FQ-TDI assay is highly accurate and reproducible both in genotyping and in allele frequency estimation.

3.8 High-Resolution Melt Analysis

In particular embodiments, the methods of the present invention utilise high-resolution melting (HRM) analysis for classifying and/or identifying bacterial or bacterium in a sample based on the SNP(s) described herein within the 16S rRNA gene, within the 16S rRNA molecule or within a DNA copy thereof.

HRM is based upon the accurate monitoring of changes in fluorescence as a PCR product (i.e., amplicon) stained with an intercalating fluorescent dye is heated through its melting temperature ($T_m$). In contrast to traditional melting, the information in HRM analysis is contained in the shape of the melting curve, rather than just the calculated $T_m$, so HRM may be considered a form of spectroscopy. HRM analysis is a single step and closed tube method, the amplification and melting can be run as a single protocol on a real-time PCR machine.

In embodiments of the present invention, the methods utilise an amplification primer pair that selectively hybridize to a target polynucleotide containing one or more of the SNPs as described herein. The amplification reaction mixture contains the fluorescent dye, which is incorporated into the resulting amplicon.

The resulting amplicon is then subjected to HRM with incremental increases in temperature (i.e., 0.01-0.5° C.) ranging from about 50° C. to about 95° C. At some point during this process, the melting temperature of the amplicon is reached and the two strands of DNA separate or "melt" apart.

The HRM is monitored in real-time using the fluorescent dye incorporated into the amplicon. The level of fluorescence of the dye is monitored as the temperature increases with the fluorescence reducing as the amount of double stranded DNA reduces. Changes in fluorescence and temperature can be plotted in a graph known as a melt curve.

As a skilled addressee will understand, the $T_m$ of the amplicon at which the two DNA strands separate is predictable, being dependent on the sequence of the nucleotide bases forming the amplicon. Accordingly, it is possible to differentiate between amplicons including an amplicon containing a polymorphism (i.e., a SNP or SNPs) as the melt curves will appear different. Indeed, in some embodiments, it is possible to differentiate between amplicons containing the same polymorphism based on differences in the surrounding DNA sequences.

HRM curves can be discriminated from one another by many different strategies. For example, in many cases, HRM curves can be discriminated on the basis of obvious differences in curve shape and/or on the basis of T, with a difference of 0.2° C. being regarded as significant. In other cases, a difference graph analysis can be used in which a defined curve is used as a baseline with other normalised curves being plotted in relation to the baseline (see Price, E. P. et al. 2007). In yet other cases, a difference graph-based method can be used involving deriving the 3rd and 97th centiles from the mean±1.96 standard deviations for the fluorescence at every temperature (see Andersson, P. et al., 2009; and Merchant-Patel, S. et al. 2008).

4. Tools, Reagents, Primers, Probes, Kits and Processing Systems

The specification explains how various SNPs can be used as 'tools' for identifying, partially identifying or classifying a bacterium, yeast organism or filamentous fungi, or diagnosing a bacterial, yeast organism or filamentous fungi infection. This SNP finding enables the inventors to develop gene/allele-based and gene product-based probes, tools, reagents, methods and assays for identifying, partially identifying or classifying a bacterium, yeast organism or filamentous fungi, or diagnosing a bacterial, yeast organism or filamentous fungi infection.

One of skill in the art could readily design, produce or manufacture a wide range of gene/allele-based and gene product-based probes, tools, reagents, methods and assays based on the information provided in the specification and especially in Tables 1 to 9 and 11.

Generally speaking, such probes, tools or reagents based on or developed in view of the SNPs outlined in the present specification may, for example, specifically bind, detect, identify, characterise or quantify the gene or part of the gene, the RNA gene product or part of the RNA gene product, or other gene products or parts thereof.

Generally speaking, such probe, tool or reagent can be for detection of a polymorphism for example at the genomic level, or at the transcription level.

Generally speaking, such probe, tool or reagent can also be an antibody or other type of molecule or chemical entity capable of detecting the gene or gene product (such as RNA).

More specifically, probes, tools and reagents may include, but are not limited to, the following:

1. An isolated, purified, synthetic or recombinant form of 16S rRNA, 16S rDNA, 18S rRNA or 18S rDNA, or a fragment thereof, including a fragment containing a SNP of interest—single stranded or double stranded.
2. A non-naturally occurring polynucleotide, recombinant polynucleotide, oligonucleotide or cDNA form of 16S rRNA, 16S rDNA, 18S rRNA or 18S rDNA, or a fragment thereof, including a fragment containing a SNP of interest—single stranded or double stranded.
3. An expression vector, recombinant cell or biological sample comprising the nucleic acid or polynucleotide of 1 or 2.

The probe, tool or reagent can be, but is not limited to, an antibody or other type of molecule or chemical entity capable of detecting the gene or gene product (RNA or polypeptide).

The at least one probe, tool or reagent can be any number or combination of the above, and the number and combination will depend on the desired result to be achieved—eg. detection of a polymorphism at the genomic level (genotyping), at the RNA level.

All the essential materials and reagents required for detecting one or more SNPs in the 16S rRNA gene or 18S rRNA gene according to the invention may be assembled together in a kit. The kits may also optionally include appropriate reagents for detection of labels, positive and negative controls, fluorescent dyes, washing solutions, blotting membranes, microtitre plates, dilution buffers and the like. For example, a nucleic acid-based detection kit for the identification of polymorphisms may include one or more of the following: (i) nucleic acid from a Gram-positive cell and/or Gram-negative cell (which may be used as a positive control); and (ii) a primer and/or probe that specifically hybridizes to at least a portion of the 16S rRNA gene or 18S rRNA gene containing the SNP position(s) to be analysed, and optionally one or more other markers, at or around the suspected SNP site. Also included may be enzymes suitable for amplifying nucleic acids including various polymerases (Reverse Transcriptase, Taq, Sequenase™ DNA ligase etc. depending on the nucleic acid amplification technique employed), deoxynucleotides and buffers to provide the necessary reaction mixture for amplification. Such kits also generally will comprise, in suitable means, distinct containers for each individual reagent and enzyme as well as for each primer or probe. The kit can also feature various devices and reagents for performing one of the assays described herein; and/or printed instructions for using the kit to identify the presence of a SNP as defined herein.

In some embodiments, the methods described generally herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to detect the presence of an SNP at a position by detecting the hybridization of a probe to a nucleic acid molecule. A processing system also can be used to determine the Gram status or identity or grouping of a bacterium on the basis of detection of one or more SNPs. In some examples, commands inputted to the processing system by a user may assist the processing system in making these determinations.

In one example, a processing system includes at least one microprocessor, a memory, an input/output device, such as a keyboard and/or display, and an external interface, interconnected via a bus. The external interface can be utilised for connecting the processing system to peripheral devices, such as a communications network, database, or storage devices. The microprocessor can execute instructions in the form of applications software stored in the memory to allow the SNP detection and/or microorganism identification or classification process to be performed, as well as to perform any other required processes, such as communicating with the computer systems. The application software may include one or more software modules, and may be executed in a suitable execution environment, such as an operating system environment, or the like.

4.1 Primers, Probes, Kits and Processing Systems for the 16S rRNA Gene or the 18S rRNA Gene The present invention provides probes and primers that may be used in the methods described herein to determine SNPs at one or more positions of the 16S rRNA gene or 18S rRNA gene so as to classify and/or identify bacteria or bacterium, yeast organism or filamentous fungi in a sample.

The primers and probes of the present invention hybridize to at least a portion of the 16S rRNA gene or the 18S rRNA gene (or 16S rRNA molecules or DNA copies thereof or 18S rRNA molecules or DNA copies thereof) containing the SNP position(s). For example, the primers may hybridize to a sequence flanking one or more SNPs, and the probe may hybridize to a sequence that includes one or more SNPs. It is well within the skill of a skilled artisan to design appropriate primers and probes for use in the methods of the present invention, based on the known sequences of the 16S rRNA gene or the 18S rRNA gene.

Non-limiting examples of primers and probes that are useful for the methods of the present invention, in which SNPs in the 16S rRNA of bacterial species at positions corresponding to positions 273, 378, 412, 440, 488, 647 and/or 653 of the 16S rRNA gene set forth in SEQ ID NO:1 are analysed, include those described in Example 1.

For example, to detect SNPs at position 273 an exemplary forward primer includes CCTCTTGCCATCGGATGTG (SEQ ID NO:16) and exemplary reverse primers include CCAGTGTGGCTGGTCATCCT (SEQ ID NO:17), CGATCCGAAAACCTTCTTCACT (SEQ ID NO:20), CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 378, exemplary forward primers include CCTCTTGCCATCGGATGTG (SEQ ID NO:16), CCTACGGGAGGCAGCAGTAG (SEQ ID NO:18), and GGGAGGCAGCAGTAGGGAAT (SEQ ID NO:19); and exemplary reverse primers include CGATCCGAAAACCTTCTTCACT (SEQ ID NO:20), CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 412, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), and AAGACGGTCTTGCTGTCACTTATAGA (SEQ ID NO:21); and exemplary reverse primers include CTATGCATCGTTGCCTTGGTAA (SEQ ID NO:22), TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 440, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), and TGATGAAGGTTTTCGGATCGT (SEQ ID NO:25); and exemplary reverse primers include TGATGTACTATTAACACATCAACCTTCCT (SEQ ID NO:26), AACGCTCGGATCTTCCGTATTA (SEQ ID NO:27), CGCTCGCCACCTACGTATTAC (SEQ ID NO:28), CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at position 488, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), TGATGAAGGTTTTCGGATCGT (SEQ ID NO:25), and GTTGTAAGAGAAGAACGAGTGTGAGAGT (SEQ ID NO:29); and exemplary reverse primers include CGTAGTTAGCCGTCCCTTTCTG (SEQ ID NO:30), GGAATTCTACCCCCCTCTACGA (SEQ ID NO:34), and GGAATTCTACCCCCCTCTACAAG (SEQ ID NO:35).

To detect SNPs at positions 647 and/or 653, exemplary forward primers include CCTCTTGCCATCGGATGTG (SEQ ID NO:16), CCTACGGGAGGCAGCAGTAG (SEQ ID NO:18), GGGAGGCAGCAGTAGGGAAT (SEQ ID NO:19), AAGACGGTCTTGCTGTCACTTATAGA (SEQ ID NO:21), TGCCGCGTGAATGAAGAA (SEQ ID NO:23), GCGTGAAGGATGAAGGCTCTA (SEQ ID NO:24), TGATGAAGGTTTTCGGATCGT (SEQ ID NO:25), GTTGTAAGAGAAGAACGAGTGTGAGAGT (SEQ ID NO:29), GCGGTTTGTTAAGTCAGATGTGAA (SEQ ID NO:31), GGTCTGTCAAGTCGGATGTGAA (SEQ ID NO:32), and TCAACCTGGGAACTCATTCGA (SEQ ID NO:33); and exemplary reverse primers include GGAATTCTACCCCCCTCTACGA (SEQ ID NO:34), and GGAATTCTACCCCCCTCTACAAG (SEQ ID NO:35).

Similarly, non-limiting examples of primers and probes that are useful for the methods of the present invention, in which SNPs in the 16S rRNA gene or 16S rRNA of bacterial species at positions corresponding to positions corresponding to positions 746, 764, 771, or 785 of the 16S rRNA gene as set forth in SEQ ID NO:43 (or positions 737, 755, 762, or 776 of the 16S rRNA gene as set forth in SEQ ID NO:1) are analysed, include those described in Table 8.

Similarly, non-limiting examples of primers and probes that are useful for the methods of the present invention, in which SNPs in the 18S rRNA gene or 18S rRNA of bacterial species at positions 343, 371, 388, 416, and 467 of the 18S rRNA gene set forth in SEQ ID NO: 37 are analysed, include those described in Table 9.

5. Applications of the Methods of the Present Invention

The methods of the present invention are useful for classifying and/or identifying bacteria, yeast organism or filamentous fungi in a sample, such as a sample from a subject or an environmental sample such as a soil or water sample or a sample taken from the surface of equipment or instruments (e.g. medical or surgical instruments) or a work surface. Such classification or identification can then be used to determine a course of treatment to remove, eradicate or reduce the number of bacteria, yeast organism or filamentous fungi. Any two or more of the methods of the present invention can be combined. For example, nucleic acid from a sample can be analysed for the presence of SNPs in a 16S rRNA gene using the methods of the present invention. This can be done so as to determine whether Gram-positive bacteria or Gram-negative bacteria are present in the sample. The bacteria can be further grouped or the identity of the bacterium may also be determined or narrowed down to one of a few possibilities. For example, as would be apparent from the disclosure above, SNPs at positions corresponding to positions 273, 378, 412, 440, 488, 647 and 653 of the 16S rRNA gene set forth in SEQ ID NO: 1 can be assessed so as to classify or even identify a bacterium in a sample.

Subjects with infections or suspected infections often present to clinicians in clinics, emergency rooms, general wards and intensive care units. Such patients often have non-diagnostic clinical signs of abnormal temperature, increased heart and respiratory rates and abnormal white cells counts. A clinician must decide whether the patient has an infection or not, the severity of the infection, whether to admit the patient to hospital (if not already in hospital), the source of infection, whether to use antibiotics, and if so, the type, route and dose of antibiotics. The presence of an infection in a patient has most typically been assessed by taking a sample from the patient and growing an organism in culture broth. Once an organism has grown it can be Gram stained and identified. However, in many infected patients (>50) it is not possible to culture an organism. Without an identified organism, a clinician must rely on clinical judgment and the use of broad spectrum antibiotics often in combinations. The indiscriminate use of broad-spectrum antibiotics, without knowledge of the pathogenic organism's identity or sensitivity, results in the development of antibiotic resistance, overuse of antibiotics, and potentially toxic side effects in patients. Blood culture is a sensitive method (1-100 cfu/mL) but only when the blood sample taken contains a viable organism, which is not always the case.

Thus, the methods of the present invention are particularly useful in assisting clinicians in determining whether the subject has an infection and if so, an appropriate course of treatment based on the classification of the bacteria, yeast organism or filamentous fungi causing the infection.

Furthermore, the methods of the present invention facilitate discrimination of Gram-positive and Gram-negative organisms within hours of taking a whole blood from a subject. The methods of the present invention also can be performed in a time-efficient manner, so that the results are available to the clinician within hours rather than days. Such attributes allow a clinician to sensitively detect the presence of a bacterium, yeast organism or filamentous fungi and to make an informed decision on treatment (such as the use of antibiotics specific to the Gram status or further grouping or identification of the bacterium). These improvements can result in a reduced number of patients admitted to hospital unnecessarily, sensitive detection of bacteria, yeast organisms and filamentous fungi, severity of infection assessed on load (and other factors), reduced use of broad-spectrum antibiotics/medicines, reduced patient time on broad spectrum antibiotics, reduced toxicity from antibiotics/medicines, reduced development of resistance to medicines (especially antibiotic resistance).

The present invention also extends to diagnosing a bacterial, yeast organism or filamentous fungi infection in a subject, and the management of the infection following a positive diagnosis. The methods described herein that analyse one or more SNPs within a 16S rRNA or 18S rRNA can be used to determine whether a subject has a bacterial, yeast organism or filamentous fungi infection and/or identify the group or species of bacteria, yeast organism or filamentous fungi in the sample. The methods described herein can be further used to classify a bacteria as Gram-positive or Gram-negative.

5.1 Management and Therapy

Based on the results of the methods of the present invention, the subject can be appropriately managed and administered therapy where required. For example, the management of a bacterial infection can include, for example, administration of therapeutic agents such as a therapeutically effective course of antibiotics.

Typically, therapeutic agents will be administered in pharmaceutical (or veterinary if the subject is a non-human subject) compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of the infection, and/or the reduction or elimination of the bacteria from the subject. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner. In determining the effective amount of the active compound(s) to be administered in the treatment or prevention of the bacterial infection, the practitioner may evaluate severity of infection, and severity of any symptom associated with the infection including, inflammation, blood pressure anomaly, tachycardia, tachypnoea, fever, chills, vomiting, diarrhoea, skin rash, headaches, confusion, muscle aches and seizures. In any event, those of skill in the art may readily determine suitable dosages of the therapeutic agents and suitable treatment regimens without undue experimentation.

The therapeutic agents may be administered in concert with adjunctive (palliative) therapies to increase oxygen supply to major organs, increase blood flow to major organs and/or to reduce the inflammatory response. Illustrative examples of such adjunctive therapies include non steroidal-anti inflammatory drugs (NSAIDs), intravenous saline and oxygen.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The disclosure of every patent, patent application and publication cited herein is hereby incorporated herein by reference in its entirety.

In order that the invention may be readily understood and put into practical effect, particular preferred embodiments will now be described by way of the following non-limiting examples.

EXAMPLES

Example 1

The aim of this experiment was to differentiate 15 of the most prevalent bacterial species frequently isolated from patients diagnosed with sepsis using the 16S rRNA SNP-HRM assay of the present invention.

Experimental Procedures

In total, the following 15 bacterial species were tested: *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae*; and *Streptococcus pyogenes*.

The bacterial species were cultured in Brain Heart Infusion broth overnight at 37° C. whereafter genomic DNA was extracted from each isolate using QIAgen DNeasy Blood and Tissue Kit (Qiagen, Australia).

16S rDNA-SNP primers (of SEQ ID NOs:16-35, made by Sigma Aldrich, Australia) were designed to amplify the regions encompassing the seven SNPs designated as follows: SNP273, SNP378, SNP412, SNP440, SNP488, SNP647 and SNP653 of the 16S rRNA gene as set forth in SEQ ID NO: 1. PCR product sizes ranged from 79 bp to 96 bp.

Real-Time PCR followed by HRM analysis was used to differentiate the 15 bacterial species. The Real-Time PCR HRM process was: 1 μl of extracted DNA (1-3 ng) was added to 19 μl of reaction mastermix containing 10 μl of the 2×SYBR green PCR Mastermix (Invitrogen, Australia) and 8 pmol of each primer. Temperature cycling for these reactions were as follows: 50° C. for 2 min, 95° C. for 2 min, followed by 40 cycles of 95° C. for 15s, 52° C. for 20s, and 72° C. for 35s, hold at 72° C. for 2 min, hold at 50° C. for 20s, HRM: ramp from 65° C. to 95° C. rising by 0.05° C. (Rotor-Gene 6000, Qiagen, Australia).

The Rotor-Gene 6000 software (version 1.7.34 or 1.7.87) was used to analyse the HRM data in multiple ways. A normalised raw melt curve depicts decreasing fluorescence versus increasing temperature, and the difference curve, which displays a user-defined curve as the baseline (i.e., the x-axis), and depicts other normalised curves in relation to that baseline. Criteria for calling melting curves as "same" or "different" using difference graphs have been developed and published previously by the inventor and her co-workers (see, e.g., Stephens, A. J., et al. 2008; Merchant-Patel, S., et al. 2010).

There are two ways that HRM curve plots can discriminate between samples. The shape of the melt curve indicates the details in the shape of the curve, and the curve shift indicates a thermal (temperature) offset of a curve from other curves.

The software allows HRM melt curve analysis using either as normalised melt curves or as difference curves as generally described above. Normalisation curve analysis allows all the HRM curves to be compared with the same starting and ending fluorescent signal level to aid interpretation and analysis. The difference curve analysis displays differences between the melt curves of each sample and a given control.

In this experiment, both the shape and shift approach was used to discriminate the HRM curves for each bacterial species tested. For determining the shift in the melting temperature for each respective bacterial species, a melting temperature difference of 0.2° C. was regarded as a significant difference between each bacterial species' melt curves.

For determining the shape differences between bacterial species, the difference curve analysis was used. An amplitude difference of >5 normalised fluorescence units is indicative that different bacterial species melt curves are different to the comparator species. Hence these differences in the shape of the curve indicate differences in the DNA sequences of each respective bacterial species.

Results

FIGS. 2 to 11 depict normalised and difference melting curves plots used to differentiate the 15 bacterial species tested in this example.

Figure 3:
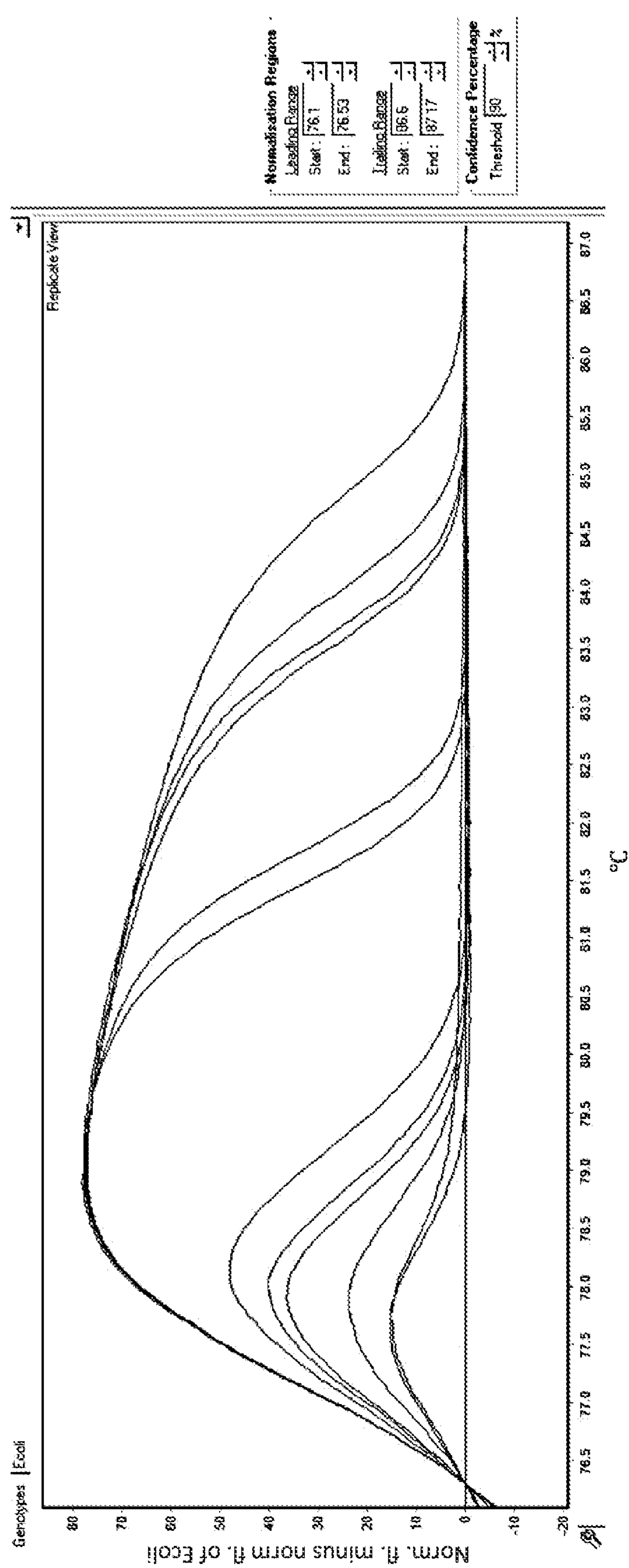
FIG. 3 shows a difference HRM curves plot for the 15 bacterial species shown in FIG. 2 with *Escherichia coli* used as a baseline.
Figure 4:
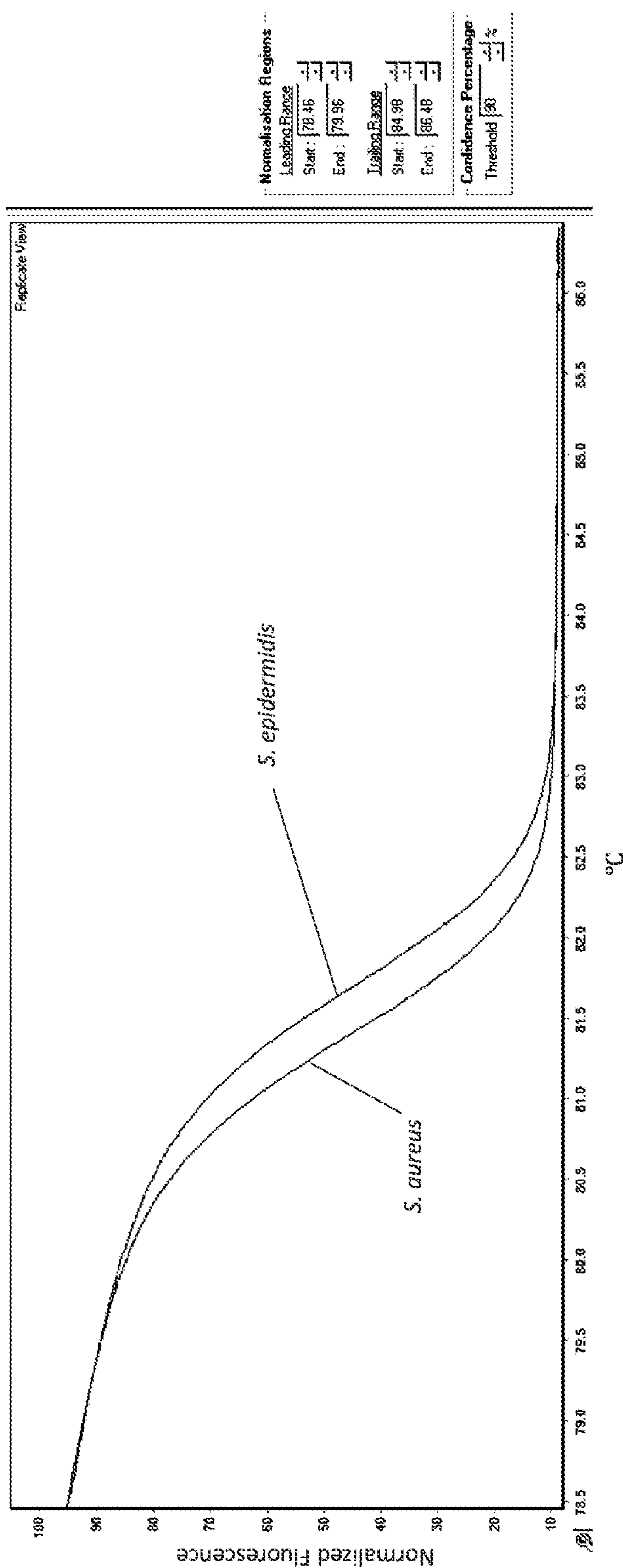
FIG. 4 shows a normalised HRM curves plot for *Staphylococcus aureus* and *Staphylococcus epidermidis* for amplicons containing a SNP at a position corresponding to position 412 in the 16S rRNA gene as set forth in SEQ ID NO:1.
Figure 5:
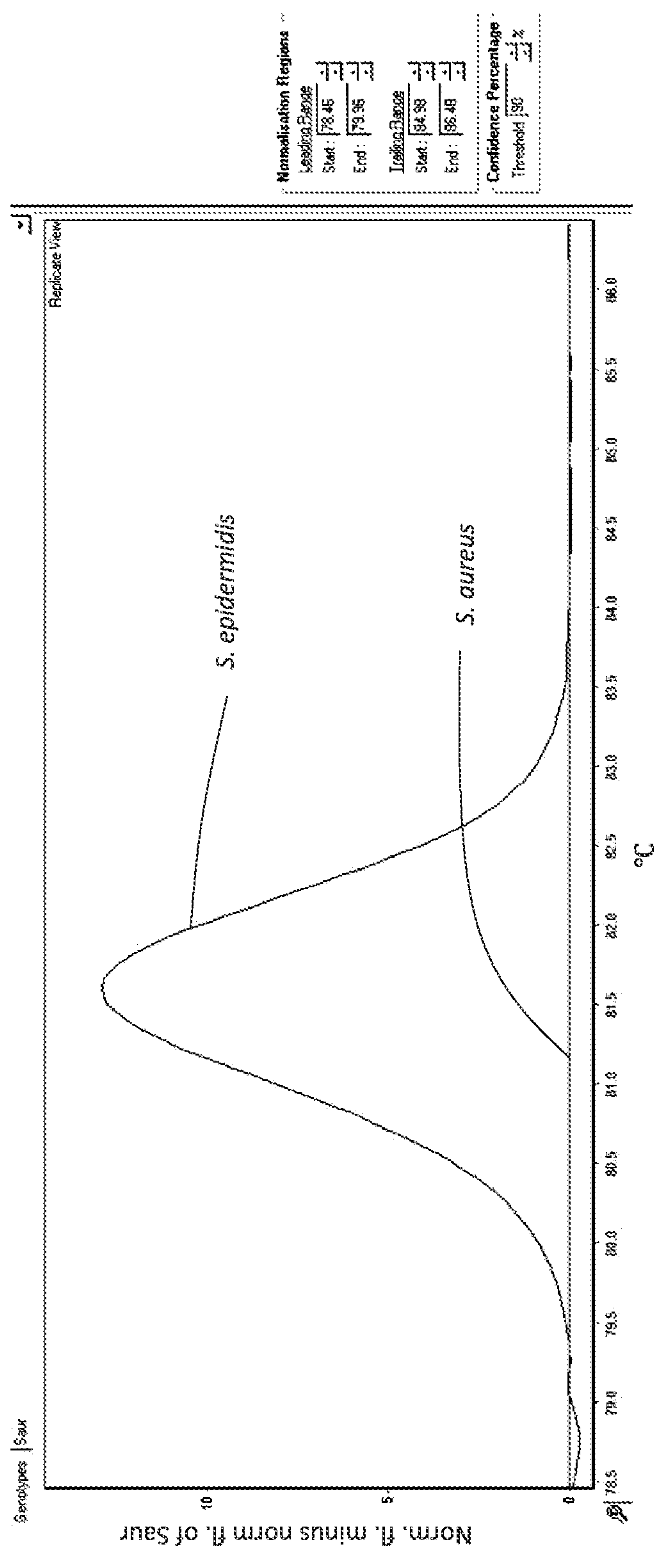
FIG. 5 shows a difference HRM curves plot for *Staphylococcus aureus* and *Staphylococcus epidermidis* as shown in FIG. 4 with *S. aureus* used as the baseline.
Figure 6:
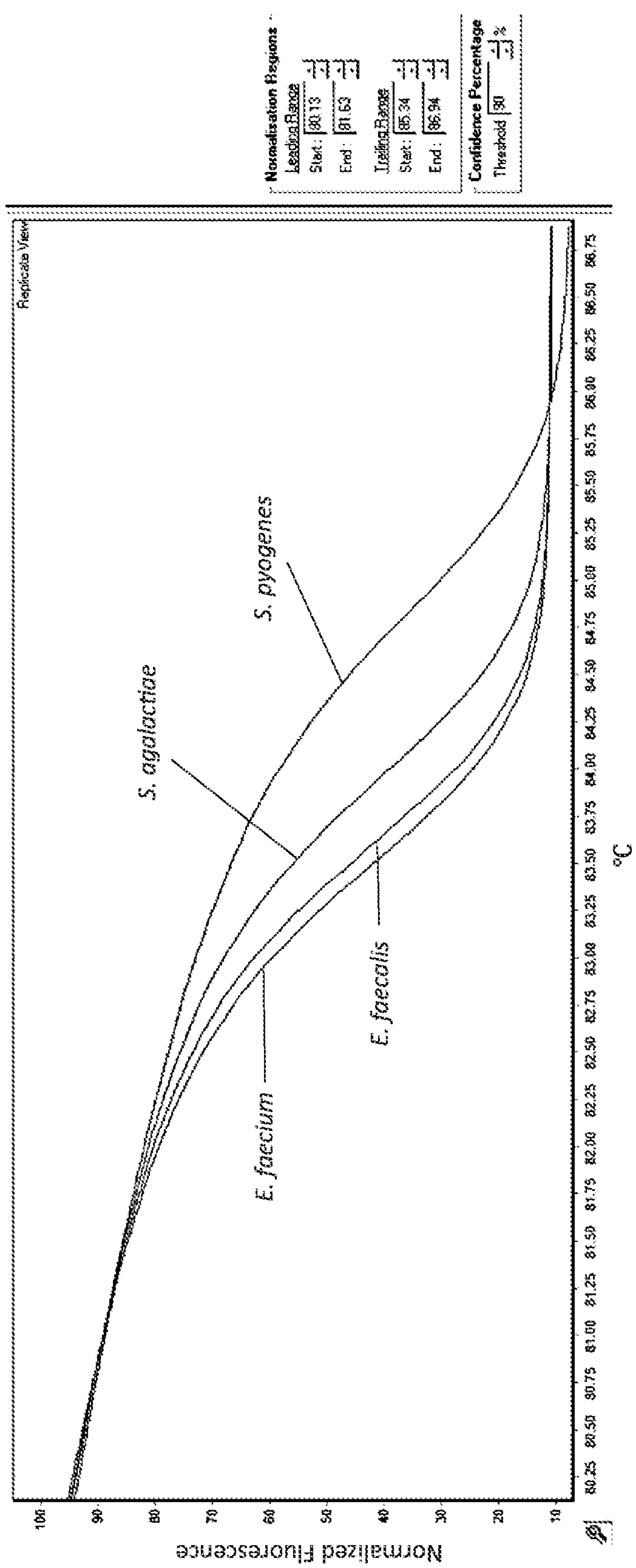
FIG. 6 shows a normalised HRM curves plot for *Enterococcus faecalis, Enterococcus faecium, Streptococcus agalactiae; Streptococcus pneumoniae* and *Streptococcus pyogenes* for amplicons containing a SNP at a position corresponding to position 378 in the 16S rRNA gene as set forth in SEQ ID NO:1.
Figure 7:
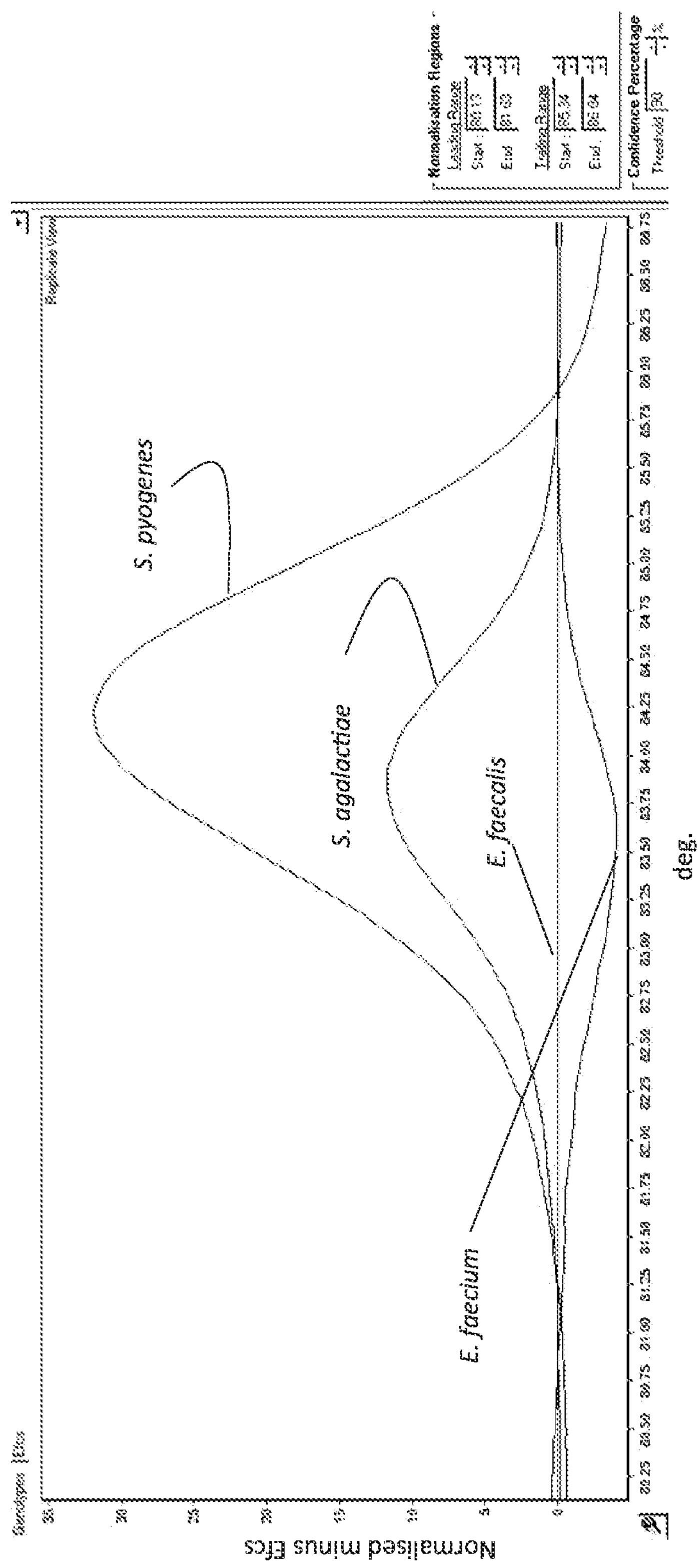
FIG. 7 shows a difference HRM curves plot for *Enterococcus faecalis, Enterococcus faecium, Streptococcus agalactiae; Streptococcus pneumoniae* and *Streptococcus pyogenes* as shown in FIG. 6 with *E. faecalis* used as the baseline.
Figure 8:
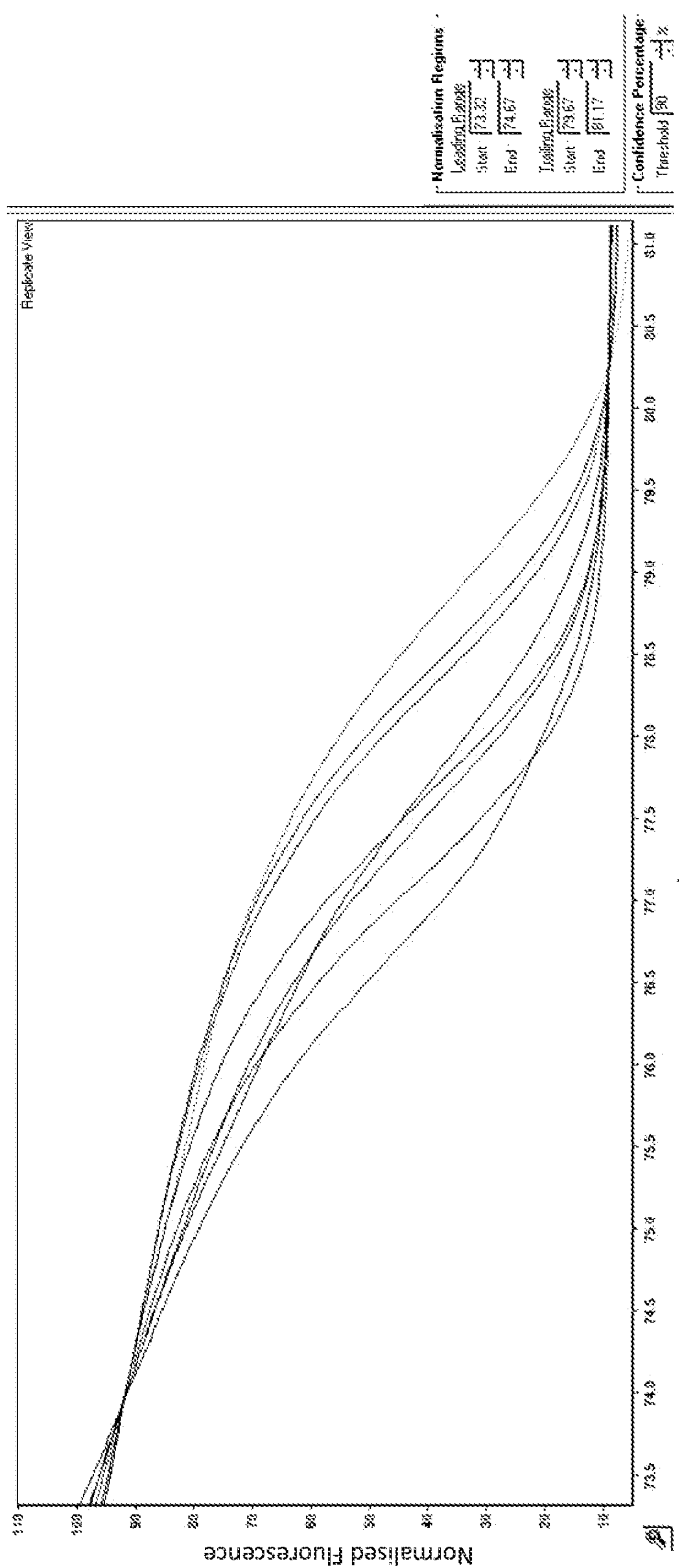
FIG. 8 shows a normalised HRM curves plot for *Escherichia coli, Enterobacter cloacae, Serratia marcescens, Acinetobacter calcoaceticus, Enterobacter aerogenes, Pseudomonas aeruginosa, Klebsiella pneumoniae* and *Proteus mirabilis* for amplicons containing a SNP at a position corresponding to position 412 in the 16S rRNA gene as set forth in SEQ ID NO:1.
Figure 9:
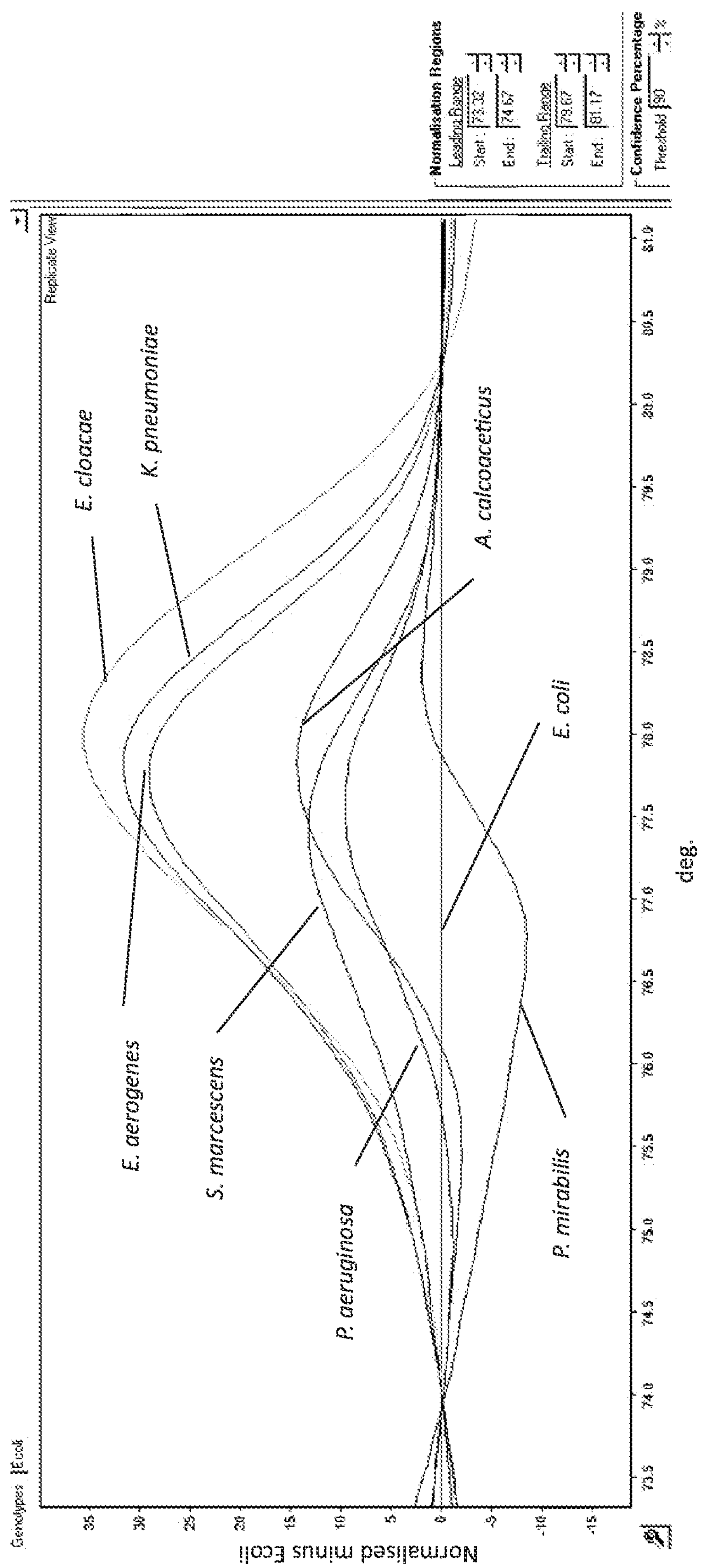
FIG. 9 shows a difference HRM curves plot for *Escherichia coli, Enterobacter cloacae, Serratia marcescens, Acinetobacter calcoaceticus, Enterobacter aerogenes, Pseudomonas aeruginosa, Klebsiella pneumoniae* and *Proteus mirabilis* as shown in FIG. 8 with *Escherichia coli* used as the baseline.
Figure 10:
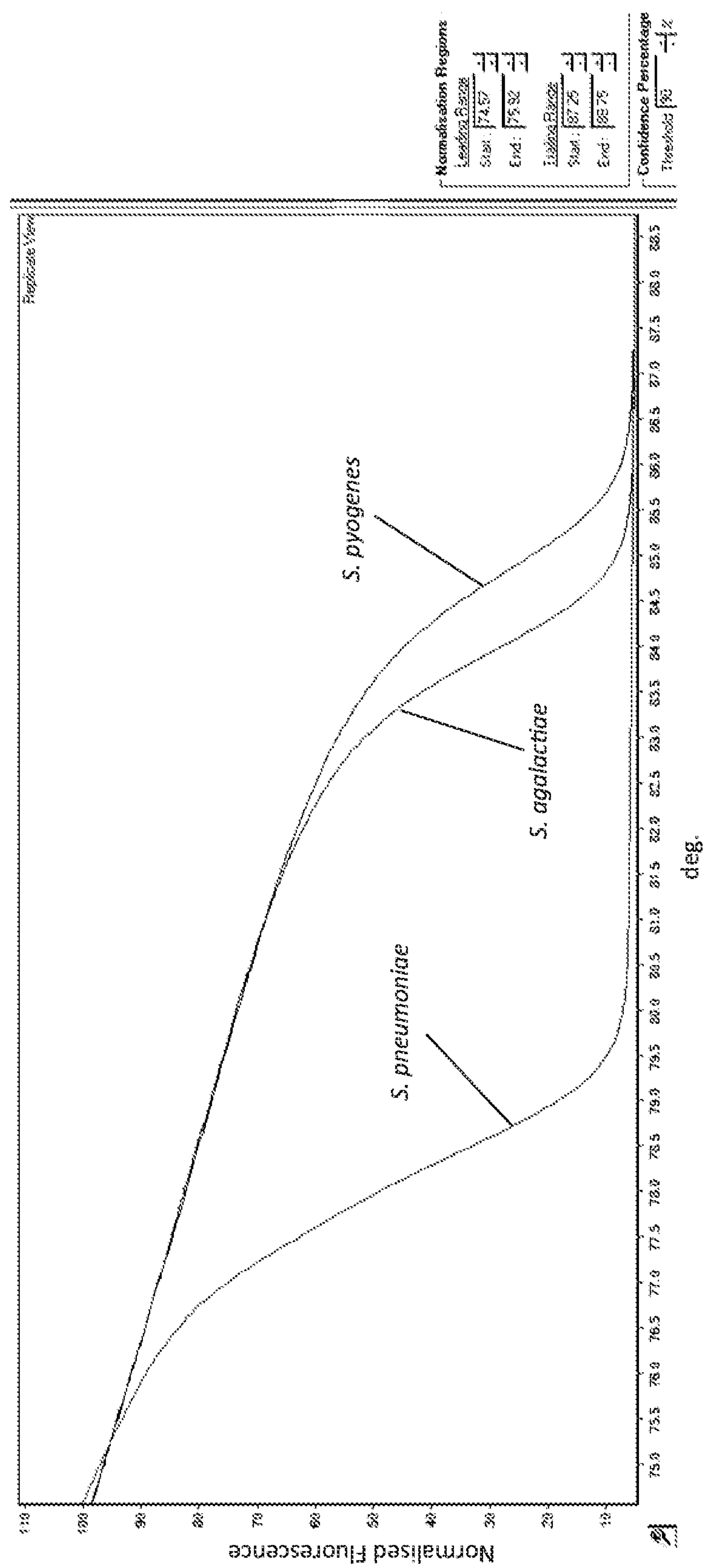
FIG. 10 shows a normalised HRM curves plot for *Streptococcus agalactiae, Streptococcus pneumoniae*, and *Streptococcus pyogenes* for amplicons containing a SNP at a position corresponding to position 378 in the 16S rRNA gene as set forth in SEQ ID NO:1.
Figure 11:
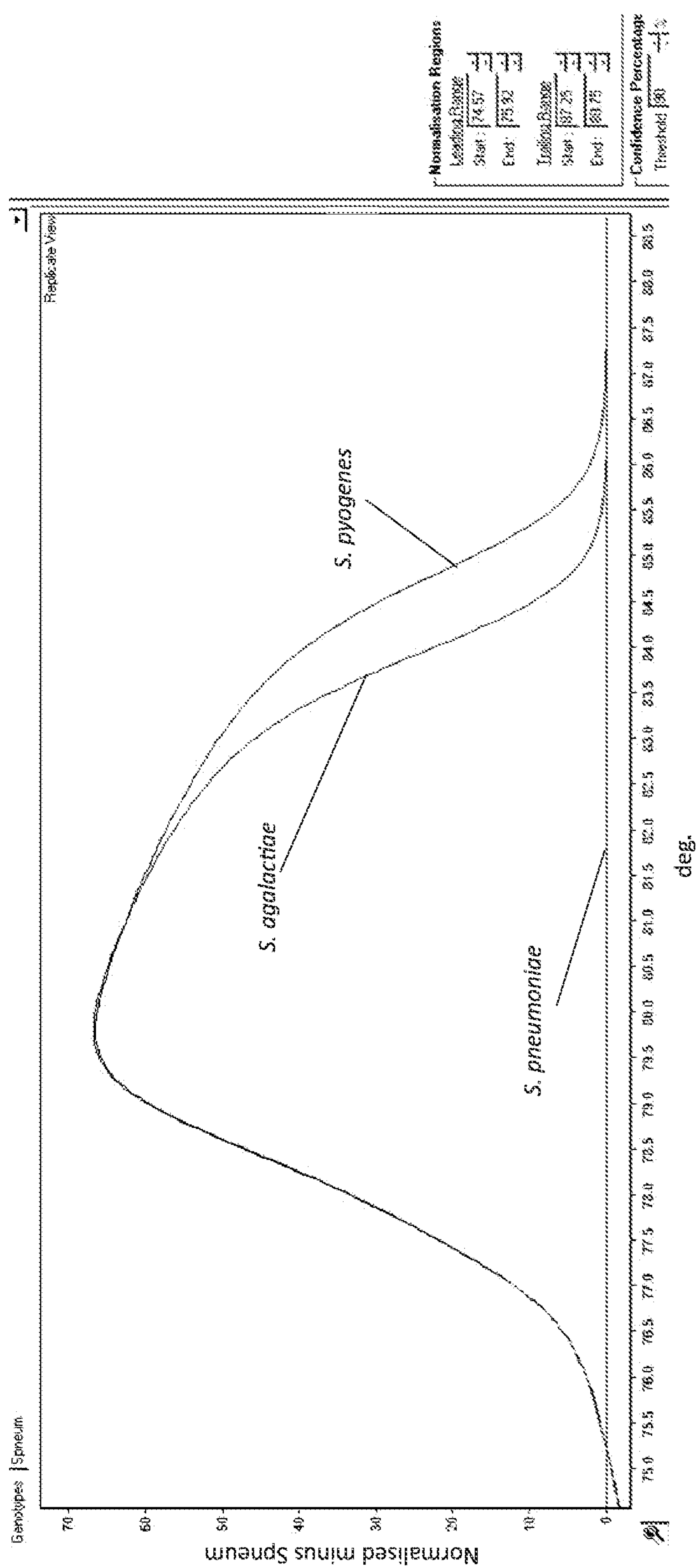
FIG. 11 shows a difference HRM curves plot for *Streptococcus agalactiae, Streptococcus pneumoniae*, and *Streptococcus pyogenes* as shown in FIG. 10 with *Streptococcus pneumoniae* used as the baseline.
Figure 12:
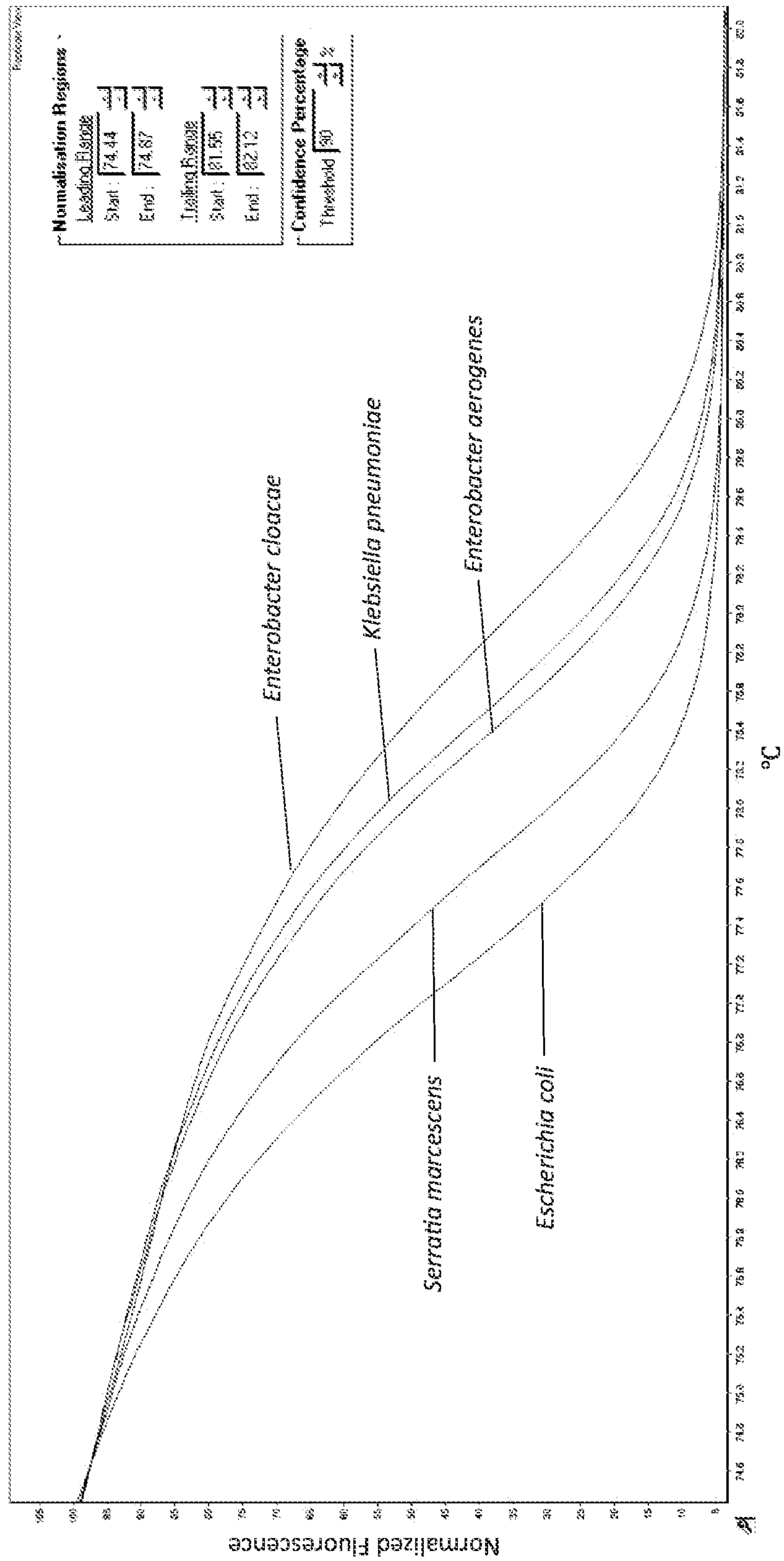
FIG. 12 shows a normalised HRM curves plot for *Escherichia coli, Klebsiella pneumoniae, Enterobacter aerogenes, Enterobacter cloacae*, and *Serratia marcescens* for amplicons containing a SNP at a position corresponding to position 412 in the 16S rRNA gene as set forth in SEQ ID NO:1.
Figure 13:
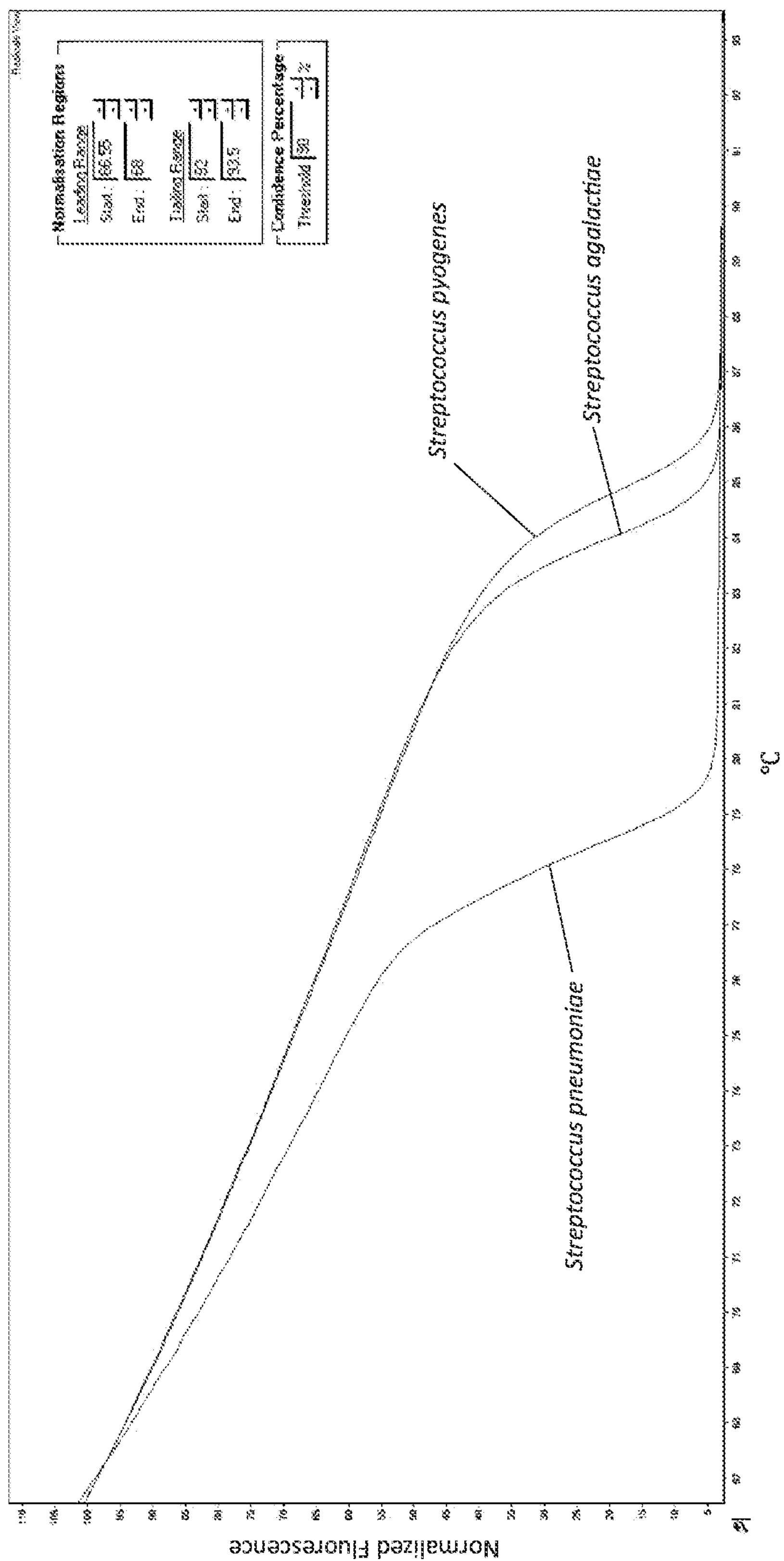
FIG. 13 shows a normalised HRM curves plot for *Streptococcus* pneumonaie, *Streptococcus agalactiae* and *Streptococcus pyogenes* for amplicons containing a SNP at a position corresponding to position 412 in the 16S rRNA gene as set forth in SEQ ID NO:1.

Each of the 15 bacterial species was designated with species specific genotypes in the HRM analysis setting of the Rotor-Gene 6000 software (version 1.7.34 or 1.7.87). For comparison of the bacterial species difference curves, *Escherichia coli* was used as the "calibrator" or "reference" (indicated as "0" on the Y-axis of the plot shown in FIG. 3. As is shown in FIG. 3, the 14 other bacterial species all showed curves that differ away from the "0" line of *Escherichia coli*. Another example of species differentiation is shown in FIG. 5, where *Staphylococcus aureus* is selected as the "calibrator" or "reference" (at the "0" position on the Y-axis) and as shown *Staphylococcus epidermidis* has a complete separate curve.

The melt curve specificity for the bacteria in urine and plasma is provided in Table 11.

TABLE 11

Bacterial speciation in urine and plasma: Melt curve specificity

| Name | Tm$ | SNP* no. |
|---|---|---|
| *E. coli* | 77.075 | 1 |
| *E. cloacae* | 79.050 | 1 |

TABLE 11-continued

Bacterial speciation in urine and plasma: Melt curve specificity

| Name | Tm$ | SNP* no. |
|---|---|---|
| *S. marcescens* | 77.810 | 1 |
| *E. aerogenes* | 78.250 | 1 |
| *K. pneumoniae* | 78.435 | 1 |
| *E. faecalis* | 83.850 | 2 |
| *E. faecium* | 83.475 | 2 |
| *S. agalactiae* | 83.925 | 2 |
| *S. pyogenes* | 84.825 | 2 |
| *S. aureus* | 81.485 | 3 |
| *S. epidermidis* | 81.700 | 3 |
| *S. pneumoniae* | 78.225 | 4 |

$Tm: PCR product melting temperature;

*SNP: Single nucleotide polymorphism.

p-value SNP1vsSNP2: <0.0001; p-value SNP2vsSNP3: 0.002; p-value SNP3vsSNP4: 0.0005.

DISCUSSION

This example demonstrates the utility of applying only seven highly discriminating SNPs to differentiate between 15 different bacterial species known to cause life-threatening diseases such as sepsis. The results also indicate that the method of the present invention is highly specific and rapid, both of which are important requirements for a DNA diagnostic assay. This method accurately determines whether two isolates are the same or different based on the DNA melt curves of the PCR products encompassing the highly discriminatory SNPs. The interrogation of these genetic targets means that this approach is especially amenable to adaption to emerging technologies such as "lab-on-chip" devices and dedicated, fully automated real-time PCR machines. Combined with rapidly advancing innovations in microfluidics, the methods of the present invention are suitable for transfer onto devices suitable for "point-of-care" diagnostics.

Example 2

To demonstrate the utility of the present invention, two hundred blood culture positive patient samples were assessed by both standard clinical microbiology and by the methods of the present invention.

The standard clinical microbiology tests were performed by a routine blood culture procedure in the laboratory utilising the BacTAlert system followed by the MALDI biotyper method for bacterial species identification. This involved entering the BacTAlert blood culture bottles into an automated, continuous-monitoring incubation that are incubated for 5-7 days. Once the blood culture bottle is flagged as positive (a minimum of 12 hours incubation), the bottle is removed from the BacTAlert instrument and an aliquot of the growth medium is removed and sub-cultured onto bacterial culture agar plates. The agar plates are incubated at 37° C. for at least 4 hours, or until visible growth appears. Thereafter, a single bacterial colony is placed onto the target plate and a matrix solution is added. The plate is inserted into the biotyper instrument and a MALDI-TOF spectrum is generated by the software. The spectrum is matched against a reference library to provide bacterial identification. The total time for this process is around 16-18 hours. The standard clinical microbiology tests were performed by Pathology Queensland.

The method used according to the present invention was to collect blood culture liquid (lmL) from 100 blood culture-negative samples after 5 days of incubation on a BacTAlert blood culture machine and stored at 4° C. until extracted. Blood culture liquid (lmL) was also collected from 200 blood-culture positive samples by staff at the Diagnostic Microbiology Department, Pathology Queensland and stored at 4° C. until DNA was extracted. Microbial DNA was isolated from all samples (blood-culture negative and blood-culture positive) using the MolYsis™ Complete 5 kit (Molzym Life Science, Germany) which enables host DNA removal, pathogen enrichment and DNA extraction from lmL of sample.

All 300 DNA extractions were subjected to testing using a real-time PCR format as follows: One microliter of extracted DNA (1 to 3 ng) was added to 19 μl of reaction mastermix containing 10 μl of the 2×SYBR green PCR Mastermix (Life Technologies, Australia) and 8 pmol of each primer. Temperature cycling for these reactions were as follows: 50° C. for 2 min, 95° C. for 2 min, followed by 40 cycles of 95° C. for 15s, 52° C. for 20s, and 72° C. for 35s, Hold at 72° C. for 2 min, Hold at 50° C. for 20s, HRM: Ramp from 65° C.-95° C. rising by 0.05° C. (RotorGeneQ, Qiagen, Australia). All samples were run in duplicate, including the relevant controls (No Template (NTC) and a positive control consisting of bacterial reference DNA for each bacterial species tested. The time to result was recorded as ±3.5 hrs.

The results were tabulated and were correlated to blood culture microbiology results obtained from Pathology Queensland at the conclusion of the study.

Results

The results of the trial are provided in Table 12.

TABLE 12

Correlation between method of the present invention and clinical microbiology results (Pathology QLD trial). Ten bacterial species were represented in 200 blood culture positive patient samples.

| Bacterial species | Gram status | Clinical microbiology result - samples positive | Method of present invention |
|---|---|---|---|
| *Staphylococcus aureus* | Positive | 56 | 55 |
| *Staphylococcus epidermidis* | Positive | 55 | 54 |
| *Enterococcus faecalis* | Positive | 11 | 11 |
| *Escherichia coli* | Negative | 50 | 50 |
| *Enterobacter cloacae* | Negative | 5 | 5 |
| *Klebsiella pneumoniae* | Negative | 4 | 4 |
| *Serratia marcescens* | Negative | 6 | 6 |
| *Streptococcus agalactiae* | Positive | 7 | 6 |
| *Streptococcus pyogenes* | Positive | 3 | 3 |
| *Streptococcus pneumoniae* | Positive | 3 | 3 |
| Total | | 200 | 198 (99% specificity) |

Advantageously, the method of the present invention was able to obtain 99% specificity when compared to the clinical microbiology result (however, it is unclear for the two samples where the clinical microbiology and the method of the present invention obtained different results which method produced the incorrect result). The method of the present invention was able to obtain the result within about 3.5 hours and with minimal handling of the patient sample. In contrast, the clinical microbiology result required more significant handling of the patient sample and took about 16-18 hours to obtain.

CITATIONS

Anderson & Borreson, 1995, *Diagnostic Molecular Pathology,* 4: 203-211.

Andersson, P., et al., 2009, *Antimicrob. Agents Chemother.* 53:2679-2683.
Ausubel et al., *Current Protocols in Molecular Biology* (John Wiley & Sons, Inc. 1994-1998.
Bullock, G. R. et al., 1985, Techniques in Immunocytochemistry, Academic Press, Orlando, Fla. Vol. 1 (1982), Vol. 2 (1983), Vol. 3 (1985).
Chard, T., 1986, An Introduction to Radioimmunoassay and Related Techniques, Elsevier Science Publishers, Amsterdam, The Netherlands (1986)
Chee, et al., 1996, *Science* 274: 610-613.
Chumanov, G. "Surface Enhanced Raman Scattering (SERS) for Discovering and Scoring Single Based Differences in DNA" Proc. Volume SPIE, 3608 (1999).
Cotton, et al., 1988, *Proc. Natl. Acad. Sci. USA,* 85:4397.
Cronin, et al., 1996, *Human Mut.* 7: 244-255.
De Risi et al, 1996, *Nat. Genet.* 14: 457-460.
DeRisi et al., 1997, *Science* 270:680-686.
Deveraux et al., 1984, *Nucleic Acids Research* 12, 387-395.
Drmanac and Drmanac, 1999, *Methods Enzymol.* 303: 165-178
Drmanac et al., 1993, *Science* 260: 1649-1652.
Drmanac et al., 1998, *Nature Biotech.* 16: 54-58.
Gibbs et al., 1989, *Nucleic Acids Research,* 17: 2347.
Gibbs, R. A. and Caskey, T., 1987, *Science,* 236:303-305.
Ginot, 1997, *Human Mutation* 10:1-10.
Hacia et al., 1996, *Nat. Genet.* 14: 441-447.
Jobs et al., 2003, *Genome Res* 13: 916-924.
Karlowsky, J. A., et al. (2004) *Ann Clin Microbiol Antimicrob.* 10; 3:7.
Kim S. & Misra A. 2007, *Ann Rev Biomed Eng.* 9:289-320.
Kneipp, K, 1997, *Physical Review Letters,* 78(9):1667-1670.
Komher, J. S. et al., 1989, *Nucl. Acids. Res.* 17: 7779-7784.
Kumar, D. et al., 2006, *Genet. Mol. Biol,* 29(2):287-289.
Kuppuswamy, M. N. et al., 1991 *Proc. Natl. Acad. Sci.* (U.S.A.) 88:1143-1147.
Levy et al., 2003, *Critical Care Medicine,* 31:1250-1256.
Liu et al, 1996, *J. Am. Chem. Soc.* 118: 1587-1594.
Lockhart et al., 1996, *Nature Biotechnol.* 14:1675-1680.
Lu, A. L. and Hsu, I. C., 1992, *Genomics,* 14(2):249-255.
Lyamichev, V. et al., 1999, *Nat Biotechnol,* 17: 292-296.
Maxam, A. M., et al., 1977, *Proc. Natl. Acad. Sci.* (U.S.A.) 74:560.
Merchant-Patel, S., et al., 2008, *Int. J. Food Microbiol.,* 128:304-308.
Merchant-Patel, S., Blackall, P. J., Templeton, J., Price, E. P., Tong, S. Y. C., Huygens, F., and Giffard, P. M., 2010, *Applied and Environmental Microbiology.,* 76(2):493-499.
Meyers, R. M., et al., 1985 *Science,* 230:1242-1246.
Milosavljevic et al., 1996, *Genomics,* 37: 77-86.
Modrich, 1991, *Ann. Rev. Genet.,* 25: 229-253.
Nagamine, C. M. et al., 1989, *Am. J. Hum. Genet,* 45:337-339.
Newton et al., 1989, *Nucl. Acids Res.* 17: 2503-2516.
Novack et al., 1986, *Proc. Natl. Acad. Sci. USA,* 83:586.
Nyren, P., et al., 1993 *Anal. Biochem.* 208: 171-175.
Orita, M. et al., 1989, *Proc Natl Acad Sci USA,* 86:2766.
Prezant, T. R., et al., 1992 *Hum. Mutat.* 1: 159-164.
Price, E. P., et al., 2007, *Appln. Environ. Microbiol,* 72:7793-7803.
Prince, J. A., et al., 2001 *Genome Res,* 11(1):152-162.
Protocols for Oligonucleotides and Analogues; Synthesis and Properties", Methods in Molecular Biology Series, Volume 20, Ed. Sudhir Agrawal, Humana ISBN: 0-89603-247-7, 1993.
Ramsay, 1998, *Nature Biotech.* 16: 40-44.
Reinhart et al., 2012, *Clinical Microbiology Reviews* 25(4): 609-634.
Saleeba, J. A., et al., 1992 *Huma. Mutat,* 1:63-69
Salimullah, et al., 2005, *Cellular and Mol. Biol. Letts,* 10: 237-245
Sapolsky and Lishutz, 1996, *Genomics* 33: 445-456
Schena et al., 1995, *Science* 270: 467.
Shalon, et al., 1996, *Genome Res.* 6: 639.
Sheffield et al., 1989, *Proc. Natl. Acad. Sci. USA* 86: 232-236
Shenk et al., 1975, *Proc. Natl. Acad. Sci. USA,* 72:989.
Shoemaker et al., 1996, *Nat. Genet.* 14: 450-456.
Smith-Sorenson et al., 1993, *Human Mutation* 2:274-285.
Sokolov, B. P., 1990, *Nucl. Acids Res.* 18: 3671.
Sooknanan et al., 1994, *Biotechniques* 17:1077-1080.
Stephens, A. J., Inman-Bamber, J., Giffard, P. M., and Huygens, F., 2008, *Clinical Chemistry.* 54(2):432-436.
Syvanen, A. C, et al., 1990 *Genomics,* 8: 684-692.
Syvanen, A. C, et al., 1993, *Amer. J. Hum. Genet.* 52: 46-59.
Syvanen, A. C., 2001, *Nat. Rev. Genet.* 2, 930-942.
Thelwell et al., 2000 *Nucleic Acid Res.* 28(19): 3752-3761.
Tijssen, P., 1985, Practice and Theory of Enzyme Immunoassays: Laboratory Techniques in Biochemistry and Molecular Biology, Elsevier Science Publishers, Amsterdam, The Netherlands.
Tyagi et al., 1996, *Proc. Natl. Acad. Sci. USA* 93:5395-5400.
Tyagi, S and Kramer, F. R., 1996, *Nat. Biotechnol,* 14: 303-308
Ugozzoli, L., et al., 1992, *GATA,* 9: 107-112.
Wartell et al., 1990 *Nucl. Acids Res.* 18:2699-2705
Weisburg W G, et al., (1991) *J Bacteriol.* 173 (2): 697-703.
Wodicka et al, 1997, *Nat. Biotech.* 15: 1-15.
Xiao and Kwok, 2003, *Genome Research,* 13(5): 932-939.
Yershov et al., 1996, *Genetics* 93: 4913-4918.

The invention claimed is:

1. A method of identifying a sepsis-associated bacterial species present in a sample, said method comprising analysing at least a portion of a bacterial 16S rRNA gene from the sample for the presence or absence of at least one single nucleotide polymorphism (SNP), wherein analysing at least a portion of the bacterial 16S rRNA gene comprises:

a) amplifying the bacterial 16S rRNA gene with oligonucleotide primers comprising SEQ ID NOs: 16-35, to produce a DNA amplification product comprising the at least one SNP, and b) using high-resolution melt analysis to analyse the DNA amplification product, thereby identifying the sepsis-associated bacterial species;

wherein the at least one SNP is at a position corresponding to at least one of positions 273, 378, 412, 440, 488, 647, and 653 of the 16S rRNA gene set forth in SEQ ID NO: 1;

the sepsis-associated bacteria is selected from the group consisting of *Acinetobacter calcoaceticus; Enterobacter aerogenes; Enterobacter cloacae; Enterococcus faecalis; Enterococcus faecium; Escherichia coli; Klebsiella pneumoniae; Proteus mirabilis; Pseudomonas aeruginosa; Serratia marcescens; Staphylococcus aureus; Staphylococcus epidermidis; Streptococcus agalactiae; Streptococcus pneumoniae* and *Streptococcus pyogenes*; and the sample is selected from the group consisting of: hair, skin, nails, biological tissue, sputum, saliva, cerebrospinal fluid, urine and blood.

2. The method of claim 1, wherein the at least one SNP in the at least a portion of the bacterial 16S rRNA gene is at least two SNPs at a position corresponding to at least two of positions 273, 378, 412, 440, 488, 647, and 653, of the 16S rRNA gene set forth in SEQ ID NO: 1.

3. The method of claim 1, further comprising treating a subject from whom the sample is collected and who is identified as having a bacterial infection, by administering to the subject an antibiotic agent for treating the bacterial infection in the subject.

4. The method of claim 2, wherein said method comprises analysing at least a portion of a bacterial 16S rRNA gene from the sample for the presence or absence of:

single nucleotide polymorphisms in the at least a portion of the bacterial 16S rRNA gene or gene product at a position corresponding to at least four of positions 273, 378, 412, 440, 488, 647, and 653 of the 16S rRNA gene set forth in SEQ ID NO: 1.

5. The method of claim 1, wherein the at least one SNP in the at least a portion of the bacterial 16S rRNA gene is at a position corresponding to at least one of positions 737, 755, 762 and 776 of the 16S rRNA gene set forth in SEQ ID NO: 1.

6. The method of claim 1, wherein said method further comprises the step of determining whether the sepsis-associated bacterial species is resistant to a therapeutic agent.

7. The method of claim 1, wherein the oligonucleotide primers comprising SEQ ID NO: 16, 21, 23, 24, 25, 29, 31, 32, and 33 are forward primers, and the oligonucleotide primers comprising SEQ ID NO: 17, 22, 26, 27, 28, 30, 34, and 35 are reverse primers.

8. A kit for identifying a sepsis-associated bacterial species in a sample, said kit comprising:

forward oligonucleotide primers consisting of SEQ ID NO: 16, 18, 19, 21, 23, 24, 25, 29, 31, 32, and 33, reverse oligonucleotide primers consisting of SEQ ID NO: 17, 20, 22, 26, 27, 28, 30, 34, and 35; and an enzyme, buffer, and/or deoxynucleotides for amplifying the bacterial 16S rRNA gene for high-resolution melt analysis.

9. The method of claim 1, wherein the sepsis-associated bacterial species is identified based on the presence or absence of the at least one SNP as follows:

(A) the sepsis-associated bacterial species is determined to be a Gram positive species when there is an A at position 273 and a T at position 653; or (B) the sepsis-associated bacterial species is determined to be a Gram positive species when there is a T at position 440; or (C) the sepsis-associated bacterial species is classified as belonging to the *Staphylococcus* genus when there is a T at position 412; or (D) the sepsis-associated bacterial species is classified as belonging to the *Enterococcus* genus when there is a G at position 647; or (E) the sepsis-associated bacterial species is identified as *Enterobacter cloacae* when there is a G at position 653; or (F) the sepsis-associated bacterial species is identified as *Streptococcus pneumoniae* when there is an A at position 378 and a T at position 488, or when there is T at positions 488 and 647; or (G) the sepsis-associated bacterial species is identified as *Streptococcus agalactiae* when there is an A at position 378, 488, and position 647; or (H) the sepsis-associated bacterial species is identified as *Streptococcus pyogenes* when there is a G at position 378 and an A at position 488 and 647; or (I) the sepsis-associated bacterial species is identified as *Acinetobacter calcoaceticus* when there is an A at positions 273, 440 and 647; or (J) the sepsis-associated bacterial species is identified as *Escherichia coli* when there is a T at position 273 and a T at position 653; or (K) the sepsis-associated bacterial species is identified as *Klebsiella pneumoniae* when there is a T at position 273, a C at positions 488 and 647 and an A at position 653; or (L) the sepsis-associated bacterial species is identified as *Proteus mirabilis* when there is a C at positions 440 and 488 and a T at position 647; or (M) the sepsis-associated bacterial species is identified as *Pseudomonas aeruginosa* when there is an A at position 440 and a T at position 647.

10. The method of claim 9, wherein:

*Staphylococcus aureus* and *Staphylococcus epidermidis* are identified when there is a T at position 412 and then distinguished from one another based on high-resolution melt curve analysis of the DNA surrounding the SNP at position 412;

*Enterococcus faecalis* and *Enterococcus faecium* are identified when there is a G at position 647 and then distinguished from one another based on high-resolution melt curve analysis of the DNA surrounding the SNP at position 647;

*Serratia marcescens* and *Enterobacter aerogenes* are identified when there is a C at positions 440 and 647 and a T at position 488 and then distinguished from one another based on high-resolution melt curve analysis of the DNA surrounding the SNPs at any one of positions 440, 488 and 647; or

*Enterococcus faecalis, Enterococcus faecium, Streptococcus agalactiae*, and *Streptococcus pyogenes* are identified in a sample based when there is an A at position 378 and then distinguished from one another based on high-resolution melt curve analysis of the DNA surrounding the SNP at position 378.

11. The method of claim 1, wherein the oligonucleotide primers consist of SEQ ID NOs: 16-35.

* * * * *